United States Patent
Gokhale et al.

(10) Patent No.: US 12,404,242 B2
(45) Date of Patent: Sep. 2, 2025

(54) COMPOSITIONS AND METHODS FOR MAKING AND USING SMALL MOLECULES IN THE TREATMENT OF CANCER

(71) Applicant: Reglagene, Inc., Houston, TX (US)

(72) Inventors: Vijay Gokhale, Houston, TX (US); Teri C. Suzuki, Houston, TX (US)

(73) Assignee: Reglagene, Inc., Houston, TX (US)

( * ) Notice: Subject to any disclaimer, the term of this patent is extended or adjusted under 35 U.S.C. 154(b) by 0 days.

(21) Appl. No.: 18/718,991

(22) PCT Filed: Dec. 16, 2022

(86) PCT No.: PCT/IB2022/062416
§ 371 (c)(1),
(2) Date: Jun. 12, 2024

(87) PCT Pub. No.: WO2023/111996
PCT Pub. Date: Jun. 22, 2023

(65) Prior Publication Data
US 2025/0109105 A1    Apr. 3, 2025

Related U.S. Application Data

(60) Provisional application No. 63/291,144, filed on Dec. 17, 2021.

(51) Int. Cl.
| C07D 213/643 | (2006.01) |
| A61K 31/426 | (2006.01) |
| A61K 31/44 | (2006.01) |
| A61K 31/505 | (2006.01) |
| C07D 239/34 | (2006.01) |
| C07D 277/34 | (2006.01) |

(52) U.S. Cl.
CPC ........ *C07D 213/643* (2013.01); *A61K 31/426* (2013.01); *A61K 31/44* (2013.01); *A61K 31/505* (2013.01); *C07D 239/34* (2013.01); *C07D 277/34* (2013.01)

(58) Field of Classification Search
CPC .......... C07D 213/643; C07D 277/34; C07D 239/34; A61K 31/426; A61K 31/44; A61K 31/505
See application file for complete search history.

(56) References Cited

U.S. PATENT DOCUMENTS

| 7,144,911 | B2 | 12/2006 | Flynn et al. |
| 7,342,037 | B2 | 3/2008 | Flynn et al. |
| 7,968,536 | B2 | 6/2011 | Cossrow et al. |
| 8,017,629 | B2 | 9/2011 | Cheng et al. |
| 8,034,954 | B2 | 10/2011 | Pacofsky et al. |
| 8,080,567 | B2 | 12/2011 | Oxford et al. |
| 8,124,632 | B2 | 2/2012 | Rossignol et al. |
| 8,158,636 | B2 | 4/2012 | Ibrahim et al. |
| 8,431,605 | B2 | 4/2013 | Hadida Ruah et al. |
| 8,703,761 | B2 | 4/2014 | Forster et al. |
| 8,722,702 | B2 | 5/2014 | Zhang et al. |
| 8,802,657 | B2 | 8/2014 | Cossrow et al. |
| 8,822,513 | B2 | 9/2014 | Lu et al. |
| 8,921,576 | B2 | 12/2014 | Ogamino et al. |
| 9,115,120 | B2 | 8/2015 | Jones et al. |
| 9,334,242 | B2 | 5/2016 | Lu et al. |
| 9,447,049 | B2 | 9/2016 | Li et al. |
| 9,550,768 | B2 | 1/2017 | Zhang et al. |
| 11,028,061 | B2 | 6/2021 | Kelly et al. |
| 11,078,171 | B2 | 8/2021 | Shapiro et al. |
| 11,084,811 | B2 | 8/2021 | Li et al. |
| 11,149,033 | B2 | 10/2021 | Min et al. |
| 2009/0036467 | A1 | 2/2009 | Rossignol et al. |
| 2009/0069310 | A1 | 3/2009 | Flynn et al. |
| 2009/0136472 | A1 | 5/2009 | Westman et al. |
| 2010/0076029 | A1 | 3/2010 | Bartolozzi et al. |
| 2010/0081644 | A1 | 4/2010 | Bartolozzi et al. |
| 2010/0152162 | A1 | 6/2010 | Uesaka et al. |
| 2010/0333138 | A1 | 12/2010 | Burgdorf et al. |
| 2011/0312932 | A1 | 12/2011 | Bartolozzi et al. |
| 2012/0010184 | A1 | 1/2012 | Bartolozzi et al. |
| 2012/0071524 | A1 | 3/2012 | Lu et al. |
| 2012/0108576 | A1 | 5/2012 | Zhang et al. |
| 2020/0024270 | A1 | 1/2020 | Li et al. |

(Continued)

FOREIGN PATENT DOCUMENTS

| EP | 2055697 A1 | 5/2009 |
| WO | 2005075435 A1 | 8/2005 |

(Continued)

OTHER PUBLICATIONS

Registry No. 1972-67-4, File REGISTRY on STN, entered STN Nov. 16, 1984.*

Patron et al. "Abstract A023: Brain penetrant small molecule for the treatment of glioblastoma." Cancer Research 84.5_Supplement_1 (2024): A023-A023.

Wager et al. "Moving beyond rules: the development of a central nervous system multiparameter optimization (CNS MPO) approach to enable alignment of druglike properties." ACS chemical neuroscience 1.6 (2010): 435-449.

Alavijeh et al. "Drug metabolism and pharmacokinetics, the blood-brain barrier, and central nervous system drug discovery." NeuroRx 2 (2005): 554-571.

(Continued)

*Primary Examiner* — Rebecca L Anderson
(74) *Attorney, Agent, or Firm* — NGUYEN TARBET IP LAW

(57) ABSTRACT

Embodiments of the instant disclosure relate to novel compounds, compositions, and methods for treating health conditions. In certain embodiments, methods of treating cancers can include administering an effective amount of at least one novel compound disclosed herein to a subject having cancer. In some embodiments, methods of treating cancers can include administering a pharmaceutical composition disclosed herein to a subject, the composition including at least one of the novel compounds disclosed herein, and optionally, one additional agent.

3 Claims, 37 Drawing Sheets

(56) References Cited

U.S. PATENT DOCUMENTS

| | | |
|---|---|---|
| 2021/0186022 A1 | 6/2021 | Pouliot et al. |
| 2022/0024912 A1 | 1/2022 | Li et al. |
| 2022/0089532 A1 | 3/2022 | Nojima et al. |
| 2022/0298168 A1 | 9/2022 | Le Bourdonnec et al. |
| 2023/0029266 A1 | 1/2023 | Cevikbas et al. |

FOREIGN PATENT DOCUMENTS

| | | | |
|---|---|---|---|
| WO | 2006004636 | A2 | 5/2006 |
| WO | 2007010273 | A2 | 1/2007 |
| WO | 2006122011 | A2 | 5/2007 |
| WO | 2008065409 | A2 | 6/2008 |
| WO | 2008090327 | A1 | 7/2008 |
| WO | 2009085256 | A1 | 7/2009 |
| WO | 2009106203 | A1 | 9/2009 |
| WO | 2010036630 | A1 | 4/2010 |
| WO | 2010133312 | A1 | 11/2010 |
| WO | 2012103583 | A1 | 8/2012 |
| WO | 2013131018 | A1 | 9/2013 |
| WO | 2016160938 | A1 | 10/2016 |
| WO | 2017006282 | A1 | 1/2017 |
| WO | 2018069863 | A1 | 4/2018 |
| WO | 2018087160 | A1 | 5/2018 |
| WO | 2019183587 | A1 | 9/2019 |
| WO | 2020198026 | A1 | 10/2020 |
| WO | 2021092240 | A1 | 5/2021 |
| WO | 2021115375 | A1 | 6/2021 |
| WO | 2021163192 | A1 | 8/2021 |
| WO | 2021216656 | A1 | 10/2021 |
| WO | 2021216660 | A1 | 10/2021 |
| WO | 2021248231 | A1 | 12/2021 |
| WO | 2021252555 | A1 | 12/2021 |
| WO | 2022063152 | A1 | 3/2022 |
| WO | 2022174031 | A1 | 8/2022 |
| WO | 2023274251 | A1 | 1/2023 |
| WO | 2023028238 | A1 | 3/2023 |

OTHER PUBLICATIONS

Sun et al. "Why 90% of clinical drug development fails and how to improve it ?. " Acta Pharmaceutica Sinica B 12.7 (2022): 3049-3062.

Van de Waterbeemd et al. "Estimation of blood-brain barrier crossing of drugs using molecular size and shape, and H-bonding descriptors." Journal of drug targeting 6.2 (1998): 151-165.

Office Action for U.S. Appl. No. 18/590,806, dated Aug. 12, 2024.

* cited by examiner

1-{4-[(5-fluoropyridin-2-yl)oxy]-3-methylphenyl}
-3-(3-methoxycyclobutanecarbonyl)urea 1-{4-[(5-cyanopyridin-2-yl)oxy]-3-methylphenyl}
-3-(3-methoxycyclobutanecarbonyl)urea

*N*-((4-((5-chloropyridin-2-yl)oxy)-3-methylphenyl)carbamoyl)-3-methoxybicyclo[1.1.1]pentane-1-carboxamide

*N*-((4-((5-chloropyrimidin-2-yl)oxy)-3-methylphenyl)carbamoyl)-3-methoxybicyclo[1.1.1]pentane-1-carboxamide

COMPOSITIONS AND METHODS FOR MAKING AND USING SMALL MOLECULES IN THE TREATMENT OF CANCER

PRIORITY

This International Application claims priority to U.S. Provisional Application No. 63/291,144, filed Dec. 17, 2021. The provisional application is incorporated herein by reference in its entirety for all purposes.

FIELD

Embodiments of the instant disclosure generally relate to novel compounds, compositions containing at least one of the novel compounds and methods for treating health conditions using one or more of the novel compound-containing compositions disclosed herein. In some embodiments, compositions including one or more novel compounds are disclosed. In certain embodiments, compositions, and methods of treating cancers, inflammatory disorders and autoimmune disorders are disclosed.

BACKGROUND

Despite advances in oncology treatment, cancer remains a leading cause of death due to its high morbidity and mortality. Small molecule therapy can be successful for treatment of some cancers; however, many have a narrow therapeutic index and are not highly selective causing unwanted drug toxicity in a subject. Poor penetrance into sanctuary sites (e.g., CNS) requires some small molecules to be administered at high concentrations which can further contribute to toxic side effects. Additionally, many cancers develop drug resistance to some small molecule therapies over time resulting in relapse of the disease.

Therefore, a need exists for creating novel small molecules for more successful treatments for cancers and other health conditions.

SUMMARY

Embodiments of the present disclosure relate to compositions and methods for treating cancers. In certain embodiments, the present disclosure provides novel compounds for treating cancers. In some embodiments, the present disclosure provides compounds having a formula as illustrated in formula (I),

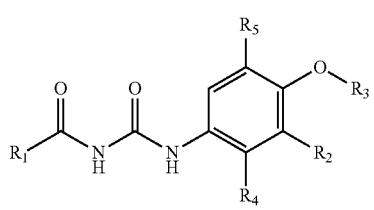

(I)

or formula (II),

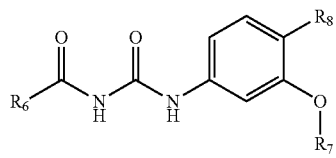

(II)

analogs, isomers, pharmaceutically acceptable salts, and prodrugs thereof;
wherein:
$R_1$ and $R_6$ are each independently selected from:

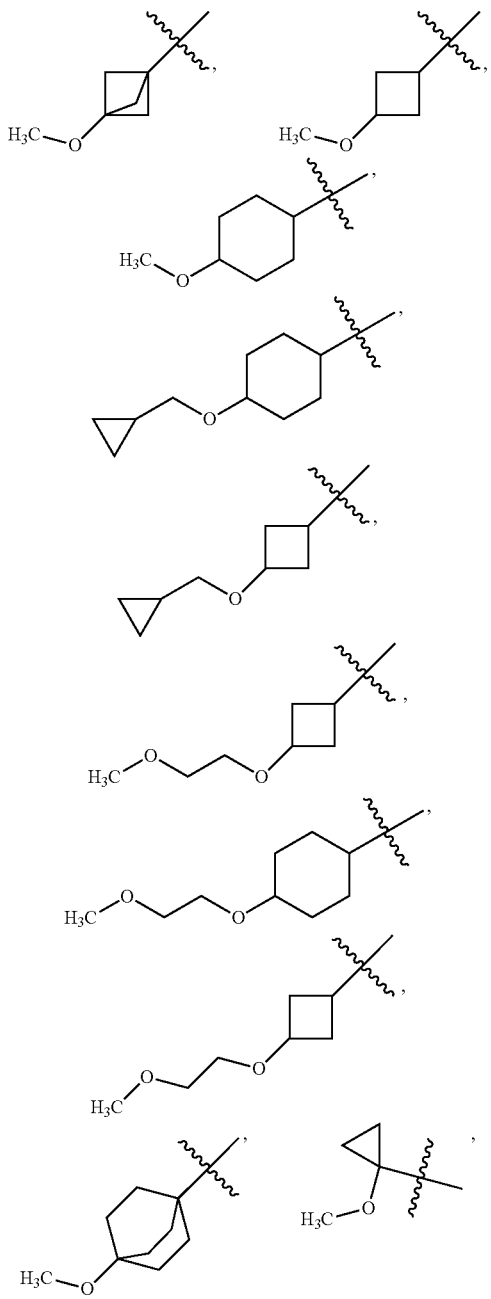

-continued

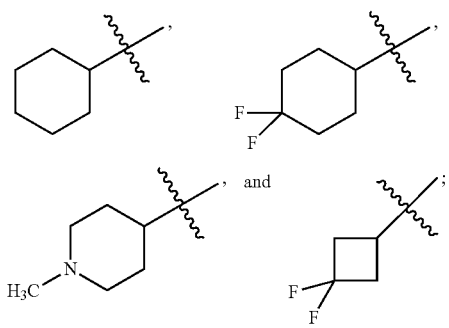

R₂ is selected from CH₃ or F;

R₃ and R₇ are each a heteroaryl, where the heteroaryl is unsubstituted or is optionally substituted with one or more groups independently selected from the group consisting of alkyl, alkenyl, alkynyl, alkoxyl, alkylsulfo, alkylamino, halogen, thiol, hydroxyl, nitro, cyano, cycloalkyl, heterocyclic alkyl, aryl, heteroaryl, cycloalkoxyl, heterocyclic alkoxyl, cycloalkylthio, and heterocyclic alkylthio;

R₄ and R₅ are each independently selected from H and F; and

R₈ is selected from CH₃ and H.

In some embodiments, compounds disclosed herein having formula (I) or formula (II) can have R₁ and R₆ having substitutions of:

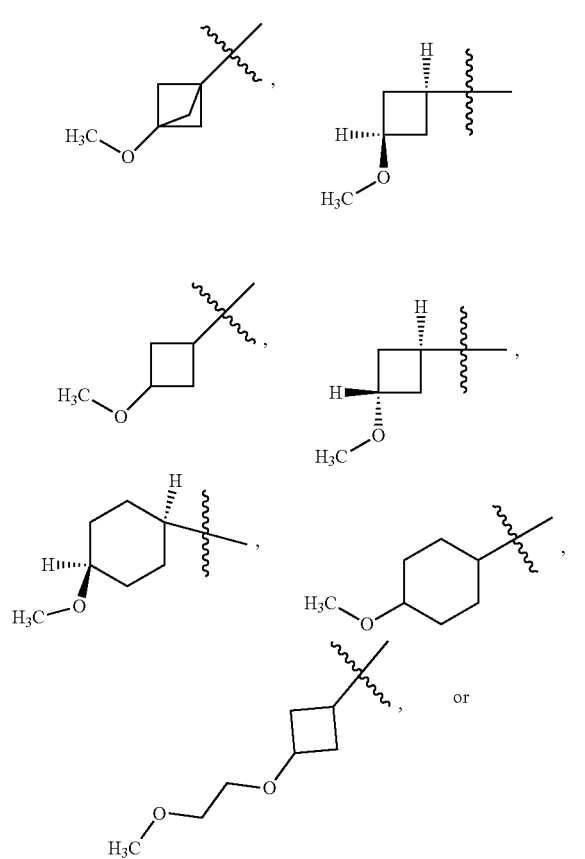

-continued

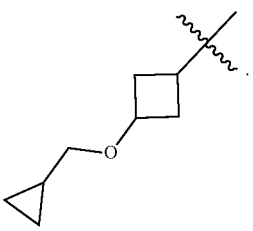

In some embodiments, compounds disclosed herein having formula (I) or formula (II) can have R₁ and R₆ having substitutions of:

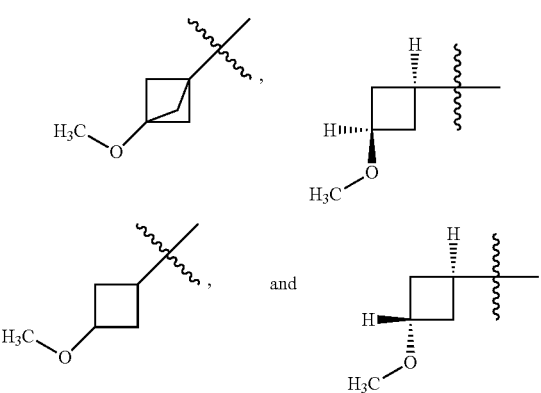

In some embodiments, compounds disclosed herein having formula (I) or formula (II) can have R₃ and R₇ having a 5- or 6-membered heteroaryl where the heteroaryl is unsubstituted or is optionally substituted with one or more groups independently selected from alkyl, alkenyl, alkynyl, alkoxyl, alkylsulfo, alkylamino, halogen, thiol, hydroxyl, nitro, cyano, cycloalkyl, heterocyclic alkyl, aryl, heteroaryl, cycloalkoxyl, heterocylic alkoxyl, cycloalkylthio, heterocylic and alkylthio.

In other embodiments, compounds disclosed herein having formula (I) or formula (II) can have R₃ and R₇ having a 5- or 6-membered heteroaryl where the heteroaryl can be an unsubstituted or is optionally substituted with one or more groups independently selected from:

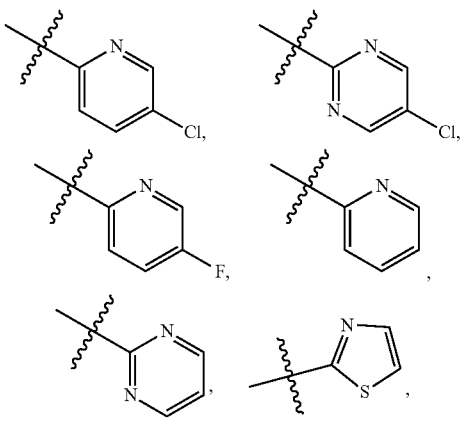

-continued

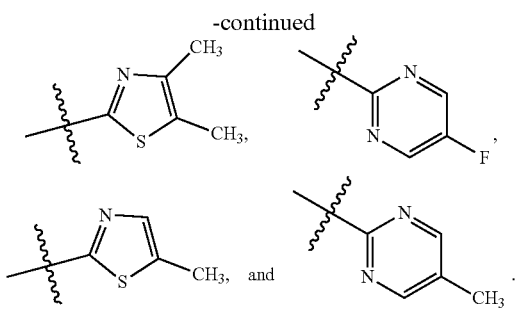

In some embodiments, compounds disclosed herein having formula (I) or formula (II) can have $R_1$ and $R_6$ having

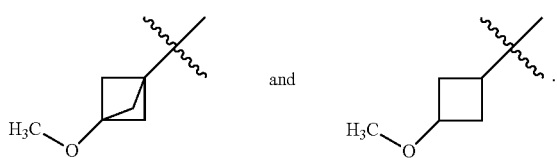

In certain embodiments, compounds disclosed herein having formula (II) can have $R_7$ having:

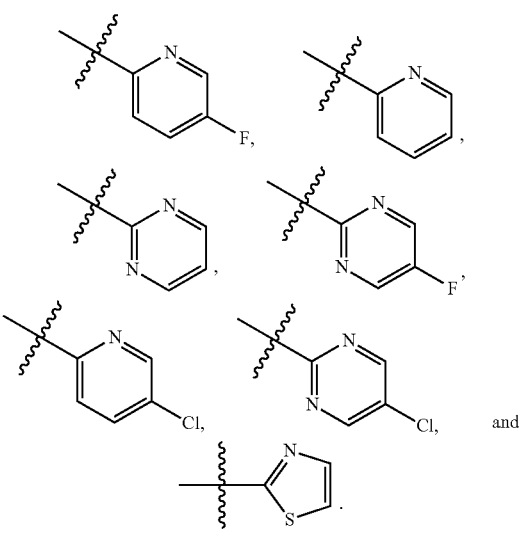

In other embodiments, compounds disclosed herein having formula (I) or formula (II) can include an $R_2$ that is $CH_3$, $R_4$ the is H, and $R_5$ that is H. In some embodiments, compounds disclosed herein having formula (II) can have an $R_8$ that is $CH_3$. In other embodiments, compounds herein having formula (I) or formula (II) can be compounds of Table 3. In some embodiments, compounds disclosed herein having formula (I) or formula (II) can be compound 19, compound 73, compound 86, compound 87, compound 88, compound 90, compound 91, compound 93, compound 94, compound 95, compound 96, compound 97, or compound 98 or a mixture thereof. In certain embodiments, these compounds can be part of a composition such as a pharmaceutically acceptable composition further including at least one excipient for use in treating a health condition or reducing onset or preventing a health condition (e.g., cancer or treatment of a tumor).

In certain embodiments, compounds disclosed herein having formula (I) can have an $EC_{50}$ ranging from about 0.05 μM to about 55 μM for decreasing cancer cell viability or for reducing tumor size or shrinking a tumor. In some embodiments, compounds disclosed herein having formula (I) can have a central nervous system multiparameter optimization (CNS MPO) score greater than or equal to 4.0 or about 4.0. In other embodiments, compounds disclosed herein having formula (I) can have a kinetic solubility ranging from about 0.1 μM to about 110 μM. In some embodiments, compounds disclosed herein having formula (I) can function in part as a cell cycle inhibitor, for example for inhibiting tumor cell expansion or aberrant cell expansion.

In certain embodiments, the present disclosure provides pharmaceutical compositions. In some embodiments, pharmaceutical compositions disclosed herein can include at least one of the compounds disclosed herein and at least one pharmaceutically acceptable excipient or carrier. In other embodiments, pharmaceutical compositions disclosed herein can further include one or more additional agents. In some embodiments, pharmaceutical compositions disclosed herein can include one or more anti-cancer, anti-microbial, or immune response promoting agents. In some embodiments, one or more additional agents can include one or more cellular immune inducing agents (e.g., cytokines or other agents).

In certain embodiments, the present disclosure provides methods for treating a subject having a health condition. In some embodiments, methods disclosed herein for treating a subject having a health condition can include administering to the subject any of the pharmaceutical compositions disclosed herein containing one or more compound disclosed herein. In some embodiments, methods disclosed herein for treating a subject having a health condition can include treating a subject having cancer. In some embodiments, methods disclosed herein for treating a subject having cancer can include treating a solid tumor. In certain embodiments, methods disclosed herein for treating a subject having cancer can include treating metastatic cancer and reducing or preventing metastasis or treating the cancer in a subject. In some embodiments, methods disclosed herein for treating a subject having cancer can include treating prostate cancer, brain cancer, pancreatic cancer, breast cancer, bone sarcoma, liver cancer, bladder cancer, kidney cancer, lung cancer, intestinal cancer, esophageal cancer or other cancer or a combination thereof.

In some embodiments, pharmaceutical compositions disclosed herein can be administered to the subject systemically, topically, subcutaneously, by inhalation, intranasally, intravenously, intradermally, intrauterine or by direct administration into a tumor of the subject. In other embodiments, pharmaceutical compositions disclosed herein can be administered to the subject orally or by inhalation. In some embodiments, pharmaceutical compositions disclosed herein can be administered to the subject intravenously.

In other embodiments, methods disclosed herein can further include administering one or more anti-cancer treatments prior to, simultaneously, or after administering an effective amount of the pharmaceutical composition to the subject.

In certain embodiments, methods disclosed herein for treating a subject having a health condition can include administering to the subject any of the compounds and/or pharmaceutical compositions disclosed herein in addition to at least one inhibitor of an ataxia telangiectasia and Rad3-related (ATR) protein, where the subject can have or be suspected of developing prostate cancer, Ewing sarcoma, or a combination thereof. In accordance with these embodiments, at least one inhibitor of an ATR protein can include, but are not limited to, Schisandrin B, NU6027, BAY 1895344, Dactolisib, EPT-46464, Torin 2, VE-821, AZ20, M4344, Ceralasertib, Berzosertib, or another comparable agent or a combination thereof. In some embodiments, at least one inhibitor of an ATR protein can include Berzosertib.

In certain embodiments, methods disclosed herein for treating a subject having a health condition can include administering to the subject any of the compounds and/or pharmaceutical compositions disclosed herein in addition to at least one inhibitor of checkpoint kinase 1 (CHK1), where the subject can have or be suspected of developing prostate cancer, Ewing sarcoma, or a combination thereof. In accordance with these embodiments, at least one inhibitor of CHK1 can include, but is not limited to, MK-8776, PF-477736, Prexasertib, Rabusertib, or other CHK1, or any combination thereof. In some embodiments, at least one inhibitor of CHK1 can include Rabusertib.

In other embodiments, methods disclosed herein for treating a subject having a health condition can include administering to the subject any of the compounds and/or pharmaceutical compositions containing at least one compound disclosed herein in addition to at least one inhibitor of PARP1 (poly(ADP)-ribose polymerase-1), where the subject can have or be suspected of developing pancreatic cancer. In accordance with these embodiments, at least one inhibitor of PARP1 can include, but is not limited to, Veliparib, Pamiparib, CEP 9722, E7016, Rucaparib, Niraparib, Talazoparib, Olaparib, or other PARPI or a combination thereof. In some embodiments, at least one inhibitor of PARPI can include Olaparib.

In certain embodiments, methods disclosed herein for treating a subject having a health condition can include administering to the subject any of the compounds and/or pharmaceutical compositions containing at least one compound disclosed herein in addition to at least one at least one chemotherapy drug, where the at least one chemotherapy drug can include at least one alkylating agent where the subject can have or be suspected of developing glioblastoma, glioma, or a combination thereof. In accordance with these embodiments, at least one alkylating agent can include chlorambucil, cyclophosphamide, thiotepa, busulfan, temozolomide, or other alkylating agent, or a combination thereof. In some embodiments, at least one alkylating agent can include temozolomide.

In some embodiments, compound 19, compound 73, compound 86, compound 87, compound 88, compound 90, compound 91, compound 93, compound 94, compound 95, compound 96, compound 97, or compound 98 compound 98, or any combination thereof can be administered alone, in any combination or in combination with at least one chemotherapy agent to treat a subject having or suspected of developing prostate cancer. In accordance with these embodiments, the at least one chemotherapy agent can include an inhibitor of an ataxia telangiectasia and Rad3-related (ATR) protein, an inhibitor of checkpoint kinase 1 (CHK1), or a combination thereof. In some embodiments, the inhibitor of an ATR protein Berzosertib and the inhibitor of checkpoint kinase 1 (CHK1) is Rabusertib. In other embodiments, compound 73 or compound 76, the inhibitor of checkpoint kinase 1 (CHK1) is Rabusertib, and where administering compound 73 or compound 76 and Rabusertib results in a synergistic reduction in viability or synergistic inhibition of expansion of prostate cancer cells in the subject when compared to administration of either compound 73, compound 76 or Rabusertib alone.

In some embodiments, compound 19, compound 73, compound 86, compound 87, compound 88, compound 90, compound 91, compound 93, compound 94, compound 95, compound 96, compound 97, or compound 98 compound 98, or any combination thereof can be administered with at least one chemotherapy agent to treat, prevent or reduce onset of glioblastoma, glioma, or a combination thereof in a subject. In accordance with these embodiments, the at least one chemotherapy agent includes, but is not limited to, at least one alkylating agent. In some embodiments, the at least one alkylating agent includes, but is not limited to, chlorambucil, cyclophosphamide, thiotepa, busulfan, temozolomide, or any combination thereof. In certain embodiments, the compound can include, but is not limited to, compound 59 or compound 19, where the at least one alkylating agent is Temozolomide, and where administering compound 59 or compound 19 and Temozolomide results in a synergistic reduction in viability of glioblastoma, glioma cancer cells in the subject when compared to administration of either compound 59, compound 19 or Temozolomide alone.

In certain embodiments, the present disclosure provides kits for storing, transporting compounds or mixtures of compounds or compositions thereof, or for practicing any of the methods disclosed herein. In some embodiments, kits disclosed herein can include one or more compounds disclosed herein and/or one or more pharmaceutical compositions disclosed herein and at least one container. In some embodiments, kits disclosed herein can be used to treat a subject having or suspected of developing cancer.

BRIEF DESCRIPTION OF THE DRAWINGS

The following drawings form part of the present specification and are included to further demonstrate certain embodiments of the present disclosure. Certain embodiments can be better understood by reference to one or more of these drawings in combination with the detailed description of specific embodiments presented herein.

Figure 6:
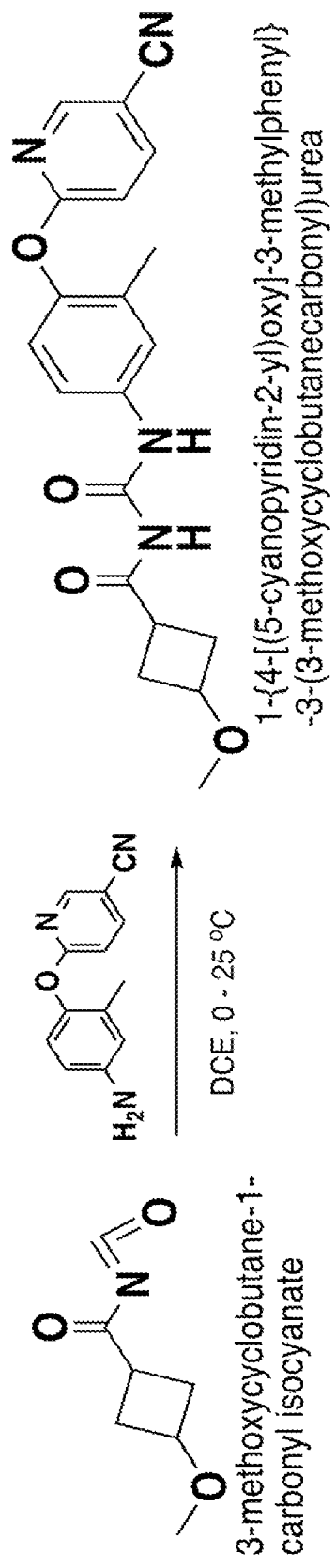

FIG. 6 represents an exemplary experiment illustrating a chemical reaction equation for synthesis of N-((4-((5-cyanopyridin-2-yl)oxy)-3-methylphenyl)carbamoyl)-3-methoxycyclobutane-1-carboxamide (Compound 16) in accordance with certain embodiments of the present disclosure.

Figure 7:
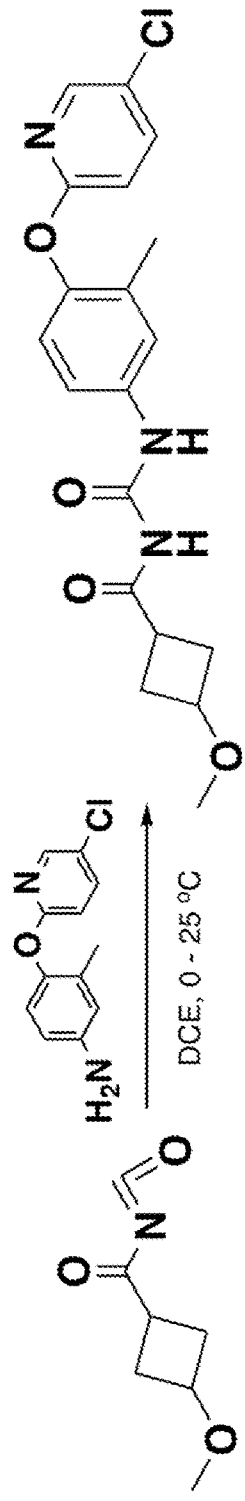

FIG. 7 represents an exemplary experiment illustrating a chemical reaction equation for synthesis of N-((4-((5-chloropyridin-2-yl)oxy)-3-methylphenyl)carbamoyl)-3-methoxycyclobutane-1-carboxamide (Compound 19) in accordance with certain embodiments of the present disclosure.

Figure 8:
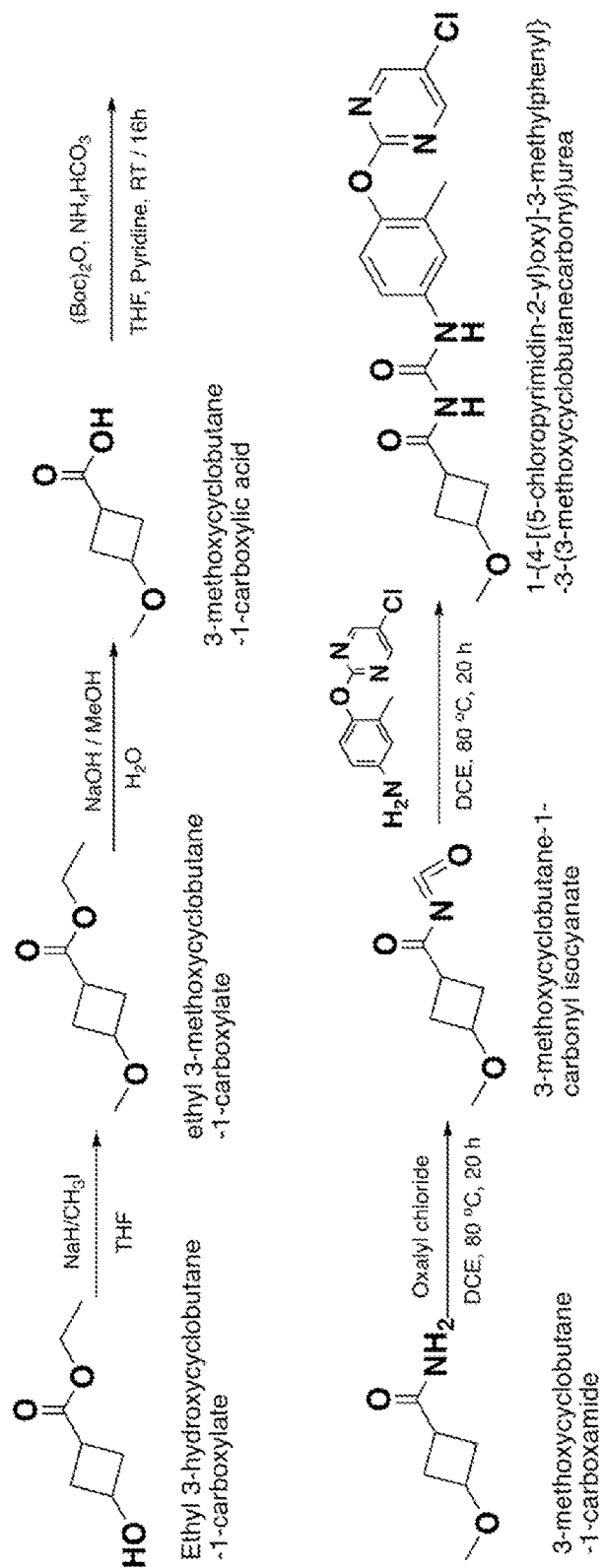

FIG. 8 represents an exemplary experiment illustrating a chemical reaction equation for synthesis of N-((4-((5-chloropyrimidin-2-yl)oxy)-3-methylphenyl)carbamoyl)-3-methoxycyclobutane-1-carboxamide (Compound 20) in accordance with certain embodiments of the present disclosure.

Figure 9:
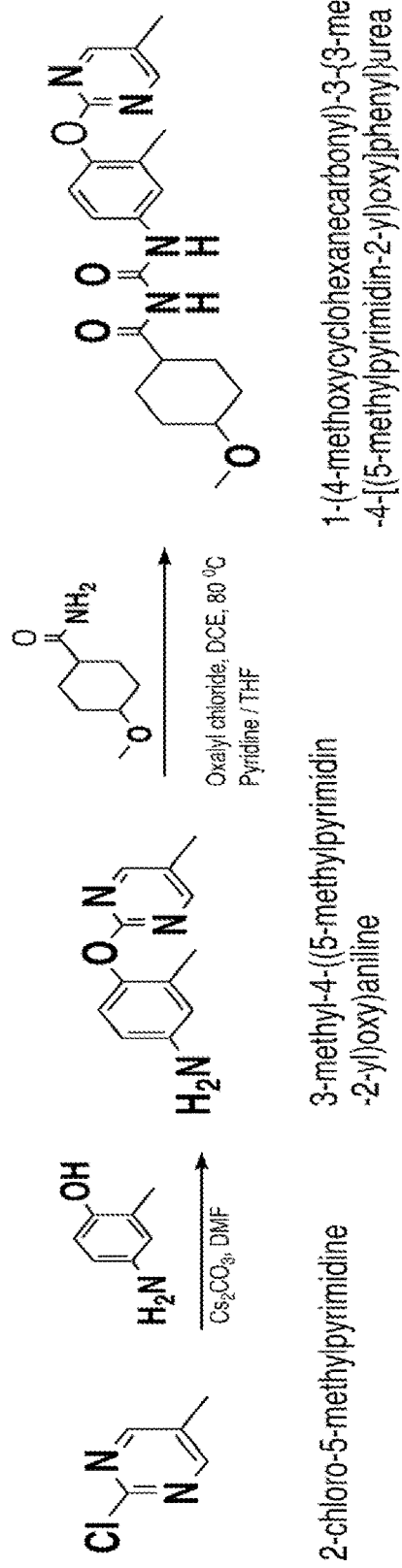

FIG. 9 represents an exemplary experiment illustrating a chemical reaction equation for synthesis of 4-methoxy-N-((3-methyl-4-((5-methylpyrimidin-2-yl)oxy)phenyl)carbamoyl)cyclohexane-1-carboxamide (Compound 27) in accordance with certain embodiments of the present disclosure.

Figure 10:
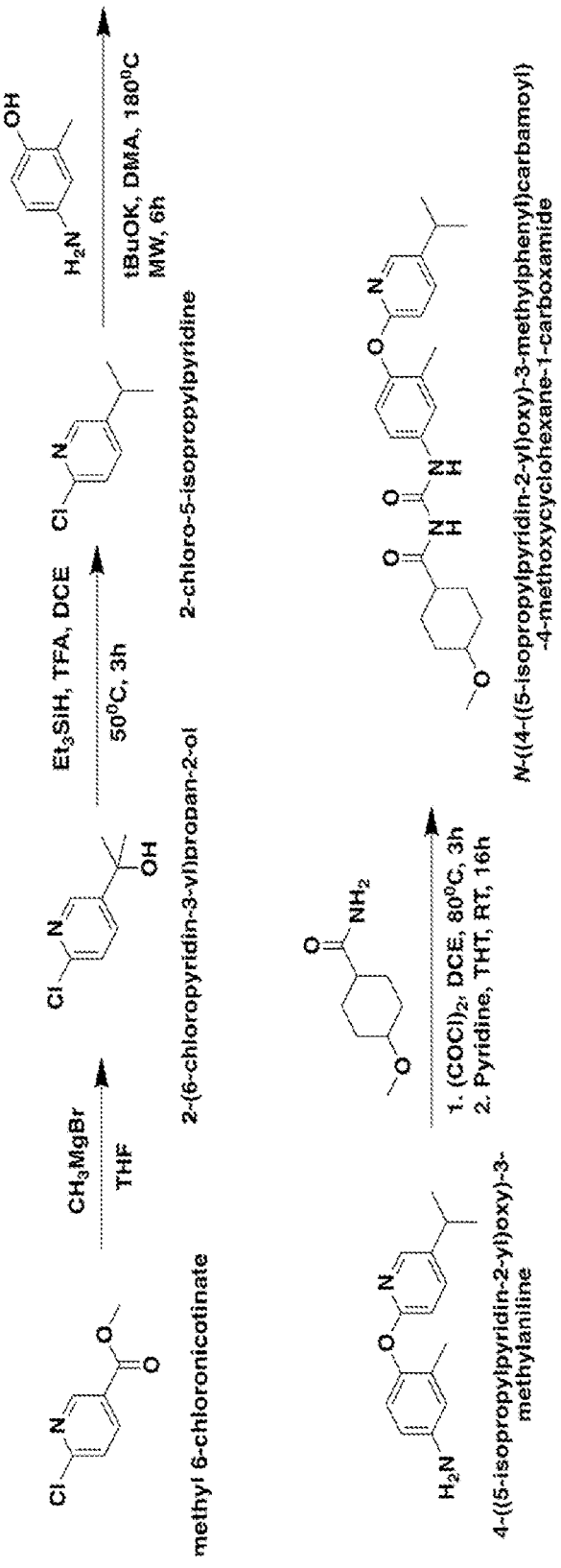

FIG. 10 represents an exemplary experiment illustrating a chemical reaction equation for synthesis of N-((4-((5-isopropylpyridin-2-yl)oxy)-3-methylphenyl)carbamoyl)-4-methoxycyclohexane-1-carboxamide (Compound 34) in accordance with certain embodiments of the present disclosure.

Figure 11:
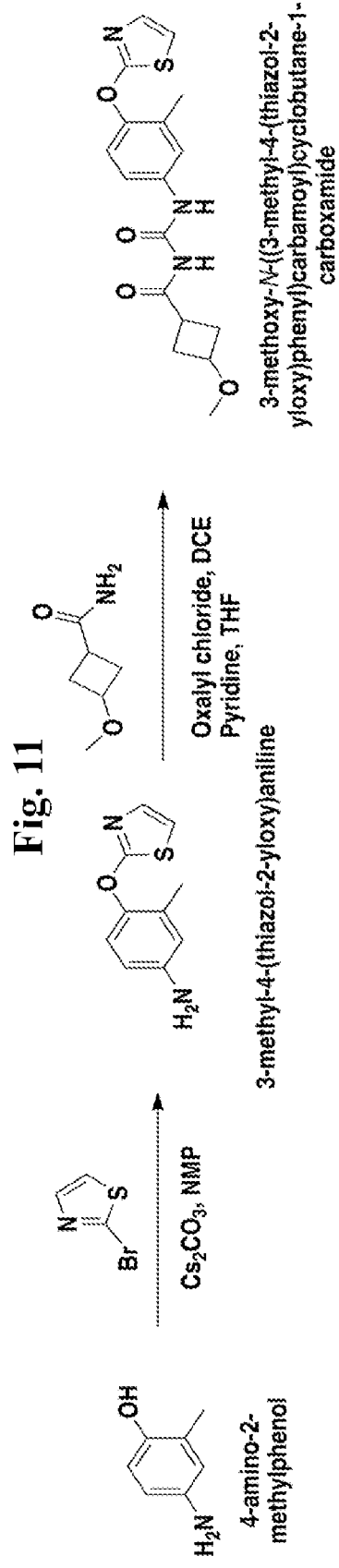

FIG. 11 represents an exemplary experiment illustrating a chemical reaction equation for synthesis of 3-methoxy-N-((3-methyl-4-(thiazol-2-yloxy)phenyl)carbamoyl)cyclobutane-1-carboxamide (Compound 45) in accordance with certain embodiments of the present disclosure.

Figure 12:
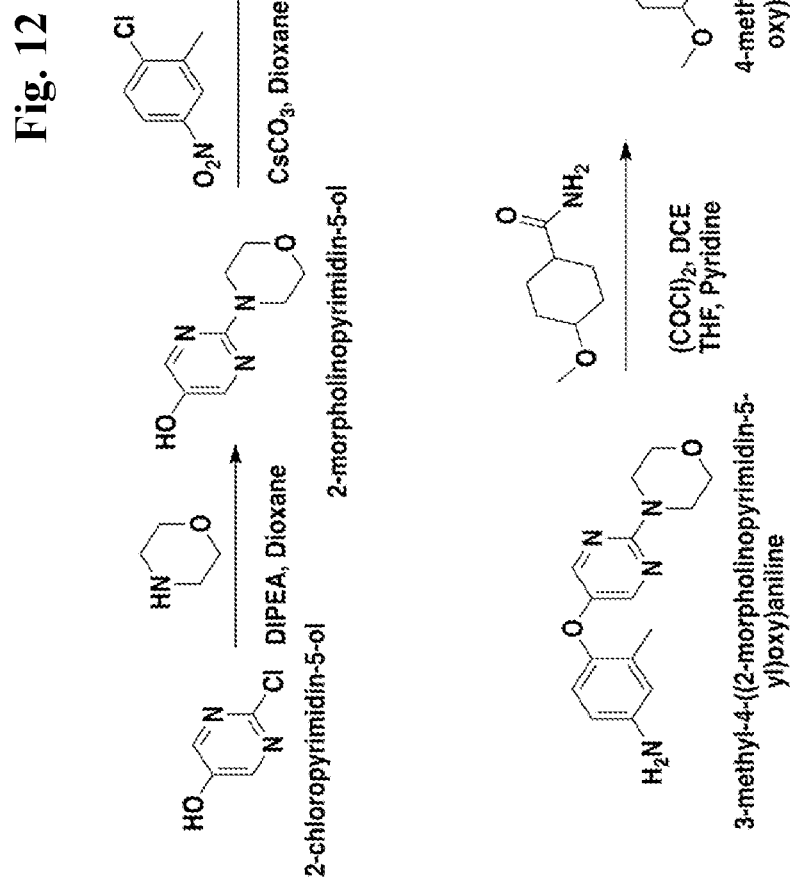

FIG. 12 represents an exemplary experiment illustrating a chemical reaction equation for synthesis of 4-methoxy-N-((3-methyl-4-((2-morpholinopyrimidin-5-yl)oxy)phenyl)carbamoyl)cyclohexane-1-carboxamide (Compound 46) in accordance with certain embodiments of the present disclosure.

Figure 13:
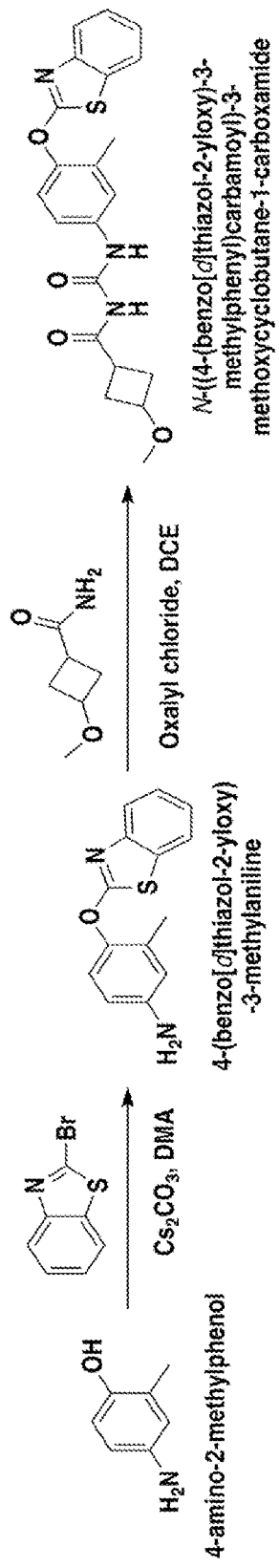

FIG. 13 represents an exemplary experiment illustrating a chemical reaction equation for synthesis of N-((4-(benzo[d]thiazol-2-yloxy)-3-methylphenyl)carbamoyl)-3-methoxycyclobutane-1-carboxamide (Compound 56) in accordance with certain embodiments of the present disclosure.

Figure 14:
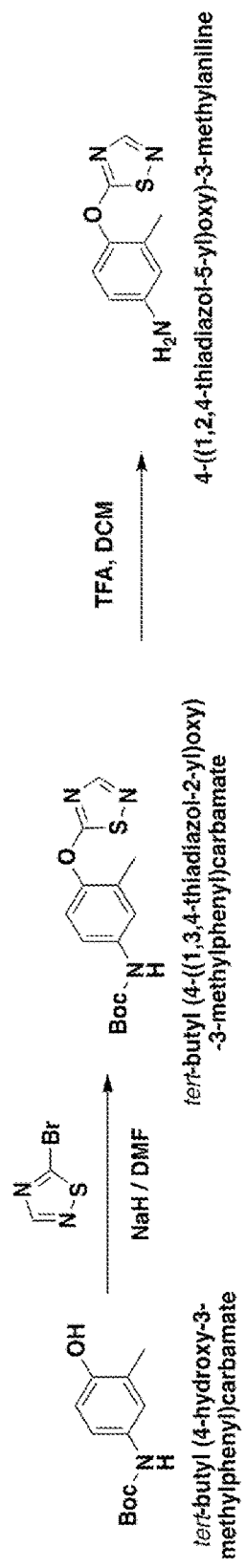
Figure 14:
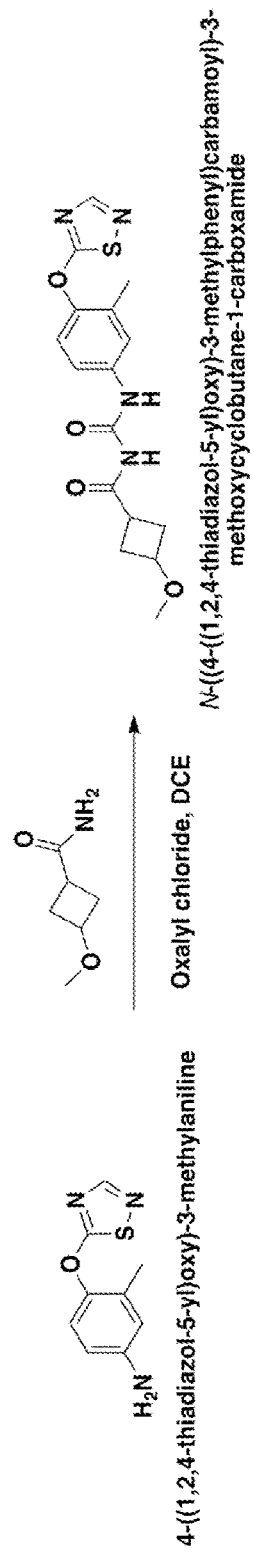

FIG. 14 represents an exemplary experiment illustrating a chemical reaction equation for synthesis of N-((4-((1,2,4-thiadiazol-5-yl)oxy)-3-methylphenyl)carbamoyl)-3-methoxycyclobutane-1-carboxamide (Compound 57) in accordance with certain embodiments of the present disclosure.

Figure 15:
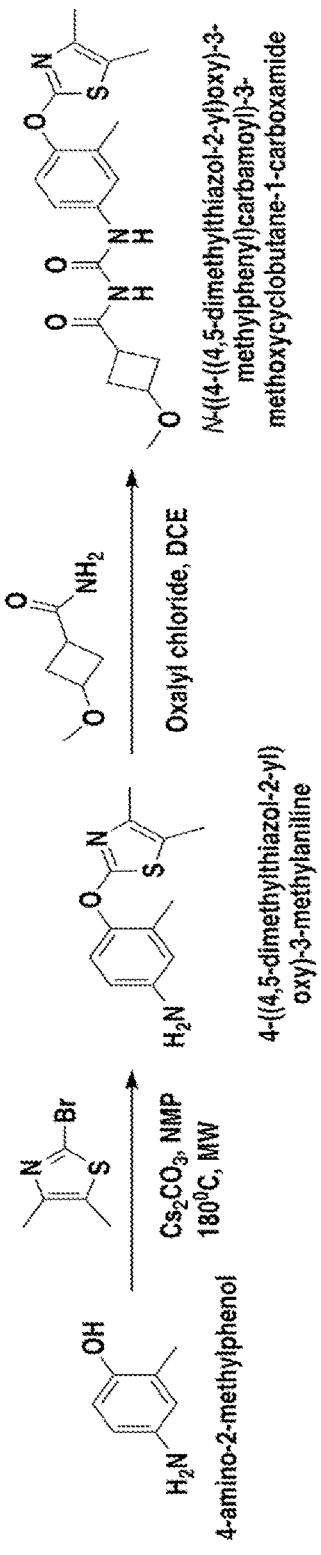

FIG. 15 represents an exemplary experiment illustrating a chemical reaction equation for synthesis of N-((4-((4,5-dimethylthiazol-2-yl)oxy)-3-methylphenyl)carbamoyl)-3-methoxycyclobutane-1-carboxamide (Compound 59) in accordance with certain embodiments of the present disclosure.

Figure 16:
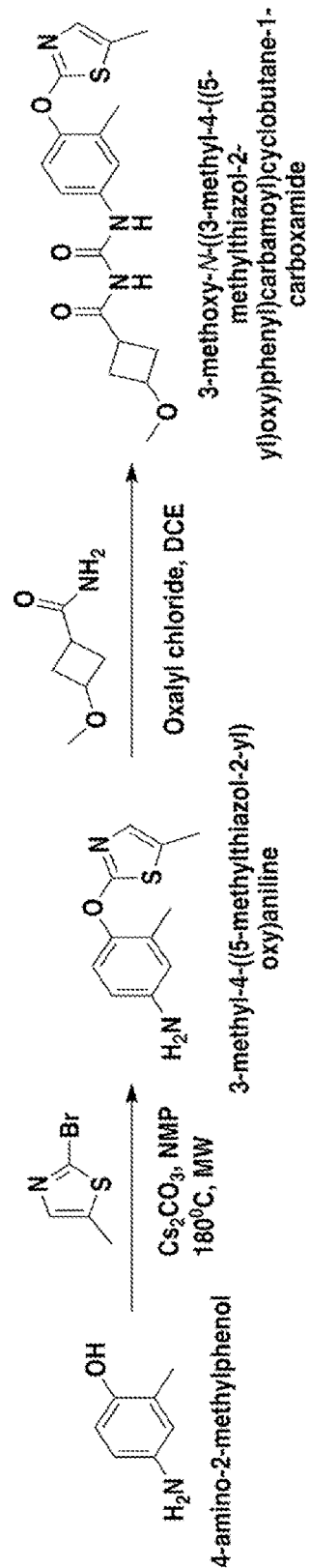

FIG. 16 represents an exemplary experiment illustrating a chemical reaction equation for synthesis of 3-methoxy-N-((3-methyl-4-((5-methylthiazol-2-yl)oxy)phenyl)carbamoyl)cyclobutane-1-carboxamide (Compound 60) in accordance with certain embodiments of the present disclosure.

Figure 17:
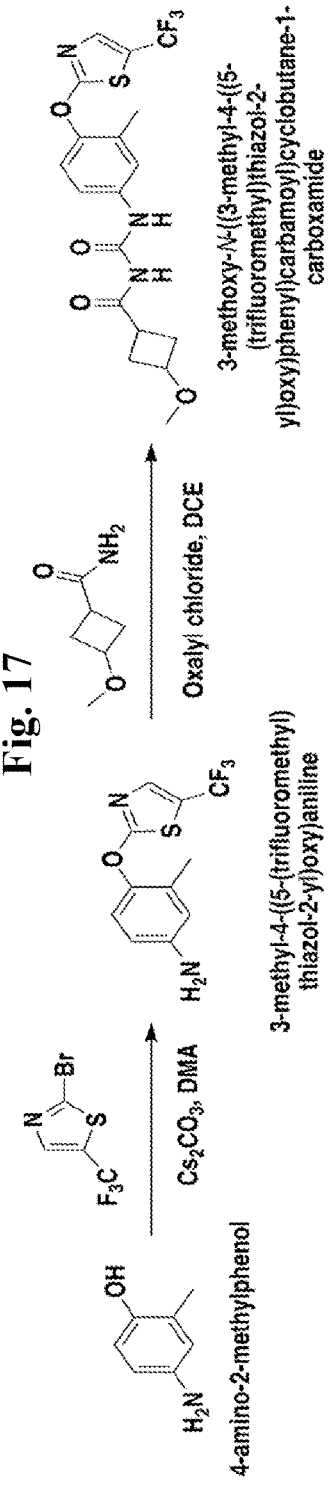

FIG. 17 represents an exemplary experiment illustrating a chemical reaction equation for synthesis of 3-methoxy-N-((3-methyl-4-((5-(trifluoromethyl)thiazol-2-yl)oxy)phenyl)carbamoyl)cyclobutane-1-carboxamide (Compound 61) in accordance with certain embodiments of the present disclosure.

Figure 18:
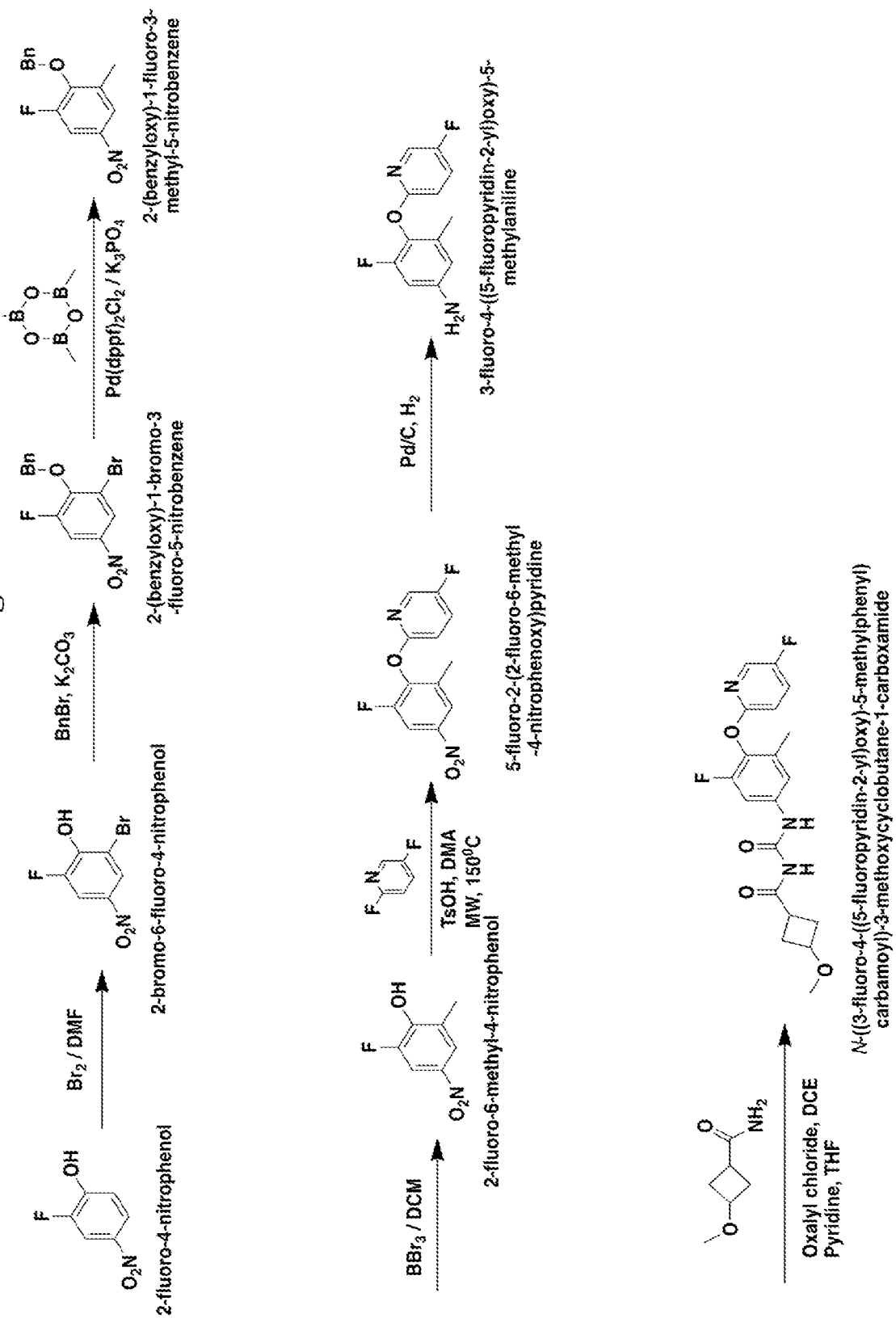

FIG. 18 represents an exemplary experiment illustrating a chemical reaction equation for synthesis of N-((3-fluoro-4-((5-fluoropyridin-2-yl)oxy)-5-methylphenyl)carbamoyl)-3-methoxycyclobutane-1-carboxamide (Compound 72) in accordance with certain embodiments of the present disclosure.

Figure 19:
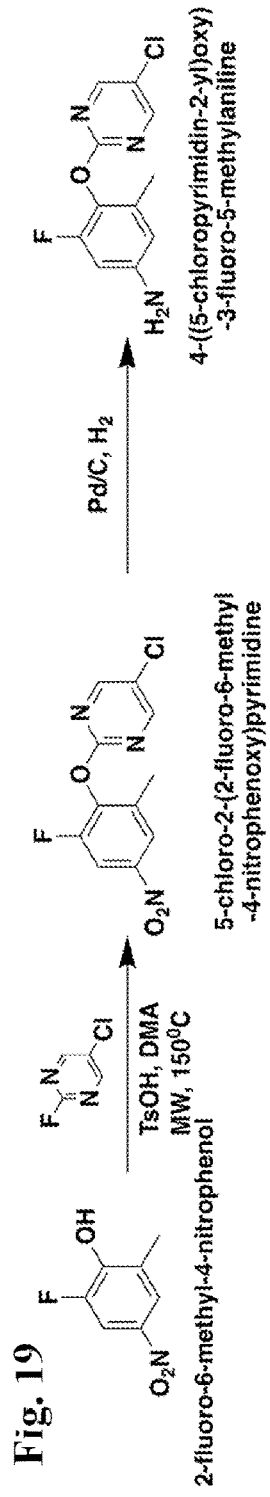

FIG. 19 represents an exemplary experiment illustrating a chemical reaction equation for synthesis of N-((4-((5-chloropyrimidin-2-yl)oxy)-3-fluoro-5-methylphenyl)carbamoyl)-3-methoxycyclobutane-1-carboxamide (Compound 73) in accordance with certain embodiments of the present disclosure.

Figure 20:
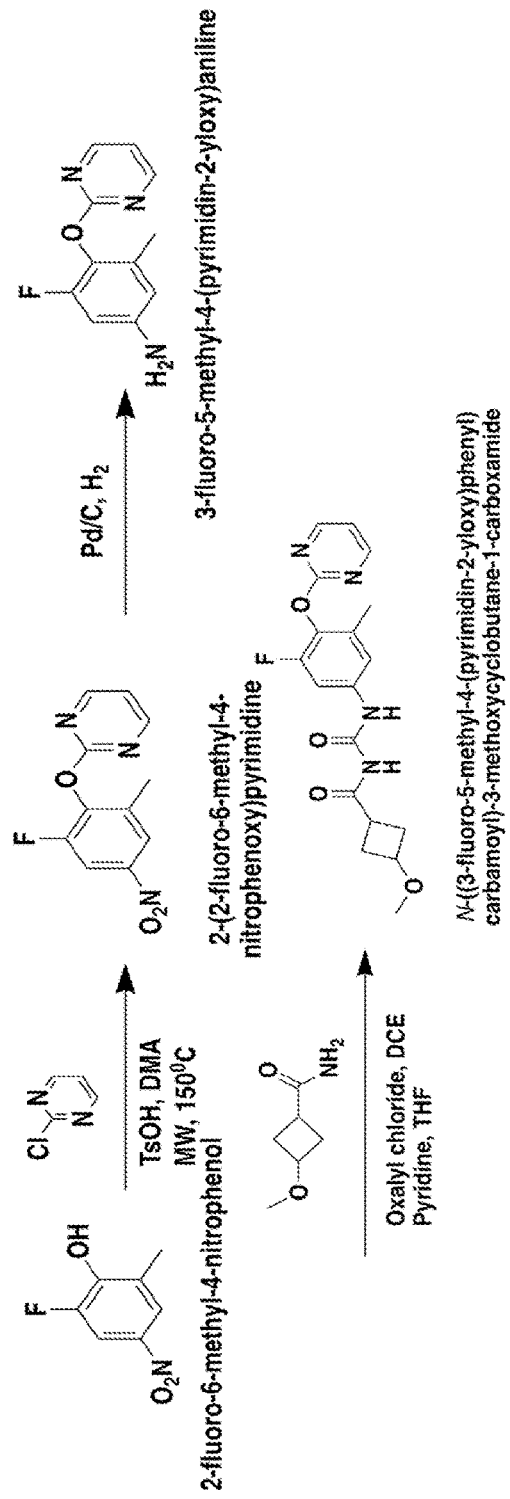

FIG. 20 represents an exemplary experiment illustrating a chemical reaction equation for synthesis of N-((3-fluoro-5-methyl-4-(pyrimidin-2-yloxy)phenyl)carbamoyl)-3-methoxycyclobutane-1-carboxamide (Compound 74) in accordance with certain embodiments of the present disclosure.

Figure 21:
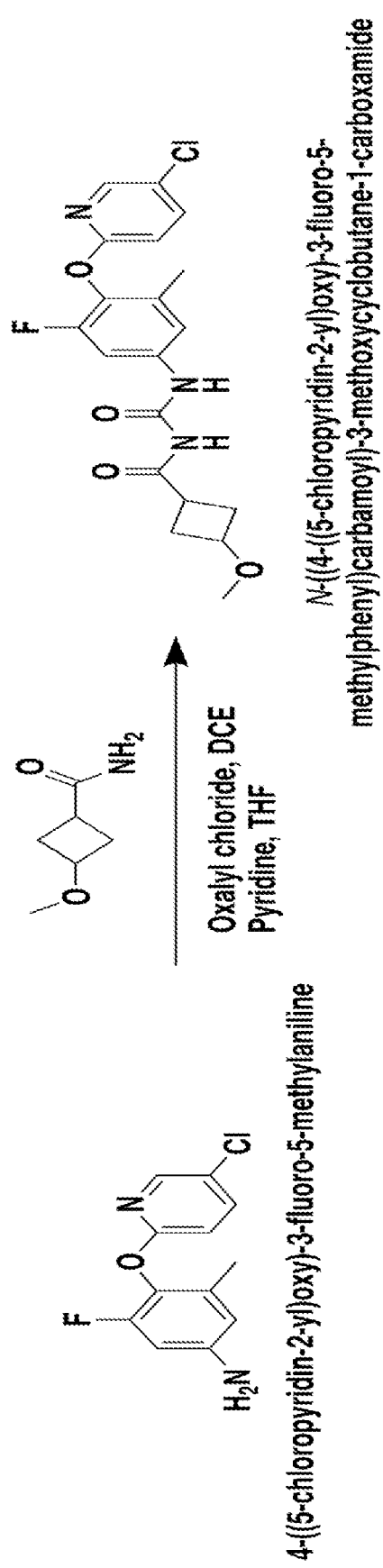

FIG. 21 represents an exemplary experiment illustrating a chemical reaction equation for synthesis of N-((4-((5-chloropyridin-2-yl)oxy)-3-fluoro-5-methylphenyl)carbamoyl)-3-methoxycyclobutane-1-carboxamide (Compound 76) in accordance with certain embodiments of the present disclosure.

Figure 22:
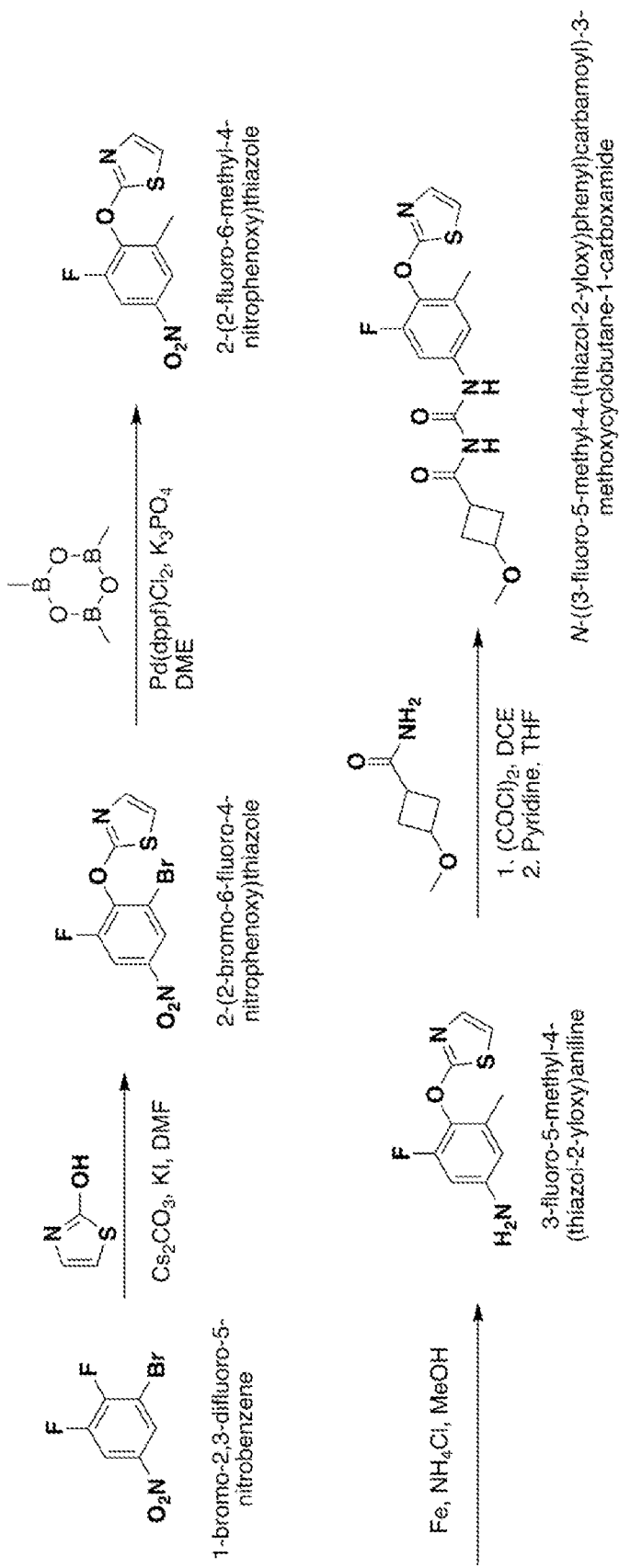

FIG. 22 represents an exemplary experiment illustrating a chemical reaction equation for synthesis of N-((3-fluoro-5-methyl-4-(thiazol-2 yloxy)phenyl)carbamoyl)-3-methoxycyclobutane-1-carboxamide (Compound 77) in accordance with certain embodiments of the present disclosure.

Figure 23:
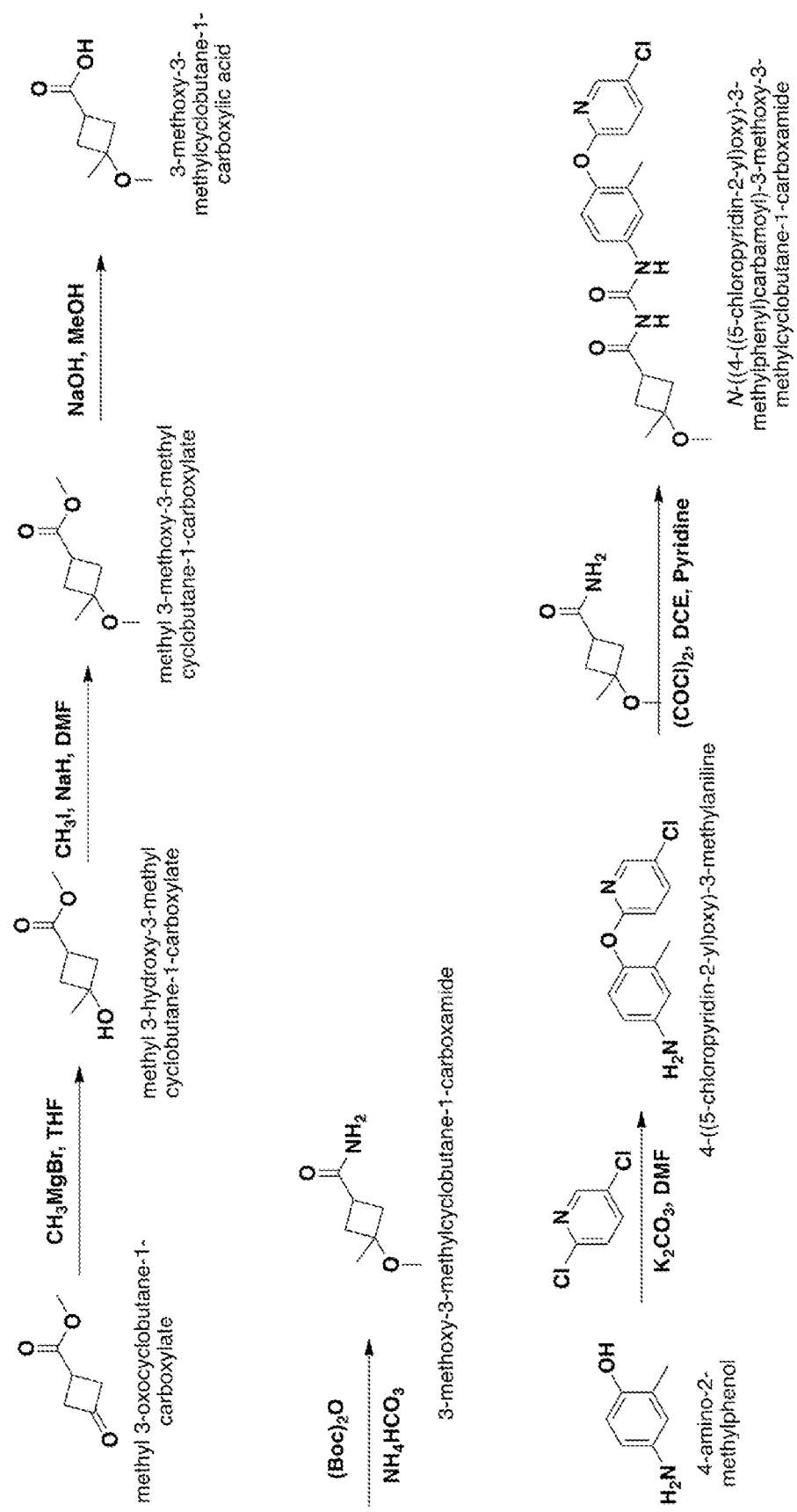

FIG. 23 represents an exemplary experiment illustrating a chemical reaction equation for synthesis of N-((4-((5-chloropyridin-2-yl)oxy)-3-methylphenyl)carbamoyl)-3-methoxy-3-methylcyclobutane-1-carboxamide (Compound 78) in accordance with certain embodiments of the present disclosure.

Figure 24:
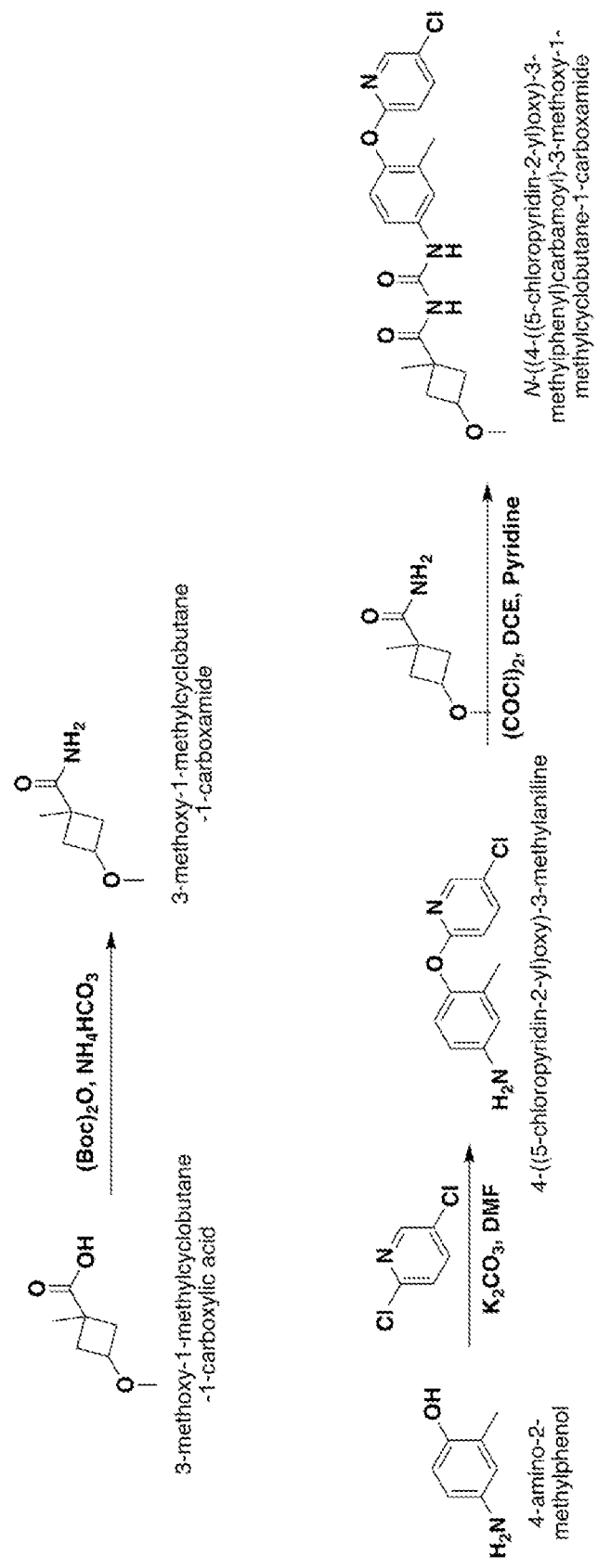

FIG. 24 represents an exemplary experiment illustrating a chemical reaction equation for synthesis of N-((4-((5-chloropyridin-2-yl)oxy)-3-methylphenyl)carbamoyl)-3-methoxy-1-methylcyclobutane-1-carboxamide (Compound 79) in accordance with certain embodiments of the present disclosure.

Figure 25:
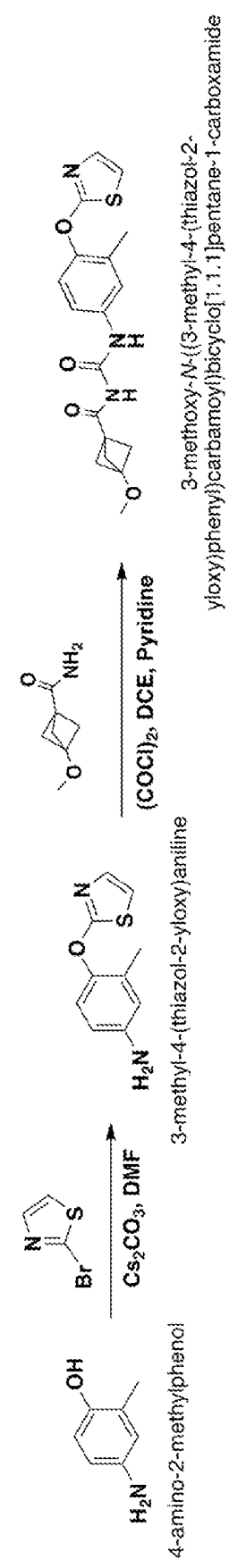

FIG. 25 represents an exemplary experiment illustrating a chemical reaction equation for synthesis of 3-methoxy-N-((3-methyl-4-(thiazol-2-yloxy)phenyl)carbamoyl)bicyclo[1.1.1]pentane-1-carboxamide (Compound 83) in accordance with certain embodiments of the present disclosure.

Figure 26:
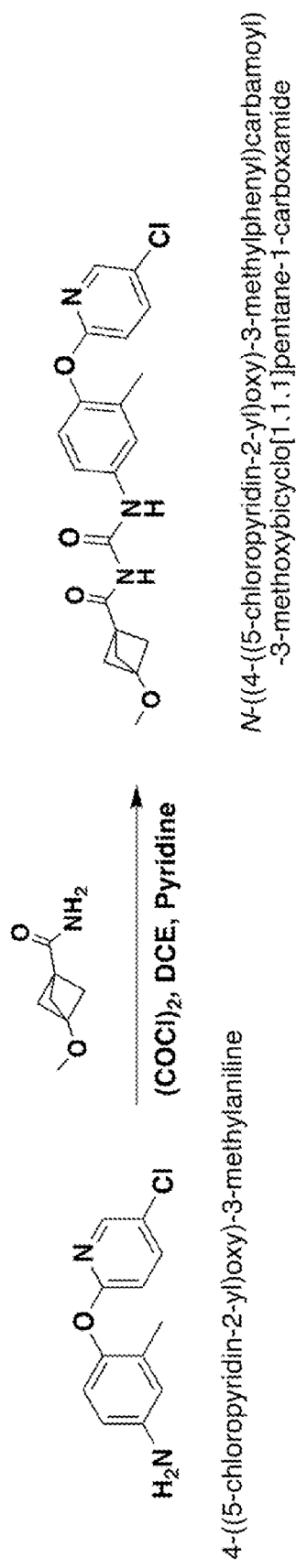

FIG. 26 represents an exemplary experiment illustrating a chemical reaction equation for synthesis of N-((4-((5-chloropyridin-2-yl)oxy)-3-methylphenyl)carbamoyl)-3-methoxybicyclo[1.1.1]pentane-1-carboxamide (Compound 84) in accordance with certain embodiments of the present disclosure.

Figure 27:
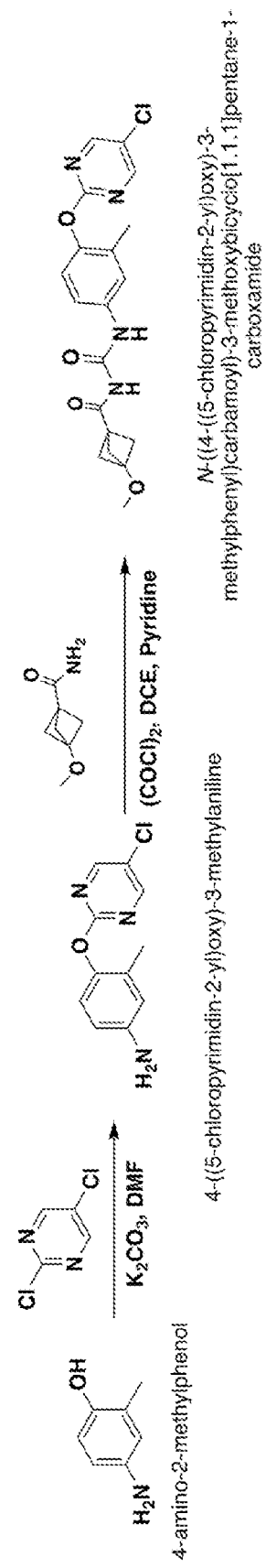

FIG. 27 represents an exemplary experiment illustrating a chemical reaction equation for synthesis of 3 N-((4-((5-chloropyrimidin-2-yl)oxy)-3-methylphenyl)carbamoyl)-3-methoxybicyclo[1.1.1]pentane-1-carboxamide (Compound 85) in accordance with certain embodiments of the present disclosure.

Figure 28:
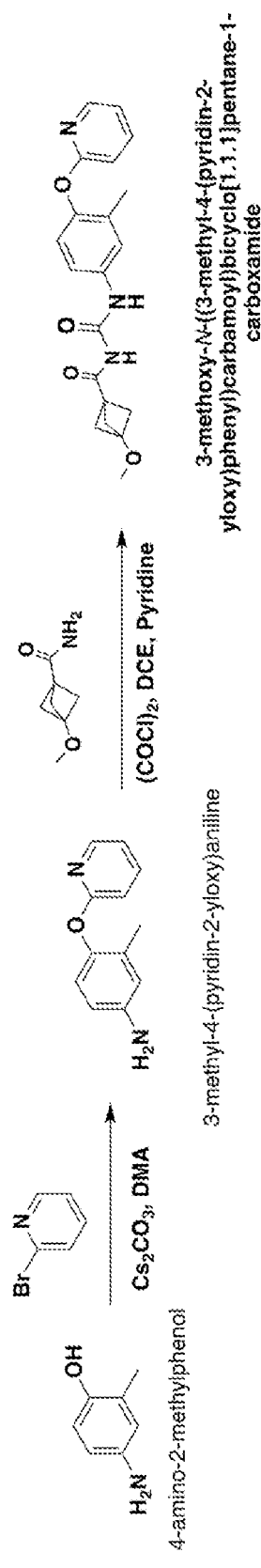

FIG. 28 represents an exemplary experiment illustrating a chemical reaction equation for synthesis of 3-methoxy-N-((3-methyl-4-(pyridin-2-yloxy)phenyl)carbamoyl)bicyclo

[1.1.1]pentane-1-carboxamide (Compound 86) in accordance with certain embodiments of the present disclosure.

Figure 29:
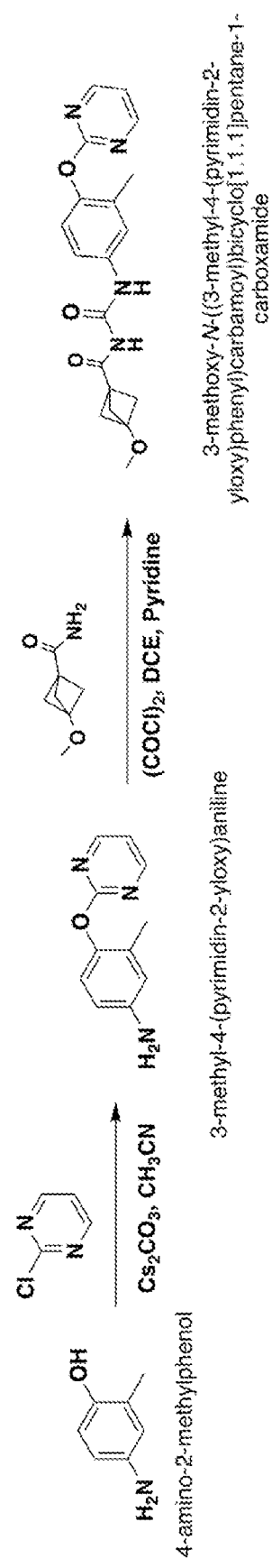

FIG. 29 represents an exemplary experiment illustrating a chemical reaction equation for synthesis of 3-methoxy-N-((3-methyl-4-(pyrimidin-2-yloxy)phenyl)carbamoyl)bicyclo[1.1.1]pentane-1-carboxamide (Compound 87) in accordance with certain embodiments of the present disclosure.

Figure 30:
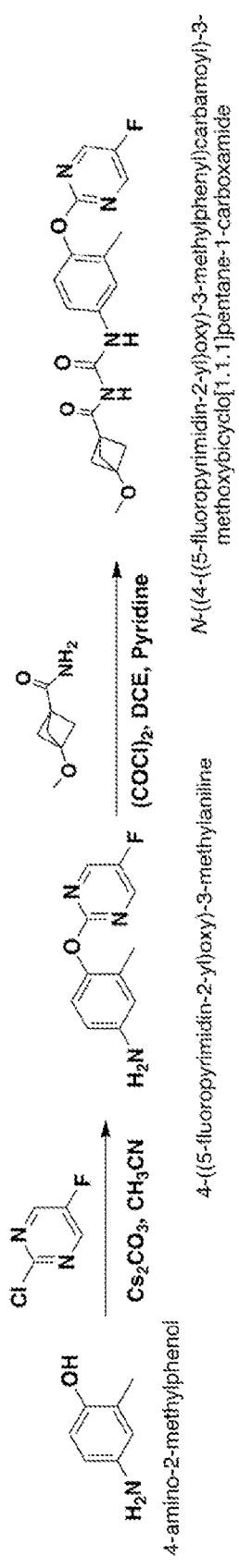

FIG. 30 represents an exemplary experiment illustrating a chemical reaction equation for synthesis of N-((4-((5-fluoropyrimidin-2-yl)oxy)-3-methylphenyl)carbamoyl)-3-methoxybicyclo[1.1.1]pentane-1-carboxamide (Compound 88) in accordance with certain embodiments of the present disclosure.

Figure 31:
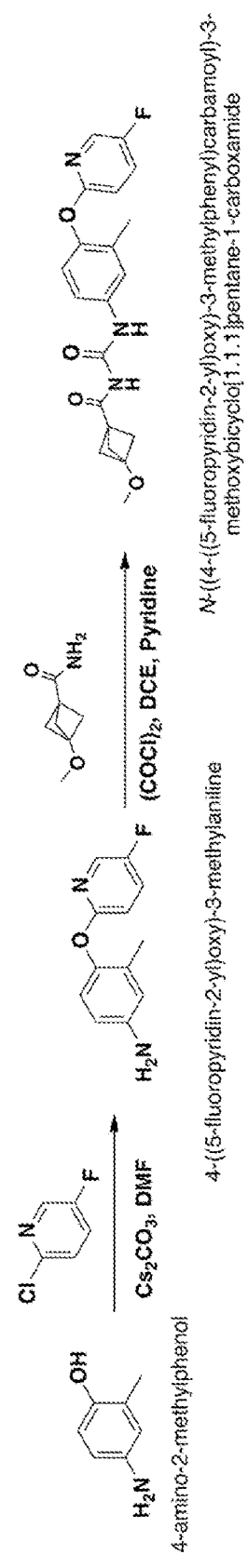

FIG. 31 represents an exemplary experiment illustrating a chemical reaction equation for synthesis of N-((4-((5-fluoropyridin-2-yl)oxy)-3-methylphenyl)carbamoyl)-3-methoxybicyclo[1.1.1]pentane-1-carboxamide (Compound 89) in accordance with certain embodiments of the present disclosure.

Figure 32:
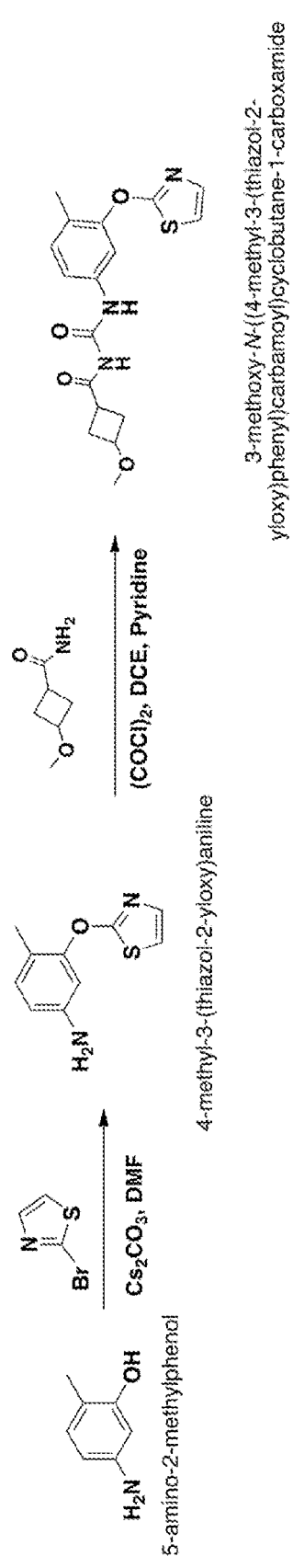

FIG. 32 represents an exemplary experiment illustrating a chemical reaction equation for synthesis of 3-methoxy-N-((4-methyl-3-(thiazol-2-yloxy)phenyl)carbamoyl)cyclobutane-1-carboxamide (Compound 93) in accordance with certain embodiments of the present disclosure.

Figure 33:
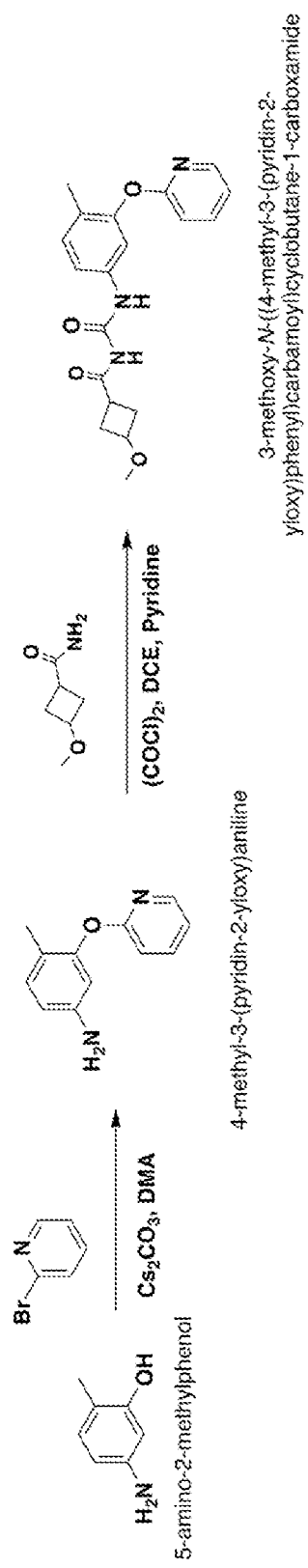

FIG. 33 represents an exemplary experiment illustrating a chemical reaction equation for synthesis of 3-methoxy-N-((4-methyl-3-(pyridin-2-yloxy)phenyl)carbamoyl)cyclobutane-1-carboxamide (Compound 94) in accordance with certain embodiments of the present disclosure.

Figure 34:
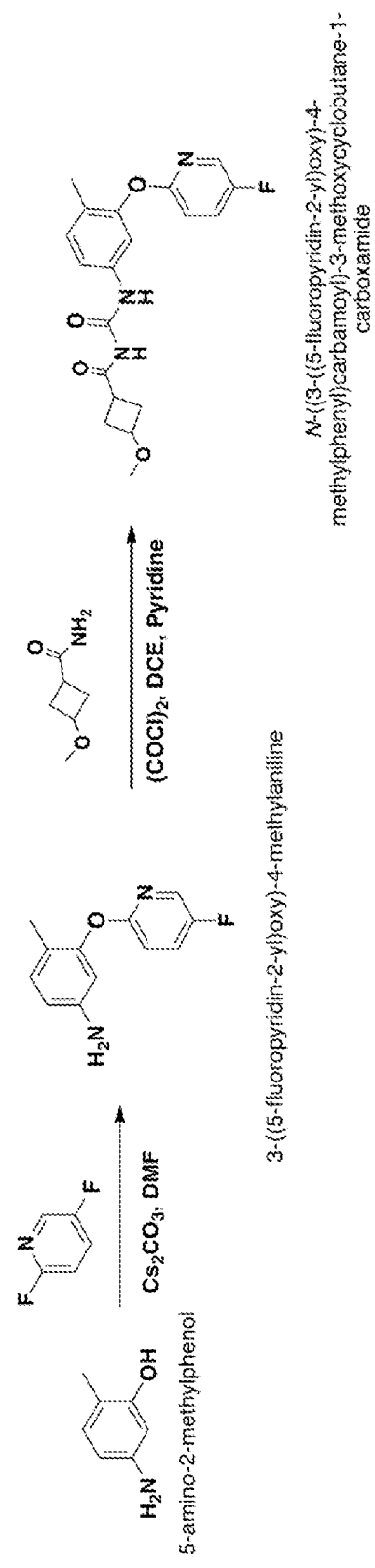

FIG. 34 represents an exemplary experiment illustrating a chemical reaction equation for synthesis of 3-methoxy-N-((4-methyl-3-(pyrimidin-2-yloxy)phenyl)carbamoyl)cyclobutane-1-carboxamide (Compound 95) in accordance with certain embodiments of the present disclosure.

Figure 35:
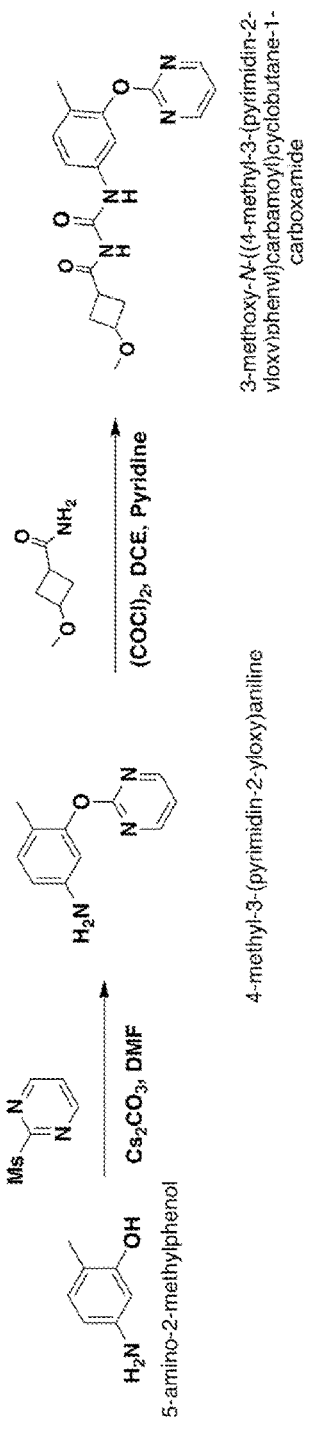

FIG. 35 represents an exemplary experiment illustrating a chemical reaction equation for synthesis of 3-methoxy-N-((4-methyl-3-(pyrimidin-2-yloxy)phenyl)carbamoyl)cyclobutane-1-carboxamide (Compound 96) in accordance with certain embodiments of the present disclosure.

Figure 36:
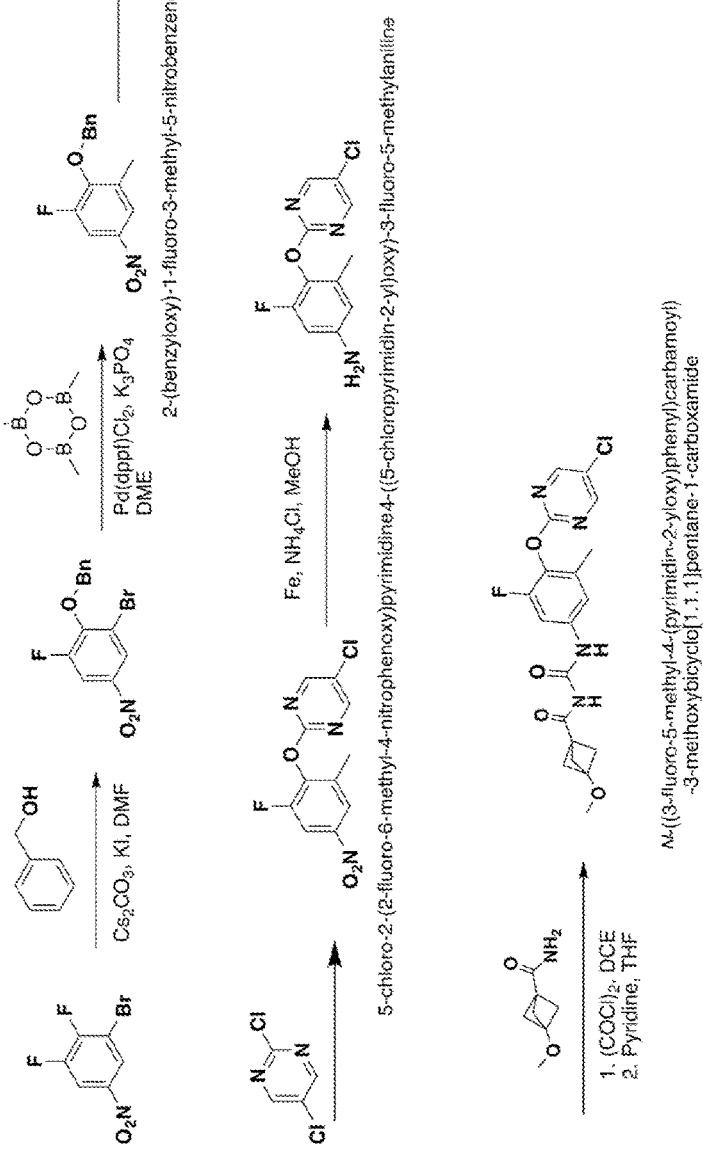

FIG. 36 represents an exemplary experiment illustrating a chemical reaction equation for synthesis of N-((4-((5-chloropyrimidin-2-yl)oxy)-3-fluoro-5-methylphenyl)carbamoyl)-3-methoxybicyclo[1.1.1]pentane-1-carboxamide (Compound 90) in accordance with certain embodiments of the present disclosure.

Figure 37:
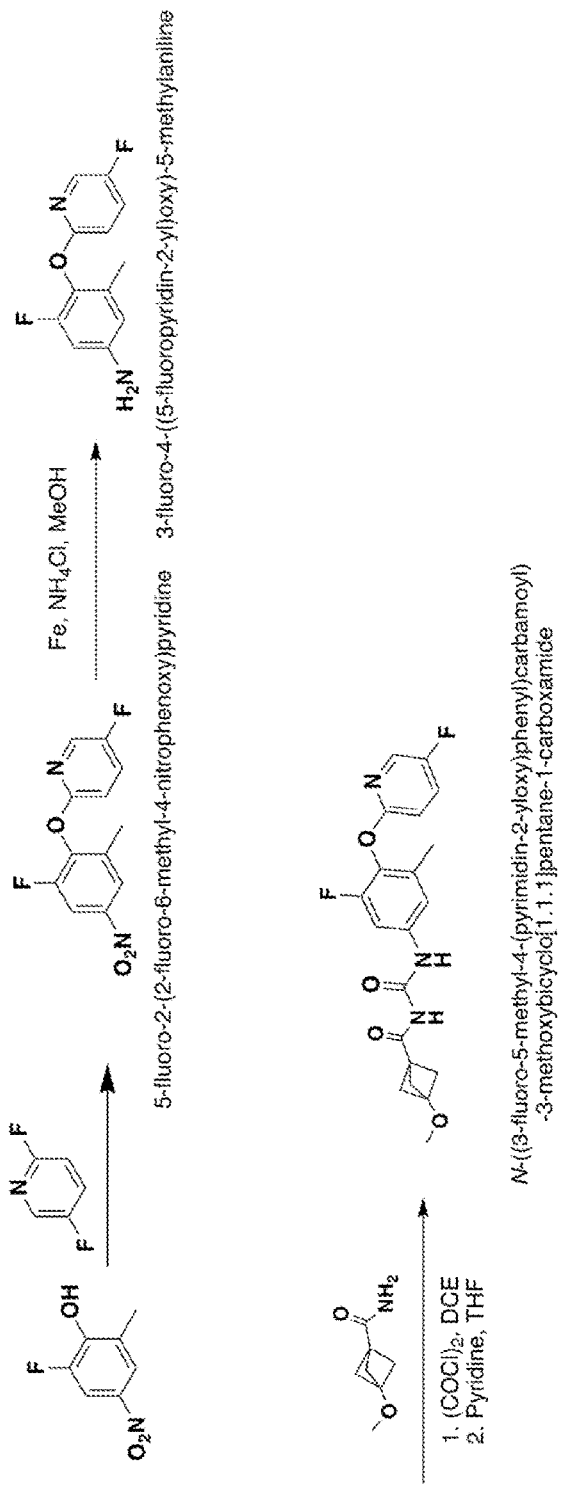

FIG. 37 represents an exemplary experiment illustrating a chemical reaction equation for synthesis of N-((3-fluoro-4-((5-fluoropyridin-2-yl)oxy)-5-methylphenyl)carbamoyl)-3-methoxybicyclo[1.1.1]pentane-1-carboxamide (Compound 91) in accordance with certain embodiments of the present disclosure.

Figure 38:
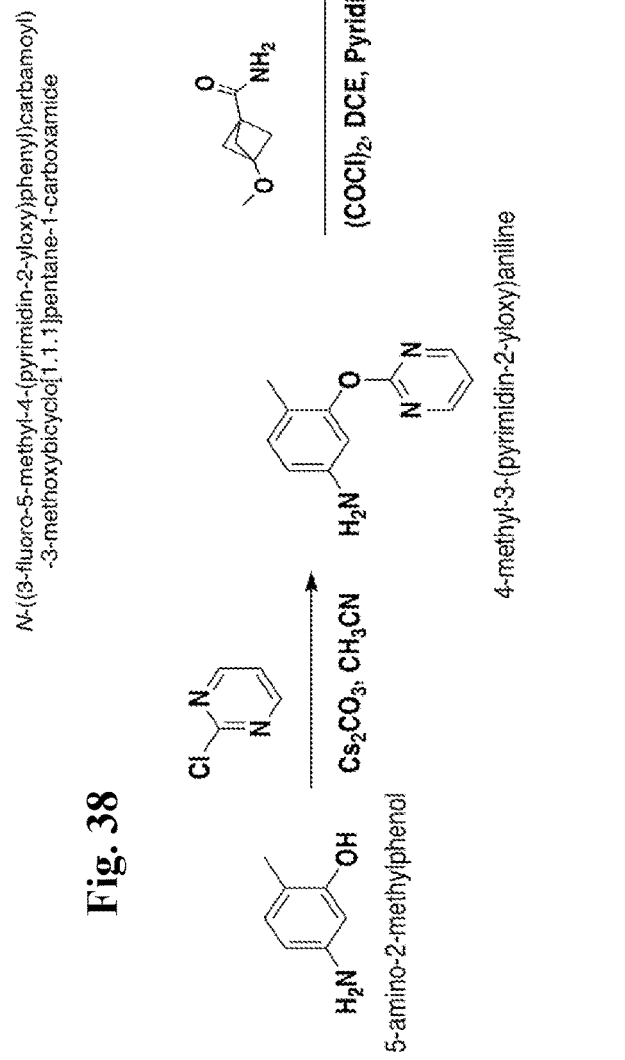

FIG. 38 represents an exemplary experiment illustrating a chemical reaction equation for synthesis of 3-methoxy-N-((4-methyl-3-(pyrimidin-2-yloxy)phenyl)carbamoyl)bicyclo[1.1.1]pentane-1-carboxamide (Compound 97) in accordance with certain embodiments of the present disclosure.

Figure 39:
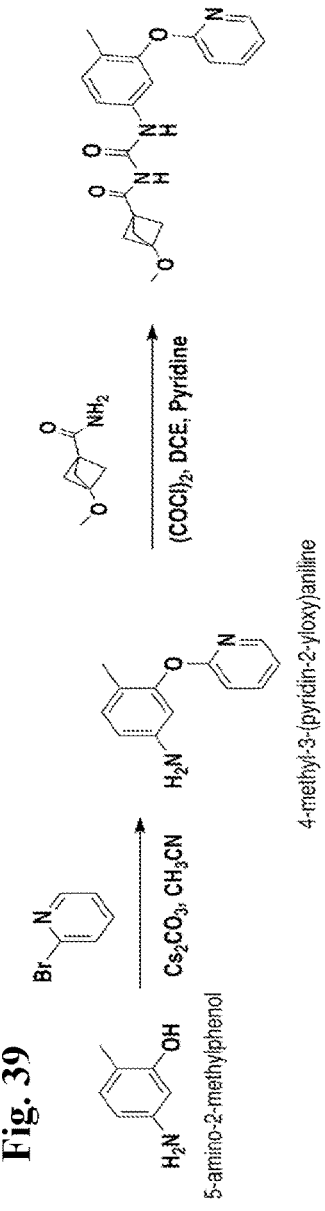

FIG. 39 represents an exemplary experiment illustrating a chemical reaction equation for synthesis of 3-methoxy-N-((4-methyl-3-(pyridin-2-yloxy)phenyl)carbamoyl)bicyclo[1.1.1]pentane-1-carboxamide (Compound 98) in accordance with certain embodiments of the present disclosure.

Figure 40:
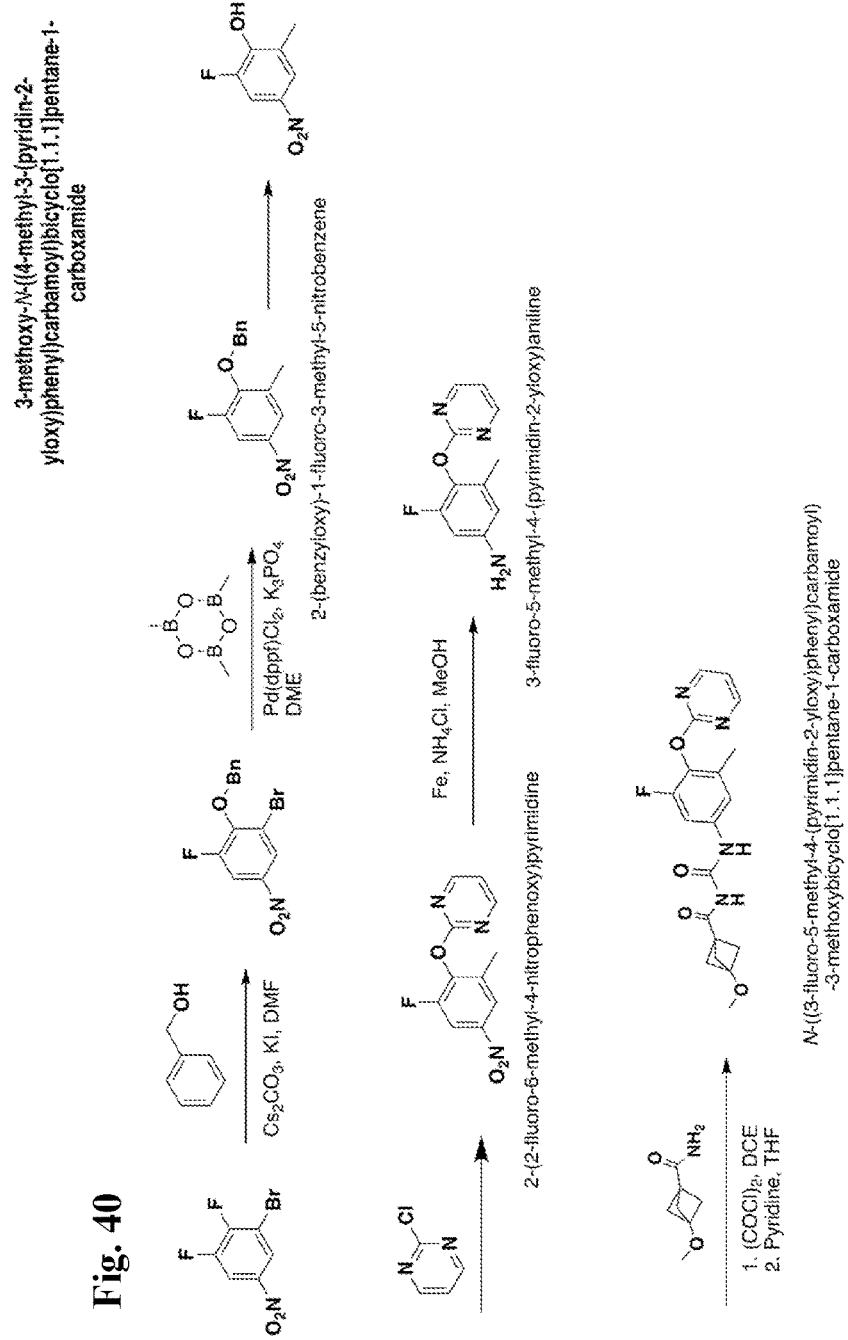

FIG. 40 represents an exemplary experiment illustrating a chemical reaction equation for synthesis of N-((3-fluoro-5-methyl-4-(pyrimidin-2-yloxy)phenyl)carbamoyl)-3-methoxybicyclo[1.1.1]pentane-1-carboxamide (Compound 92) in accordance with certain embodiments of the present disclosure.

Figure 41A:
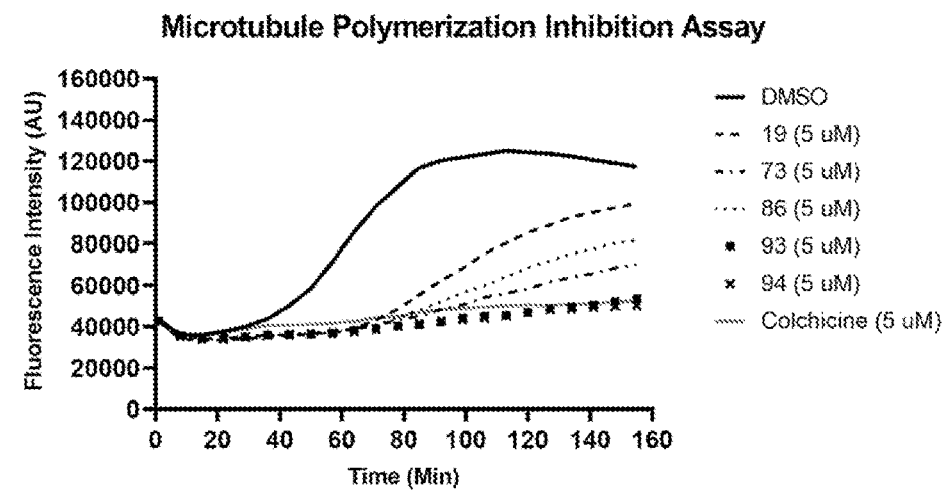
Figure 41B:
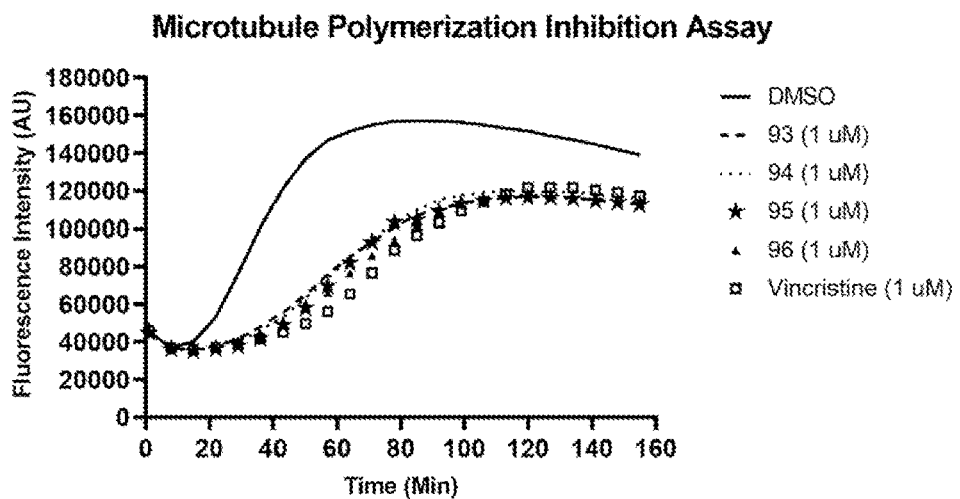
Figure 41C:
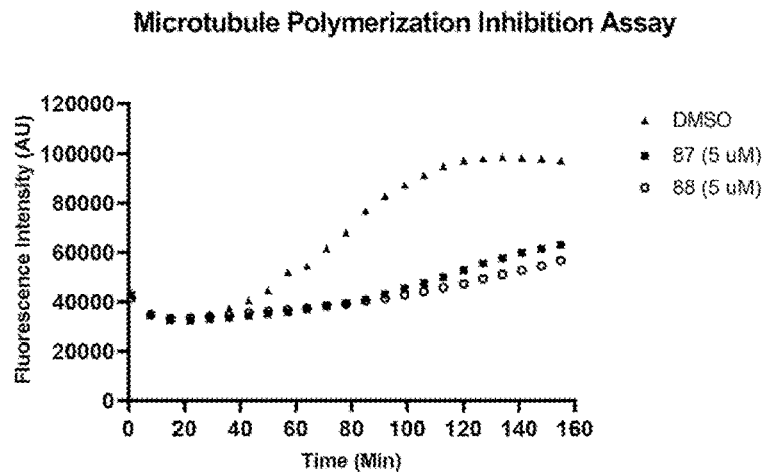

FIG. 41A-41C represent exemplary experiments illustrating inhibition of tubulin polymerization. FIG. 41A illustrates effects of compounds 19, 73, 86, 93 and 94 at 5 uM concentration. FIG. 41B illustrates effects of compounds 93, 94, 95 and 96 at 1 uM concentration.

FIG. 41C illustrates effects of compounds 73, 86, 87 and 88 at 5 uM concentration in accordance with certain embodiments of the present disclosure. Colchicine and vincristine are positive controls.

Figure 42A:
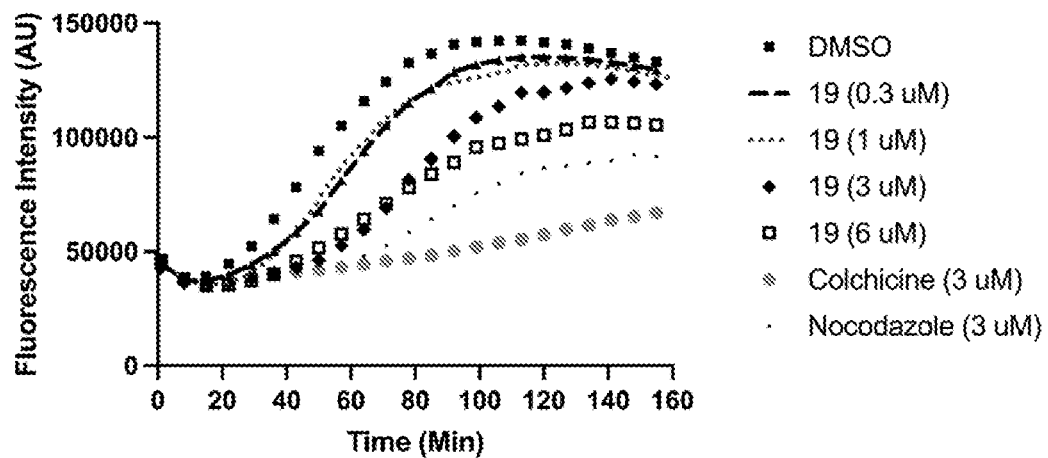
Figure 42B:
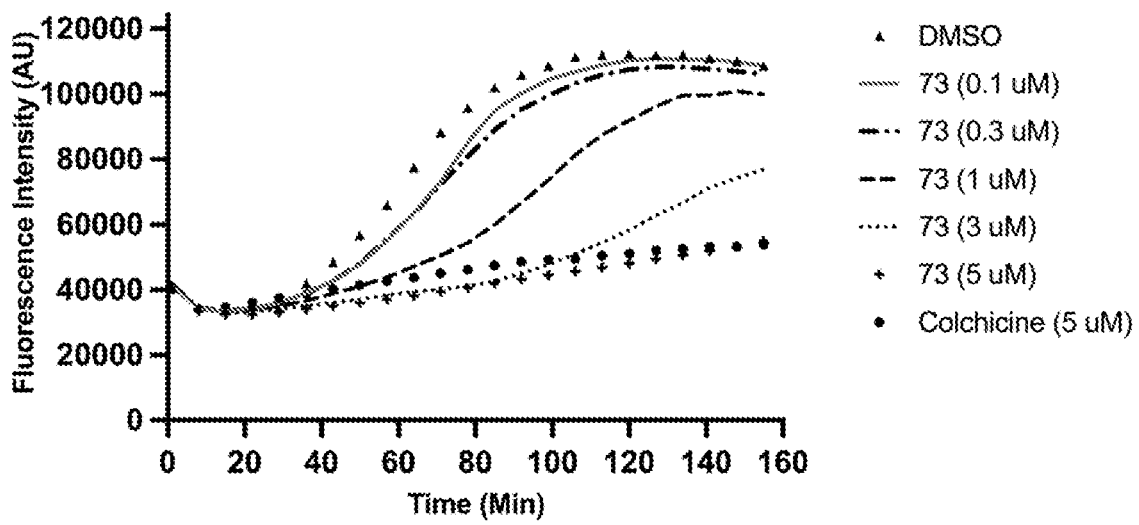

FIG. 42A-42B represent exemplary experiments illustrating inhibition of tubulin polymerization. FIG. 42A illustrates effects of compound 19 at 0.3, 1, 3 and 6 uM concentrations.

FIG. 42B illustrates effects of compound 73 at 0.1, 0.3, 1, 3 and 6 uM concentration in accordance with certain embodiments of the present disclosure. Colchicine and nocodazole are positive controls.

Figure 43:
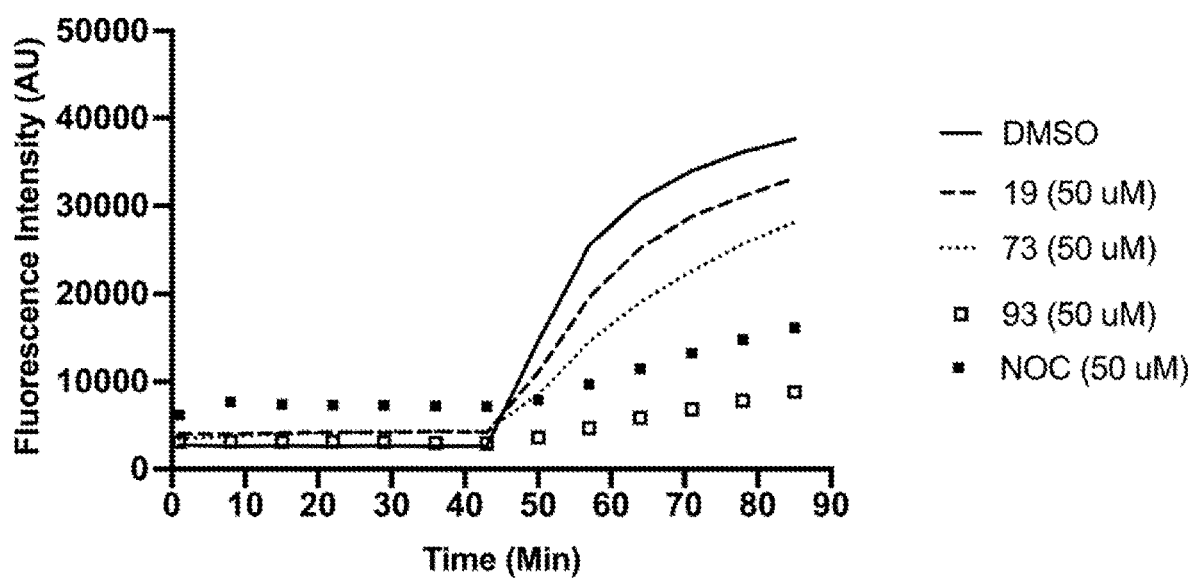

FIG. 43 represent fluorescence-based colchicine competitive binding assay with compounds 19, 73 and 93 at 50 uM concentration in accordance with certain embodiments of the present disclosure. Nocodazole (NOC) is positive control.

Figure 44:
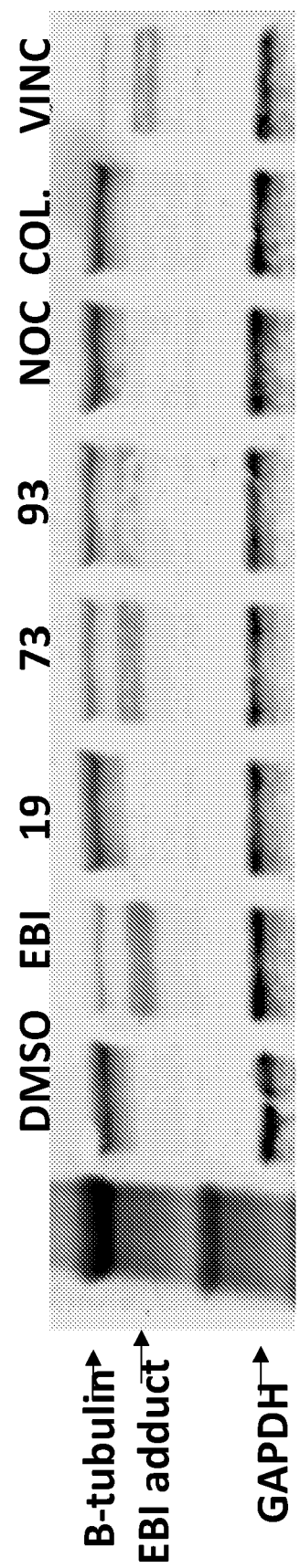

FIG. 44 represent N,N'-ethylene-bis(iodoacetamide) (EBI) competition assay with compounds 19, 73 and 93 in MCF7 cell lines showing binding of compounds in colchicine binding site in accordance with certain embodiments of the present disclosure. Colchicine (COL) and nocodazole (NOC) are positive controls while vincristine (VINC) is negative control.

Figure 45A:
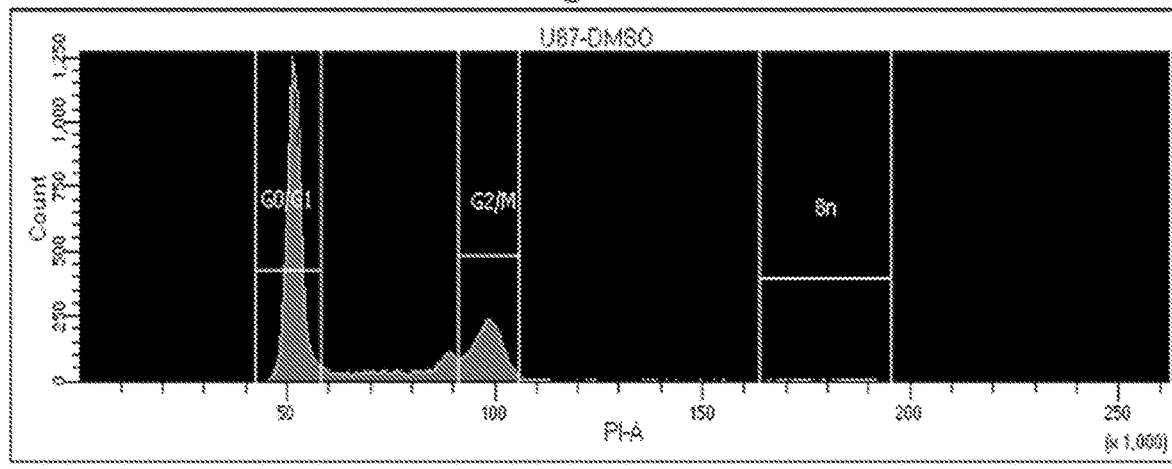
Figure 45B:
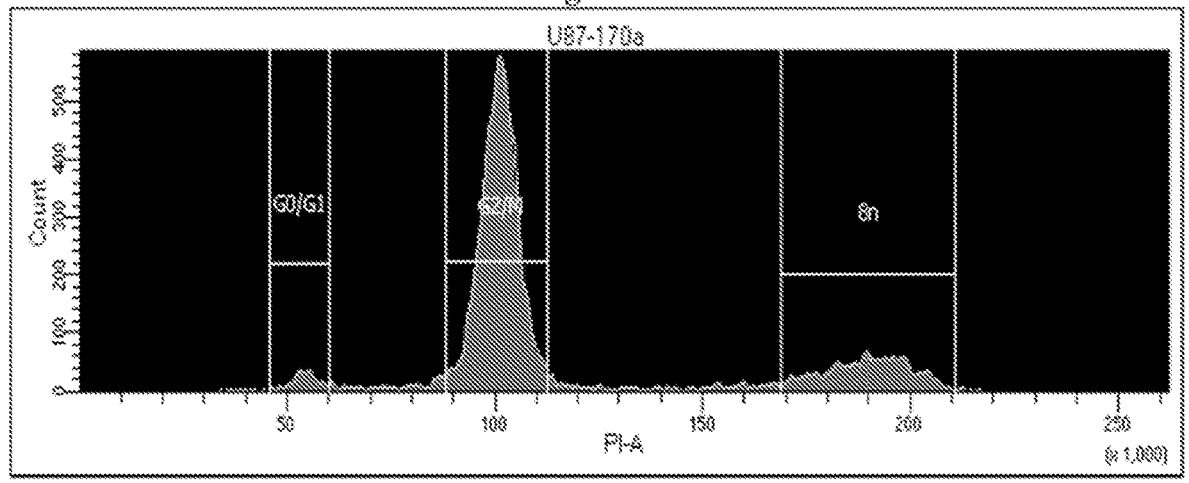
Figure 45C:
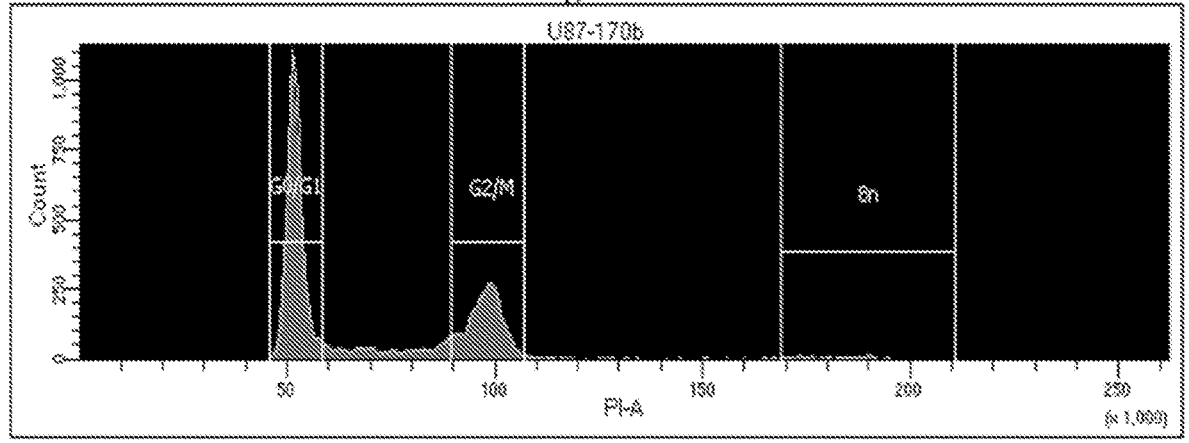

FIG. 45A-45C represent exemplary experiments illustrating cell cycle distribution of U87 cells following treatment with DMSO (FIG. 45A), Compound 1 A (FIG. 45B), or Compound 1B (FIG. 45C) in accordance with certain embodiments of the present disclosure.

Figure 46A:
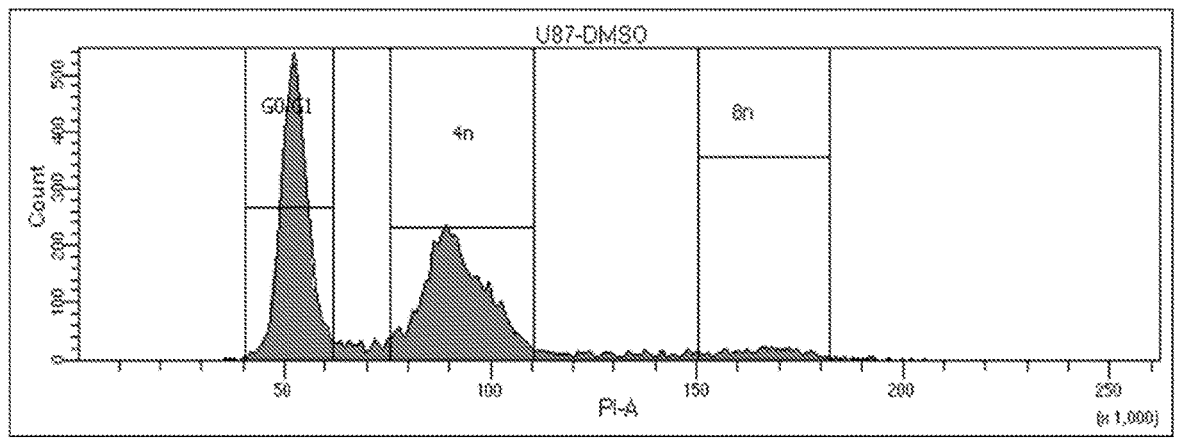
Figure 46B:
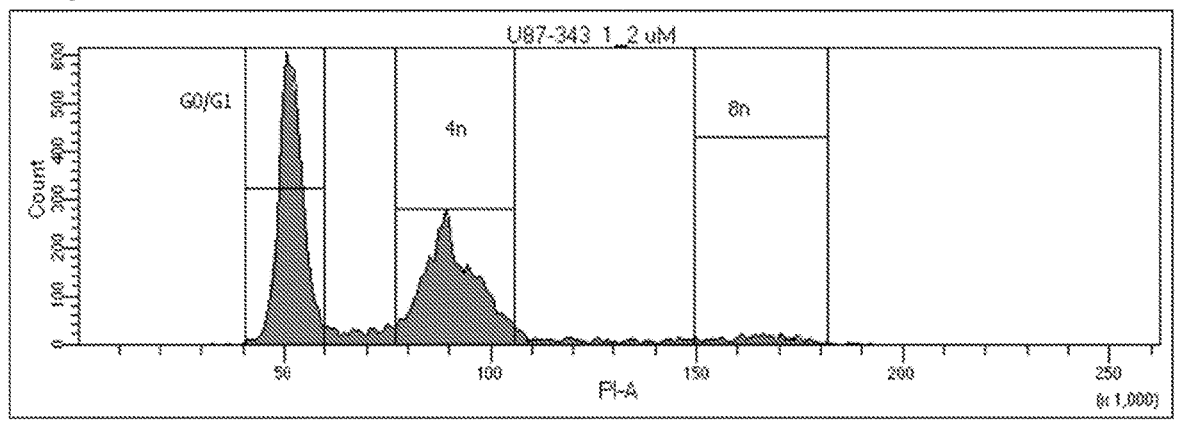
Figure 46C:
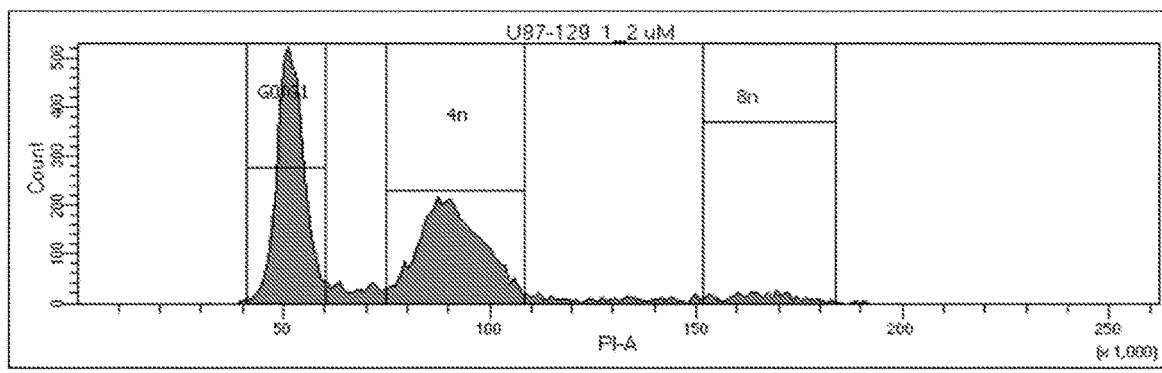

FIGS. 46A-46C represent exemplary experiments illustrating cell cycle distribution of U87 cells following treatment with DMSO (FIG. 46A), Compound 53 (FIG. 46B), or Compound 71 (FIG. 46C) in accordance with certain embodiments of the present disclosure.

Figure 47A:
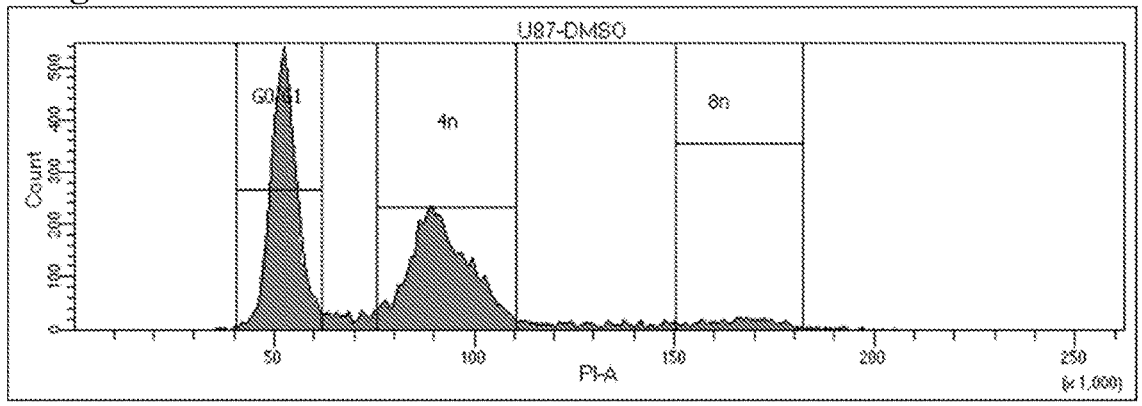
Figure 47B:
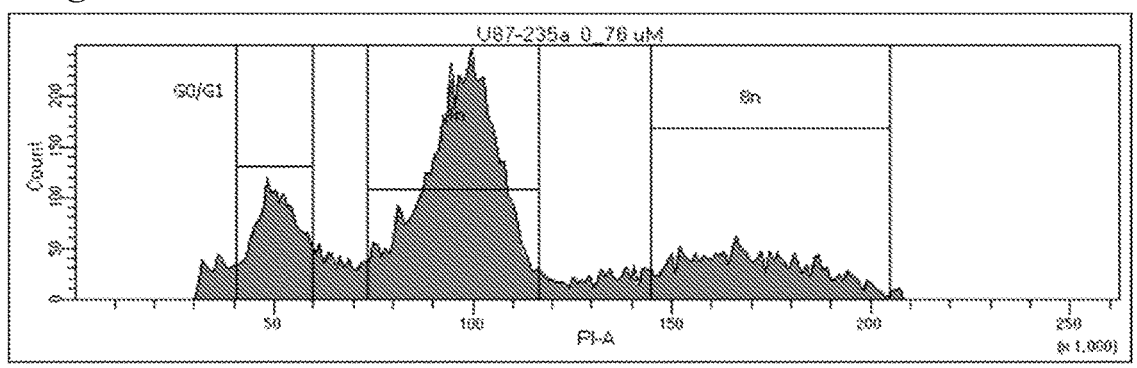
Figure 47C:
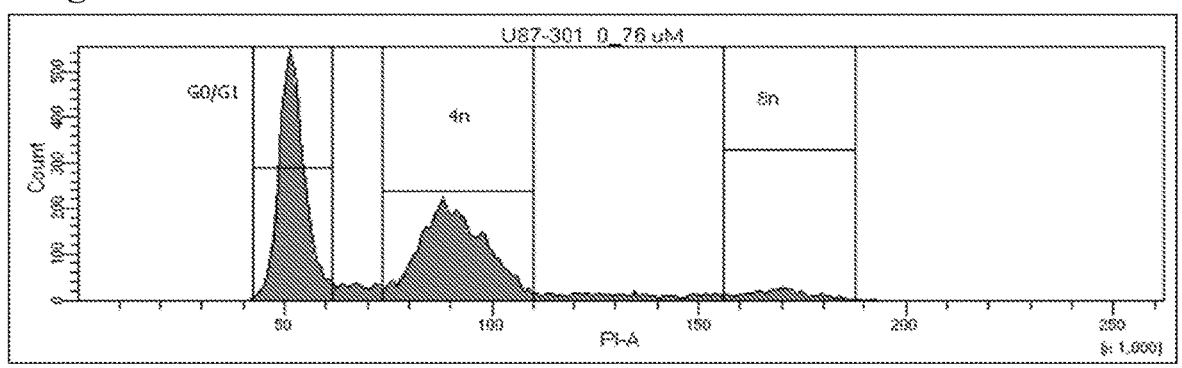

FIGS. 47A-47C represent exemplary experiments illustrating cell cycle distribution of U87 cells following treatment with DMSO (FIG. 47A), Compound 19A (FIG. 478), or Compound 40 (FIG. 47C) in accordance with certain embodiments of the present disclosure.

Figure 48A:
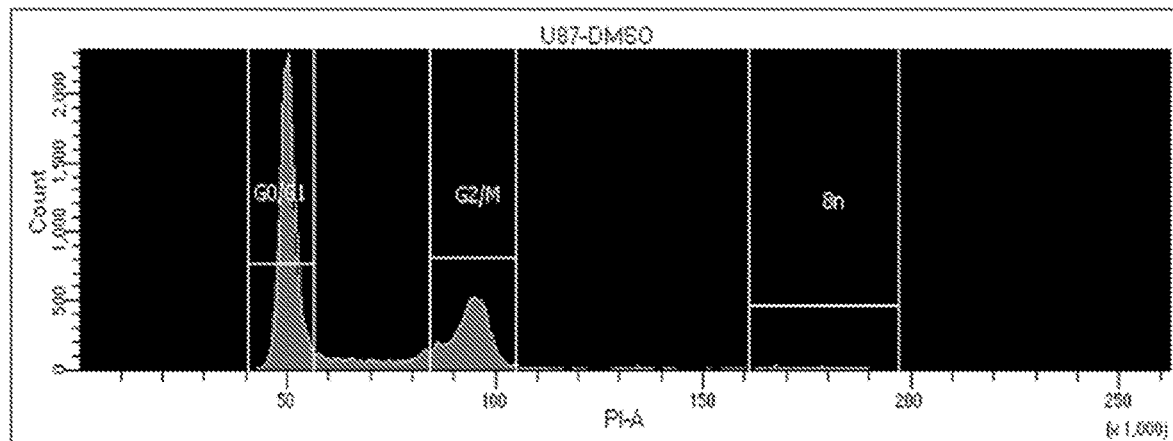
Figure 48B:
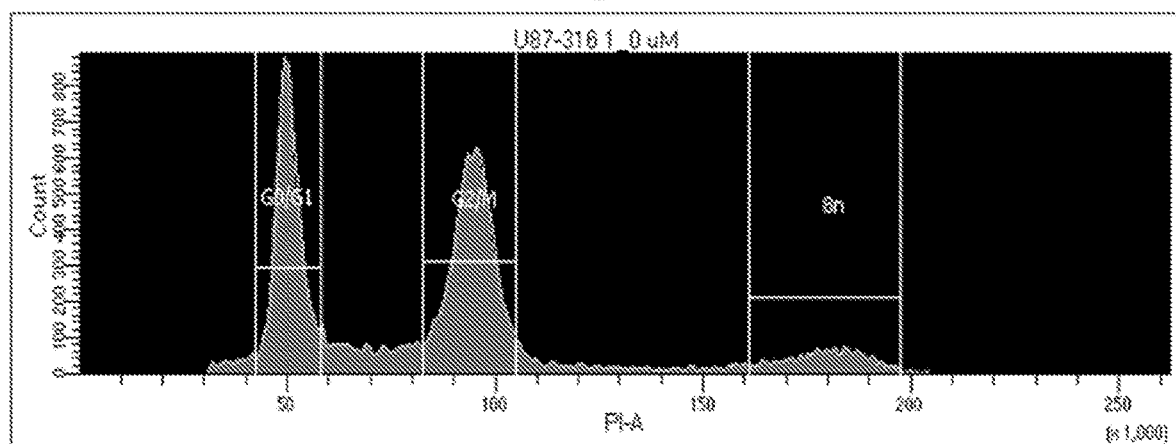
Figure 48C:
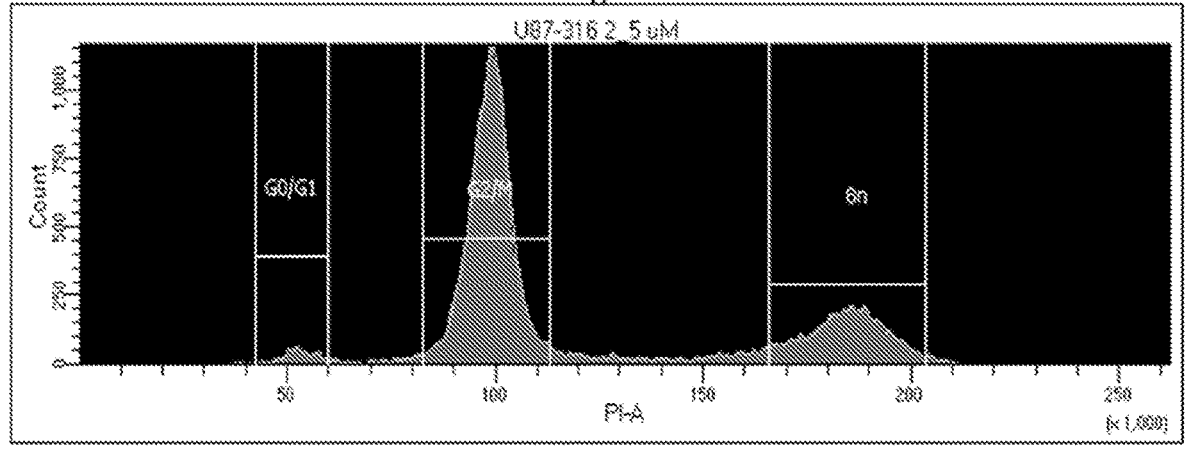

FIGS. 48A-48C represent exemplary experiments illustrating cell cycle distribution of U87 cells following treatment with DMSO (DMSO (FIG. 48A), 1.0 μM Compound 45A (FIG. 48B), or 2.5 μM Compound 45A (FIG. 48C), in accordance with certain embodiments of the present disclosure.

FIGS. 49A-49E represent exemplary experiments illustrating cell cycle distribution of U87 cells following treatment with DMSO (DMSO (FIG. 49A), 150 nM Compound 93 (FIG. 49B), 150 nM Compound 94 (FIG. 49C), 150 nM Compound 95 (FIG. 49D), and 150 nM Compound 96 (FIG. 49E) in accordance with certain embodiments of the present disclosure.

FIGS. 50A-50D represent exemplary experiments illustrating cell cycle distribution of U87 cells following treatment with DMSO (DMSO (FIG. 50A), 30 nM Compound 90 (FIG. 505), 30 nM Compound 97 (FIG. 50C), and 10 nM Compound 98 (FIG. 50D) in accordance with certain embodiments of the present disclosure.

Figure 51:
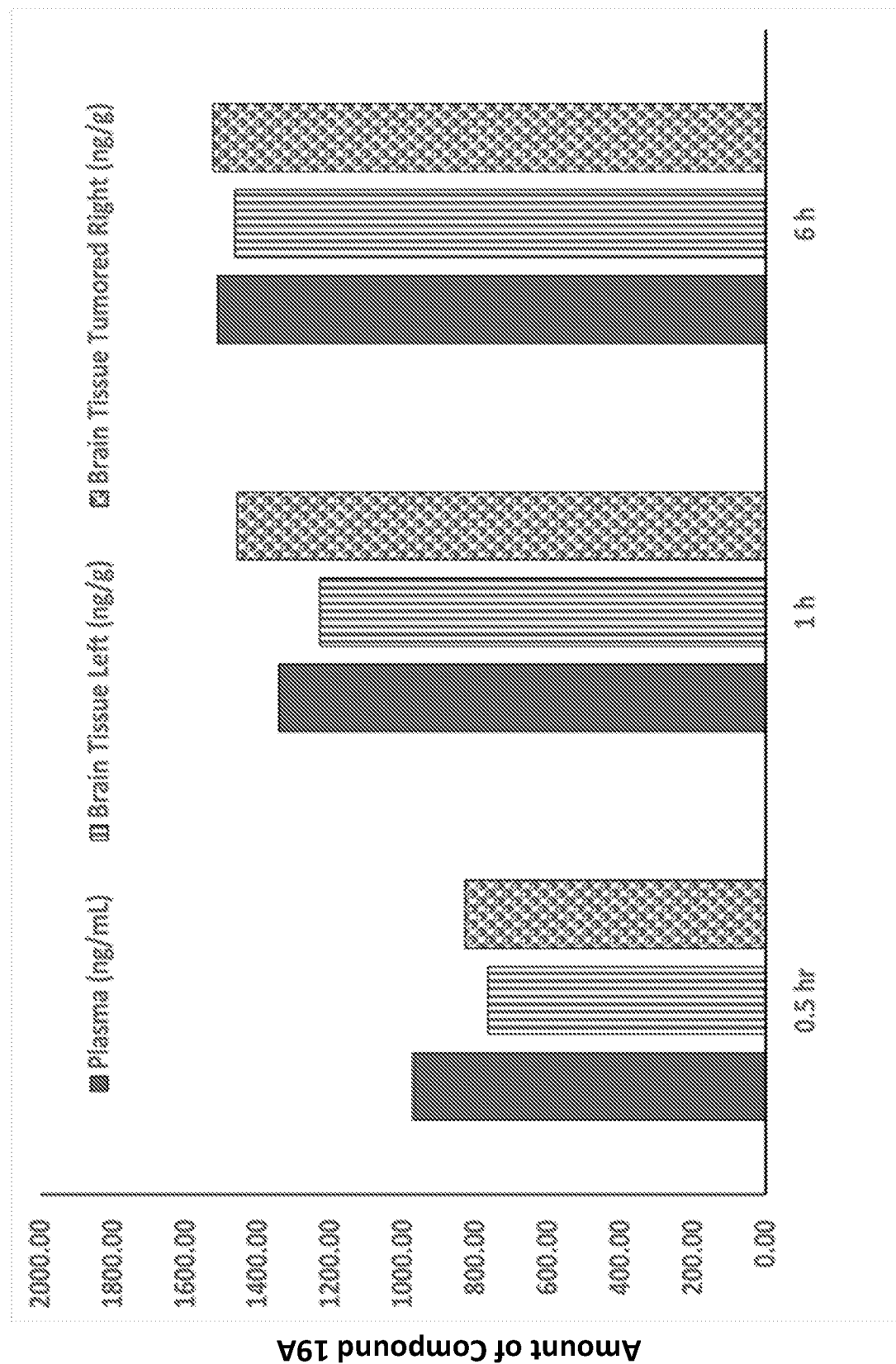

FIG. 51 represents an exemplary experiment illustrating concentration of Compound 19A in plasma, healthy brain tissue, and brain tumor tissue after administration to a rodent model in accordance with certain embodiments of the present disclosure.

Figure 52A:
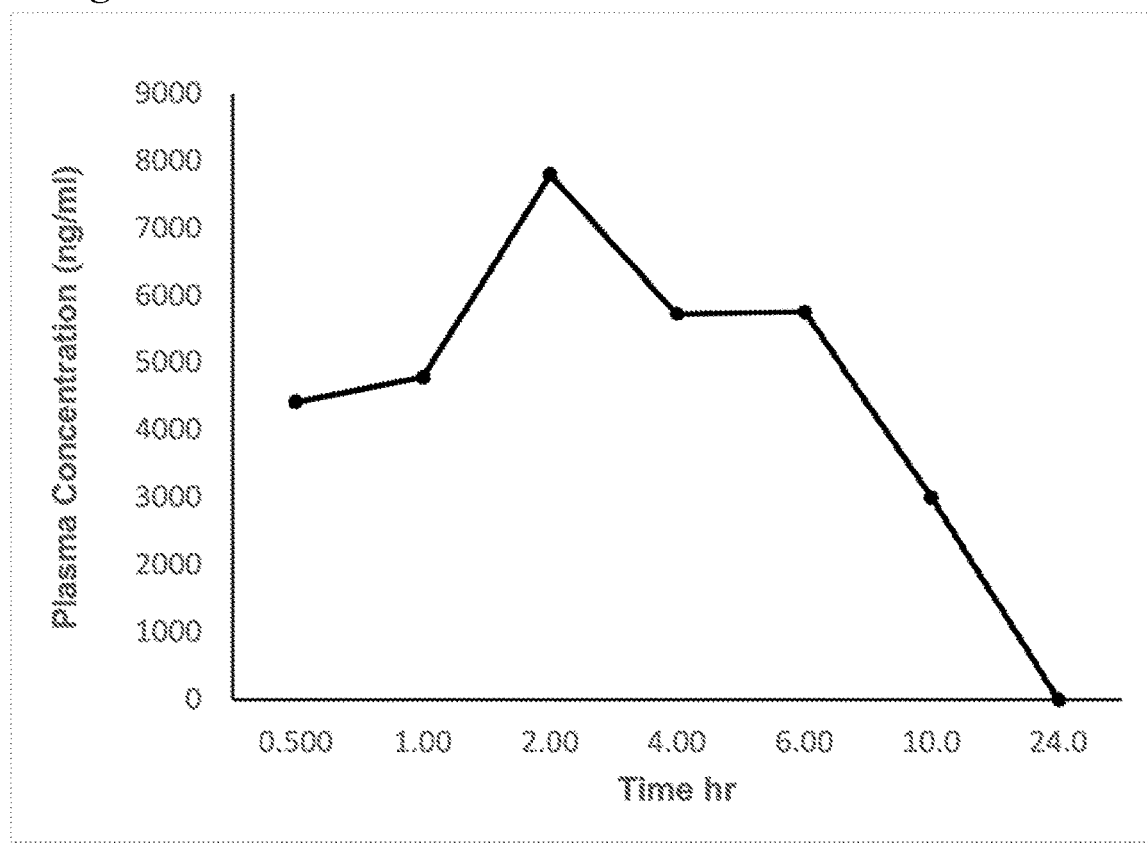
Figure 52B:
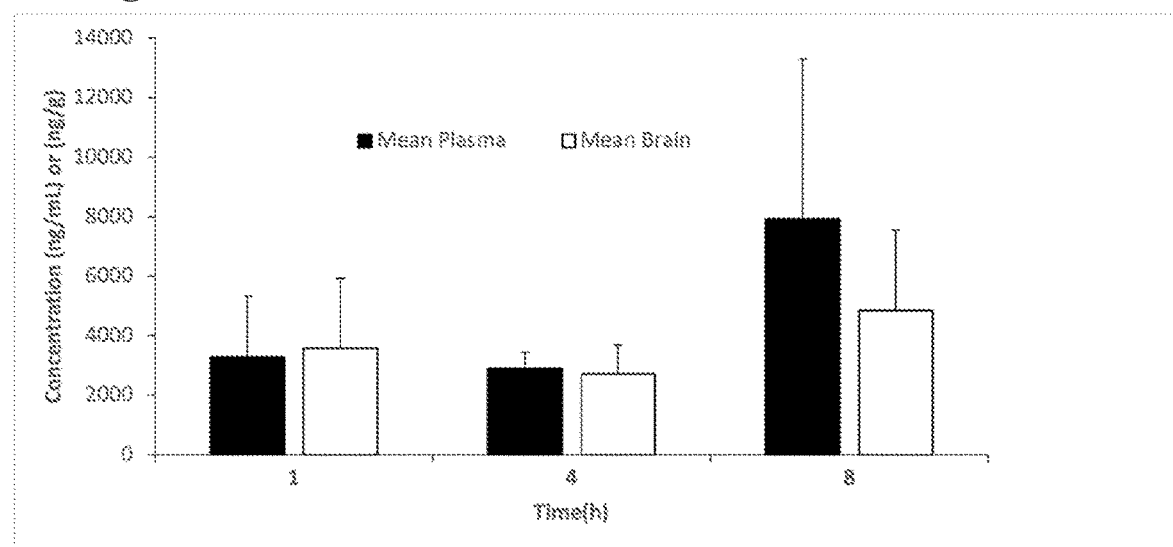

FIG. 52A-52B represent an exemplary experiment illustrating concentration of Compound 19A in plasma after oral dose (FIG. 52A); FIG. 52B represents levels of Compound 19A in plasma and brain tissue after administration to a rodent model in accordance with certain embodiments of the present disclosure.

Figure 53A:
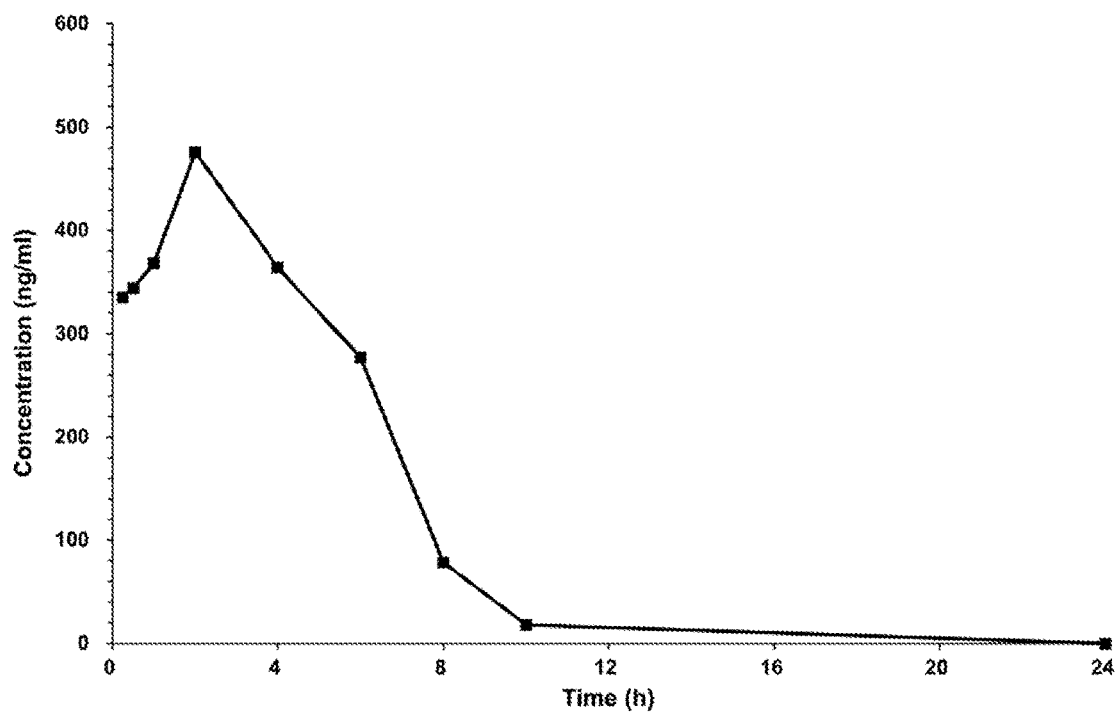
Figure 53B:
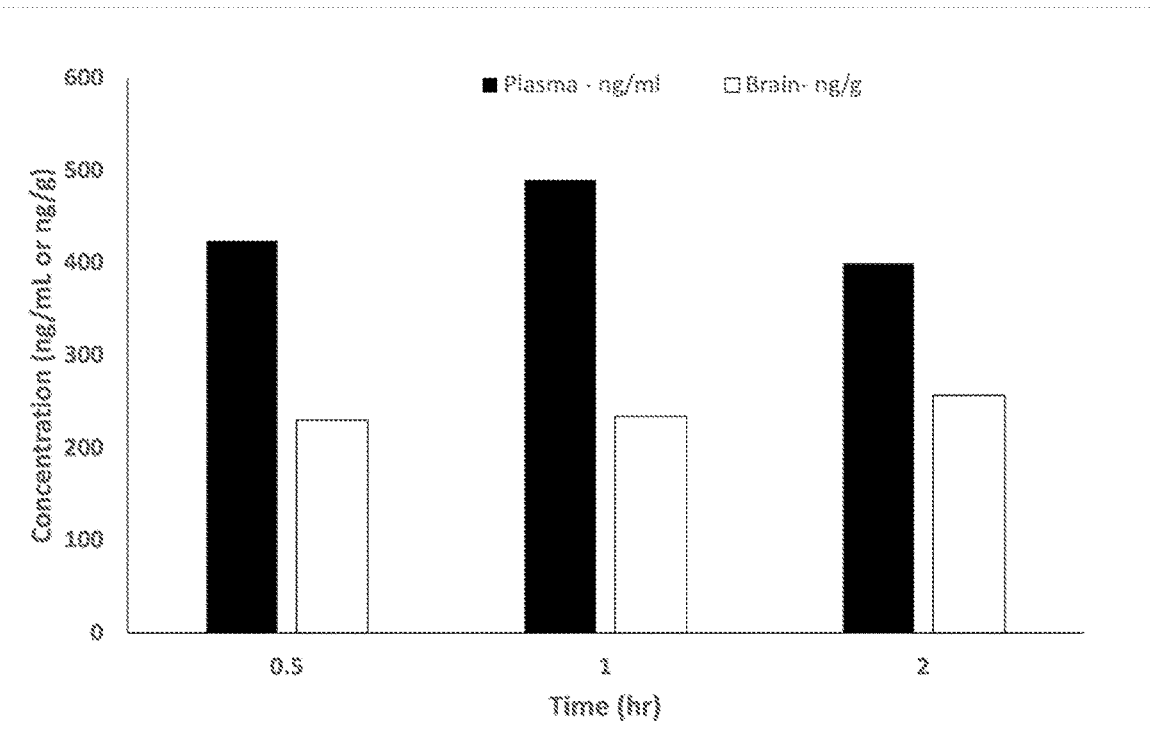

FIG. 53A-53B represent an exemplary experiment illustrating concentration of Compound 98 in plasma after oral dose (FIG. 53A); FIG. 53B represents levels of Compound 98 in plasma and brain tissue after administration to a rodent model in accordance with certain embodiments of the present disclosure.

DEFINITIONS

As used herein, the term "about," can mean relative to the recited value, e.g., amount, dose, temperature, time, percentage, etc., ±10%, 9%, 8%, ±7%, 6%, 5%, 4%, 3%, ±2%, or +1%.

As used herein, "analog," refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

As used herein, "isomers" refers to compounds having the same number and kind of atoms, and hence the same molecular weight, but differing in respect to the structural arrangement or configuration of the atoms.

As used herein, "alkyl" refers to a saturated aliphatic hydrocarbon group including $C_1$-$C_{20}$ straight chain and branched chain groups. Representative examples include, but are not limited to methyl, ethyl, n-propyl, isopropyl, n-butyl, isobutyl, tert-butyl, sec-butyl, n-pentyl, 1,1-dimethyl propyl, 1,2-dimethyl propyl, 2,2-dimethyl propyl, I-ethyl propyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and the isomers of branched chain thereof. An alkyl group can be a lower alkyl having 1 to 6 carbon atoms. Representative examples include, but are not limited to methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl and etc. The alkyl group can be substituted or unsubstituted. When substituted, the substituent group(s) can have one or more groups independently selected from the group consisting of alkyl, alkenyl, alkynyl, alkoxyl, alkylsulfo, alkylamino, halogen, thiol, hydroxyl, nitro, cyano, cycloalkyl, heterocyclic alkyl, aryl, heteroaryl, cycloalkoxyl, heterocyclic alkoxyl, cycloalkylthio, heterocyclic alkylthio, carbonyl, carboxy or carboxylic ester.

As used herein, "cycloalkyl" refers to saturated and/or partially unsaturated monocyclic or polycyclic hydrocarbon group and have 3 to 20 carbon atoms. Representative examples of monocyclic cycloalkyl include, but are not limited to cyclopropyl, cyclobutyl, cyclopentyl, cyclopentenyl, cyclohexyl, cyclohexenyl, cyclohexadienyl, cycloheptyl, cycloheptatrienyl, cyclooctyl and etc. Polycyclic cycloalkyl includes the cycloalkyl having Spiro ring, fused ring and bridged ring.

As used herein, "heteroaryl" refers to an 5-14 membered aryl having 1 to 4 heteroatoms selected from the group consisting of O, S, and N as ring atoms, the remaining ring atoms being C. Examples of heteroaryl groups are furan, thiophene, pyridine, pyrrole, N-alkyl pyrrole, pyrimidine, pyrazine, imidazole, tetrazolyl, and the like. Heteroaryl herein can be fused to aryl, heterocyclic alkyl or cycloalkyl, wherein the ring connected with parent structure is heteroaryl. Heteroaryls herein can be substituted or unsubstituted. When substituted, the substituent group(s) can be one or more groups independently selected from the group consisting of alkyl, alkenyl, alkynyl, alkoxyl, alkylsulfo, alkylamino, halogen, thiol, hydroxyl, nitro, cyano, cycloalkyl, heterocyclic alkyl, aryl, heteroaryl, cycloalkoxyl, heterocyclic alkoxyl, cycloalkylthio, heterocyclic alkylthio, carbonyl, carboxy or carboxylic ester.

As used herein, "hydroxyl" refers to an —OH group. As used herein, "hydroxyalkyl" refers to -alkyl-OH, wherein alkyl as defined above. As used herein, "halo" or "halogen" refers to fluoro, chloro, bromo, or iodo. As used herein, "thiol" refers to an organosulfur compound according to the form R—SH, where R represents an alkyl or other organic substituent. As used herein, "carbonyl" refers to —C(═O)—. As used herein, "nitro" refers to —NO$_2$. As used herein, "cyano" refers to —CN. As used herein, "amino" refers to —NH$_2$. As used herein, "carboxy" refers to —C(═O)OH. As used herein, "carboxylic ester" refers to —C(═O)O-alkyl.

As used herein, "optionally substituted" indicates that a group can be unsubstituted or substituted with one or more substituents as defined herein. As used herein, "substituted" in reference to a group indicates that a hydrogen atom attached to a member atom within a group is replaced. It should be understood that the term "substituted" includes the provision that such substitution be in accordance with the permitted valence of the substituted atom and the substituent and that the substitution results in a stable compound (e.g. one that does not spontaneously undergo transformation such as by rearrangement, cyclization, or elimination). In certain embodiments, a single atom can be substituted with more than one substituent as long as such substitution is in accordance with the permitted valence of the atom. Suitable substituents are defined herein for each substituted or optionally substituted group.

As used herein, "pharmaceutically acceptable" refers to those compounds, materials, compositions, and dosage forms which can be, within the scope of sound medical judgment, suitable for use in contact with the tissues of human beings and animals without excessive toxicity, irritation, or other problem or complication, commensurate with a reasonable benefit/risk ratio.

As used herein, "individual", "subject", "host", and "patient" can be used interchangeably and refer to any mammalian subject regarding diagnosis, treatment, prophylaxis or therapy is desired; for example, humans (e.g., adults, adolescents, children, infants and a fetus), pets, livestock, horses or other animals.

As used herein, "treat," "treating" or "treatment" can refer to administering an agent disclosed herein and reversing, ameliorating, or inhibiting onset or inhibiting progression of a health condition or disease or a symptom of the health condition or disease.

DETAILED DESCRIPTION

In the following sections, certain exemplary compositions and methods are described to detail certain embodiments of the invention. It will be obvious to one skilled in the art that practicing the certain embodiments does not require the employment of all or even some of the specific details outlined herein, but rather that concentrations, times, and other specific details can be modified through routine experimentation. In some cases, well known methods, or components have not been included in the description.

The present disclosure is based, at least in part, on the discovery of microtubule destabilizing agents for therapeutic use in treating health conditions such as cancer. As shown herein, therapeutic compounds and methods of using the therapeutic compounds have been identified. Current agents used for cancer are either not effective, or unsafe.

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules of the compound are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods. Additional aspects of the disclosure are described below.

I. Compounds

One aspect of the present disclosure encompasses compounds for use to treat health conditions in a subject or of use as combination therapies in treatment, reducing onset or amelioration of a health condition in a subject in need thereof. In some embodiments, a compound can include a compound according to formula (I),

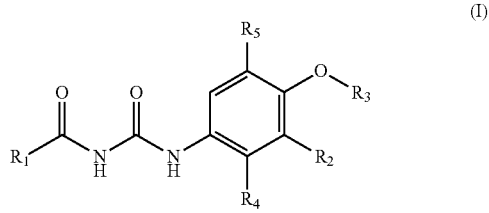

an analog, an isomer, a pharmaceutically acceptable salt, and/or a prodrug thereof; $R_1$ is selected from:

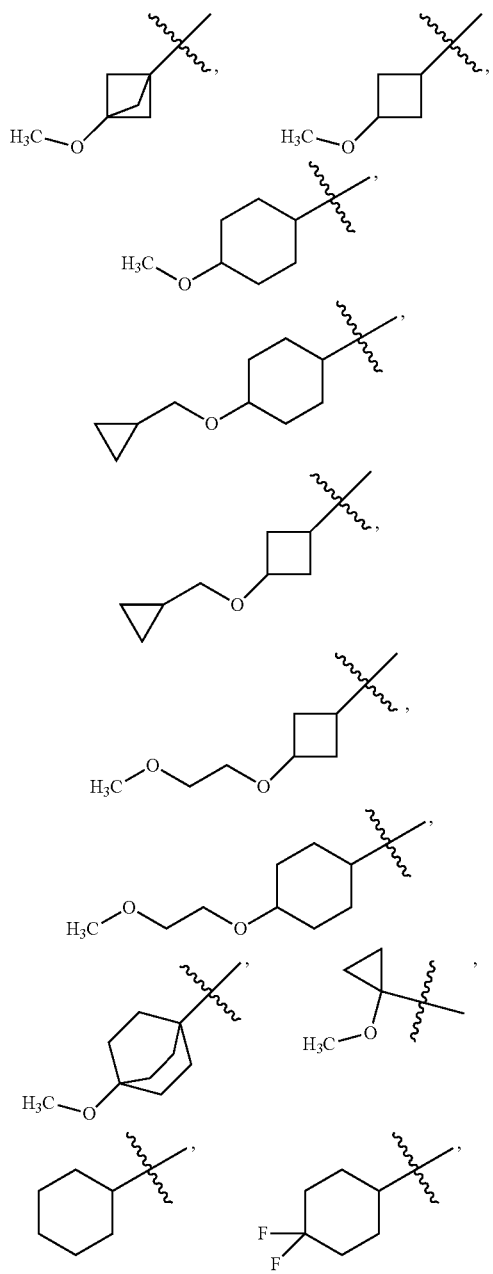

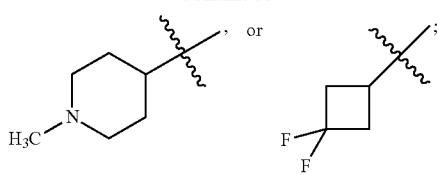

$R_2$ is $CH_3$ or F; $R_3$ is a heteroaryl, wherein the heteroaryl is unsubstituted or is optionally substituted with one or more groups independently selected from alkyl, alkenyl, alkynyl, alkoxyl, alkylsulfo, alkylamino, halogen, thiol, hydroxyl, nitro, cyano, cycloalkyl, heterocyclic alkyl, aryl, heteroaryl, cycloalkoxyl, heterocyclic alkoxyl, cycloalkylthio, and heterocyclic alkylthio; $R_4$ and $R_5$ are each independently selected from H and F.

In some embodiments, $R_1$ of compounds of formula (I) disclosed herein is selected from:

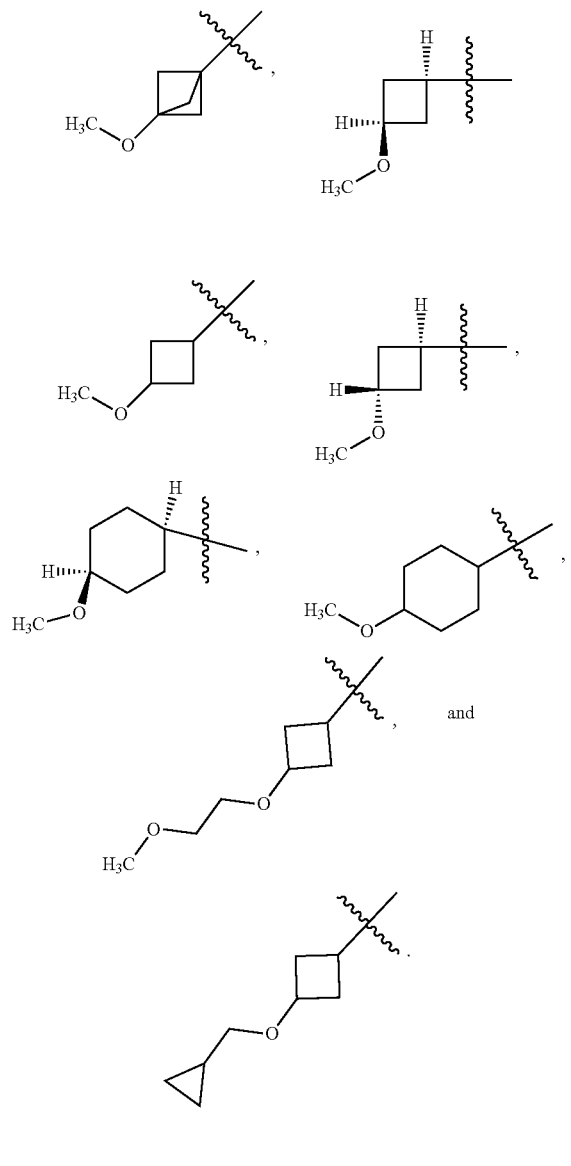

In some embodiments, $R_1$ of compounds of formula (I) disclosed herein is selected from:

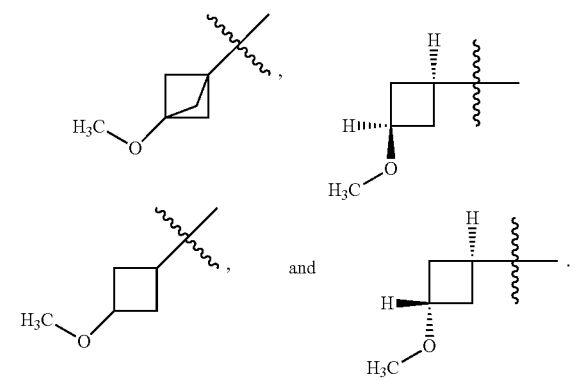

In some embodiments, $R_3$ of compounds of formula (I) disclosed herein is a 5- or 6-membered heteroaryl where the heteroaryl is unsubstituted or is optionally substituted with one or more groups independently selected from alkyl, alkenyl, alkynyl, alkoxyl, alkylsulfo, alkylamino, halogen, thiol, hydroxyl, nitro, cyano, cycloalkyl, heterocyclic alkyl, aryl, heteroaryl, cycloalkoxyl, heterocyclic alkoxyl, cycloalkylthio, heterocyclic alkylthio. In other embodiments, $R_3$ is a 5- or 6-membered heteroaryl unsubstituted or optionally substituted with one or more groups independently selected from the group consisting of alkyl, alkenyl, alkynyl, alkoxyl, alkylsulfo, alkylamino, halogen, thiol, hydroxyl, nitro, cyano, cycloalkyl, heterocyclic alkyl, aryl, heteroaryl, cycloalkoxyl, heterocyclic alkoxyl, cycloalkylthio, heterocyclic alkylthio.

In some embodiments, $R_3$ of compounds of formula (I) disclosed herein is a 5- or 6-membered heteroaryl where the heteroaryl is unsubstituted or is optionally substituted with one or more groups independently selected from alkyl, alkenyl, alkynyl, alkoxyl, alkylsulfo, alkylamino, halogen, thiol, hydroxyl, nitro, cyano, cycloalkyl, heterocyclic alkyl, aryl, heteroaryl, cycloalkoxyl, heterocyclic alkoxyl, cycloalkylthio, heterocyclic alkylthio. In other embodiments, $R_3$ is a 5- or 6-membered heteroaryl unsubstituted or optionally substituted with one or more groups independently selected from the group consisting of alkyl, alkylamino, halogen, alkylhalide, cyano, cycloalkyl, heterocyclic alkyl, aryl, heteroaryl, cycloalkoxyl, and heterocyclic alkoxyl, cycloalkylthio, and heterocyclic alkylthio.

In some embodiments, $R_3$ of compounds of formula (I) disclosed herein is selected from:

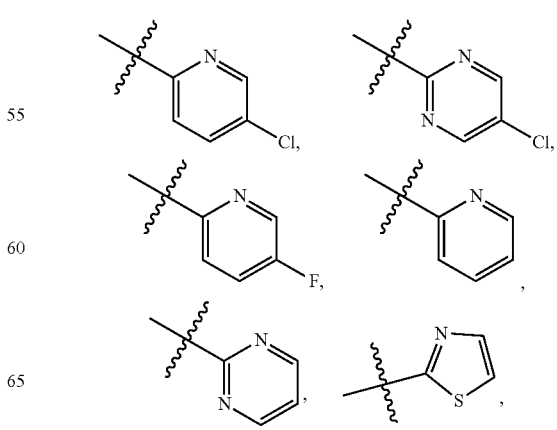

-continued

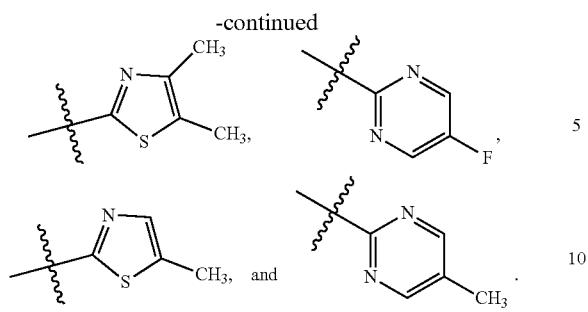

In some embodiments, $R_2$ is $CH_3$. In some embodiments, $R_4$ is H. In other embodiments, $R_5$ is H. In some embodiments, $R_8$ is $CH_3$.

In certain embodiments, compounds of formula (I) can have $R_1$, $R_2$, $R_3$, $R_4$, and/or $R_5$ as indicated in Table 1. In other embodiments, compounds of the present disclosure can include any one of the compounds provided in Table 1.

TABLE 1

| Compound | $R_1$ | $R_2$ | $R_3$ | $R_4$ | $R_5$ | Name |
|---|---|---|---|---|---|---|
| 1 | 4-methoxycyclohexyl | —$CH_3$ | 5-chloropyrimidin-2-yl | —H | —H | 3-{4-[(5-chloropyrimidin-2-yl)oxy]-3-methylphenyl}-1-(4-methoxycyclohexanecarbonyl)urea |
| 2 | oxetan-3-yl | —$CH_3$ | 5-chloropyrimidin-2-yl | —H | —H | 1-{4-[(5-chloropyrimidin-2-yl)oxy]-3-methylphenyl}-3-(oxetane-3-carbonyl)urea |
| 3 | cyclopentyl | —$CH_3$ | 5-chloropyrimidin-2-yl | —H | —H | 1-{4-[(5-chloropyrimidin-2-yl)oxy]-3-methylphenyl}-3-cyclopentanecarbonylurea |
| 4 | tetrahydropyran-4-yl | —$CH_3$ | 5-chloropyrimidin-2-yl | —H | —H | 3-{4-[(5-chloropyrimidin-2-yl)oxy]-3-methylphenyl}-1-(oxane-4-carbonyl)urea |

TABLE 1-continued

| Compound | R₁ | R₂ | R₃ | R₄ | R₅ | Name |
|---|---|---|---|---|---|---|
| 5 | (3R)-oxolan-3-yl | —CH₃ | 5-chloropyrimidin-2-yl | —H | —H | rac-1-{4-[(5-chloropyrimidin-2-yl)oxy]-3-methylphenyl}-3-[(3R)-oxolane-3-carbonyl]urea |
| 6 | 4-methoxycyclohexyl | —CH₃ | 5-cyanopyridin-2-yl | —H | —H | 3-{4-[(5-cyanopyridin-2-yl)oxy]-3-methylphenyl}-1-(4-methoxycyclohexanecarbonyl)urea |
| 7 | 4-methoxycyclohexyl | —CH₃ | 5-chloropyridin-2-yl | —H | —H | 3-{4-[(5-chloropyridin-2-yl)oxy]-3-methylphenyl}-1-(4-methoxycyclohexanecarbonyl)urea |
| 8 | 4-methoxycyclohexyl | —CH₃ | 5-fluoropyrimidin-2-yl | —H | —H | 3-{4-[(5-fluoropyrimidin-2-yl)oxy]-3-methylphenyl}-1-(4-methoxycyclohexanecarbonyl)urea |
| 9 | 4-methoxycyclohexyl | —CH₃ | 5-fluoropyridin-2-yl | —H | —H | 3-{4-[(5-fluoropyridin-2-yl)oxy]-3-methylphenyl}-1-(4-methoxycyclohexanecarbonyl)urea |
| 10 | 4-methoxycyclohexyl | —CH₃ | pyrimidin-2-yl | —H | —H | 1-(4-methoxycyclohexanecarbonyl)-3-[3-methyl-4-(pyrimidin-2-yloxy)phenyl]urea |
| 11 | 4-methoxycyclohexyl | —CH₃ | 1,3-thiazol-2-yl | —H | —H | 1-(4-methoxycyclohexanecarbonyl)-3-[3-methyl-4-(1,3-thiazol-2-yloxy)phenyl]urea |
| 12 | 4-methoxycyclohexyl | —F | 5-chloropyridin-2-yl | —H | —H | 3-{4-[(5-chloropyridin-2-yl)oxy]-3-fluorophenyl}-1-(4-methoxycyclohexanecarbonyl)urea |

TABLE 1-continued

| Compound | R₁ | R₂ | R₃ | R₄ | R₅ | Name |
|---|---|---|---|---|---|---|
| 13 | 4-methoxycyclohexyl | —F | pyrimidin-2-yl | —H | —H | 3-[3-fluoro-4-(pyrimidin-2-yloxy)phenyl]-1-(4-methoxycyclohexanecarbonyl)urea |
| 14 | 4-methoxycyclohexyl | —F | 5-chloropyrimidin-2-yl | —H | —H | 3-{4-[(5-chloropyrimidin-2-yl)oxy]-3-fluorophenyl}-1-(4-methoxycyclohexanecarbonyl)urea |
| 15 | 3-methoxycyclobutyl | —CH₃ | 5-fluoropyridin-2-yl | —H | —H | 1-{4-[(5-fluoropyridin-2-yl)oxy]-3-methylphenyl}-3-(3-methoxycyclobutanecarbonyl)urea |
| 16 | 3-methoxycyclobutyl | —CH₃ | 5-cyanopyridin-2-yl | —H | —H | 1-{4-[(5-cyanopyridin-2-yl)oxy]-3-methylphenyl}-3-(3-methoxycyclobutanecarbonyl)urea |
| 17 | 3-methoxycyclobutyl | —CH₃ | 5-fluoropyrimidin-2-yl | —H | —H | 1-{4-[(5-fluoropyrimidin-2-yl)oxy]-3-methylphenyl}-3-(3-methoxycyclobutanecarbonyl)urea |
| 18 | 3-methoxycyclobutyl | —CH₃ | pyrimidin-2-yl | —H | —H | 3-(3-methoxycyclobutanecarbonyl)-1-[3-methyl-4-(pyrimidin-2-yloxy)phenyl]urea |
| 19 | 3-methoxycyclobutyl | —CH₃ | 5-chloropyridin-2-yl | —H | —H | 1-{4-[(5-chloropyridin-2-yl)oxy]-3-methylphenyl}-3-(3-methoxycyclobutanecarbonyl)urea |

TABLE 1-continued

| Compound | R₁ | R₂ | R₃ | R₄ | R₅ | Name |
|---|---|---|---|---|---|---|
| 20 | 3-methoxycyclobutyl | —CH₃ | 5-chloropyrimidin-2-yl | —H | —H | 1-{4-[(5-chloropyrimidin-2-yl)oxy]-3-methylphenyl}-3-(3-methoxycyclobutanecarbonyl)urea |
| 21 | 4-methoxycyclohexyl | —CH₃ | 1,3-oxazol-2-yl | —H | —H | 1-(4-methoxycyclohexanecarbonyl)-3-[3-methyl-4-(1,3-oxazol-2-yloxy)phenyl]urea |
| 22 | 4-methoxycyclohexyl | —CH₃ | pyridazin-3-yl | —H | —H | 1-(4-methoxycyclohexanecarbonyl)-3-[3-methyl-4-(pyridazin-3-yloxy)phenyl]urea |
| 23 | 4-methoxycyclohexyl | —H | 5-chloropyrimidin-2-yl | —F | —H | 3-{4-[(5-chloropyrimidin-2-yl)oxy]-2-fluorophenyl}-1-(4-methoxycyclohexanecarbonyl)urea |
| 24 | 4-methoxycyclohexyl | —H | 5-chloropyridin-2-yl | —F | —H | 3-{4-[(5-chloropyridin-2-yl)oxy]-2-fluorophenyl}-1-(4-methoxycyclohexanecarbonyl)urea |
| 25 | 4-methoxycyclohexyl | —H | pyrimidin-2-yl | —F | —H | 3-[2-fluoro-4-(pyrimidin-2-yloxy)phenyl]-1-(4-methoxycyclohexanecarbonyl)urea |
| 26 | 4-methoxycyclohexyl | —CH₃ | 1,3,4-thiadiazol-2-yl | —H | —H | 1-(4-methoxycyclohexanecarbonyl)-3-[3-methyl-4-(1,3,4-thiadiazol-2-yloxy)phenyl]urea |
| 27 | 4-methoxycyclohexyl | —CH₃ | 5-methylpyrimidin-2-yl | —H | —H | 1-(4-methoxycyclohexanecarbonyl)-3-{3-methyl-4-[(5-methylpyrimidin-2-yl)oxy]phenyl}urea |

TABLE 1-continued

| Compound | R₁ | R₂ | R₃ | R₄ | R₅ | Name |
|---|---|---|---|---|---|---|
| 28 | 4-methoxycyclohexyl | —CH₃ | 1-methyl-1H-imidazol-2-yl | —H | —H | 1-(4-methoxycyclohexanecarbonyl)-3-{3-methyl-4-[(1-methyl-1H-imidazol-2-yl)oxy]phenyl}urea |
| 29 | 4-methoxycyclohexyl | —CH₃ | 5-(trifluoromethyl)pyrimidin-2-yl | —H | —H | 1-(4-methoxycyclohexanecarbonyl)-3-(3-methyl-4-{[5-(trifluoromethyl)pyrimidin-2-yl]oxy}phenyl)urea |
| 30 | 4-methoxycyclohexyl | —CH₃ | 5-(propan-2-yl)pyrimidin-2-yl | —H | —H | 1-(4-methoxycyclohexanecarbonyl)-3-(3-methyl-4-{[5-(propan-2-yl)pyrimidin-2-yl]oxy}phenyl)urea |
| 31 | 4-methoxycyclohexyl | —CH₃ | 5-cyclopropylpyrimidin-2-yl | —H | —H | 3-{4-[(5-cyclopropylpyrimidin-2-yl)oxy]-3-methylphenyl}-1-(4-methoxycyclohexanecarbonyl)urea |
| 32 | 4-methoxycyclohexyl | —CH₃ | 5-methylpyridin-2-yl | —H | —H | 1-(4-methoxycyclohexanecarbonyl)-3-{3-methyl-4-[(5-methylpyridin-2-yl)oxy]phenyl}urea |
| 33 | 4-methoxycyclohexyl | —CH₃ | 5-(trifluoromethyl)pyridin-2-yl | —H | —H | 4-methoxy-N-((3-methyl-4-((5-(trifluoromethyl)pyridin-2-yl)oxy)phenyl)carbamoyl)cyclohexane-1-carboxamide |
| 34 | 4-methoxycyclohexyl | —CH₃ | 5-isopropylpyridin-2-yl | —H | —H | N-((4-((5-isopropylpyridin-2-yl)oxy)-3-methylphenyl)carbamoyl)-4-methoxycyclohexane-1-carboxamide |

TABLE 1-continued

| Compound | R₁ | R₂ | R₃ | R₄ | R₅ | Name |
|---|---|---|---|---|---|---|
| 35 | 3-methoxycyclobutyl | —CH₃ | 5-(4-methylpiperazin-1-yl)pyrimidin-2-yl | —H | —H | 3-methoxy-N-((3-methyl-4-((2-(4-methylpiperazin-1-yl)pyrimidin-5-yl)oxy)phenyl)carbamoyl)cyclobutane-1-carboxamide |
| 36 | 4-methoxycyclohexyl | —CH₃ | 5-(4-methylpiperazin-1-yl)pyrimidin-2-yl | —H | —H | 4-methoxy-N-((3-methyl-4-((2-(4-methylpiperazin-1-yl)pyrimidin-5-yl)oxy)phenyl)carbamoyl)cyclohexane-1-carboxamide |
| 37 | 4-(cyclopropylmethoxy)cyclohexyl | —F | 5-chloropyrimidin-2-yl | —H | —H | N-((4-((5-chloropyrimidin-2-yl)oxy)-3-fluorophenyl)carbamoyl)-4-(cyclopropylmethoxy)cyclohexane-1-carboxamide |
| 38 | 4-(cyclopropylmethoxy)cyclohexyl | —CH₃ | 5-chloropyrimidin-2-yl | —H | —H | N-((4-((5-chloropyrimidin-2-yl)oxy)-3-methylphenyl)carbamoyl)-4-(cyclopropylmethoxy)cyclohexane-1-carboxamide |
| 39 | 3-(cyclopropylmethoxy)cyclobutyl | —CH₃ | thiazol-2-yl | —H | —H | 3-(cyclopropylmethoxy)-N-((3-methyl-4-(thiazol-2-yloxy)phenyl)carbamoyl)cyclobutane-1-carboxamide |
| 40 | 3-(cyclopropylmethoxy)cyclobutyl | —CH₃ | 5-chloropyridin-2-yl | —H | —H | N-((4-((5-chloropyridin-2-yl)oxy)-3-methylphenyl)carbamoyl)-3-(cyclopropylmethoxy)cyclobutane-1-carboxamide |

TABLE 1-continued

| Compound | R₁ | R₂ | R₃ | R₄ | R₅ | Name |
|---|---|---|---|---|---|---|
| 41 | cyclopropylmethoxy-cyclobutyl | —CH₃ | 5-chloropyrimidin-2-yl | —H | —H | N-((4-((5-chloropyrimidin-2-yl)oxy)-3-methylphenyl)carbamoyl)-3-(cyclopropylmethoxy)cyclobutane-1-carboxamide |
| 42 | 4-methoxycyclohexyl | —CH₃ | pyrimidin-5-yl | —H | —H | 4-methoxy-N-((3-methyl-4-(pyrimidin-5-yloxy)phenyl)carbamoyl)cyclohexane-1-carboxamide |
| 43 | 3-methoxycyclobutyl | —CH₃ | pyrimidin-5-yl | —H | —H | 3-methoxy-N-((3-methyl-4-(pyrimidin-5-yloxy)phenyl)carbamoyl)cyclobutane-1-carboxamide |
| 44 | 3-methoxycyclobutyl | —CH₃ | 2-morpholinopyrimidin-5-yl | —H | —H | 3-methoxy-N-((3-methyl-4-((2-morpholinopyrimidin-5-yl)oxy)phenyl)carbamoyl)cyclobutane-1-carboxamide |
| 45 | 3-methoxycyclobutyl | —CH₃ | thiazol-2-yl | —H | —H | 3-methoxy-N-((3-methyl-4-(thiazol-2-yloxy)phenyl)carbamoyl)cyclobutane-1-carboxamide |
| 46 | 4-methoxycyclohexyl | —CH₃ | 2-morpholinopyrimidin-5-yl | —H | —H | 4-methoxy-N-((3-methyl-4-((2-morpholinopyrimidin-5-yl)oxy)phenyl)carbamoyl)cyclohexane-1-carboxamide |
| 47 | 3-(2-methoxyethoxy)cyclobutyl | —CH₃ | thiazol-2-yl | —H | —H | N-((4-((5-chloropyrimidin-2-yl)oxy)-3-methylphenyl)carbamoyl)-3-(2-methoxyethoxy)cyclobutane-1-carboxamide |

TABLE 1-continued

| Compound | R₁ | R₂ | R₃ | R₄ | R₅ | Name |
|---|---|---|---|---|---|---|
| 48 | (cyclobutyl with CH₃ and OCH₂CH₂OCH₃) | —CH₃ | (5-chloropyrimidin-2-yl) | —H | —H | N-((4-((5-chloropyrimidin-2-yl)oxy)-3-methylphenyl)carbamoyl)-3-(2-methoxyethoxy)cyclobutane-1-carboxamide |
| 49 | (cyclobutyl with CH₃ and OCH₂CH₂OCH₃) | —CH₃ | (5-chloropyridin-2-yl) | —H | —H | N-((4-((5-chloropyridin-2-yl)oxy)-3-methylphenyl)carbamoyl)-3-(2-methoxyethoxy)cyclobutane-1-carboxamide |
| 50 | (cyclohexyl with CH₃ and OCH₂CH₂OCH₃) | —CH₃ | (5-chloropyrimidin-2-yl) | —H | —H | N-((4-((5-chloropyrimidin-2-yl)oxy)-3-methylphenyl)carbamoyl)-4-(2-methoxyethoxy)cyclohexanecarboxamide |
| 51 | (4-methoxycyclohexyl) | —CH₃ | (2-(2-oxa-6-azaspiro[3.3]heptan-6-yl)pyrimidin-5-yl) | —H | —H | N-((4-((2-(2-oxa-6-azaspiro[3.3]heptan-6-yl)pyrimidin-5-yl)oxy)-3-methylphenyl)carbamoyl)-4-methoxycyclohexanecarboxamide |
| 52 | (3-methoxycyclobutyl) | —CH₃ | (2-(2-oxa-6-azaspiro[3.3]heptan-6-yl)pyrimidin-5-yl) | —H | —H | -((4-((2-(2-oxa-6-azaspiro[3.3]heptan-6-yl)pyrimidin-5-yl)oxy)-3-methylphenyl)carbamoyl)-3-methoxycyclobutanecarboxamide |
| 53 | (4-hydroxycyclohexyl) | —CH₃ | (5-chloropyrimidin-2-yl) | —H | —H | N-((4-((5-chloropyrimidin-2-yl)oxy)-3-methylphenyl)carbamoyl)-4-hydroxycyclohexane-1-carboxamide |

TABLE 1-continued

| Compound | R₁ | R₂ | R₃ | R₄ | R₅ | Name |
|---|---|---|---|---|---|---|
| 54 | H₃C-O-CH₂CH₂-O-cyclohexyl | —F | 5-chloropyrimidin-2-yl | —H | —H | N-((4-((5-chloropyrimidin-2-yl)oxy)-3-fluorophenyl)carbamoyl)-4-(2-methoxyethoxy)cyclohexane-1-carboxamide |
| 55 | 3-methoxycyclobutyl | —CH₃ | 1,3,4-thiadiazol-2-yl | —H | —H | N-((4-((1,3,4-thiadiazol-2-yl)oxy)-3-methylphenyl)carbamoyl)-3-methoxycyclobutanecarboxamide |
| 56 | 3-methoxycyclobutyl | —CH₃ | benzo[d]thiazol-2-yl | —H | —H | N-((4-(benzo[d]thiazol-2-yloxy)-3-methylphenyl)carbamoyl)-3-methoxycyclobutane-1-carboxamide |
| 57 | 3-methoxycyclobutyl | —CH₃ | 1,2,4-thiadiazol-5-yl | —H | —H | N-((4-((1,2,4-thiadiazol-5-yl)oxy)-3-methylphenyl)carbamoyl)-3-methoxycyclobutane-1-carboxamide |
| 58 | 3-methoxycyclobutyl | —CH₃ | pyrimidin-2-yl | —H | —H | 3-methoxy-N-((3-methyl-4-(pyrazin-2-yloxy)phenyl)carbamoyl)cyclobutane-1-carboxamide |
| 59 | 3-methoxycyclobutyl | —CH₃ | 4,5-dimethylthiazol-2-yl | —H | —H | N-((4-((4,5-dimethylthiazol-2-yl)oxy)-3-methylphenyl)carbamoyl)-3-methoxycyclobutane-1-carboxamide |
| 60 | 3-methoxycyclobutyl | —CH₃ | 5-methylthiazol-2-yl | —H | —H | 3-methoxy-N-((3-methyl-4-((5-methylthiazol-2-yl)oxy)phenyl)carbamoyl)cyclobutane-1-carboxamide |
| 61 | 3-methoxycyclobutyl | —CH₃ | 5-(trifluoromethyl)thiazol-2-yl | —H | —H | 3-methoxy-N-((3-methyl-4-((5-(trifluoromethyl)thiazol-2-yl)oxy)phenyl)carbamoyl)cyclobutane-1-carboxamide |

TABLE 1-continued

| Compound | R₁ | R₂ | R₃ | R₄ | R₅ | Name |
|---|---|---|---|---|---|---|
| 62 | 3-methoxycyclobutyl | —CH₃ | 5-cyanothiazol-2-yl | —H | —H | N-((4-((5-cyanothiazol-2-yl)oxy)-3-methylphenyl)carbamoyl)-3-methoxycyclobutane-1-carboxamide |
| 63 | 4-methoxybicyclo[2.2.2]octan-1-yl | —CH₃ | thiazol-2-yl | —H | —H | 4-methoxy-N-((3-methyl-4-(thiazol-2-yloxy)phenyl)carbamoyl)bicyclo[2.2.2]octane-1-carboxamide |
| 64 | 4-methoxybicyclo[2.2.2]octan-1-yl | —CH₃ | 5-chloropyrimidin-2-yl | —H | —H | N-((4-((5-chloropyrimidin-2-yl)oxy)-3-methylphenyl)carbamoyl)-4-methoxybicyclo[2.2.2]octane-1-carboxamide |
| 65 | 1-methoxycyclopropyl | —CH₃ | 5-chloropyridin-2-yl | —H | —H | N-((4-((5-chloropyridin-2-yl)oxy)-3-methylphenyl)carbamoyl)-1-methoxycyclopropane-1-carboxamide |
| 66 | 1-methoxycyclopropyl | —CH₃ | 5-chloropyrimidin-2-yl | —H | —H | N-((4-((5-chloropyrimidin-2-yl)oxy)-3-methylphenyl)carbamoyl)-1-methoxycyclopropane-1-carboxamide |
| 67 | 1-methoxycyclopropyl | —CH₃ | 5-fluoropyridin-2-yl | —H | —H | N-((4-((5-fluoropyridin-2-yl)oxy)-3-methylphenyl)carbamoyl)-1-methoxycyclopropane-1-carboxamide |
| 68 | 1-methoxycyclopropyl | —CH₃ | thiazol-2-yl | —H | —H | 1-methoxy-N-((3-methyl-4-(thiazol-2-yloxy)phenyl)carbamoyl)cyclopropane-1-carboxamide |
| 69 | 1-methoxycyclopropyl | —CH₃ | pyrimidin-2-yl | —H | —H | 1-methoxy-N-((3-methyl-4-(pyrimidin-2-yloxy)phenyl)carbamoyl)cyclopropane-1-carboxamide |

TABLE 1-continued

| Compound | R₁ | R₂ | R₃ | R₄ | R₅ | Name |
|---|---|---|---|---|---|---|
| 70 | cyclohexyl | —F | 5-chloropyrimidin-2-yl | —H | —H | N-((4-((5-chloropyrimidin-2-yl)oxy)-3-fluorophenyl)carbamoyl)cyclohexanecarboxamide |
| 71 | cyclohexyl | —CH₃ | 5-chloropyrimidin-2-yl | —H | —H | N-((4-((5-chloropyrimidin-2-yl)oxy)-3-methylphenyl)carbamoyl)cyclohexanecarboxamide |
| 72 | 3-methoxycyclobutyl | —CH₃ | 5-fluoropyridin-2-yl | —H | —F | N-((3-fluoro-4-((5-fluoropyridin-2-yl)oxy)-5-methylphenyl)carbamoyl)-3-methoxycyclobutane-1-carboxamide |
| 73 | 3-methoxycyclobutyl | —CH₃ | 5-chloropyrimidin-2-yl | —H | —F | N-((4-((5-chloropyrimidin-2-yl)oxy)-3-fluoro-5-methylphenyl)carbamoyl)-3-methoxycyclobutane-1-carboxamide |
| 74 | 3-methoxycyclobutyl | —CH₃ | pyrimidin-2-yl | —H | —F | N-((3-fluoro-5-methyl-4-(pyrimidin-2-yloxy)phenyl)carbamoyl)-3-methoxycyclobutane-1-carboxamide |
| 75 | 4-methoxycyclohexyl | —CH₃ | 5-cyclopropylpyridin-2-yl | —H | —H | N-((4-((5-cyclopropylpyridin-2-yl)oxy)-3-methylphenyl)carbamoyl)-4-methoxycyclohexane-1-carboxamide |
| 76 | 3-methoxycyclobutyl | —CH₃ | 5-chloropyridin-2-yl | —H | —F | N-((4-((5-chloropyridin-2-yl)oxy)-3-fluoro-5-methylphenyl)carbamoyl)-3-methoxycyclobutane-1-carboxamide |

TABLE 1-continued

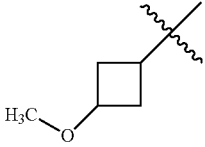 [SMILES: *C1CC(OC)C1]

| Compound | R₁ | R₂ | R₃ | R₄ | R₅ | Name |
|---|---|---|---|---|---|---|
| 77 | 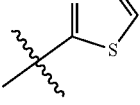 | —CH₃ | 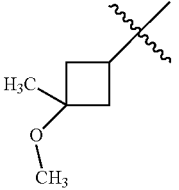 | —H | —F | N-((3-fluoro-5-methyl-4-(thiazol-2-yloxy)phenyl)carbamoyl)-3-methoxycyclobutane-1-carboxamide |
| 78 | 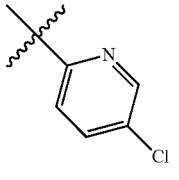 [SMILES: *c1ccc(Cl)cn1] | —CH₃ | 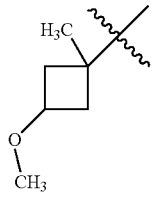 [SMILES: *C1(C)CC(OC)C1] | —H | —H | N-((4-((5-chloropyridin-2-yl)oxy)-3-methylphenyl)carbamoyl)-3-methoxy-3-methylcyclobutane-1-carboxamide |
| 79 | 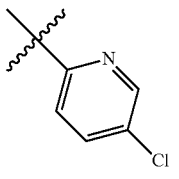 [SMILES: *c1ccc(Cl)cn1] | —CH₃ | 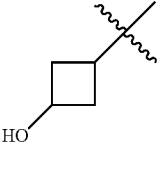 [SMILES: *C1CC(O)C1] | —H | —H | N-((4-((5-chloropyridin-2-yl)oxy)-3-methylphenyl)carbamoyl)-3-methoxy-1-methylcyclobutane-1-carboxamide |
| 80 | 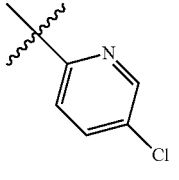 [SMILES: *c1ccc(Cl)cn1] | —CH₃ | 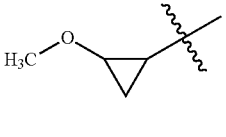 | —H | —H | N-((4-((5-chloropyridin-2-yl)oxy)-3-methylphenyl)carbamoyl)-3-hydroxycyclobutane-1-carboxamide |
| 81 | 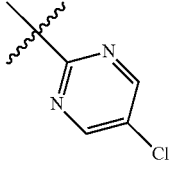 [SMILES: *c1ncc(Cl)cn1] | —CH₃ | 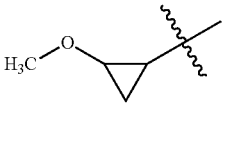 | —H | —H | N-((4-((5-chloropyrimidin-2-yl)oxy)-3-methylphenyl)carbamoyl)-2-methoxycyclopropane-1-carboxamide |
| 82 | 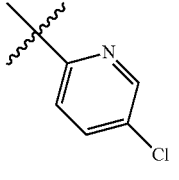 [SMILES: *c1ccc(Cl)cn1] | —CH₃ | 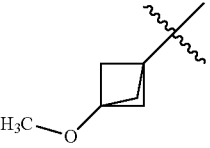 | —H | —H | N-((4-((5-chloropyridin-2-yl)oxy)-3-methylphenyl)carbamoyl)-2-methoxycyclopropane-1-carboxamide |
| 83 | 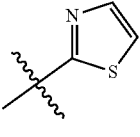 [SMILES: *c1nccs1] | —CH₃ | | —H | —H | 3-methoxy-N-((3-methyl-4-(thiazol-2-yloxy)phenyl)carbamoyl)bicyclo[1.1.1]pentane-1-carboxamide |

TABLE 1-continued

| Compound | R₁ | R₂ | R₃ | R₄ | R₅ | Name |
|---|---|---|---|---|---|---|
| 84 | 3-methoxybicyclo[1.1.1]pentane (H₃C-O-) | —CH₃ | 5-chloropyridin-2-yl | —H | —H | N-((4-((5-chloropyridin-2-yl)oxy)-3-methylphenyl)carbamoyl)-3-methoxybicyclo[1.1.1]pentane-1-carboxamide |
| 85 | 3-methoxybicyclo[1.1.1]pentane | —CH₃ | 5-chloropyrimidin-2-yl | —H | —H | N-((4-((5-chloropyrimidin-2-yl)oxy)-3-methylphenyl)carbamoyl)-3-methoxybicyclo[1.1.1]pentane 1-carboxamide |
| 86 | 3-methoxybicyclo[1.1.1]pentane | —CH₃ | pyridin-2-yl | —H | —H | 3-methoxy-N-((3-methyl-4-(pyridin-2-yloxy)phenyl)carbamoyl)bicyclo[1.1.1]pentane-1-carboxamide |
| 87 | 3-methoxybicyclo[1.1.1]pentane | —CH₃ | pyrimidin-2-yl | —H | —H | 3-methoxy-N-((3-methyl-4-(pyrimidin-2-yloxy)phenyl)carbamoyl)bicyclo[1.1.1]pentane-1-carboxamide |
| 88 | 3-methoxybicyclo[1.1.1]pentane | —CH₃ | 5-fluoropyrimidin-2-yl | —H | —H | N-((4-((5-fluoropyrimidin-2-yl)oxy)-3-methylphenyl)carbamoyl)-3-methoxybicyclo[1.1.1]pentane-1-carboxamide |
| 89 | 3-methoxybicyclo[1.1.1]pentane | —CH₃ | 5-fluoropyridin-2-yl | —H | —H | N-((4-((5-fluoropyridin-2-yl)oxy)-3-methylphenyl)carbamoyl)-3-methoxybicyclo[1.1.1]pentane-1-carboxamide |
| 90 | 3-methoxybicyclo[1.1.1]pentane | —CH₃ | 5-chloropyrimidin-2-yl | —H | —F | N-((4-((5-chloropyrimidin-2-yl)oxy)-3-fluoro-5-methylphenyl)carbamoyl)-3-methoxybicyclo[1.1.1]pentane-1-carboxamide |
| 91 | 3-methoxybicyclo[1.1.1]pentane | —CH₃ | 5-fluoropyridin-2-yl | —H | —F | N-((3-fluoro-4-((5-fluoropyridin-2-yl)oxy)-5-methylphenyl)carbamoyl)-3-methoxybicyclo[1.1.1]pentane-1-carboxamide |

TABLE 1-continued

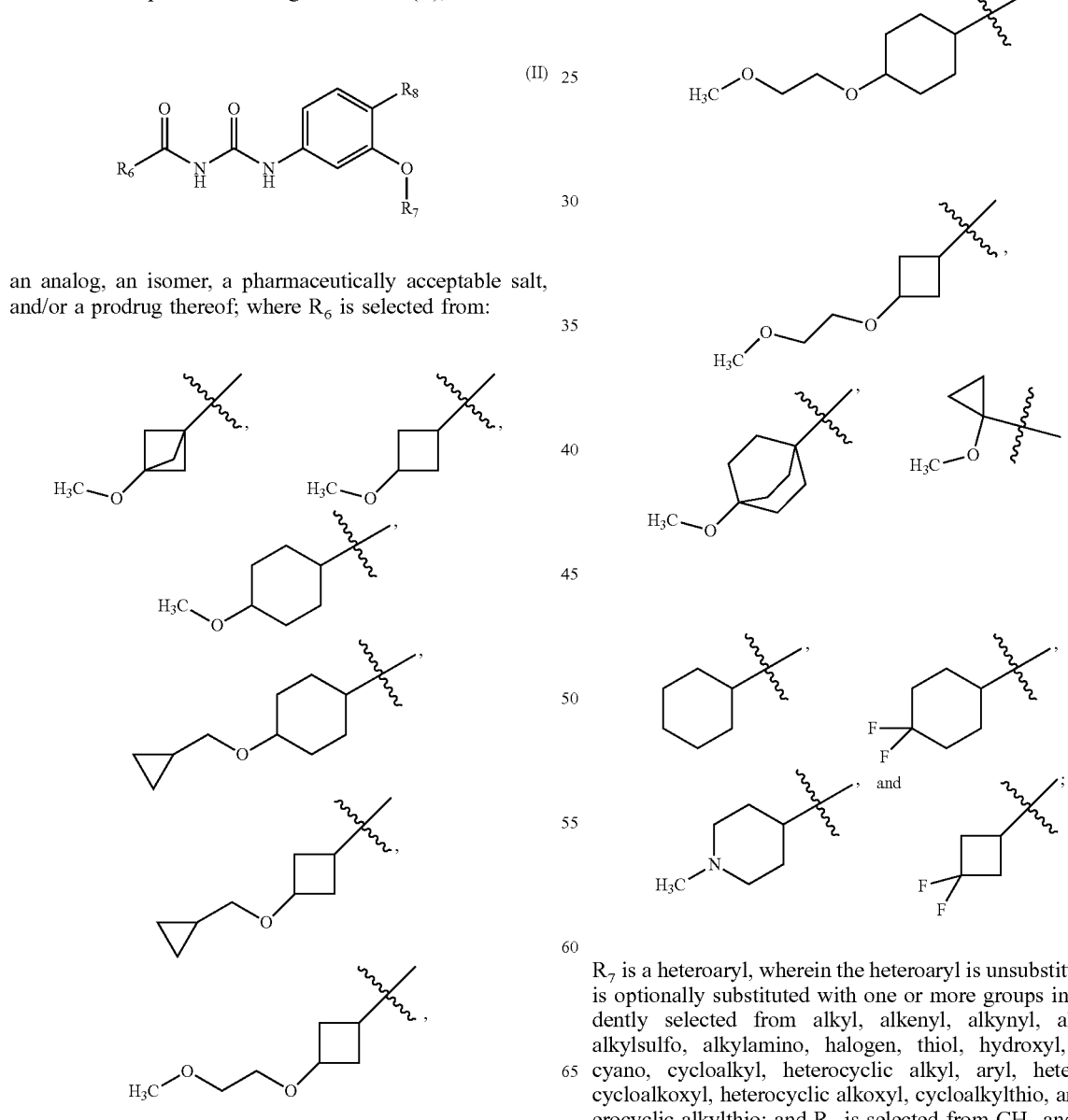

| Compound | R₁ | R₂ | R₃ | R₄ | R₅ | Name |
|---|---|---|---|---|---|---|
| 92 | (methoxybicyclo[1.1.1]pentyl) | —CH₃ | (pyrimidin-2-yl) | —H | —F | N-((3-fluoro-5-methyl-4-(pyrimidin-2-yloxy)phenyl)carbamoyl)-3-methoxybicyclo[1.1.1]pentane-1-carboxamide |

In some embodiments, a compound provided herein includes a compound according to formula (II), an analog, an isomer, a pharmaceutically acceptable salt, and/or a prodrug thereof; where $R_6$ is selected from:

$R_7$ is a heteroaryl, wherein the heteroaryl is unsubstituted or is optionally substituted with one or more groups independently selected from alkyl, alkenyl, alkynyl, alkoxyl, alkylsulfo, alkylamino, halogen, thiol, hydroxyl, nitro, cyano, cycloalkyl, heterocyclic alkyl, aryl, heteroaryl, cycloalkoxyl, heterocyclic alkoxyl, cycloalkylthio, and heterocyclic alkylthio; and $R_8$ is selected from $CH_3$ and H.

In some embodiments, $R_6$ is selected from:

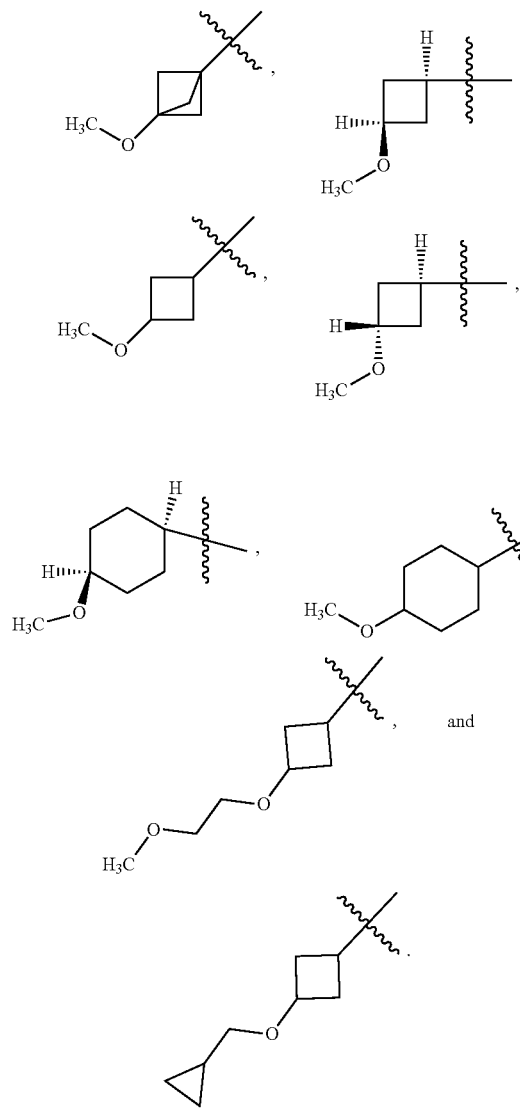

In some embodiments, $R_6$ is selected from:

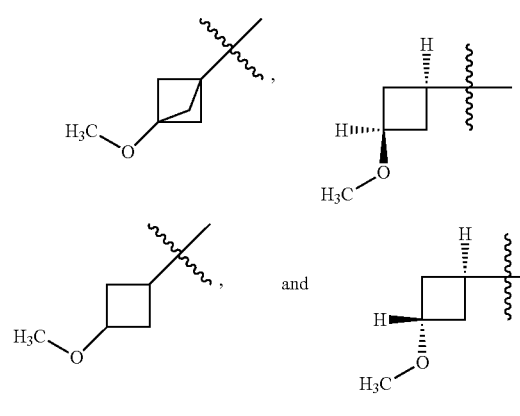

In some embodiments, $R_6$ is:

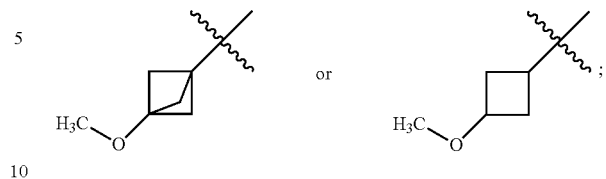

In some embodiments, $R_7$ is a 5- or 6-membered heteroaryl unsubstituted or optionally substituted with one or more groups independently selected from the group consisting of alkyl, alkylamino, halogen, alkylhalide, cyano, cycloalkyl, heterocyclic alkyl, aryl, heteroaryl, cycloalkoxyl, and heterocyclic alkoxyl, cycloalkylthio, and heterocyclic alkylthio.

In other embodiments, $R_7$ is a 5- or 6-membered heteroaryl unsubstituted or optionally substituted with one or more groups selected from:

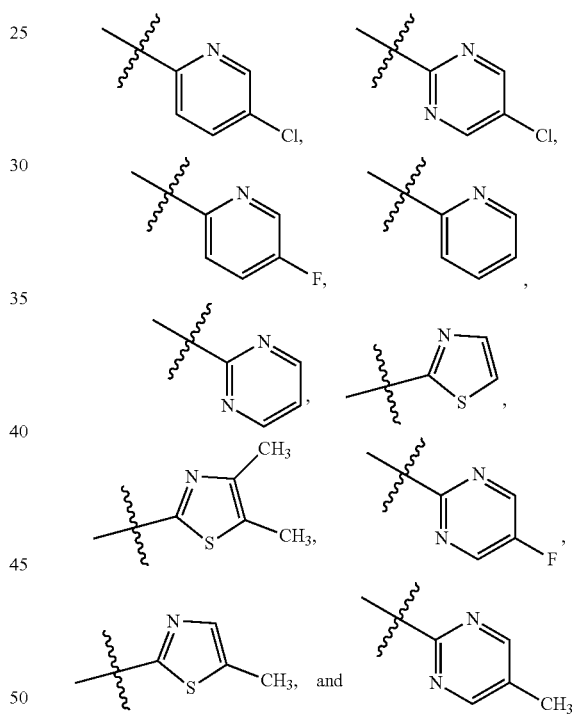

In some embodiments, $R_7$ is selected from:

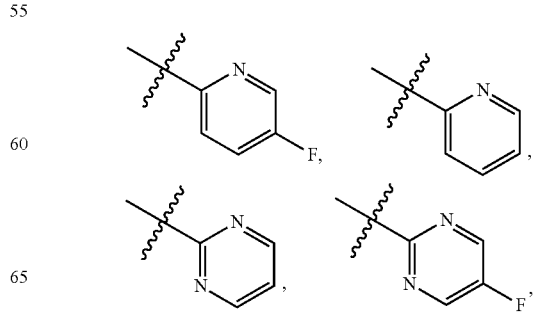

-continued

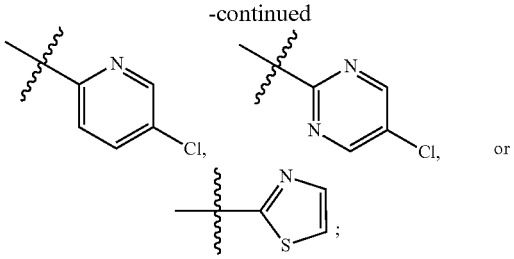

and

In other embodiments, $R_8$ is $CH_3$.

In other embodiments, compounds of formula (I) can include an $R_6$, $R_7$, and/or $R_8$ as indicated in Table 2. In other embodiments, compounds of the present disclosure can include any one of the compounds provided in Table 2.

TABLE 2

| Compound | $R_6$ | $R_7$ | $R_8$ | Name |
|---|---|---|---|---|
| 93 | methoxycyclobutyl | thiazol-2-yl | —$CH_3$ | 3-methoxy-N-((4-methyl-3-(thiazol-2-yloxy)phenyl)carbamoyl)cyclobutane-1-carboxamide |
| 94 | methoxycyclobutyl | pyridin-2-yl | —$CH_3$ | 3-methoxy-N-((4-methyl-3-(pyridin-2-yloxy)phenyl)carbamoyl)cyclobutane-1-carboxamide |
| 95 | methoxycyclobutyl | 5-fluoropyridin-2-yl | —$CH_3$ | N-((3-((5-fluoropyridin-2-yl)oxy)-4-methylphenyl)carbamoyl)-3-methoxycyclobutane-1-carboxamide |
| 96 | methoxycyclobutyl | pyrimidin-2-yl | —$CH_3$ | 3-methoxy-N-((4-methyl-3-(pyrimidin-2-yloxy)phenyl)carbamoyl)cyclobutane-1-carboxamide |
| 97 | methoxybicyclo[1.1.1]pentyl | pyrimidin-2-yl | —$CH_3$ | 3-methoxy-N-((4-methyl-3-(pyrimidin-2-yloxy)phenyl)carbamoyl)bicyclo[1.1.1]pentane-1-carboxamide |

TABLE 2-continued

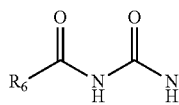

| Compound | R<sub>6</sub> | R<sub>7</sub> | R<sub>8</sub> | Name |
|---|---|---|---|---|
| 98 | 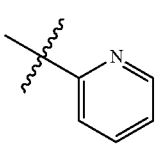 [SMILES: *c1ccccn1] | 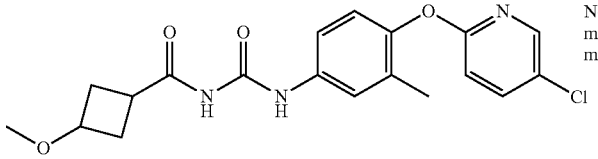 | —CH$_3$ | 3-methoxy-N-((4-methyl-3-(pyridin-2-yloxy)phenyl)carbamoyl)bicyclo[1.1.1]pentane-1-carboxamide |

In additional embodiments, compounds of the present disclosure can be any one of the compounds provided in Table 3 or a combination thereof.

TABLE 3

| Compound | Structure | Name |
|---|---|---|
| 19 | 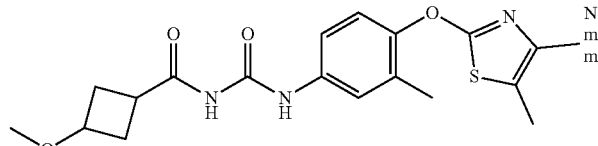 | N-((4-((5-chloropyridin-2-yl)oxy)-3-methylphenyl)carbamoyl)-3-methoxycyclobutane-1-carboxamide |
| 59 | 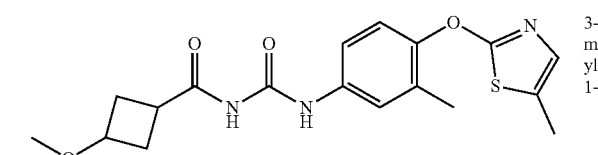 | N-((4-((4,5-dimethylthiazol-2-yl)oxy)-3-methylphenyl)carbamoyl)-3-methoxycyclobutane-1-carboxamide |
| 60 | 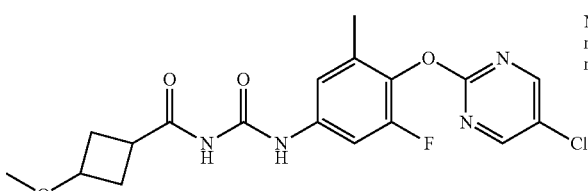 | 3-methoxy-N-((3-methyl-4-((5-methylthiazol-2-yl)oxy)phenyl)carbamoyl)cyclobutane-1-carboxamide |
| 73 | 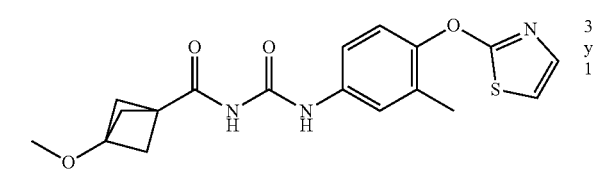 | N-((4-((5-chloropyrimidin-2-yl)oxy)-3-fluoro-5-methylphenyl)carbamoyl)-3-methoxycyclobutane-1-carboxamide |
| 83 | 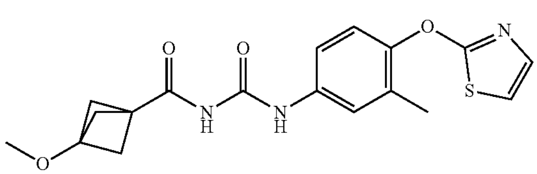 [SMILES: COC12CC(C(=O)NC(=O)Nc3ccc(Oc4nccs4)c(C)c3)(C1)C2] | 3-methoxy-N-((3-methyl-4-(thiazol-2-yloxy)phenyl)carbamoyl)bicyclo[1.1.1]pentane-1-carboxamide |

TABLE 3-continued

| Compound | Structure | Name |
|---|---|---|
| 84 | 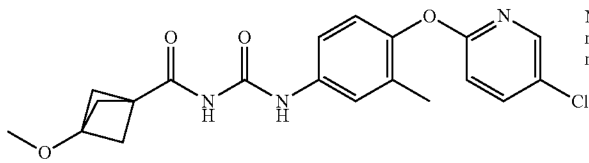 [SMILES: COC12CC(C(=O)NC(=O)Nc3ccc(Oc4ccc(Cl)cn4)c(C)c3)(C1)C2] | N-((4-((5-chloropyridin-2-yl)oxy)-3-methylphenyl)carbamoyl)-3-methoxybicyclo[1.1.1]pentane-1-carboxamide |
| 85 | 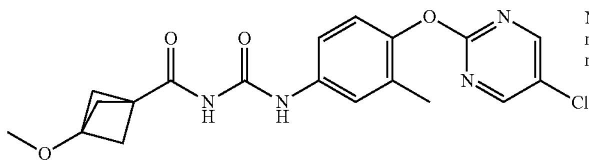 [SMILES: COC12CC(C(=O)NC(=O)Nc3ccc(Oc4ncc(Cl)cn4)c(C)c3)(C1)C2] | N-((4-((5-chloropyrimidin-2-yl)oxy)-3-methylphenyl)carbamoyl)-3-methoxybicyclo[1.1.1]pentane-1-carboxamide |
| 86 | 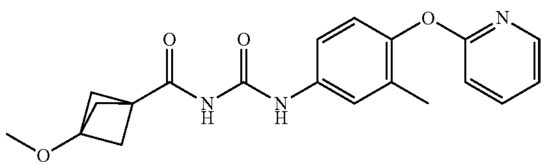 [SMILES: COC12CC(C(=O)NC(=O)Nc3ccc(Oc4ccccn4)c(C)c3)(C1)C2] | 3-methoxy-N-((3-methyl-4-(pyridin-2-yloxy)phenyl)carbamoyl)bicyclo[1.1.1]pentane-1-carboxamide |
| 87 | 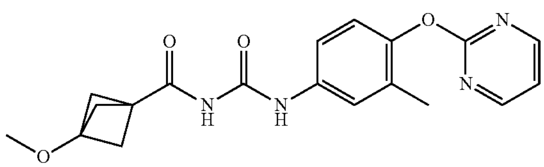 [SMILES: COC12CC(C(=O)NC(=O)Nc3ccc(Oc4ncccn4)c(C)c3)(C1)C2] | 3-methoxy-N-((3-methyl-4-(pyrimidin-2-yloxy)phenyl)carbamoyl)bicyclo[1.1.1]pentane-1-carboxamide |
| 88 | 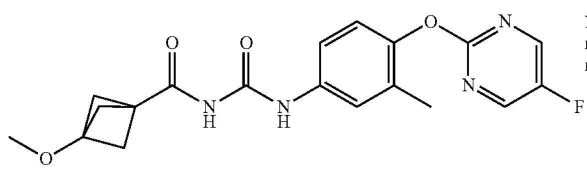 | N-((4-((5-fluoropyrimidin-2-yl)oxy)-3-methylphenyl)carbamoyl)-3-methoxybicyclo[1.1.1]pentane-1-carboxamide |
| 89 | 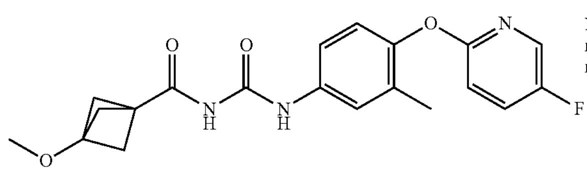 | N-((4-((5-fluoropyridin-2-yl)oxy)-3-methylphenyl)carbamoyl)-3-methoxybicyclo[1.1.1]pentane-1-carboxamide |
| 90 | 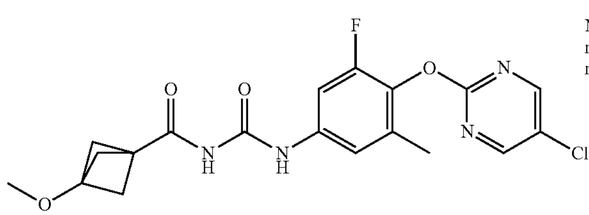 [SMILES: COC12CC(C(=O)NC(=O)Nc3cc(C)c(Oc4ncc(Cl)cn4)c(F)c3)(C1)C2] | N-((4-((5-chloropyrimidin-2-yl)oxy)-3-fluoro-5-methylphenyl)carbamoyl)-3-methoxybicyclo[1.1.1]pentane-1-carboxamide |
| 91 | 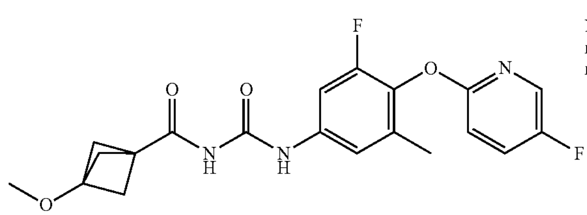 | N-((3-fluoro-4-((5-fluoropyridin-2-yl)oxy)-5-methylphenyl)carbamoyl)-3-methoxybicyclo[1.1.1]pentane-1-carboxamide |
| 93 | 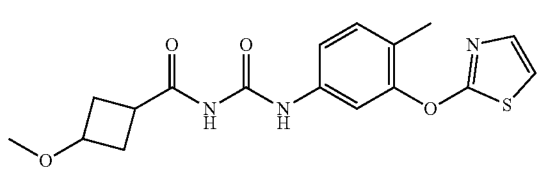 [SMILES: COC1CC(C(=O)NC(=O)Nc2ccc(C)c(Oc3nccs3)c2)C1] | 3-methoxy-N-((4-methyl-3-(thiazol-2-yloxy)phenyl)carbamoyl)cyclobutane-1-carboxamide |

TABLE 3-continued

| Compound | Structure | Name |
|---|---|---|
| 94 | 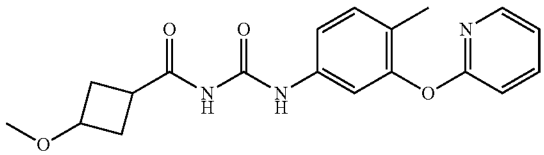 [SMILES: COC1CC(C(=O)NC(=O)Nc2ccc(C)c(Oc3ccccn3)c2)C1] | 3-methoxy-N-((4-methyl-3-(pyridin-2-yloxy)phenyl)carbamoyl)cyclobutane-1-carboxamide |
| 95 | 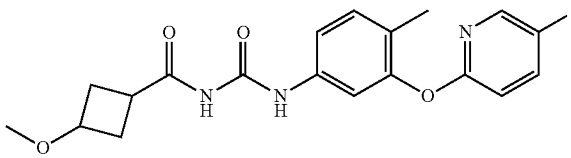 | FN-((3-((5-fluoropyridin-2-yl)oxy)-4-methylphenyl)carbamoyl)-3-methoxycyclobutane-1-carboxamide |
| 96 | 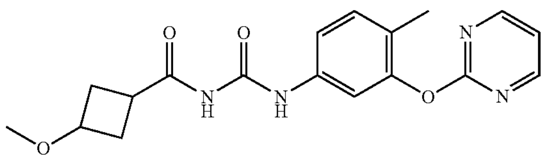 [SMILES: COC1CC(C(=O)NC(=O)Nc2ccc(C)c(Oc3ncccn3)c2)C1] | 3-methoxy-N-((4-methyl-3-(pyrimidin-2-yloxy)phenyl)carbamoyl)cyclobutane-1-carboxamide |
| 97 | 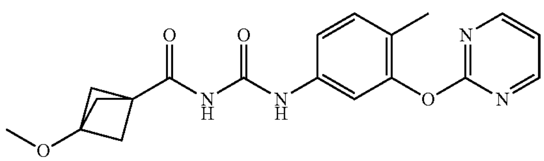 [SMILES: COC12CC(C(=O)NC(=O)Nc3ccc(C)c(Oc4ncccn4)c3)(C1)C2] | 3-methoxy-N-((4-methyl-3-(pyrimidin-2-yloxy)phenyl)carbamoyl)bicyclo[1.1.1]pentane-1-carboxamide |
| 98 | 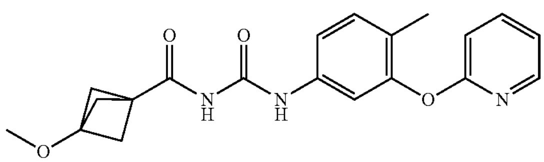 [SMILES: COC12CC(C(=O)NC(=O)Nc3ccc(C)c(Oc4ccccn4)c3)(C1)C2] | 3-methoxy-N-((4-methyl-3-(pyridin-2-yloxy)phenyl) carbamoyl)bicyclo[1.1.1]pentane-1-carboxamide |

In some embodiments, compounds of the present disclosure can include isomers of one or more of the compounds of formula (I) or the compounds of formula (II). In other embodiments, compounds disclosed herein can contain carbon-carbon double bonds and/or carbon-nitrogen double bonds in the E or Z configuration, wherein the term "E" represents higher order substituents on opposite sides of the carbon-carbon or carbon-nitrogen double bond and the term "Z" represents higher order substituents on the same side of the carbon-carbon or carbon-nitrogen double bond as determined by the Cahn-Ingold-Prelog Priority Rules. In some embodiments, compounds can be in a composition as a mixture of "E" and "Z" isomers. In some embodiments, compounds disclosed herein can have substituents around a cycloalkyl and/or heterocycloalkyl. In some embodiments, compounds of the present disclosure can include isomers of any one of the compounds of formula (I) or the compounds of formula (II) and be designated as being of a "cis" or "trans" configuration.

In some embodiments, compounds of the present disclosure can be a cis or trans isomer of any one of the compounds of formula (I) or the compounds of formula (II) disclosed herein. In accordance with these embodiments, compounds of the present disclosure can be a cis or a trans isomer of any one of the compounds of formula (I) provided in Table 1, the compounds of formula (II) provided in Table 2, or the compounds provided in Table 3. In other embodiments, compounds of formula (I) or compounds of formula (II) disclosed herein can be a cis or a trans isomer of formula (I) or formula (II) as provided in Table 4.

TABLE 4

| Compound | $R_1$ | Isomers | NMR d ppm (Protons values for a and b) protons a and b) |
|---|---|---|---|
| 1A | | cis | 3.38 – 3.35<br>2.50 – 2.47 |
| 1B | | trans | 3.09 – 3.07<br>2.48 – 2.36 |

TABLE 4-continued
| Compound | R₁ | Isomers (Protons a and b) | NMR d ppm values for protons a and b |
|---|---|---|---|
| 6A | 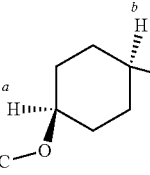 | cis | 3.42 – 3.35<br>2.48 – 2.39 |
| 6B | | trans | 3.14 – 3.04<br>2.43 – 2.30 |
| 7A | | cis | 3.42 – 3.38<br>2.49 – 2.45 |
| 7B | | trans | 3.23 – 3.09<br>2.49 – 2.37 |
| 11A | | cis | 3.41 – 3.34<br>2.49 – 2.41 |
| 11B | | trans | 3.15 – 3.04<br>2.44 – 2.31 |
| 14A | | cis | 3.38 – 3.33<br>2.50 – 2.43 |
| 14B | 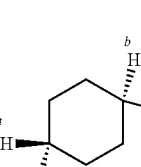 | trans | 3.12 – 3.06<br>2.41 – 2.35 |
| 15A | | cis | 3.86 – 3.70<br>2.87 – 2.73 |
| 15B | | trans | 3.80 – 3.40<br>3.24 – 3.15 |
| 16A | | cis | 3.84 – 3.72<br>2.88 – 2.75 |
| 16B | | trans | 4.05 – 3.98<br>3.24 – 3.15 |
| 17A | | cis | 3.84 – 3.75<br>2.81 – 2.70 |
| 17B | | trans | 4.04 – 3.95<br>3.23 – 3.15 |

TABLE 4-continued

| Compound | R₁ | Isomers (Protons a and b) | NMR d ppm (values for protons a and b) |
|---|---|---|---|
| 18A | methoxycyclobutyl | cis | 3.86 – 3.74, 2.86 – 2.78 |
| 18B | methoxycyclobutyl | Trans | 4.01 – 3.96, 3.21 – 3.18 |
| 19A | methoxycyclobutyl | cis | 3.84 – 3.74, 2.81 – 2.74 |
| 19B | methoxycyclobutyl | trans | 4.06 – 3.92, 3.26 – 3.15 |
| 20A | methoxycyclobutyl | cis | 3.85 – 3.73, 2.87 – 2.76 |
| 20B | methoxycyclobutyl | trans | 4.08 – 3.92, 3.19 – 3.12 |
| 26A | methoxycyclohexyl | cis | 3.38, 2.49 – 2.48 |
| 26B | methoxycyclohexyl | trans | 3.12 – 3.06, 2.41 – 2.34 |
| 27A | methoxycyclohexyl | cis | 3.37 – 3.31, 2.48 – 2.41 |
| 27B | methoxycyclohexyl | trans | 3.15 – 3.04, 2.45 – 2.31 |
| 31A | methoxycyclohexyl | cis | 3.37 – 3.31, 2.48 – 2.41 |
| 31B | methoxycyclohexyl | trans | 3.15 – 3.04, 2.45 – 2.31 |
| 34A | methoxycyclohexyl | cis | 2.93 – 2.86, 2.43 – 2.35 |
| 34B | methoxycyclohexyl | trans | 3.20 – 3.12, 2.33 – 2.30 |

TABLE 4-continued

| Compound | $R_1$ | Isomers | NMR d ppm (Protons values for a and b) protons a and b |
|---|---|---|---|
| 45A | (structure with H$^a$, H$^b$, OCH$_3$) | cis | 3.83 – 3.75<br>2.86 – 2.77 |
| 45B | (structure with H$^a$, H$^b$, OCH$_3$) | trans | 4.03 – 3.96<br>3.22 – 3.17 |

In some embodiments, compounds of the present disclosure can contain asymmetrically substituted carbon atoms in the R or S configuration, in which the terms "R" and "S" are as defined as known in the art. In accordance with some embodiments disclosed herein, compounds having asymmetrically substituted carbon atoms with equal amounts of R and S configurations can be racemic at those carbon atoms. In certain embodiments, the present disclosure can include racemic mixtures, relative and absolute stereoisomers, and/or mixtures of relative and absolute stereoisomers.

In other embodiments, compounds disclosed herein can be in the form of an ester prodrug. The term "ester" herein can refer a compound which is produced by modifying a functional group (e.g., hydroxyl, carboxyl, amino or the like group). Examples of an "ester" include "esters formed with a hydroxyl group" and "esters formed with a carboxyl group." The term "ester" can mean an ester whose ester residue is a "conventional protecting group" or a "protecting group removable in vivo by a biological method such as hydrolysis." In some embodiments, the term "conventional protecting group" can mean a protecting group removable by a chemical method such as hydrogenolysis, hydrolysis, electrolysis or photolysis. In other embodiments, the term "protecting group removable in vivo by a biological method such as hydrolysis" can mean a protecting group removable in vivo by a biological method such as hydrolysis to produce a free acid or its salt.

In certain embodiments, compounds of the present disclosure can be in the form of a pharmaceutically acceptable salt. By "salt" or "pharmaceutically acceptable salt", it is meant those salts which are, within the scope of sound medical judgment, suitable for use in contact with the tissues of humans and lower animals without undue toxicity, irritation, and allergic response, commensurate with a reasonable benefit to risk ratio, and effective for their intended use. A "pharmacologically acceptable salt" can refer to a salt, which can be formed when a compound herein has an acidic group such as carboxyl or a basic group such as amino or imino. In some embodiments, a salt of a compound herein formed with an acidic group herein can include alkali metal salts such as a sodium salt, potassium salt or lithium salt, alkaline earth metal salts such as a calcium salt or magnesium salt, metal salts such as an aluminum salt or iron salt; amine salts, e.g., inorganic salts such as an ammonium salt and organic salts such as a t-octylamine salt, dibenzylamine salt, morpholine salt, glucosamine salt, phenylglycine alkyl ester salt, ethylenediamine salt, N-methylglucamine salt, guanidine salt, diethylamine salt, triethylamine salt, dicyclohexylamine salt, N,N'-dibenzylethylenediamine salt, chloroprocaine salt, procaine salt, diethanolamine salt, N-benzylphenethylamine salt, piperazine salt, tetramethylammonium salt or tris(hydroxymethyl)aminomethane salt; and amino acid salts such as a glycine salt, lysine salt, arginine salt, ornithine salt, glutamate or aspartate. In some embodiments, a salt of a compound herein formed with a basic group herein can include hydro-halides such as a hydrofluoride, hydrochloride, hydrobromide or hydroiodide, inorganic acid salts such as a nitrate, perchlorate, sulfate or phosphate; lower alkanesulfonates such as a methanesulfonate, trifluoromethanesulfonate or ethanesulfonate, arylsulfonates such as a benzenesulfonate or p-toluenesulfonate, organic acid salts such as an acetate, malate, fumarate, succinate, citrate, ascorbate, tartrate, oxalate or maleate; and amino acid salts such as a glycine salt, lysine salt, arginine salt, ornithine salt, glutamate or aspartate. In certain embodiments, when a pharmacologically acceptable salt of a compound herein remains in the atmosphere or is recrystallized, it can absorb water to form a hydrate of use in formulations disclosed herein.

In certain embodiments, compounds of the present disclosure can include, but is not limited to, compounds in a solid or a liquid form. In some embodiments, compounds of the present disclosure can be in an amorphous form. In other embodiments, compounds of the present disclosure can be in a crystal form. In accordance with some embodiments herein, compounds having a solid state can exist in crystalline or non-crystalline form, or as a mixture thereof. In some embodiments, compounds herein in crystalline form can be used to form pharmaceutically acceptable solvates. A skilled artisan can appreciate that pharmaceutically acceptable solvates can be formed wherein solvent molecules are incorporated into the crystalline lattice during crystallization. In accordance with some embodiments, solvates for use herein can involve nonaqueous solvents such as ethanol, isopropanol, DMSO, acetic acid, ethanolamine, and EtOAc, or they can involve water as the solvent incorporated into the crystalline lattice. Solvates wherein water is the solvent that is incorporated into the crystalline lattice are typically referred to as "hydrates." Hydrates include stoichiometric hydrates as well as compositions containing variable amounts of water. The present disclosure encompasses all such solvates.

In certain embodiments, compounds of the present disclosure can exist in crystalline form, including the various solvates thereof, can exhibit polymorphism (e.g., the capacity to occur in different crystalline structures). These different crystalline forms are referred to herein as "polymorphs." Polymorphs have the same chemical composition but differ in packing, geometrical arrangement, and other descriptive properties of the crystalline solid state. Polymorphs, therefore, can have different physical properties such as shape, density, hardness, deformability, stability, and dissolution properties. Polymorphs typically exhibit different melting points, IR spectra, and X-ray powder diffraction patterns, NMR signatures, which can be used for identification. In certain embodiments, compounds of the present disclosure can be polymorphs. In certain embodiments, compounds of the present disclosure can be polymorphs that are identified by their melting points, IR spectra, X-ray powder diffraction patterns, NMR signatures, or any combination thereof. In some embodiments, different polymorphs of compounds herein can be produced by changing and/or adjusting the reaction conditions and/or reagents, used in making the compound. For example (but not limited to), changes in temperature, pressure, or solvent can result in polymorphs. In some embodiments, different polymorphs of compounds herein can spontaneously convert to another polymorph.

In certain embodiments and further to the previous paragraphs, compounds disclosed herein (e.g., a compound according to Formula I) can have kinetic solubility. Higher kinetic solubility can be important in bioavailability of formulations, such as oral, inhalable, topical, subcutaneous and/or intravenous formulations. In some embodiments, compounds disclosed herein can have a kinetic solubility of at least about 0.1 μM. In some embodiments, compounds disclosed herein can have a kinetic solubility ranging from about 0.1 μM to about 110 μM (e.g., about 0.1 μM, about 0.5 μM, about 1 μM, about 5 μM, about 10 μM, about 20 μM, about 30 μM, about 40 μM, about 50 μM, about 60 μM, about 70 μM, about 80 μM, about 90 μM, about 100 μM, about 110 μM or any concentration in between). In some embodiments, compounds disclosed herein can maintain a kinetic solubility for about 1 hour to about 48 hours (e.g., about 1 hour, about 3 hours, about 6 hours, about 12 hours, about 24 hours, about 36 hours, 48 hours or any time in between or greater than 48 hours). In some embodiments, compounds disclosed herein can maintain a kinetic solubility ranging from about 0.1 μM to about 110 μM (e.g., about 0.1 μM, about 0.5 μM, about 1 μM, about 5 μM, about 10 μM, about 20 μM, about 30 μM, about 40 μM, about 50 μM, about 60 μM, about 70 μM, about 80 μM, about 90 μM, about 100 μM, about 110 μM or any concentration in between or greater) for about 1 hour to about 48 hours (e.g., about 1 hour, about 3 hours, about 6 hours, about 12 hours, about 24 hours, about 36 hours, 48 hours or any time in between or longer). In some embodiments, compounds disclosed herein can maintain a kinetic solubility at temperatures ranging from about 4° C. to about 80° C. (e.g., about 4° C., about 6° C., about 8° C., about 10° C., about 20° C., about 30° C., about 40° C., about 50° C., about 60° C., about 70° C., about 80° C. or in between). In some embodiments, compounds disclosed herein can maintain a kinetic solubility ranging from about 0.1 μM to about 110 μM (e.g., about 0.1 μM, about 0.5 μM, about 1 μM, about 5 μM, about 10 μM, about 20 μM, about 30 μM, about 40 μM, about 50 μM, about 60 μM, about 70 μM, about 80 μM, about 90 μM, about 100 μM, about 110 μM or in between) at temperatures ranging from about 4° C. to about 80° C. (e.g., about 4° C., about 6° C., about 8° C., about 10° C., about 20° C., about 30° C., about 40° C., about 50° C., about 60° C., about 70° C., about 80° C. or in between). In some embodiments, compounds disclosed herein can maintain a kinetic solubility ranging from about 0.1 μM to about 110 μM (e.g., about 0.1 μM, about 0.5 μM, about 1 μM, about 5 μM, about 10 μM, about 20 μM, about 30 μM, about 40 μM, about 50 μM, about 60 μM, about 70 μM, about 80 μM, about 90 μM, about 100 μM, about 110 μM) at room temperature (i.e., 25° C.±3° C.). In some embodiments, compounds herein can maintain a kinetic solubility ranging from about 0.1 μM to about 110 μM (e.g., about 0.1 μM, about 0.5 μM, about 1 μM, about 5 μM, about 10 μM, about 20 μM, about 30 μM, about 40 μM, about 50 μM, about 60 μM, about 70 μM, about 80 μM, about 90 μM, about 100 μM, about 110 μM) at room temperature (e.g., 25° C.±3° C.) for about 1 hours to about 48 hours (e.g., about 1 hour, about 3 hours, about 6 hours, about 12 hours, about 24 hours, about 36 hours, 48 hours or more depending on the compound).

In certain embodiments, compounds disclosed herein (e.g., a compound according to Formula I) can have a central nervous system multiparameter optimization (CNS MPO) score. The CNS MPO score is determined by an algorithm that uses a weighted scoring function to assess six fundamental physicochemical properties [(a) lipophilicity, calculated partition coefficient (ClogP); (b) calculated distribution coefficient at about pH 7.4 (ClogD); (c) molecular weight (MW); (d) topological polar surface area (TPSA); (e) number of hydrogen-bond donors (HBDs); and (f) most basic center ($pK_a$)]. The algorithm assigns a compound a collective score ranging from 0 to 6, wherein higher CNS MPO scores are indicative of the compound's capability of crossing the blood-brain-barrier (BBB). In some embodiments, compounds herein can have a CNS MPO score indicative of BBB permeability. In some embodiments, compounds disclosed herein can have a CNS MPO score greater than or equal to 4.0.

In certain embodiments and further to the previous paragraphs, compounds disclosed herein (e.g., a compound according to Formula I) can decrease viability or induce cell killing of at least one cancer cell. In some embodiments, compounds disclosed herein can decrease viability or induce cell killing of at least one cancer cell by about 10% to about 99% or up to 100% (e.g., about 1%, about 25%, about 50%, about 75%, about 99%) compared to not using a compound or mixture of compounds disclosed herein. In some embodiments, compounds disclosed herein can have a half maximal effective concentration (i.e., $EC_{50}$) for decreasing cancer cell viability of at least about 0.05 μM. In some embodiments, compounds disclosed herein can have an $EC_{50}$ for decreasing or inhibiting cancer cell viability or killing cancer cells ranging from about 0.05 μM to about 55 μM (e.g., about 0.05 μM, about 0.1 μM, about 0.15 μM, about 0.25 μM, about 0.5 μM, about 0.75 μM, about 1 μM, about 2 μM, about 5 μM, about 10 μM, about 15 μM, about 20 μM, about 25 μM, about 30 μM, about 35 μM, about 40 μM, about 45 μM, about 50 μM, up to about 55 μM).

In certain embodiments and further to the previous paragraphs, compounds disclosed herein (e.g., a compound according to Formula I) can include a cell cycle inhibitor or other anti-tumor agent. Cell cycle inhibitors reduce or stop cell cycle progression through various mechanisms. Cell cycle arrest can be induced at different stages, decreasing the rate of cell division and the number of actively cycling cells. In some embodiments, compounds disclosed herein can arrest a cell cycle at $G_2M$. In other embodiments, compounds herein can arrest proliferation of at least one cancer cell at the $G_2M$ cell cycle stage.

In some embodiments, a compound according to the instant disclosure is 3-methoxy-N-((3-methyl-4-(thiazol-2-yloxy)phenyl)carbamoyl)bicyclo[1.1.1]pentane-1-carboxamide,

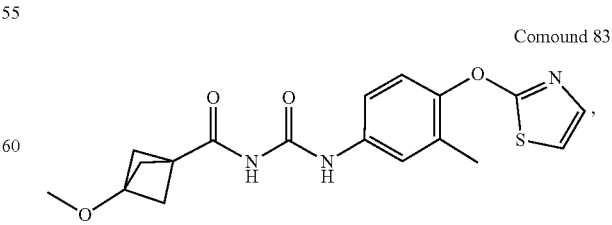

Comound 83 an analog thereof, an isomer thereof, a pharmaceutically acceptable salt thereof, a prodrug thereof, a polymorph thereof, or any combination thereof. In some embodiments, the compound has an $EC_{50}$ ranging from about 0.04 µM to about 0.08 µM in cancer cell viability and a kinetic solubility ranging from about 1.5 µM to about 3.5 µM.

In some embodiments, a compound according to the instant disclosure is N-((4-((5-chloropyridin-2-yl)oxy)-3-methylphenyl)carbamoyl)-3-methoxybicyclo[1.1.1]pentane-1-carboxamide, Compound 84

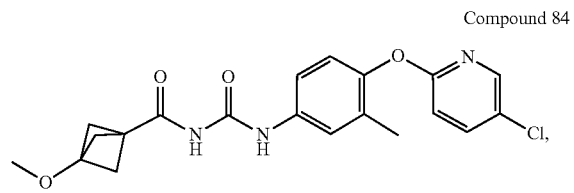 [SMILES: COC12CC(C(=O)NC(=O)Nc3ccc(Oc4ccc(Cl)cn4)c(C)c3)(C1)C2]

an analog thereof, an isomer thereof, a pharmaceutically acceptable salt thereof, a prodrug thereof, a polymorph thereof, or any combination thereof. In some embodiments, the compound has an $EC_{50}$ ranging from about 0.01 µM to about 0.16 µM in cancer cell viability.

In some embodiments, the compound is N-((4-((5-chloropyrimidin-2-yl)oxy)-3-methylphenyl)carbamoyl)-3-methoxybicyclo[1.1.1]pentane-1-carboxamide, Compound 85

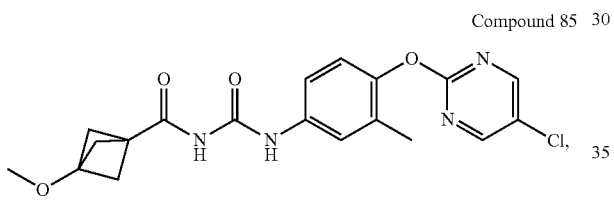

an analog thereof, an isomer thereof, a pharmaceutically acceptable salt thereof, a prodrug thereof, a polymorph thereof, or any combination thereof. In some embodiments, the compound has an $EC_{50}$ ranging from about 0.04 µM to 0.08 µM in cancer cell viability and a kinetic solubility ranging from about 1.5 µM to about 3.5 µM.

In some embodiments, the compound is 3-methoxy-N-((3-methyl-4-(pyridin-2-yloxy)phenyl)carbamoyl)bicyclo[1.1.1]pentane-1-carboxamide, Compound 86

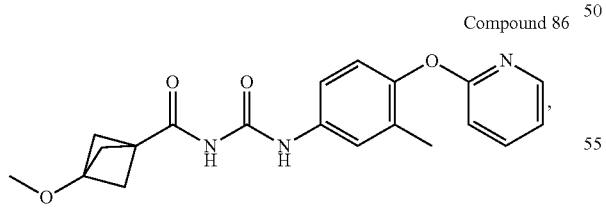

an analog thereof, an isomer thereof, a pharmaceutically acceptable salt thereof, a prodrug thereof, a polymorph thereof, or any combination thereof. In some embodiments, the compound has an $EC_{50}$ ranging from (about 0.26) about 0.1 µM to about 0.4 µM in cancer cell viability.

In some embodiments, the compound is 3-methoxy-N-((3-methyl-4-(pyrimidin-2-yloxy)phenyl)carbamoyl)bicyclo[1.1.1]pentane-1-carboxamide, Compound 87

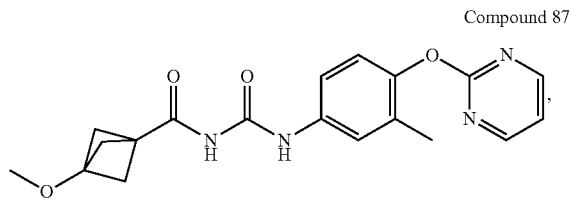 [SMILES: COC12CC(C(=O)NC(=O)Nc3ccc(Oc4ccccn4)c(C)c3)(C1)C2]

an analog thereof, an isomer thereof, a pharmaceutically acceptable salt thereof, a prodrug thereof, a polymorph thereof, or any combination thereof. In some embodiments, the compound has an $EC_{50}$ ranging from about 0.5 µM to about 4.0 µM in cancer cell viability and a kinetic solubility ranging from about 25.0 µM to about 30.0 µM.

In some embodiments, the compound is N-((4-((5-fluoropyrimidin-2-yl)oxy)-3-methylphenyl)carbamoyl)-3-methoxybicyclo[1.1.1]pentane-1-carboxamide, Compound 88

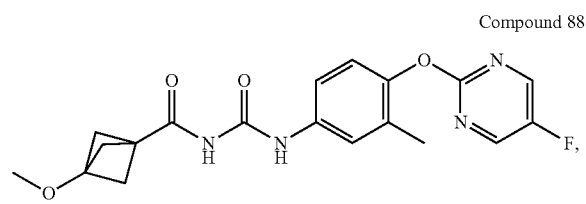 [SMILES: COC12CC(C(=O)NC(=O)Nc3ccc(Oc4ncc(F)cn4)c(C)c3)(C1)C2]

an analog thereof, an isomer thereof, a pharmaceutically acceptable salt thereof, a prodrug thereof, a polymorph thereof, or any combination thereof. In some embodiments, the compound has an $EC_{50}$ ranging from about 0.5 µM to about 4.0 µM in cancer cell viability and a kinetic solubility ranging from about 85.0 µM to about 91.0 µM.

In some embodiments, the compound is N-((4-((5-fluoropyridin-2-yl)oxy)-3-methylphenyl)carbamoyl)-3-methoxybicyclo[1.1.1]pentane-1-carboxamide, Compound 89

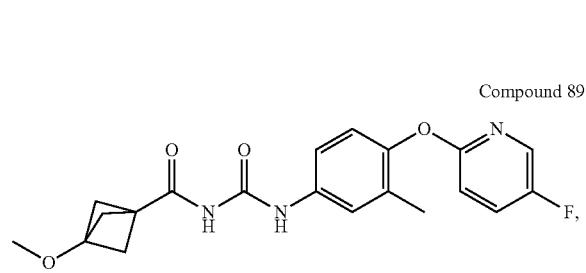 [SMILES: COC12CC(C(=O)NC(=O)Nc3ccc(Oc4ccc(F)cn4)c(C)c3)(C1)C2]

an analog thereof, an isomer thereof, a pharmaceutically acceptable salt thereof, a prodrug thereof, a polymorph thereof, or any combination thereof. In some embodiments, the compound has an $EC_{50}$ ranging from about 0.05 µM to about 0.35 µM in cancer cell viability.

In some embodiments, the compound is N-((4-((5-chloropyrimidin-2-yl)oxy)-3-fluoro-5-methylphenyl)carbamoyl)-3-methoxybicyclo[1.1.1]pentane-1-carboxamide, Compound 90

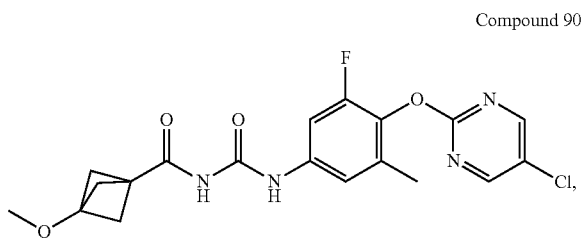 [SMILES: COC12CC(C(=O)NC(=O)Nc3cc(C)c(Oc4ncc(Cl)cn4)c(F)c3)(C1)C2]

an analog thereof, an isomer thereof, a pharmaceutically acceptable salt thereof, a prodrug thereof, a polymorph thereof, or any combination thereof. In some embodiments, the compound has an $EC_{50}$ ranging from about 0.065 μM to about 0.034 μM in cancer cell viability and a kinetic solubility ranging from about 1.5 μM to about 3.5 μM.

In some embodiments, the compound is N-((3-fluoro-4-((5-fluoropyridin-2-yl)oxy)-5-methylphenyl)carbamoyl)-3-methoxybicyclo[1.1.1]pentane-1-carboxamide, Compound 94

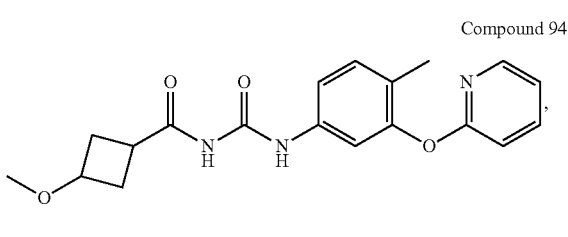

an analog thereof, an isomer thereof, a pharmaceutically acceptable salt thereof, a prodrug thereof, a polymorph thereof, or any combination thereof. In some embodiments, the compound has an $EC_{50}$ ranging from about 0.002 μM to about 0.007 μM in cancer cell viability and a kinetic solubility ranging from about 10.0 μM to about 14.0 μM.

In some embodiments, the compound is N-((3-((5-fluoropyridin-2-yl)oxy)-4-methylphenyl)carbamoyl)-3-methoxycyclobutane-1-carboxamide, Compound 91

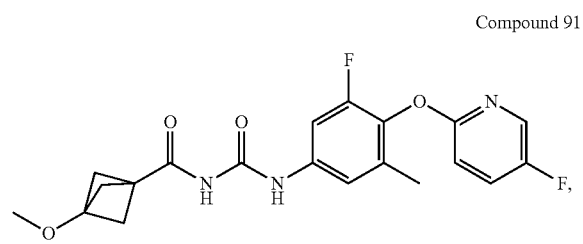 [SMILES: COC12CC(C(=O)NC(=O)Nc3cc(C)c(Oc4ccc(F)cn4)c(F)c3)(C1)C2]

an analog thereof, an isomer thereof, a pharmaceutically acceptable salt thereof, a prodrug thereof, a polymorph thereof, or any combination thereof. In some embodiments, the compound has an $EC_{50}$ ranging from about 0.087 μM to about 0.63 μM in cancer cell viability.

In some embodiments, the compound is 3-methoxy-N-((4-methyl-3-(thiazol-2-yloxy)phenyl)carbamoyl)cyclobutane-1-carboxamide, Compound 95

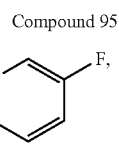

an analog thereof, an isomer thereof, a pharmaceutically acceptable salt thereof, a prodrug thereof, a polymorph thereof, or any combination thereof. In some embodiments, the compound has an $EC_{50}$ ranging from about 0.005 μM to about 0.03 μM in cancer cell viability and a kinetic solubility ranging from about 5.0 μM to about 9.0 μM.

In some embodiments, the compound is 3-methoxy-N-((4-methyl-3-(pyrimidin-2-yloxy)phenyl)carbamoyl)cyclobutane-1-carboxamide, Compound 93

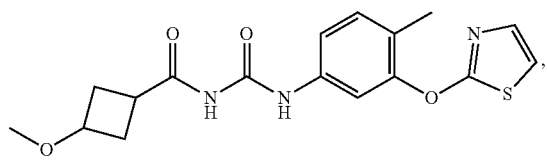

an analog thereof, an isomer thereof, a pharmaceutically acceptable salt thereof, a prodrug thereof, a polymorph thereof, or any combination thereof. In some embodiments, the compound has an $EC_{50}$ ranging from about 0.01 μM to about 0.05 μM in cancer cell viability and a kinetic solubility ranging from about 7.0 μM to about 11.0 μM.

In some embodiments, the compound is 3-methoxy-N-((4-methyl-3-(pyridin-2-yloxy)phenyl)carbamoyl)cyclobutane-1-carboxamide, Compound 96

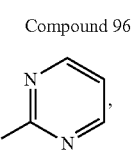

an analog thereof, an isomer thereof, a pharmaceutically acceptable salt thereof, a prodrug thereof, a polymorph thereof, or any combination thereof. In some embodiments, the compound has an $EC_{50}$ ranging from about 0.02 μM to about 0.06 μM in cancer cell viability and a kinetic solubility ranging from about 13.0 μM to about 17.0 μM. 1. In some embodiments, the compound is 3-methoxy-N-((4-methyl-3-(pyrimidin-2-yloxy)phenyl)carbamoyl)bicyclo[1.1.1]pentane-1-carboxamide, Compound 97

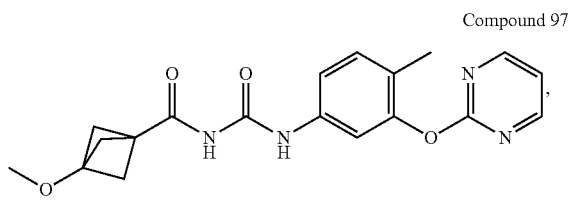 [SMILES: COC12CC(C(=O)NC(=O)Nc3ccc(C)c(Oc4ncccn4)c3)(C1)C2]

an analog thereof, an isomer thereof, a pharmaceutically acceptable salt thereof, a prodrug thereof, a polymorph thereof, or any combination thereof. In some embodiments, the compound has an $EC_{50}$ ranging from about 0.02 µM to about 0.011 µM in cancer cell viability and a kinetic solubility ranging from about 4.0 µM to about 8.0 µM.

In some embodiments, the compound is 3-methoxy-N-((4-methyl-3-(pyridin-2-yloxy)phenyl)carbamoyl)bicyclo[1.1.1]pentane-1-carboxamide, Compound 98

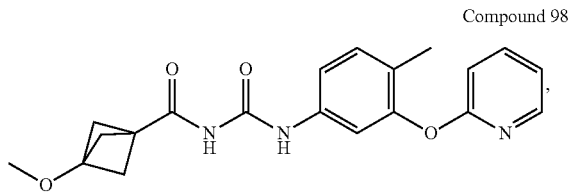

an analog thereof, an isomer thereof, a pharmaceutically acceptable salt thereof, a prodrug thereof, a polymorph thereof, or any combination thereof. In some embodiments, the compound has an $EC_{50}$ ranging from about 0.02 µM to about 0.07 µM in cancer cell viability.

II. Pharmaceutical Compositions

Another aspect of the instant disclosure includes pharmaceutical compositions. The pharmaceutical composition include at least one compound according to the instant disclosure for use to treat health conditions in a subject in need thereof. The compound can be as described, for example as described in Section I.

In some embodiments, pharmaceutical compositions can include at least one compound disclosed herein and at least one pharmaceutically acceptable carrier. In certain embodiments, pharmaceutical compositions can include pharmaceutically acceptable carriers, excipients, and/or stabilizers are nontoxic to recipients at dosages and/or concentrations used to practice the methods disclosed herein.

In certain embodiments, weight fraction of the excipient or combination of excipients in the composition can be about 99% or less, about 97% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

In some embodiments, the pharmaceutically acceptable excipient can be a diluent, a binder, a filler, a buffering agent, a pH modifying agent, a disintegrant, a dispersant, a preservative, a lubricant, taste-masking agent, a flavoring agent, or a coloring agent and can be as described herein below in Sections II (A-L). The concentrations and types of excipients utilized to form pharmaceutical compositions disclosed herein and contemplated herein can be selected according to known principles of pharmaceutical science and knowledge in the art.

A. Diluent

In some embodiments, the excipient can be a diluent. The diluent can be compressible (i.e., plastically deformable) or abrasively brittle. Non-limiting examples of suitable compressible diluents include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lactitol, mannitol, malitol, sorbitol, xylitol, maltodextrin, and trehalose. Non-limiting examples of suitable abrasively brittle diluents include dibasic calcium phosphate (anhydrous or dihydrate), calcium phosphate tribasic, calcium carbonate, and magnesium carbonate.

B. Binder

In another embodiment, the excipient can be a binder. Suitable binders include, but are not limited to, starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, polypeptides, oligopeptides, and combinations thereof.

C. Filler

In another embodiment, the excipient can be a filler. Suitable fillers include, but are not limited to, carbohydrates, inorganic compounds, and polyvinylpyrrolidone. By way of non-limiting example, the filler can be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

D. Buffering Agent

In still another embodiment, the excipient can be a buffering agent. Representative examples of suitable buffering agents include, but are not limited to, phosphates, carbonates, citrates, tris buffers, and buffered saline salts (e.g., Tris buffered saline or phosphate buffered saline).

E. pH Modifier

In various embodiments, the excipient can be a pH modifier. By way of non-limiting example, the pH modifying agent can be sodium carbonate, sodium bicarbonate, sodium citrate, citric acid, or phosphoric acid.

F. Disintegrant

In a further embodiment, the excipient can be a disintegrant. The disintegrant can be non-effervescent or effervescent. Suitable examples of non-effervescent disintegrants include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. Non-limiting examples of suitable effervescent disintegrants include sodium bicarbonate in combination with citric acid and sodium bicarbonate in combination with tartaric acid.

G. Dispersant

In yet another embodiment, the excipient can be a dispersant or dispersing enhancing agent. Suitable dispersants can include, but are not limited to, starch, alginic acid, polyvinylpyrrolidones, guar gum, kaolin, bentonite, purified wood cellulose, sodium starch glycolate, isoamorphous silicate, and microcrystalline cellulose.

H. Excipient

In another alternate embodiment, the excipient can be a preservative. Non-limiting examples of suitable preservatives include antioxidants, such as BHA, BHT, vitamin A, vitamin C, vitamin E, or retinyl palmitate, citric acid, sodium citrate; chelators such as EDTA or EGTA; and antimicrobials, such as parabens, chlorobutanol, or phenol.

I. Lubricant

In a further embodiment, the excipient can be a lubricant. Non-limiting examples of suitable lubricants include minerals such as talc or silica; and fats such as vegetable stearin, magnesium stearate, or stearic acid.

J. Taste-Masking Agent

In yet another embodiment, the excipient can be a taste-masking agent. Taste-masking materials include cellulose ethers; polyethylene glycols; polyvinyl alcohol; polyvinyl alcohol and polyethylene glycol copolymers; monoglycerides or triglycerides; acrylic polymers; mixtures of acrylic polymers with cellulose ethers; cellulose acetate phthalate; and combinations thereof.

K. Flavoring Agent

In an alternate embodiment, the excipient can be a flavoring agent. Flavoring agents can be chosen from synthetic flavor oils and flavoring aromatics and/or natural oils, extracts from plants, leaves, flowers, fruits, and combinations thereof.

L. Coloring Agent

In still a further embodiment, the excipient can be a coloring agent. Suitable color additives include, but are not limited to, food, drug and cosmetic colors (FD&C), drug and cosmetic colors (D&C), or external drug and cosmetic colors (Ext. D&C).

Other pharmaceutically acceptable carriers, excipients, and/or stabilizers can include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

III. Dosage forms

One aspect of the instant disclosure encompasses a dosage form comprising a compound according to the instant disclosure. In some embodiments, the dosage form includes a pharmaceutical composition comprising a compound according to the instant disclosure. The compound can be as described in Section I and the pharmaceutical compositions cam be as described in Section II herein above.

In certain embodiments, pharmaceutical compositions disclosed herein can be in unit dosage forms such as tablets, pills, capsules, powders, granules, solutions or suspensions, or suppositories, for oral, parenteral or rectal administration, or administration by inhalation or insufflation. In some embodiments, for preparing solid compositions such as tablets, the principal active ingredient (e.g., a compound disclosed herein) can be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid pre-formulation composition containing a homogeneous mixture of a compound according to the present invention, or a non-toxic pharmaceutically acceptable salt thereof. When referring to these pre-formulation compositions as homogeneous, it is meant that the active ingredient is dispersed evenly throughout the composition so that the composition can be readily subdivided into equally effective unit dosage forms such as tablets, pills and capsules. In some embodiments, solid pre-formulation compositions herein can then subdivided into unit dosage forms of the type described above containing from 0.1 mg to about 500 mg (e.g., about 0.1 mg, about 0.5 mg, about 1.0 mg, about 5.0 mg, about 10 mg, about 25 mg, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg or higher or a concentration in between) of a compound disclosed herein.

In some embodiments, tablets and/or pills disclosed herein can be coated or otherwise compounded to provide a dosage form affording the advantage of prolonged action. In some embodiments, a tablet and/or pill herein can have an inner dosage and an outer dosage component, the latter being in the form of an envelope over the former. In accordance with embodiments herein, the two components can be separated by an enteric layer that serves to resist disintegration in the stomach and permits the inner component to pass intact into the duodenum or to be delayed in release. In some embodiments, tablets and/or pills disclosed herein can include one or more materials that can be used for such enteric layers or coatings, such materials including a number of polymeric acids and mixtures of polymeric acids with such materials as shellac, cetyl alcohol and cellulose acetate. Non-limiting surface-active agents (surfactants) suitable for use herein can include non-ionic agents, such as polyoxyethylenesorbitans (e.g., Tween™ 20, 40, 60, 80 or 85) and other sorbitans (e.g., Span™ 20, 40, 60, 80 or 85). In some embodiments, compositions herein with a surface-active agent can have between about 0.05 and about 5% surface-active agent. In some embodiments, other ingredients can be added to pharmaceutical compositions herein, for example mannitol or other pharmaceutically acceptable vehicles, if necessary.

In some embodiments, pharmaceutical compositions disclosed herein can be tablets. In accordance with some embodiments herein, tablets contemplated herein can contain excipients such as microcrystalline cellulose, lactose, sodium citrate, calcium carbonate, dibasic calcium phosphate and glycine, disintegrants such as starch (preferably corn, potato or tapioca starch), sodium starch glycolate, croscarmellose sodium and certain complex silicates, and granulation binders such as polyvinylpyrrolidone, hydroxypropylmethylcellulose (HPMC), hydroxy-propylcellulose (HPC), sucrose, gelatin and acacia. In accordance with some embodiments disclosed herein, tablets contemplated can contain lubricating agents such as magnesium stearate, stearic acid, glyceryl behenate and talc. In some embodiments, pharmaceutical compositions can be solid compositions employed as fillers in gelatin capsules. In accordance with some embodiments herein, excipients included in gelatin capsules contemplated herein can include lactose, starch, cellulose, milk sugar or high molecular weight polyethylene glycols.

In certain embodiments, pharmaceutical compositions disclosed herein can include emulsions. In some embodiments, emulsions disclosed herein can be prepared using commercially available fat emulsions, such as Intralipid™, Liposyn™, Infonutrol™ Lipofundin™ and Lipiphysan™. The active ingredient (e.g., the one or more aminopeptidase inhibitors and/or one or more platinum-based chemotherapeutics) can be either dissolved in a pre-mixed emulsion composition or alternatively it can be dissolved in an oil (e.g., soybean oil, safflower oil, cottonseed oil, sesame oil, corn oil or almond oil) and an emulsion formed upon mixing with a phospholipid (e.g., egg phospholipids, soybean phospholipids or soybean lecithin) and water. In some embodiments, other ingredients can be added to the compositions disclosed herein, for example glycerol or glucose, to adjust the tonicity of the emulsion. In other embodiments, emulsions can contain up to 20% oil, for example, between about 5% and about 20%. In some embodiments, emulsions can have fat droplets between about 0.1 μm and about 1.0 μm and/or have a pH in the range of about 5.5 to about 8.0.

In certain embodiments, pharmaceutical compositions disclosed herein can be formulated for parenteral administration, such as intravenous, intracerebroventricular injection, intra-cisterna magna injection, intra-parenchymal injection, or a combination thereof. In some embodiments, pharmaceutical compositions herein formulated for parenteral administration can include one or more sterile liquids as pharmaceutically acceptable carriers. Non-limiting examples of sterile liquids suitable for use as pharmaceutically acceptable carriers herein can be water and oil, including those of petroleum, animal, vegetable, or synthetic origin, such as peanut oil, soybean oil, mineral oil, and the like. Saline solutions and aqueous dextrose, polyethylene glycol (PEG) and glycerol solutions can also be employed as liquid carriers, particularly for injectable solutions. Pharmaceutical compositions disclosed herein can further include additional ingredients, for example preservatives, buffers, tonicity agents, antioxidants and stabilizers, nonionic wetting or clarifying agents, viscosity-increasing agents, and the like. In some embodiments, pharmaceutical compositions disclosed herein can be packaged in single unit dosages or in multi-dosage forms.

In some embodiments, pharmaceutical compositions herein suitable for parenteral administration can include aqueous and non-aqueous sterile injection solutions which can further contain anti-oxidants, buffers, bacteriostats and solutes which render the formulation isotonic with the blood of the intended recipient; and aqueous and non-aqueous sterile suspensions which can include suspending agents and thickening agents. Aqueous solutions can be suitably buffered (preferably to a pH of about 3.0 to about 9.0 or about 5.0 to about 8.5 or about 6.5 to about 8.0). The preparation of suitable parenteral formulations under sterile conditions is readily accomplished by standard pharmaceutical techniques well known to those skilled in the art.

In some embodiments, pharmaceutical compositions described herein can further include an anti-microbial agent, a chemotherapeutic agent, and/or other anti-cancer therapeutic or antibody. In accordance with these embodiments, the anti-microbial agent can, in an example, be an anti-viral, bactericidal agent, anti-fungal, or anti-bacterial agent. For example, the anti-microbial agent can be an anti-bacterial agent (antibiotic) such as doxycycline or other antibiotics such as a general antibiotic.

IV. Methods

Another aspect of the present disclosure relates to methods for treating a health condition in a subject having, is suspected of developing, or is at risk of developing a health condition. In accordance with these embodiments, the methods can include administering to the subject a therapeutically effective amount of a compound according to the instant disclosure alone or as combination therapies in treatment, reducing onset or amelioration of a health condition in a subject in need thereof. The compound can be in the form of a therapeutic composition comprising the compound according to the instant disclosure or can be a dosage form comprising the compound according to the instant disclosure. The health condition can be cancer. Various embodiments of the method and health conditions are described herein below. The compound, the therapeutic composition, and the dosage form can be as described herein above in Sections I, II, and III, respectively.

A. Cancer

In some embodiments, the health condition is cancer, a neoplasm, a metastasis, a tumor, or a combination thereof. Accordingly, in certain embodiments, a method of the instant disclosure includes treating or ameliorating or preventing onset of cancer, a neoplasm, a metastasis, a tumor, or a combination thereof in a subject in need thereof. The neoplasm can be malignant or benign, the cancer can be primary or metastatic; the neoplasm or cancer can be early stage or late stage. Non-limiting examples of neoplasms or cancers that can be treated include acute lymphoblastic leukemia, acute myeloid leukemia, adrenocortical carcinoma, AIDS-related cancers, AIDS-related lymphoma, anal cancer, appendix cancer, astrocytomas (childhood cerebellar or cerebral), basal cell carcinoma, bile duct cancer, bladder cancer, bone cancer, brainstem glioma, brain tumors (cerebellar astrocytoma, cerebral astrocytoma/malignant glioma, ependymoma, medulloblastoma, supratentorial primitive neuroectodermal tumors, visual pathway and hypothalamic gliomas), breast cancer, bronchial adenomas/carcinoids, Burkitt lymphoma, carcinoid tumors (childhood, gastrointestinal), carcinoma of unknown primary, central nervous system lymphoma (primary), cerebellar astrocytoma, cerebral astrocytoma/malignant glioma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma in the Ewing family of tumors, extracranial germ cell tumor (childhood), extragonadal germ cell tumor, extrahepatic bile duct cancer, eye cancers (intraocular melanoma, retinoblastoma), gallbladder cancer, gastric (stomach) cancer, gastrointestinal carcinoid tumor, gastrointestinal stromal tumor, germ cell tumors (childhood extracranial, extragonadal, ovarian), gestational trophoblastic tumor, gliomas (adult, childhood brain stem, childhood cerebral astrocytoma, childhood visual pathway and hypothalamic), gastric carcinoid, hairy cell leukemia, head and neck cancer, hepatocellular (liver) cancer, Hodgkin lymphoma, hypopharyngeal cancer, hypothalamic and visual pathway glioma (childhood), intraocular melanoma, islet cell carcinoma, Kaposi sarcoma, kidney cancer (renal cell cancer), laryngeal cancer, leukemias (acute lymphoblastic, acute myeloid, chronic lymphocytic, chronic myelogenous, hairy cell), lip and oral cavity cancer, liver cancer (primary), lung cancers (non-small cell, small cell), lymphomas (AIDS-related, Burkitt, cutaneous T-cell, Hodgkin, non-Hodgkin, primary central nervous system), macroglobulinemia (Waldenstrom), malignant fibrous histiocytoma of bone/osteosarcoma, medulloblastoma (childhood), melanoma, intraocular melanoma, Merkel cell carcinoma, mesotheliomas (adult malignant, childhood), metastatic squamous neck cancer with occult primary, mouth cancer, multiple endocrine neoplasia syndrome (childhood), multiple myeloma/plasma cell neoplasm, mycosis fungoides, myelodysplastic syndromes, myelodysplastic/myeloproliferative diseases, myelogenous leukemia (chronic), myeloid leukemias (adult acute, childhood acute), multiple myeloma, myeloproliferative disorders (chronic), nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer (surface epithelial-stromal tumor), ovarian germ cell tumor, ovarian low malignant potential tumor, pancreatic cancer, pancreatic cancer (islet cell), paranasal sinus and nasal cavity cancer, parathyroid cancer, penile cancer, pharyngeal cancer, pheochromocytoma, pineal astrocytoma, pineal germinoma, pineoblastoma, and supratentorial primitive neuroectodermal tumors (childhood), pituitary adenoma, plasma cell neoplasia, pleuropulmonary blastoma, primary central nervous system lymphoma, prostate cancer, rectal cancer, renal cell carcinoma (kidney cancer), renal pelvis and ureter transitional cell cancer, retinoblastoma, rhabdomyosarcoma (childhood), salivary gland cancer, sarcoma (Ewing family of tumors, Kaposi, soft tissue, uterine), Sezary syndrome, skin cancers (nonmelanoma, melanoma), skin carcinoma (Merkel cell), small cell lung cancer, small intestine cancer, soft tissue sarcoma, squamous cell carcinoma, squamous neck cancer with occult primary (metastatic), stomach cancer, supratentorial primitive neuroectodermal tumor (childhood), T-Cell lymphoma (cutaneous), testicular cancer, throat cancer, thymoma (childhood), thymoma and thymic carcinoma, thyroid cancer, thyroid cancer (childhood), transitional cell cancer of the renal pelvis and ureter, trophoblastic tumor (gestational), enknown primary site (adult, childhood), ureter and renal pelvis transitional cell cancer, urethral cancer, uterine cancer (endometrial), uterine sarcoma, vaginal cancer, visual pathway and hypothalamic glioma (childhood), vulvar cancer, Waldenstrom macroglobulinemia, and Wilms tumor (childhood).

In some embodiments, methods of treating or ameliorating cancer, a metastasis, a tumor, or a combination thereof in a subject can include, but are not limited to, administration of an effective amount of any the compounds and/or pharmaceutical compositions described herein. "An effective amount" as used herein refers to a dose of any the compounds and/or pharmaceutical compositions herein that is sufficient to confer a therapeutic effect on a subject having or suspected of developing cancer, a tumor, or any combination thereof and further treating the cancer. In certain embodiments, a therapeutic effect for a subject having or suspected of having a tumor can include reducing the symptoms or consequences of the cancer, such as reducing expansion of, shrinking of a tumor, killing tumor cells, preventing the occurrence of metastases from a primary tumor, reducing the number of tumor cells of a tumor, primary tumor and/or a metastatic tumor, inhibiting the growth of tumor cells of a primary tumor and/or a metastatic tumor, eliminating tumor cells in a subject by killing the cells or preventing propagation or expansion of the solid tumor cells and the like.

In some embodiments, the cancer comprises prostate cancer, brain cancer, cancer that metastasizes to the brain, pancreatic cancer, lung cancer, breast cancer, bone sarcoma, kidney cancer, skin cancer such as melanoma, liver cancer, bladder cancer, Ewing sarcoma, glioblastoma, high grade glioma, or any combination thereof. In some embodiments, the cancer is prostate cancer. In some embodiments, the cancer is breast cancer.

In some embodiments and further to the paragraphs above, the cancer is brain cancer. Non-limiting examples of brain cancer include astrocytomas (childhood cerebellar or cerebral), brainstem glioma, brain tumors (cerebellar astrocytoma, cerebral astrocytoma/malignant glioma, ependymoma, medulloblastoma, supratentorial primitive neuroectodermal tumors, visual pathway and hypothalamic gliomas), cerebellar astrocytoma, cerebral astrocytoma/malignant glioma, gliomas (adult, childhood brain stem, childhood cerebral astrocytoma, childhood visual pathway and hypothalamic). In some embodiments, the cancer is glioblastoma. In some embodiments, the cancer is glioma. In some embodiments, the cancer is high grade gliomas. In some embodiments, the cancer is cancer that metastasizes to the brain. As used herein, the term "cancer that metastasizes to the brain" has the meaning commonly understood by a person skilled in the art. More specifically, although it is recognized that any cancer can spread to the brain, the term "cancer that metastasizes to the brain" is used in the art to refer to the types of non-brain cancers that are most likely to cause brain metastases. Non-limiting examples of cancers that are most likely to cause brain metastases include lung, breast, colon, kidney, and melanoma. In some embodiments, the cancer is lung cancer, brain metastasis from lung cancer, breast cancer, brain metastasis from breast cancer, brain metastasis from colon cancer, colon cancer, brain metastasis from kidney cancer, kidney cancer, melanoma, or brain metastasis from melanoma.

In some embodiments and further to paragraphs above, the cancer is prostate cancer, brain cancer, cancer that metastasizes to the brain, lung cancer, breast cancer, melanoma, Ewing sarcoma, glioblastoma, high grade glioma, or any combination thereof. In some embodiments, a method of the instant disclosure includes treating a brain cancer. In some embodiments, a method of the instant disclosure includes treating a cancer that metastasizes to the brain. In some embodiments, a method of the instant disclosure includes treating glioblastoma. In some embodiments, a method of the instant disclosure includes treating high grade gliomas. In some embodiments, a method of the instant disclosure includes Ewing's sarcoma.

B. Subject

In some embodiments, the subject can be human, livestock animal, a companion animal, a lab animal, or a zoological or wild animal, reptile or bird. Non-limiting examples of suitable livestock animals can include pigs, cows, goats, sheep, llamas and alpacas. Non-limiting examples of companion animals can include pets such as dogs, cats, rabbits, horses and birds. As used herein, a "zoological animal" refers to an animal that can be found in a zoo. Such animals can include non-human primates, large cats, wolves, and bears. Non-limiting examples of a laboratory animal can include rodents, canines, felines, and non-human primates. In some embodiments, the subject is a human subject such as a fetus, child, infant, adolescent, young adult, adult or elderly adult.

In some embodiments, a subject can be any subject for whom treatment or therapy is desired. In other embodiments, a subject to be treated by the methods described herein can be a human patient having, suspected of having, or at risk of developing cancer. In some embodiments, a subject can have or can be suspected of having cancer, a metastasis, a tumor, or any combination thereof. In some embodiments, a subject can have or can be suspected of having one or more primary tumors, one or more metastatic tumors such as solid tumors or any combination thereof. In some embodiments, a subject can be a mammal. In some embodiments, a subject can be a human patient. In other embodiments, a human patient such as an adult, child, adolescent, toddler, young adult or infant or fetus who is in need of the methods herein can be identified by routine medical examination, e.g., laboratory tests, biopsy, magnetic resonance imaging (MRI) scans, ultrasound exams, and the like. In some embodiments, the subject to be treated by the method described herein can have undergone or is being subjected to an anti-cancer therapy, for example, chemotherapy, radiotherapy, immunotherapy, and/or surgery.

In some embodiments, a subject to be treated by the methods described herein can be a human patient having, suspected of having, or at risk of developing prostate cancer, brain cancer, pancreatic cancer, breast cancer, bone sarcoma, liver cancer, bladder cancer, or any combination thereof. In some embodiments, a subject to be treated by the methods described herein can be a human patient having, suspected of having, or at risk of developing adenocarcinoma of the prostate (e.g., acinar adenocarcinoma and/or prostatic ductal adenocarcinoma). In certain embodiments, a subject to be treated by the methods described herein can be a human patient having, suspected of having, or at risk of developing astrocytoma, glioblastoma, and/or meningioma. In some embodiments, a subject to be treated by the methods described herein can be a human patient having, suspected of having, or at risk of developing exocrine pancreatic cancer (e.g., adenocarcinoma, squamous cell carcinoma, adenosquamous carcinoma, colloid carcinoma) and/or neuroendocrine pancreatic cancer. In some embodiments, a subject to be treated by the methods described herein can be a human patient having, suspected of having, or a risk for developing ductal carcinoma in situ, invasive ductal carcinoma, inflammatory breast cancer, and/or metastatic breast cancer. In some embodiments, a subject to be treated by the methods disclosed herein can be a human subject having, suspected of having, or at risk of developing osteosarcoma, chondrosarcoma, poorly differentiated round/spindle cell tumors, Ewing sarcoma, hemangioendothelioma, angiosarcoma, fibrosarcoma/myofibrosarcoma, chordoma, adamantinoma, liposarcoma, leiomyosarcoma, malignant peripheral nerve sheath tumor, rhabdomyosarcoma, synovial sarcoma, and/or malignant solitary fibrous tumor. In some embodiments, a subject to be treated by the methods disclosed herein can be a human subject having, suspected of having, or at risk of developing hepatocellular carcinoma (HCC), fibrolamellar HCC, cholangiocarcinoma, hemangiocarcinoma, secondary liver cancer, and/or hepatoblastoma. In some embodiments, a subject to be treated by the methods described herein can be a human patient having, suspected of having, or at risk of developing urothelial carcinoma, squamous cell carcinomas, adenocarcinomas, and/or small-cell carcinomas of the bladder.

C. Administering

A composition of the instant disclosure can be administered to a subject by several different means or any method known in the art. For example, a composition can generally be administered parenterally, buccally, nasally, by inhalation, intraperitoneally, intrauterine, intratumorally, intravascularly, transdermally, subcutaneously, rectally, or intrapulmonarily. The term parenteral as used herein includes subcutaneous, intravenous, intramuscular, intrathecal, or intrasternal injection, or infusion techniques. Topical administration can also involve the use of transdermal administration such as transdermal patches or iontophoresis devices. The compositions can be formulated in dosage unit formulations for administration comprising conventional nontoxic pharmaceutically acceptable adjuvants, carriers, excipients, and vehicles as described in Section II.

Actual dosage levels of active ingredients in a therapeutic composition of the disclosure can be varied so as to administer an amount of substituted phenethylamines that is effective to achieve the desired therapeutic response for a particular subject. A selected dosage level can depend upon a variety of factors, including the substituted phenethylamine in a composition, the activity of the therapeutic composition, formulation, the combination with other drugs or treatments, disease and longevity, and the physical condition and prior medical history of the subject being treated. Determination of the proper dosage for a particular situation is within the skill of the practitioner.

In some embodiments, a composition of the disclosure is administered as needed, upon development or shortly before development of symptoms. In some embodiments, the composition is administered regularly by following a prescribed treatment schedule. For instance, a composition of the instant disclosure can be administered routinely, at various intervals. For instance, compositions can be administered daily, weekly, monthly, or over several months. In some embodiments, compositions are administered daily. In other embodiments, compositions are administered weekly. In yet other embodiments, compositions are administered monthly. Compositions can also be administered every three to six months. As it will be recognized in the art, the duration of treatment can and will vary and can be determined experimentally.

Administration of the compositions described herein can also be carried out as part of a treatment regimen that can include multiple instances of administration of one or more compositions comprising substituted phenethylamines. Such a regimen can be designed as a method of immediately treating a condition and/or as a method of long-term maintenance of the health of a subject after having been treated for a condition (e.g., prevention). For instance, a treatment regimen can be designed to delay the onset of the condition of interest in a subject. It will be appreciated that determination of appropriate treatment regimens is within the skill of practitioners in the art.

It will also be appreciated by those skilled in the art that a composition of the present disclosure can be co-administered with other therapeutic agents before, after, and/or during treatment with a composition of the disclosure. The term "co-administer" refers to administration of more than one active ingredient at the same time, just prior to, or just after the administration of one or more additional therapies. The compounds of the disclosure can be administered alone or can be co-administered to the patient. Co-administration is meant to include simultaneous or sequential administration of the compounds individually or in combination. Dosage amounts and intervals can be adjusted individually to provide levels of the administered compound effective for the particular clinical indication being treated. This will provide a therapeutic regimen that is commensurate with the severity of the individual's disease state.

In some embodiments, when the health condition is cancer, pharmaceutical compositions herein can be administered alone or in combination with a platinum-based chemotherapeutic. As used herein, a "platinum-based chemotherapeutic" is a chemotherapeutic that is an organic compound which contains platinum as an integral part of the molecule. In some embodiments, compositions of use herein can contain one or more platinum-based chemotherapeutics including, but not limited to, cisplatin, carboplatin, nedaplatin, triplatin tetranitrate, phenanthriplatin, picoplatin, satraplatin or a combination thereof. In some embodiments, a platinum-based chemotherapeutic can be administered separately from a compound disclosed herein or a derivative thereof. In some embodiments, compositions containing a platinum-based chemotherapeutic of use herein can contain a concentration of the platinum-based chemotherapeutic at about 1 mg/ml to about 100 mg/ml (e.g., about 1 mg/ml, about 5 mg/ml, about 10 mg/ml, about 20 mg/ml, about 30 mg/ml, about 40 mg/ml, about 50 mg/ml, about 60 mg/ml, about 80 mg/ml, about 100 mg/ml or more or any concentration in between). In certain embodiments, platinum-based chemotherapeutic agents can be administered to a subject alone or in combination with at least one compound disclosed herein daily, every other day, twice weekly, every other day, every other week, weekly or monthly or other suitable dosing regimen.

In other embodiments, pharmaceutical compositions disclosed herein can be administered alone or in combination with at least one immunomodulatory agent. Non-limiting examples of such immunomodulatory agents include, but are not limited to, anti-PD1, anti-PD-L1, anti-CTLA-4, anti-OX40, anti-CD137, etc. Non-limiting examples of PD-1 inhibitors include, but are not limited to, anti-PD-1 antibodies, such as pembrolizumab, nivolumab, and cemiplimab. Non-limiting examples of PD-L1 inhibitors can include atezolizumab, durvalumab, and avelumab. A non-limiting example of a CTLA-4 inhibitor is the anti-CTLA-4 antibody ipilimumab. In some embodiments, an immunomodulatory agent can be one or more inhibitors that target a checkpoint molecule selected from CD40, GITR, LAG-3, OX40, TIGIT and TIM-3. In certain embodiments, immunomodulatory agents can be administered to a subject alone or in combination with at least one compound disclosed herein daily, every other day, twice weekly, every other day, every other week, weekly or monthly or other suitable dosing regimen.

In some embodiments, pharmaceutical compositions disclosed herein can be administered alone or in combination with at least one or more small molecules. Non-limiting examples of such small molecules can include, but are not limited to, imatinib, dasatinib, nilotinib, bosutinib, regorafenib, ponatinib, sunitinib, sorafenib, erdafitinib, lenvatinib, pazopanib, afatinib, gefitinib, osimertinib, vandetanib, erlotinib, lapatinib, dacomitinib, neratinib, ribociclib, abemaciclib, palbociclib, cabozantinib, crizotinib, axitinib, alectinib, vemurafenib, encorafenib, dabrafenib, olaparib, rucaparib, talazoparib, niraparib, larotrectinib, entrectinib, lorlatinib, ibrutinib, cobimetinib, binimetinib, trametinib, brigatinib, cgilteritinib, ceritinib, ivosidenib, carfilzomib, marizomib, alpelisib, duvelisib, copanlisib, and the like.

In some embodiments, a subject treated with any of the methods herein can have completed an additional cancer therapeutic regimen, be receiving an additional cancer therapeutic regimen, or can receive an additional cancer therapeutic regimen following treatment disclosed herein. In some embodiments, an additional therapeutic regimen of use to treat cancer disclosed herein can include administering one or more anti-cancer therapeutics.

In other embodiments, an additional therapeutic regimen for use in compositions and methods disclosed herein can include administering an immunomodulatory agent. In some embodiments, a subject can be treated with an immunomodulatory agent before, during, or after administration of a compound and/or pharmaceutical composition disclosed herein.

In certain embodiments, an additional therapeutic regimen in combination therapies disclosed herein can include administering radiation. In some embodiments, a subject can be treated by radiation therapy by at least one of before, during or after administration of a compound and/or pharmaceutical composition disclosed herein. In some embodiments, a subject can be treated by radiation therapy at least 12 hours, about 24 hours, about 2 days, about 3 days, about 4 days, about 5 days, about 6 days, about 1 week, or about 2 weeks before and/or after administration of a compound and/or pharmaceutical composition disclosed herein. In other embodiments, a subject can be treated by radiation therapy using ionizing radiation. In some embodiments, a subject can be treated by radiation therapy delivered by a linear accelerator. In some embodiments, a subject can be treated by radiation therapy delivered directly to a tumor. In certain embodiments, radiation therapy can be delivered directly to a tumor at a dose of radiation ranging from about 2 Gy to about 150 Gy (e.g., about 2, about 5, about 10, about 20, about 30, about 40, about 50, about 75, about 100, about 125, about 150 Gy or other suitable radiation range or dose). In certain embodiments, at least one compound herein can be administered with radiation to treat a subject having or suspected of developing a brain cancer. In some embodiments, at least one compound herein can be administered with radiation to treat a subject having or suspected of developing glioblastoma, glioma, or a combination. In some embodiments, compound 19 can be administered with radiation to treat a subject having or suspected of developing glioblastoma, glioma, or a combination.

In some embodiments, an additional therapeutic regimen for use herein can include administering a chemotherapeutic agent. In certain embodiments, a chemotherapeutic agent can include, but is not limited to, Doxorubicin, Melphlan, Roscovitine, Mitomycin C, Hydroxyurea, 5-Fluorouracil, Cisplatin, Ara-C, Etoposide, Gemcitabine, Bortezomib, Sunitinib, Sorafenib, Sodium Valproate, a HDAC Inhibitor, or Dacarbazine. More examples of additional chemotherapeutic agents include, but are not limited to, HDAC inhibitors such as FR01228, Trichostatin A, SAHA and/or PDX101. In some embodiments, the cell cycle inhibitor is a DNA synthesis inhibitor. As used herein, a "DNA synthesis inhibitor" can include a chemotherapeutic agent that inhibits or prevents the synthesis of DNA by a cancer cell. Examples of DNA synthesis inhibitors include but are not limited to AraC (cytarabine), 6-mercaptopurine, 6-thioguanine, 5-fluorouracil, capecitabine, floxuridine, gemcitabine, decitabine, vidaza, fludarabine, nelarabine, cladribine, clofarabine, pentostatin, thiarabine, troxacitabine, sapacitabine or forodesine. More examples of additional chemotherapeutic agents include, but are not limited to, FLT3 inhibitors such as Semexanib (SCT5416), Sunitinib (SU 11248), Midostaurin (PKC412), Lestautinib (CEP-701), Tandutinib (MLN518), CHIR-258, Sorafenib (BAY-43-9006) and/or KW-2449. More non-limiting examples of additional chemotherapeutic agents include farnesyltransferase inhibitors such as tipifarnib (R1 15777, Zarnestra), lonafarnib (SCH66336, Sarasar™) and/or BMS-214662. Other examples of additional chemotherapeutic agents include, but are not limited to, topoisomerase II inhibitors such as the epipodophyllotoxins etoposide, teniposide, anthracyclines doxorubicin and/or 4-epi-doxorubicin. More non-limiting examples of additional chemotherapeutic agents include P-glycoprotein modulators such as zosuquidar trihydrochloride (Z.3HCL), vanadate, or verapamil. More non-limiting examples of additional chemotherapeutic agents include hypomethylating agents such as 5-aza-cytidine or 2' deoxyazacitidine.

In certain embodiments, compounds disclosed herein can be administered in combination with one or more anticancer therapeutics to treat at least one type of cancer in a subject. In some embodiments, at least one compound herein can be administered with at least one inhibitor of an ataxia telangiectasia and Rad3-related (ATR) protein to treat a subject having or suspected of having prostate cancer. In some embodiments, at least one compound herein can be administered with at least one inhibitor of an ATR protein to treat a subject having or suspected of having Ewing sarcoma. Non-limiting examples of inhibitors of ATR proteins (i.e., ATR inhibitors) suitable for use herein can include Schisandrin B, NU6027, BAY 1895344, Dactolisib (NVP-BEZ235), EPT-46464, Torin 2, VE-821, AZ20, M4344 (VX-803), Ceralasertib (AZD6738), Berzosertib (M6620, VX-970), and the like. In certain embodiments, at least one compound herein can be administered with Berzosertib to treat a subject having or suspected of having Ewing sarcoma and/or prostate cancer. In some embodiments, N-((4-((5-chloropyridin-2-yl)oxy)-3-methylphenyl)carbamoyl)-3-methoxycyclobutane-1-carboxamide (Compound 19) can be administered with at least one ATR inhibitor to treat a subject having or suspected of having Ewing sarcoma and/or prostate cancer. In other embodiments, 3-methoxy-N-((3-methyl-4-(thiazol-2-yloxy)phenyl)carbamoyl)cyclobutane-1-carboxamide (Compound 45) can be administered with at least one ATR inhibitor to treat a subject having or suspected of having Ewing sarcoma and/or prostate cancer. In certain embodiments, N-((4-((5-chloropyridin-2-yl)oxy)-3-methylphenyl)carbamoyl)-3-methoxycyclobutane-1-carboxamide (Compound 19) can be administered with Berzosertib to treat a subject having or suspected of having Ewing sarcoma and/or prostate cancer. In some embodiments, 3-methoxy-N-((3-methyl-4-(thiazol-2-yloxy)phenyl)carbamoyl)cyclobutane-1-carboxamide (Compound 45) can be administered with Berzosertib to treat a subject having or suspected of having Ewing sarcoma and/or prostate cancer.

In other embodiments, at least one compound disclosed herein can be administered with at least one inhibitor of serine threonine kinase Checkpoint kinase 1 (CHK1) to treat a subject having or suspected of having prostate cancer. In certain embodiments, at least one compound herein can be administered with at least one inhibitor of CHK1 to treat a subject having or suspected of developing Ewing sarcoma. Non-limiting examples of CHK1 inhibitors of use herein can include MK-8776 (SCH 900776), PF-477736, Prexasertib (LY2606368), Rabusertib (LY2603618), and the like. In certain embodiments, at least one compound herein can be administered with Rabusertib to treat a subject having or suspected of developing Ewing sarcoma and/or prostate cancer. In some embodiments, N-((4-((5-chloropyridin-2-yl)oxy)-3-methylphenyl)carbamoyl)-3-methoxycyclobutane-1-carboxamide (Compound 19) can be administered with at least one CHK1 inhibitor to treat a subject having or suspected of developing Ewing sarcoma and/or prostate cancer. In some embodiments, 3-methoxy-N-((3-methyl-4-(thiazol-2-yloxy)phenyl)carbamoyl)cyclobutane-1-carboxamide (Compound 45) can be administered with at least one CHK1 inhibitor to treat a subject having or suspected of developing Ewing sarcoma and/or prostate cancer. In some embodiments, N-((4-((5-chloropyridin-2-yl)oxy)-3-methylphenyl)carbamoyl)-3-methoxycyclobutane-1-carboxamide (Compound 19) can be administered with Rabusertib to treat a subject having or suspected of developing Ewing sarcoma and/or prostate cancer. In some embodiments, 3-methoxy-N-((3-methyl-4-(thiazol-2-yloxy)phenyl)carbamoyl)cyclobutane-1-carboxamide (Compound 45) can be administered with Rabusertib to treat a subject having or suspected of developing Ewing sarcoma and/or prostate cancer.

In certain embodiments, compound 19, compound 73, compound 86, compound 87, compound 88, compound 90, compound 91, compound 93, compound 94, compound 95, compound 96, compound 97, or compound 98 compound 98, or any combination thereof can be administered with at least one chemotherapy agent to treat a subject having or suspected of developing prostate cancer, wherein the at least one chemotherapy agent can include an inhibitor of an ataxia telangiectasia and Rad3-related (ATR) protein, an inhibitor of checkpoint kinase 1 (CHK1), or a combination thereof. In some embodiments, the inhibitor of an ATR protein Berzosertib and the inhibitor of checkpoint kinase 1 (CHK1) is Rabusertib. In some embodiments, compound 73 or compound 76, the inhibitor of checkpoint kinase 1 (CHK1) is Rabusertib, and wherein administering compound 73 or compound 76 and Rabusertib results in a synergistic reduction in viability of prostate cancer cells in the subject when compared to administration of either compound 73 or compound 76 or Rabusertib alone.

In some embodiments, at least one compound disclosed herein can be administered with at least one inhibitor of PARP1 (poly(ADP)-ribose polymerase-1) to treat a subject having or suspected of developing pancreatic cancer. Non-limiting examples of PARP1 inhibitors suitable for use herein can include Veliparib, Pamiparib (BGB-290), CEP 9722, E7016, Rucaparib, Niraparib, Talazoparib, Olaparib, and the like. In some embodiments, at least one compound herein can be administered with Olaparib to treat a subject having or suspected of developing pancreatic cancer. In other embodiments, N-((4-((5-chloropyridin-2-yl)oxy)-3-methylphenyl)carbamoyl)-3-methoxycyclobutane-1-carboxamide (Compound 19) can be administered with at least one PARP1 inhibitor to treat a subject having or suspected of developing pancreatic cancer. In certain embodiments, 3-methoxy-N-((3-methyl-4-(thiazol-2-yloxy)phenyl)carbamoyl)cyclobutane-1-carboxamide (Compound 45) can be administered with at least one PARP1 inhibitor to treat a subject having or suspected of developing pancreatic cancer. In other embodiments, N-((4-((5-chloropyridin-2-yl)oxy)-3-methylphenyl)carbamoyl)-3-methoxycyclobutane-1-carboxamide (Compound 19) can be administered with Olaparib to treat a subject having or suspected of developing pancreatic cancer. In some embodiments, 3-methoxy-N-((3-methyl-4-(thiazol-2-yloxy)phenyl)carbamoyl)cyclobutane-1-carboxamide (Compound 45) can be administered with Olaparib to treat a subject having or suspected of developing pancreatic cancer.

In some embodiments, at least one compound herein can be administered with at least one chemotherapy agent to treat a subject having or suspected of developing glioblastoma and/or glioma, where the at least one chemotherapy agent is an alkylating agent. Non-limiting examples of alkylating agents suitable for use herein can include chlorambucil, cyclophosphamide, thiotepa, busulfan, temozolomide, and the like. In some embodiments, at least one compound herein can be administered with temozolomide to treat a subject having or suspected of having glioblastoma and/or glioma. In some embodiments, N-((4-((5-chloropyridin-2-yl)oxy)-3-methylphenyl)carbamoyl)-3-methoxycyclobutane-1-carboxamide (Compound 19) can be administered with at least one alkylating agent to treat a subject having or suspected of developing glioblastoma and/or glioma. In some embodiments, 3-methoxy-N-((3-methyl-4-(thiazol-2-yloxy)phenyl)carbamoyl)cyclobutane-1-carboxamide (Compound 45) can be administered with at least one alkylating agent to treat a subject having or suspected of developing glioblastoma and/or glioma. In some embodiments, N-((4-((5-chloropyridin-2-yl)oxy)-3-methylphenyl)carbamoyl)-3-methoxycyclobutane-1-carboxamide (Compound 19) can be administered with temozolomide to treat a subject having or suspected of developing glioblastoma and/or glioma. In some embodiments, 3-methoxy-N-((3-methyl-4-(thiazol-2-yloxy)phenyl)carbamoyl)cyclobutane-1-carboxamide (Compound 45) can be administered with temozolomide to treat a subject having or suspected of developing glioblastoma and/or glioma.

In some embodiments and further to the disclosure herein, compound 19, compound 73, compound 86, compound 87, compound 88, compound 90, compound 91, compound 93, compound 94, compound 95, compound 96, compound 97, or compound 98 compound 98, or any combination thereof can be administered before, during and/or after at least one chemotherapy agent to treat glioblastoma, glioma, or a combination thereof in a subject, where the at least one chemotherapy agent includes at least one alkylating agent. In some embodiments, the at least one alkylating agent includes, but is not limited to, chlorambucil, cyclophosphamide, thiotepa, busulfan, temozolomide, or any combination thereof. In some embodiments, the compound is compound 59 or compound 19, wherein the at least one alkylating agent is Temozolomide, and wherein administering compound 59 or compound 19 and Temozolomide results in a synergistic reduction in viability of glioblastoma, glioma cancer cells in the subject when compared to administration of either compound 59 or compound 19 or Temozolomide alone.

V. Kits

In certain embodiments, kits are provided herein for use in treating or alleviating a targeted disease or condition treatable by use of a compound disclosed herein such as cancer and/or a tumor as described herein. In some embodiments, the kit can include instructions for use in accordance with any of the methods described herein. In other embodiments, instructions can include a description of administering a compound and/or pharmaceutical composition disclosed herein to a subject at risk of the target disease. In certain embodiments, kits disclosed herein can include instructions for using the components of the kit, for example relating to the use of a compound and/or pharmaceutical composition disclosed herein. In accordance with embodiments herein, kits can include instructions that provide information as to dosage, dosing schedule, and route of administration for the intended treatment.

In some embodiments, kits disclosed herein can include at least one container. In accordance with embodiments herein, containers can be any container such as tubes, vials, bottles, syringe, such as unit doses, bulk packages (e.g., multi-dose packages) or sub-unit doses. Instructions supplied in the kits of the invention can be written instructions on a label or package insert (e.g., a paper sheet included in the kit), but machine-readable instructions (e.g., instructions carried on a magnetic or optical storage disk) are also acceptable. The label or package insert indicates that the composition is used for treating, delaying the onset and/or alleviating the disease, such as cancer or a tumor. Instructions can be provided for practicing any of the methods described herein.

Kits disclosed herein can include suitable packaging. Suitable packaging includes, but is not limited to, vials, bottles, jars, flexible packaging (e.g., sealed Mylar or plastic bags), and the like. Also contemplated herein are packages for use in combination with a specific device, such as an inhaler, nasal administration device (e.g., an atomizer) or an infusion device such as a minipump. A kit can have a sterile access port (for example the container can be an intravenous solution bag or a vial having a stopper pierceable by a hypodermic injection needle). The container can also have a sterile access port (for example the container can be an intravenous solution bag or a vial having a stopper pierceable by a hypodermic injection needle). At least one active agent in the composition can be a compound disclosed herein.

Kits can optionally provide additional components such as buffers and interpretive information. Normally, the kit includes a container and a label or package insert(s) on or associated with the container. In some embodiments, the invention provides articles of manufacture including contents of the kits described above.

EXAMPLES

The following examples are included to illustrate certain embodiments. It should be appreciated by those of skill in the art that the techniques disclosed in the examples which follow represent techniques discovered to function well in the practice of the claimed methods, compositions and apparatus. However, those of skill in the art should, in light of the present disclosure, appreciate that changes can be made in some embodiments which are disclosed and still obtain a like or similar result without departing from the spirit and scope of embodiments of the inventions.

Example 1

Figure 1:
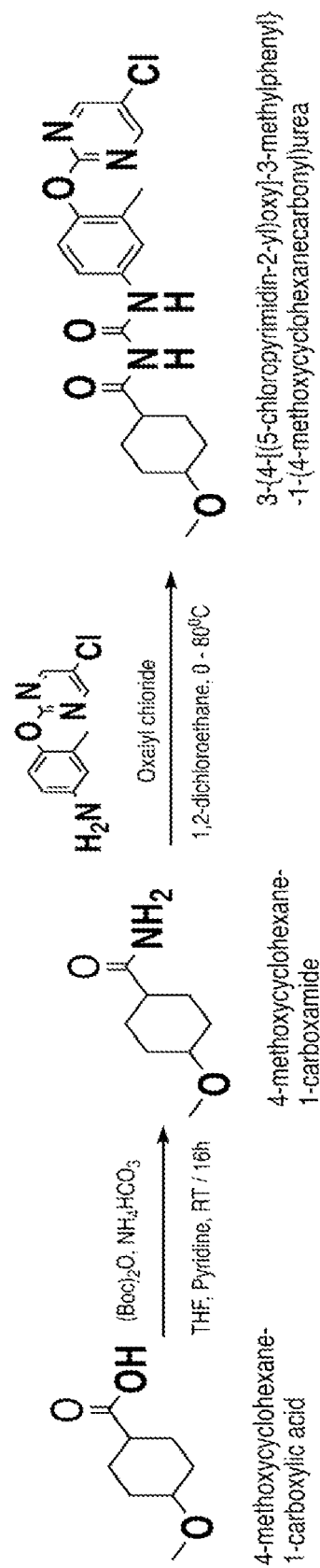
FIG. 1 represents an exemplary experiment illustrating a chemical reaction equation for synthesis of N-((4-((5-chloropyrimidin-2-yl)oxy)-3-methylphenyl)carbamoyl)-4-methoxycyclohexane-1-carboxamide (Compound 1) in accordance with certain embodiments of the present disclosure.

In one exemplary method, N-((4-((5-chloropyrimidin-2-yl)oxy)-3-methylphenyl)carbamoyl)-4-methoxycyclohexane-1-carboxamide (Compound 1) was synthesized. FIG. 1 illustrates the chemical reaction equation for synthesis of Compound 1.

4-methoxycyclohexane-1-carboxamide. 4-Methoxycyclohexane-1-carboxylic acid (500 mg, 3.16 mmol), pyridine (0.7 mL, 8.34 mmol), di-tert-butyl dicarbonate (758 mg, 3.48 mmol) and ammonium bicarbonate (375 mg, 4.74 mmol) were added to freshly distilled THF (20 mL). The reaction mixture was stirred at room temperature for 16 hours, then petroleum ether was added, and the precipitate was filtered. The filter cake was dried to afford 4-methoxycyclohexane-1-carboxamide (380 mg, 2.41 mmol) (Yield 76%) as a white solid. The crude intermediate was used directly in the next step.

N-((4-((5-chloropyrimidin-2-yl)oxy)-3-methylphenyl) carbamoyl)-4-methoxycyclohexane-1-carboxamide. To a solution of 4-methoxycyclohexane-1-carboxamide (200 mg, 1.27 mmol) in 1,2-dichloroethane (8 mL) at room temperature was added oxalyl chloride (242 mg, 1.91 mmol). The reaction mixture was heated at 80° C. for 6 hours and then concentrated. The resulting mixture was dissolved in 1,2-dichloroethane (8 mL). The resultant solution was cooled to 0° C. and then treated with 4-((5-chloropyrimidin-2-yl)oxy)-3-methylaniline (200 mg, 0.85 mmol). The mixture was allowed to gradually warm up to room temperature and stirred for 16 hours. The mixture was concentrated, and the residue was purified by preparative HPLC to afford compound 1 (130 mg, 0.31 mmol) (Yield 36%) as a white solid.

In an exemplary method, (1H) NMR spectra was recorded on Bruker 400 MHz machine with TMS (tetramethyl silane) as internal standard. $^1$HNMR (DMSO-d6): 10.68-1.66 (m, 1H), 10.60-10.57 (m, 1H), 8.74 (s, 2H), 7.47-7.41 (m, 2H), 7.11-7.09 (m, 1H), 3.41-3.37 (m, 0.5H), 3.24-3.21 (m, 3H), 3.12-3.07 (m, 0.5 H), 2.48-2.35 (m, 1H), 2.11-2.06 (m, 1H), 2.05 (s, 3H), 1.92-1.83 (m, 2H), 1.69-1.62 (m, 1H), 1.61-1.52 (m, 1H), 1.49-1.35 (m, 2H), 1.14-1.03 (m, 1H).

In another exemplary method, HPLC analysis was performed with UV detectors at 214 nm, and 254 nm wavelength and low-resolution mass spectrometry. LC-MS (ESI$^+$): m/z 419 (M+H)$^+$.

Example 2

Figure 2:
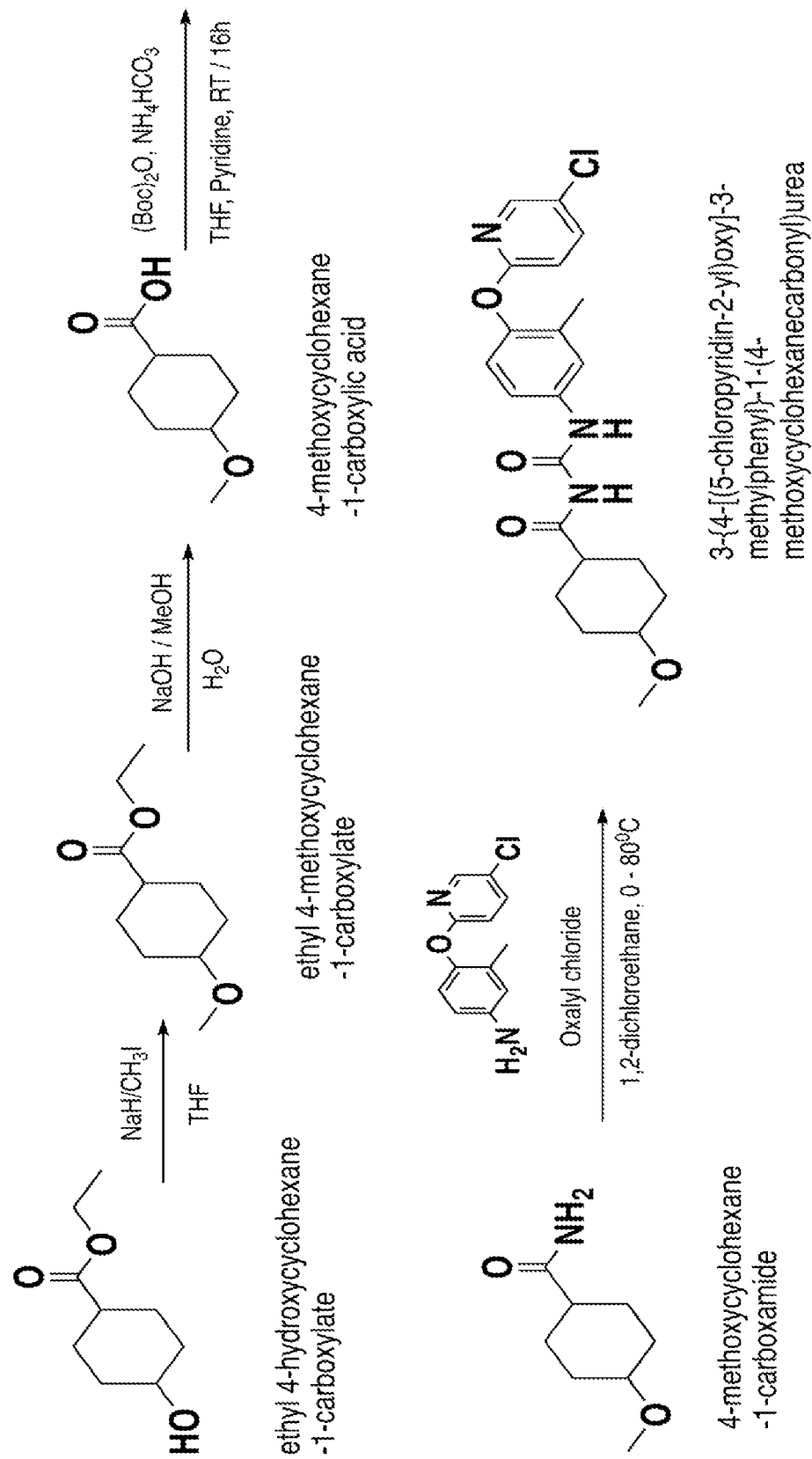
FIG. 2 represents an exemplary experiment illustrating a chemical reaction equation for synthesis of N-((4-((5-chloropyridin-2-yl)oxy)-3-methylphenyl)carbamoyl)-4-methoxycyclohexane-1-carboxamide (Compound 7) in accordance with certain embodiments of the present disclosure.

In another exemplary method, N-((4-((5-chloropyridin-2-yl)oxy)-3-methylphenyl)carbamoyl)-4-methoxycyclohexane-1-carboxamide (Compound 7) was synthesized. FIG. 2 illustrates the chemical reaction equation for synthesis of Compound 7.

Ethyl 4-methoxycyclohexane-1-carboxylate. The mixture of ethyl 4-hydroxycyclohexane-1-carboxylate (27.5 g, 0.16 mol), NaH (9.5 g, 0.24 mol) in THF (500 mL) was stirred at 0° C. for 30 minutes. CH$_3$I (45.3 g, 0.32 mol) was added at 0° C. After 30 minutes of stirring, the reaction mixture was warmed up to room temperature and kept stirring overnight. The reaction was quenched with brine (300 mL), the mixture was then extracted with ethyl acetate (300 mL×3), dried over Na$_2$SO$_4$, filtered and concentrated under reduced pressure to afford ethyl 4-methoxycyclohexane-1-carboxylate (19.88 g, 0.09 mmol) (Yield 66%) as a yellow liquid. The crude intermediate was used in the next step without further purification. $^1$H NMR (400 MHz, DMSO-d6) δ 4.14-3.97 (m, 2H), 3.32-3.25 (m, 0.5H), 3.22-3.19 (m, 3H), 3.15-3.0 (m, 0.5H), 2.47-2.17 (m, 1H), 2.04-1.78 (m, 2H), 1.73-1.43 (m, 4H), 1.41-1.26 (m, 2H), 1.24-1.06 (m, 3H).

4-methoxycyclohexane-1-carboxylic acid. The solution of ethyl 4-methoxycyclohexane-1-carboxylate (19.88 g, 0.11 mol), NaOH (17.08 g, 0.43 mol) in MeOH/H$_2$O (110 ml, v/v=10:1) was stirred at room temperature overnight. MeOH was evaporated at reduced pressure and the residual aqueous solution was treated with HCl to pH=4. The mixture was extracted with ethyl acetate (300 mL×3), dried over Na$_2$SO$_4$, filtered and concentrated under reduced pressure to afford 4-methoxycyclohexane-1-carboxylic acid (8.6 g, 0.05 mmol) (Yield 51%) as a yellow liquid. $^1$H NMR (400 MHz, DMSO-d6) δ 12.05 (s, 1H), 3.32-3.25 (m, 0.5H), 3.22-3.19 (m, 3H), 3.15-3.0 (m, 0.5H), 2.32-2.08 (m, 1H), 2.02-1.92 (m, 1H), 1.91-1.83 (m, 1H), 1.73-1.60 (m, 2H), 1.58-1.21 (m, 3H), 1.18-1.03 (m, 1H).

4-methoxycyclohexane-1-carboxamide. 4-methoxycyclohexane-1-carboxylic acid (2 g, 12.64 mmol), pyridine (2.6 mL, 32.87 mmol), di-tert-butyl dicarbonate (3.03 g, 13.91 mmol) and ammonium bicarbonate (1.50 g, 18.96 mmol) were added to THF (80 mL). The reaction mixture was stirred at room temperature for 16 hours, then petroleum ether was added, and the precipitate was filtered. The filter cake was dried to afford 4-methoxycyclohexane-1-carboxamide (1.3 g, 8.28 mmol) (Yield 65%) as a white solid. $^1$H NMR (400 MHz, DMSO-d6) δ 7.27-7.07 (m, 1H), 6.74-6.56 (m, 1H), 3.32-3.25 (m, 0.5H), 3.22-3.19 (m, 3H), 3.15-3.0 (m, 0.5H), 2.15-1.94 (m, 2H), 1.84-1.69 (m, 2H), 1.68-1.52 (m, 1H), 1.48-1.22 (m, 3H), 1.13-0.98 (m, 1H).

4-((5-chloropyridin-2-yl)oxy)-3-methylaniline. A solution of 4-amino-2-methylphenol (2.0 g, 16.25 mmol), 2,5-dichloropyridine (2.64 g, 17.87 mmol), Cs$_2$CO$_3$ (13.24 g, 40.63 mmol), CuI (0.62 g, 3.25 mmol) in DMF (30 mL) was stirred at 130° C. for 18 hours. After quenching the reaction, the reaction mixture was extracted with ethyl acetate (300 mL×3). The organic layer was washed with brine (300 mL), dried over Na$_2$SO$_4$, filtered and concentrated. The crude product was purified by flash column chromatography (Petroleum Ether:Ethyl Acetate=5:1) to get 4-((5-chloropyridin-2-yl)oxy)-3-methylaniline (2.3 g, 9.80 mmol) (Yield 61%) as a brown solid. LC-MS (ESI$^+$): m/z 235 (M+H)$^+$.

N-((4-((5-chloropyridin-2-yl)oxy)-3-methylphenyl)carbamoyl)-4-methoxycyclohexane-1-carboxamide (Compound 7). To a solution of 4-methoxycyclohexane-1-carboxamide (334 mg, 2.13 mmol) in 1,2-dichloroethane (10 mL) at room temperature was added oxalyl chloride (0.54 mL, 6.44 mmol). The reaction mixture was heated at 80° C. for 20 hours and then concentrated. The resulting residue was dissolved in 1,2-dichloroethane (8 mL), the resultant solution was cooled to 0° C. and then treated with 4-((5-chloropyridin-2-yl)oxy)-3-methylaniline (100 mg, 0.43 mmol). The mixture was allowed to gradually warm to room temperature and stirred for 16 hours. The mixture was concentrated and the residue was purified by preparative HPLC to afford N-((4-((5-chloropyridin-2-yl)oxy)-3-methylphenyl)carbamoyl)-4-methoxycyclohexane-1-carboxamide (58.4 mg, 0.14 mmol). N-((4-((5-chloropyridin-2-yl)oxy)-3-methylphenyl)carbamoyl)-4-methoxycyclohexane-1-carboxamide was synthesized using as per the procedure for Compound 1. Yield 32%. NMR and HPLC analysis were performed as described in exemplary methods herein. $^1$H NMR (400 MHz, DMSO-d6) δ 10.69-10.62 (m, 1H), 10.62-10.52 (m, 1H), 8.16-8.15 (m, 1H), 7.95-7.92 (m, 1H), 7.45-7.38 (m, 2H), 7.08-7.01 (m, 2H), 3.41-3.37 (m, 0.5H), 3.24-3.21 (m, 3H), 3.16-3.0 (m, 0.5H), 2.47-2.30 (m, 1H), 2.08-2.06 (m, 1H), 2.04 (s, 3H), 1.88-1.86 (m, 2H), 1.69-1.40 (m, 2H), 1.39-1.36 (m, 2H), 1.10-1.06 (m, 1H). LC-MS (ESI$^+$): m/z 418 (M+H)$^+$.

Example 3

Figure 3:
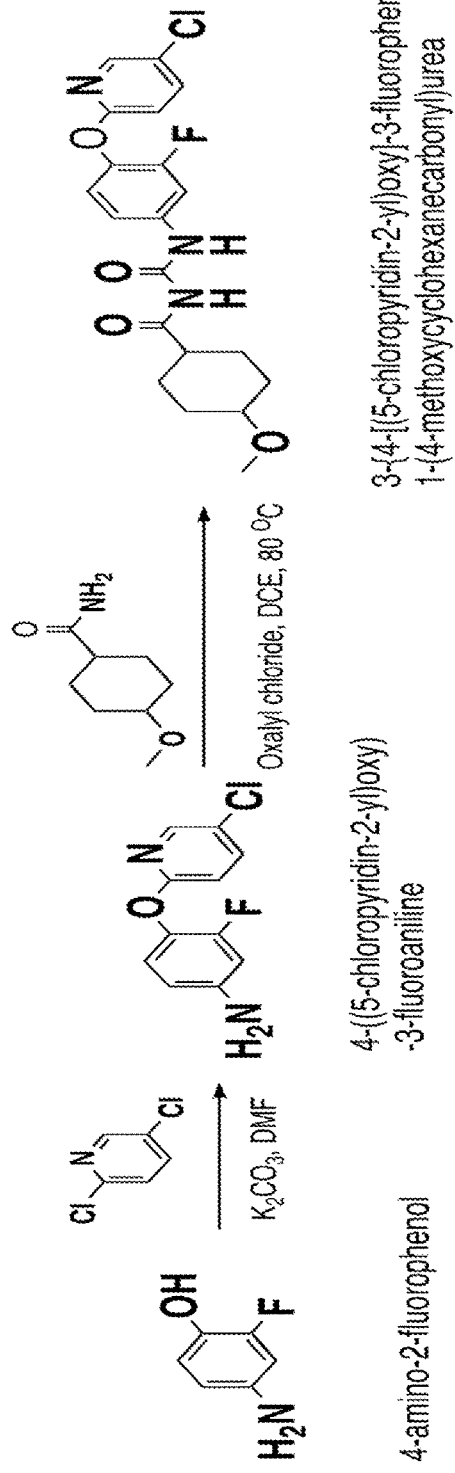
FIG. 3 represents an exemplary experiment illustrating a chemical reaction equation for synthesis of N-((4-((5-chloropyridin-2-yl)oxy)-3-fluorophenyl)carbamoyl)-4-methoxycyclohexane-1-carboxamide (Compound 12) in accordance with certain embodiments of the present disclosure.

In another exemplary method, N-((4-((5-chloropyridin-2-yl)oxy)-3-fluorophenyl)carbamoyl)-4-methoxycyclohexane-1-carboxamide (Compound 12) was synthesized. FIG. 3 illustrates the chemical reaction equation for synthesis of Compound 12.

4-((5-chloropyridin-2-yl)oxy)-3-fluoroaniline. A solution of 4-amino-2-fluorophenol (500 mg, 3.93 mmol), 2,5-dichloropyridine (582 mg, 3.93 mmol), K$_2$CO$_3$ (13.24 g, 40.63 mmol) in DMF (10 mL) was stirred at room temperature for 18 hours. After quenching the reaction, the reaction mixture was extracted with ethyl acetate (300 mL×3). The organic layer was washed with brine (300 mL), dried over Na$_2$SO$_4$, filtered and concentrated. The crude product was purified by flash column chromatography (Petroleum Ether:Ethyl Acetate=3:1) to get 4-((5-chloropyridin-2-yl)oxy)-3-fluoroaniline (370 mg, 1.55 mmol) (Yield 39%) as a yellow solid. LC-MS (ESI⁺): m/z 239 (M+H)⁺.

N-((4-((5-chloropyridin-2-yl)oxy)-3-fluorophenyl)carbamoyl)-4-methoxycyclohexane-1-carboxamide. N-((4-((5-chloropyridin-2-yl)oxy)-3-fluorophenyl)carbamoyl)-4-methoxycyclohexane-1-carboxamide was synthesized using procedure similar to Compound 1. (Yield 11%) LC-MS (ESI⁺): m/z 422 (M+H)⁺. ¹H NMR (400 MHz, DMSO-d6) δ 10.79-10.61 (m, 2H), 8.19-8.14 (m, 1H), 8.02-7.94 (m, 1H), 7.72-7.65 (m, 1H), 7.35-7.24 (m, 2H), 7.23-7.15 (m, 1H), 3.41-3.37 (m, 0.5H), 3.26-3.17 (m, 3H), 3.16-3.03 (m, 0.5H), 2.48-2.30 (m, 1H), 2.11-1.99 (m, 1H), 1.94-1.81 (m, 2H), 1.75-1.51 (m, 2H), 1.48-1.32 (m, 2H), 1.15-1.01 (m, 1H).

Example 4

Figure 4:
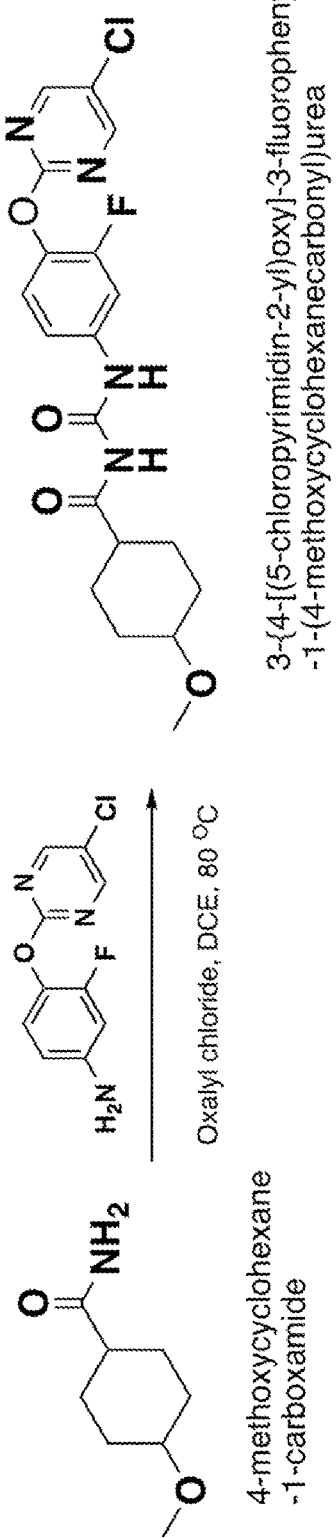
FIG. 4 represents an exemplary experiment illustrating a chemical reaction equation for synthesis of N-((4-((5-chloropyrimidin-2-yl)oxy)-3-fluorophenyl)carbamoyl)-4-methoxycyclohexane-1-carboxamide (Compound 14) in accordance with certain embodiments of the present disclosure.

In another exemplary method, N-((4-((5-chloropyrimidin-2-yl)oxy)-3-fluorophenyl)carbamoyl)-4-methoxycyclohexane-1-carboxamide (Compound 14) was synthesized. FIG. 4 illustrates the chemical reaction equation for synthesis of Compound 14.

N-((4-((5-chloropyrimidin-2-yl)oxy)-3-fluorophenyl)carbamoyl)-4-methoxycyclohexane-1-carboxamide was synthesized using procedure similar to Compound 1. LC-MS (ESI⁺): m/z 423.5 (M+H)⁺.

Compound 14A: Yield 4.4%. ¹H NMR (400 MHz, DMSO-d6) δ 10.72-10.70 (m, 2H), 8.79 (s, 2H), 7.74-7.70 (m, 1H), 7.38-7.32 (m, 2H), 3.38-3.33 (m, 1H), 3.21 (s, 3H), 2.50-2.43 (m, 1H), 1.89-1.85 (m, 2H), 1.71-1.62 (m, 2H), 1.58-1.54 (m, 2H), 1.43-1.36 (m, 2H).

Compound 14B: Yield 4.4%. ¹H NMR (400 MHz, DMSO-d6) δ 10.75-10.67 (m, 2H), 8.79 (s, 2H), 7.74-7.70 (m, 1H), 7.38-7.32 (m, 2H), 3.24 (s, 3H), 3.12-3.06 (m, 1H), 2.41-2.35 (m, 1H), 2.07-2.04 (m, 2H), 1.90-1.87 (m, 2H), 1.47-1.37 (m, 2H), 1.13-1.03 (m, 2H).

Example 5

Figure 5:
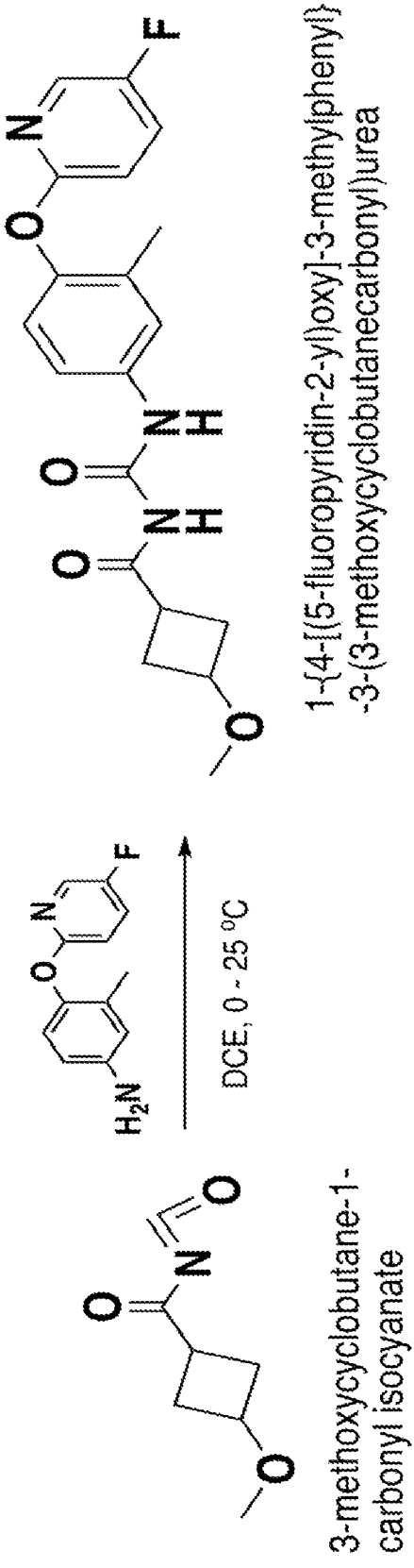
FIG. 5 represents an exemplary experiment illustrating a chemical reaction equation for synthesis of N-((4-((5-fluoropyridin-2-yl)oxy)-3-methylphenyl)carbamoyl)-3- methoxycyclobutane-1-carboxamide (Compound 15) in accordance with certain embodiments of the present disclosure.

In another exemplary method, N-((4-((5-fluoropyridin-2-yl)oxy)-3-methylphenyl)carbamoyl)-3-methoxycyclobutane-1-carboxamide (Compound 15) was synthesized. FIG. 5 illustrates the chemical reaction equation for synthesis of Compound 15.

1-{4-[(5-fluoropyridin-2-yl)oxy]-3-methylphenyl}-3-(3-methoxycyclobutanecarbonyl) urea. A three-necked round bottom flask equipped with magnetic stirrer were charged with 4-((5-fluoropyridin-2-yl)oxy)-3-methylaniline (150 mg, 0.69 mmol) and DCE (30 mL), a solution of 3-methoxycyclobutane-1-carbonyl isocyanate (160 mg, 1.03 mmol) in DCE (5 mL) was added dropwise via syringe at 0° C. under N₂. The mixture was allowed to gradually warm to room temperature and stirred for 16 hours. The mixture was concentrated and the residue was purified by preparative HPLC to afford two isomers of N-((4-((5-fluoropyridin-2-yl)oxy)-3-methylphenyl)carbamoyl)-3-methoxycyclobutanecarboxamide.

Compound 15A: 45.8 mg, 0.12 mmol; Compound 15B: 17.0 mg, 0.05 mmol (Yield 24%) as a white solid. NMR and HPLC analysis were performed as described in exemplary methods herein. LC-MS (ESI⁺): m/z 374 (M+H)⁺. Compound 15A: ¹H NMR (400 MHz, DMSO-d6) δ 10.66 (s, 1H), 10.52 (s, 1H), 8.09 (d, J=3.2 Hz, 1H), 7.88-7.71 (m, 1H), 7.51-7.31 (m, 2H), 7.13-6.91 (m, 2H), 3.86-3.70 (m, 1H), 3.13 (s, 3H), 2.87-2.73 (m, 1H), 2.41-2.40 (m, 2H), 2.09-1.91 (m, 5H). Compound 15B: ¹H NMR (400 MHz, DMSO-d6) δ 10.65 (s, 1H), 10.54 (s, 1H), 8.09 (d, J=3.2 Hz, 1H), 7.85-7.72 (m, 1H), 7.49-7.33 (m, 2H), 7.11-6.95 (m, 2H), 3.80-3.40 (m, 1H), 3.24-3.15 (m, 1H), 3.13 (s, 3H), 2.41-2.40 (m, 2H), 2.17-2.08 (m, 2H), 2.05 (s, 3H).

Example 6

In another exemplary method, N-((4-((5-cyanopyridin-2-yl)oxy)-3-methylphenyl)carbamoyl)-3-methoxycyclobutane-1-carboxamide (Compound 16) was synthesized. FIG. 6 illustrates the chemical reaction equation for synthesis of Compound 16.

N-((4-((5-cyanopyridin-2-yl)oxy)-3-methylphenyl)carbamoyl)-3-methoxycyclobutane-1-carboxamide was synthesized as per the procedure for Compound 15. LC-MS (ESI⁺): m/z 381 (M+H)⁺.

Compound 16A: ¹H NMR (400 MHz, DMSO-d6) δ 10.67 (s, 1H), 10.55 (s, 1H), 8.62 (d, J=2.0 Hz, 1H), 8.31 (dd, J=8.4, 2.4 Hz, 1H), 7.52-7.38 (m, 2H), 7.23 (d, J=8.4 Hz, 1H), 7.07 (d, J=8.4 Hz, 1H), 3.84-3.72 (m, 1H), 3.13 (s, 3H), 2.88-2.75 (m, 1H), 2.41 (m, 2H), 2.08-1.94 (m, 5H).

Compound 16B: ¹H NMR (400 MHz, DMSO-d6) δ 10.67 (s, 1H), 10.56 (d, J=9.6 Hz, 1H), 8.61 (d, J=2.0 Hz, 1H), 8.30 (dd, J=8.4, 2.0 Hz, 1H), 7.56-7.36 (m, 2H), 7.22 (d, J=8.4 Hz, 1H), 7.07 (d, J=8.4 Hz, 1H), 4.05-3.98 (m, 1H), 3.24-3.15 (m, 1H), 3.13 (s, 3H), 2.41 (m, 2H), 2.17-2.07 (m, 2H), 2.02 (s, 3H).

Example 7

In another exemplary method, N-((4-((5-chloropyridin-2-yl)oxy)-3-methylphenyl)carbamoyl)-3-methoxycyclobutane-1-carboxamide (Compound 19) was synthesized. FIG. 7 illustrates the chemical reaction equation for synthesis of Compound 19.

1-{4-[(5-chloropyridin-2-yl)oxy]-3-methylphenyl}-3-(3-methoxycyclobutanecarbonyl) urea was synthesized as per the procedure for compound 15 (Yield 11%), yielding two isomers, Compound 19A and Compound 19B. NMR and HPLC analysis were performed as described in exemplary methods herein. LC-MS (ESI⁺): m/z 390 (M+H)⁺. Compound 19A: ¹H NMR (400 MHz, DMSO-d6) δ 10.67 (s, 1H), 10.53 (s, 1H), 8.16 (d, J=2.6 Hz, 1H), 7.95 (dd, J=8.8, 2.7 Hz, 1H), 7.50-7.34 (m, 2H), 7.05 (dd, J=16.5, 8.4 Hz, 2H), 3.84-3.74 (m, 1H), 3.14 (s, 3H), 2.81 (dd, J=16.8, 8.4 Hz, 1H), 2.47-2.36 (m, 2H), 2.11-1.93 (m, 5H). Compound 19B: ¹H NMR (400 MHz, DMSO-d6) δ 10.66 (s, 1H), 10.55 (s, 1H), 8.15 (d, J=2.8 Hz, 1H), 7.94 (dd, J=8.8, 2.7 Hz, 1H), 7.49-7.36 (m, 2H), 7.05 (dd, J=16.0, 8.4 Hz, 2H), 4.06-3.92 (m, 1H), 3.26-3.15 (m, 1H), 3.13 (s, 3H), 2.41-2.40 (m, 2H), 2.17-2.06 (m, 2H), 2.05 (s, 3H).

Example 8

In another exemplary method, N-((4-((5-chloropyrimidin-2-yl)oxy)-3-methylphenyl)carbamoyl)-3-methoxycyclobutane-1-carboxamide (Compound 20) was synthesized. FIG. 8 illustrates the chemical reaction equation for synthesis of Compound 20.

Ethyl 3-methoxycyclobutane-1-carboxylate. Ethyl 3-hydroxycyclobutane-1-carboxylate (5 g, 34.68 mmol) was dissolved in dry THF (100 mL) and cooled to 0° C. NaH (1.25 g, 52.02 mmol) was then added in portions during a period of 10 minutes. The reaction mixture was stirred at 0° C. for 30 minutes, then warmed up to room temperature and kept stirring overnight. Quenched with brine (300 mL), the mixture was then extracted with ethyl acetate (100 mL×3), dried over Na₂SO₄, filtered and concentrated under reduced pressure to afford ethyl 3-methoxycyclobutane-1-carboxylate (4.4 g, 27.8 mmol) (yield 80%) as a yellow liquid. The crude intermediate was used in the next step without further purification.

3-methoxycyclobutane-1-carboxylic acid. To a solution of ethyl 3-methoxycyclobutane-1-carboxylate (4.4 g, 27.81 mmol) in MeOH/$H_2O$ (100 mL, 10:1) was added NaOH (1.33 g, 55.63 mmol) and stirred at room temperature overnight. MeOH was evaporated at reduced pressure and the residual aqueous solution was treated with HCl to pH=4. The mixture was extracted with ethyl acetate (100 mL×3), dried over $Na_2SO_4$, filtered and concentrated under reduced pressure to afford 3-methoxycyclobutane-1-carboxylic acid (3.2 g, 24.6 mmol) (Yield=88%) as a yellow liquid. $^1$H NMR (400 MHz, DMSO-d6) δ 12.13 (s, 1H), 3.79-3.67 (m, 1H), 3.11 (d, J=2.4 Hz, 3H), 2.59-2.53 (m, 1H), 2.44-2.29 (m, 2H), 1.97-1.86 (m, 2H).

3-methoxycyclobutane-1-carboxamide. To a solution of 3-methoxycyclobutane-1-carboxylic acid (3 g, 23.05 mmol) in THF (70 mL) was added pyridine (4.74 g, 59.94 mmol), $(BOC)_2O$ (5.53 g, 25.36 mmol) and $NH_4HCO_3$ (2.73 g, 34.58 mmol), the reaction mixture was stirred at room temperature for 20 hours under $N_2$, then petroleum ether was added and the precipitate was filtered. The filter cake was dried to afford 4-methoxycyclohexane-1-carboxamide (2.1 g, 16.28 mmol) (yield 70%) as a white solid. $^1$H NMR (400 MHz, DMSO-d6) δ 7.19 (s, 1H), 6.74 (s, 1H), 3.78-3.61 (m, 1H), 3.10 (s, 3H), 2.47-2.39 (m, 1H), 2.27 (m, 2H), 1.94-1.83 (m, 2H).

3-methoxycyclobutane-1-carbonyl isocyanate. To a solution of 3-methoxycyclobutane-1-carboxamide (1.5 g, 11.62 mmol) in DCE (80 mL) was added dropwise. Oxalyl chloride (2.9 ml, 34.86 mmol) with stirring at 0° C., then the reaction mixture was refluxed at 80° C. for 20 hours under $N_2$. The reaction mixture was concentrated under reduced pressure to provide product as an oil (1.3 g, 8.39 mmol) (yield 72%). The crude product was used directly for the next step without purification.

N-((4-((5-chloropyrimidin-2-yl)oxy)-3-methylphenyl) carbamoyl)-3-methoxycyclobutane-1-carboxamide. N-((4-((5-chloropyrimidin-2-yl)oxy)-3-methylphenyl)carbamoyl)-3-methoxycyclobutane-1-carboxamide was synthesized using the procedure as per compound 1 (Yield 13%) yielding two isomers, Compound 20A and Compound 20B. NMR and HPLC analysis were performed as described in exemplary methods herein. LC-MS (ESI$^+$): m/z 391 (M+H)$^+$. Compound 20A: $^1$H NMR (400 MHz, DMSO-d6) δ 10.67 (s, 1H), 10.54 (s, 1H), 8.74 (s, 2H), 7.46-7.39 (m, 2H), 7.10-7.08 (m, 1H), 3.85-3.73 (m, 1H), 3.13 (s, 3H), 2.87-2.76 (m, 1H), 2.46-2.37 (m, 2H), 2.08-1.96 (m, 5H). Compound 20B: $^1$H NMR (400 MHz, DMSO-d6) δ 10.67 (s, 1H), 10.57 (s, 1H), 8.75 (s, 2H), 7.52-7.35 (m, 2H), 7.10 (d, J=8.4 Hz, 1H), 4.08-3.92 (m, 1H), 3.19-3.12 (m, 1H), 2.42-2.40 (m, 2H), 2.19-2.08 (m, 2H), 2.06 (s, 3H).

Example 9

In another exemplary method, 4-methoxy-N-((3-methyl-4-((5-methylpyrimidin-2-yl)oxy)phenyl)carbamoyl)cyclohexane-1-carboxamide (Compound 27) was synthesized. FIG. 9 illustrates the chemical reaction equation for synthesis of Compound 27.

4-methoxy-N-((3-methyl-4-((5-methylpyrimidin-2-yl) oxy)phenyl)carbamoyl)cyclohexane-1-carboxamide was synthesized as per Compound 1, yielding two isomers, Compound 27A and Compound 27B. NMR and HPLC analysis were performed as described in exemplary methods herein. LC-MS (ESI$^+$): m/z 399.8 (M+H)$^+$. Compound 27A: Yield 4.3%; $^1$H NMR (400 MHz, DMSO-d$_6$) δ 10.67-10.51 (m, 2H), 8.48-8.42 (m, 2H), 7.46-7.42 (m, 1H), 7.41-7.36 (m, 1H), 7.05-7.01 (m, 1H), 3.37-3.31 (m, 1H), 3.21 (s, 3H), 2.48-2.41 (m, 1H), 2.20 (s, 3H), 2.03 (s, 3H), 1.92-1.82 (m, 2H), 1.74-1.51 (m, 2H), 1.61-1.51 (m, 2H), 1.45-1.32 (m, 2H). Compound 27B: Yield 6.3%; $^1$H NMR (400 MHz, DMSO-d$_6$) δ 10.71-10.51 (m, 2H), 8.48-8.42 (m, 2H), 7.46-7.42 (m, 1H), 7.41-7.36 (m, 1H), 7.05-7.01 (m, 1H), 3.23 (s, 3H), 3.15-3.04 (m, 1H), 2.45-2.31 (m, 1H), 2.20 (s, 3H), 2.11-2.04 (m, 2H), 2.03 (s, 3H), 1.93-1.82 (m, 2H), 1.49-1.34 (m, 2H), 1.16-1.01 (m, 2H).

Example 10

In another exemplary method, N-((4-((5-isopropylpyridin-2-yl)oxy)-3-methylphenyl)carbamoyl)-4-methoxycyclohexane-1-carboxamide (Compound 34) was synthesized. FIG. 10 illustrates the chemical reaction equation for synthesis of Compound 34.

2-(6-chloropyridin-3-yl)propan-2-ol. To a solution of methyl 6-chloronicotinate (1.00 g, 5.83 mmol) in THF (8 mL) was added a solution of methyl magnesium bromide (5.83 mL, 17.48 mmol) in THF (15 mL) at 0° C., the mixture was stirred at 0° C. for 3 hours. Saturated aqueous ammonium chloride was added to the reaction mixture, then extracted with ethyl acetate. The organic layer was washed with saturated brine, dried over anhydrous magnesium sulfate. The solvent was evaporated under reduced pressure to give 2-(6-chloro-3-pyridyl)-2-propanol (1.00 g, crude) as a yellow solid. LC-MS (ESI$^+$): m/z 172.1 (M+H)$^+$.

2-chloro-5-isopropylpyridine. To a solution of 2-(6-chloropyridin-3-yl)propan-2-ol (1.00 g, 5.83 mmol) in dry dichloromethane (25 mL) was added dropwise triethyl silane (3.52 g, 29.15 mmol) and trifluoroacetic acid (7.19 g, 58.3 mmol) at 0° C. The resulting mixture was warmed up to room temperature (RT) and stirred overnight. The mixture was poured into ice-water and basified with saturated sodium bicarbonate to pH 4-5 and extracted with dichloromethane (200 mL*3). The combined organic layers were washed with brine, dried over sodium sulfate and concentrated. The residue was purified by column chromatography silica gel (Petroleum Ether:Ethyl Aceate=1:1) to give 2-chloro-5-isopropylpyridine (0.73 g, 4.69 mmol) (Yield: 80.4%) as a yellow solid.

4-((5-isopropylpyridin-2-yl)oxy)-3-methylaniline. A solution of 4-amino-2-methylphenol (0.29 g, 2.36 mmol), 2-chloro-5-isopropylpyridine (0.35 g, 2.36 mmol), potassium tert-butylate (0.49 g, 3.55 mmol) in DMA (5 mL) was irradiated under microwave at 180° C. for 6 hours. After quenching the reaction, the reaction mixture was extracted with ethyl acetate (300 mL*3). The organic layer was washed with brine (300 mL), dried over $Na_2SO_4$, filtered and concentrated. The crude product was purified by flash column chromatography (DCM:MeOH=20:1) to get 4-((5-isopropylpyridin-2-yl)oxy)-3-methylaniline (0.20 g, 1.03 mmol) (Yield 43.3%) as a brown solid. LC-MS (ESI$^+$): m/z 243.1 (M+H)$^+$.

N-((4-((5-isopropylpyridin-2-yl)oxy)-3-methylphenyl) carbamoyl)-4-methoxycyclohexane-1-carboxamide (Compound 34). NMR and HPLC analysis were performed as described in exemplary methods herein. Compound 34A: (29.0 mg, 0.07 mmol) (Yield 8%). LC-MS (ESI$^+$): m/z 426.6 (M+H)$^+$. $^1$H NMR (400 MHz, CDCl$_3$) δ 10.60 (s, 1H), 8.90 (s, 1H), 8.05-8.04 (m, 1H), 7.57-7.54 (m, 1H), 7.45-7.45 (m, 1H), 7.39-7.36 (m, 1H), 7.01-6.99 (m, 1H), 6.79-6.76 (m, 1H), 3.46 (s, 1H), 3.31 (s, 3H), 2.93-2.86 (m, 1H), 2.40-2.35

(m, 1H), 2.18 (s, 3H), 2.04-2.00 (m, 2H), 1.93-1.83 (m, 2H), 1.75-1.71 (m, 2H), 1.51-1.44 (m, 2H), 1.26 (s, 3H), 1.23 (s, 3H). Compound 34B: (20.6 mg, 0.05 mmol) (Yield 6%). LC-MS (ESI$^+$): m/z 426.6 (M+H)$^+$. $^1$H NMR (400 MHz, CDCl$_3$) δ 10.55 (s, 1H), 8.92 (s, 1H), 8.03 (s, 1H), 7.55-7.53 (m, 1H), 7.44-744 (m, 1H), 7.38-7.36 (m, 1H), 7.02-7.00 (m, 1H), 6.79-6.77 (m, 1H), 3.34 (s, 3H), 3.20-3.12 (m, 1H), 2.92-2.86 (m, 1H), 2.33-2.32 (m, 1H), 2.30 (s, 1H), 2.27 (s, 2H), 2.18 (s, 1H), 2.07-2.04 (m, 2H), 1.63-1.53 (m, 2H), 1.32-1.31 (m, 2H), 1.25 (s, 3H), 1.24 (s, 3H).

Example 11

In another exemplary method, 3-methoxy-N-((3-methyl-4-(thiazol-2-yloxy)phenyl)carbamoyl)cyclobutane-1-carboxamide (Compound 45) was synthesized. FIG. 11 illustrates the chemical reaction equation for synthesis of Compound 45.

3-methyl-4-(thiazol-2-yloxy)aniline. A solution of 4-amino-2-methylphenol (4.00 g, 32.5 mmol), 2-bromothiazole (5.30 g, 32.5 mmol), cesium carbonate (21.20 g, 65 mmol), in NMP (50 mL) was irradiated under microwave at 180° C. for 1 hour. After quenching the reaction, the reaction mixture was extracted with ethyl acetate (300 mL×3). The organic layer was washed with brine (300 mL), dried over Na$_2$SO$_4$, filtered and concentrated. The crude product was purified by flash column chromatography (Petroleum Ether:Ethyl Acetate=2:1) to get 3-methyl-4-(thiazol-2-yloxy)aniline (5.50 g, 26.7 mmol) (Yield 82%) as a brown solid. LC-MS (ESI$^+$): m/z 147.6 (M+H)$^+$.

3-methoxy-N-((3-methyl-4-(thiazol-2-yloxy)phenyl)carbamoyl)cyclobutane-1-carboxamide (Compound 45). NMR and HPLC analysis were performed as described in exemplary methods herein. Compound 45A: 87.2 mg, 0.24 mmol (Yield 24.9%) as a white solid. LC-MS (ESI$^+$): m/z 362.5 (M+H)$^+$. $^1$H NMR (400 MHz, DMSO-d$_6$) δ 10.70 (s, 1H), 10.59 (s, 1H), 7.52-7.52 (m, 1H), 7.49-7.46 (m, 1H), 7.26-7.23 (m, 2H), 7.17-7.16 (m, 1H), 3.83-3.75 (m, 1H), 3.75 (s, 3H), 2.86-2.77 (m, 1H), 2.44-2.38 (m, 2H), 2.16 (s, 3H), 2.05-1.98 (m, 2H). Compound 45B: 30.1 mg, 0.08 mmol (Yield 8.7%) as a white solid. LC-MS (ESI$^+$): m/z 362.5 (M+H)$^+$. $^1$H NMR (400 MHz, DMSO-d$_6$) δ 10.70 (s, 1H), 10.62 (s, 1H), 7.52 (s, 1H), 7.49-7.46 (m, 1H), 7.26-7.23 (m, 2H), 7.17-7.16 (m, 1H), 4.03-3.96 (m, 1H), 3.22-3.17 (m, 1H), 3.14 (s, 3H), 2.44-2.39 (m, 2H), 2.17 (s, 3H), 2.14-2.09 (m, 2H).

Example 12

In another exemplary method, 4-methoxy-N-((3-methyl-4-((2-morpholinopyrimidin-5-yl)oxy)phenyl)carbamoyl)cyclohexane-1-carboxamide (Compound 46) was synthesized. FIG. 12 illustrates the chemical reaction equation for synthesis of Compound 46.

4-methoxy-N-((3-methyl-4-((2-morpholinopyrimidin-5-yl)oxy)phenyl)carbamoyl)cyclohexane-1-carboxamide. To a solution of 4-methoxycyclohexane-1-carboxamide (115.0 mg, 0.73 mmol) in 1,2-dichloroeathane (10 mL) at room temperature was added oxalyl chloride (0.06 mL, 0.73 mmol). The reaction mixture was heated at 80° C. for 20 hours, and then concentrated. The resulting residue was dissolved in 1,2-dichloroethane (8 mL), the resultant solution was cooled to 0° C. and then treated with 3-methyl-4-((2-morpholinopyrimidin-5-yl)oxy)aniline (150.0 mg, 0.52 mmol). The mixture was allowed to gradually warm to room temperature and stirred for 16 hours. The mixture was concentrated and the residue was purified by preparative HPLC to afford 4-methoxy-N-((3-methyl-4-((2-morpholinopyrimidin-5-yl)oxy)phenyl)carbamoyl)cyclohexane-1-carboxamide ide (38.4 mg, 0.08 mmol) (Yield 15.7%) as a white solid. LC-MS (ESI$^+$): m/z 470.7 (M+H)$^+$. $^1$H NMR (400 MHz, DMSO-d$_6$) δ 10.63-10.59 (m, 1H), 10.53-10.48 (m, 1H), 8.24 (s, 2H), 7.44-7.43 (m, 1H), 7.32-7.27 (m, 1H), 6.75-6.72 (m, 1H), 3.69-3.62 (m, 8H), 3.36-3.38 (s, 0.5H), 3.24-3.20 (m, 3H), 3.09-3.06 (m, 0.5H), 2.45-2.34 (m, 1H), 2.25 (s, 3H), 2.08-2.02 (m, 1H), 1.89-1.84 (m, 2H), 1.73-1.52 (m, 2H), 1.45-1.37 (m, 2H), 1.12-1.03 (m, 1H).

Example 13

In another exemplary method, N-((4-(benzo[d]thiazol-2-yloxy)-3-methylphenyl)carbamoyl)-3-methoxycyclobutane-1-carboxamide (Compound 56) was synthesized. FIG. 13 illustrates the chemical reaction equation for synthesis of Compound 56.

4-(benzo[d]thiazol-2-yloxy)-3-methylaniline. A solution of 4-amino-2-methylphenol (0.50 g, 4.06 mmol), 2-bromobenzo[d]thiazole (0.96 g, 4.46 mmol), Cs$_2$CO$_3$ (1.98 g, 6.09 mmol), in DMA (5 mL) was irradiated in microwave reactor at 160° C. for 1 hour. After quenching the reaction, the reaction mixture was extracted with ethyl acetate (300 mL×3). The organic layer was washed with brine (300 mL), dried over Na$_2$SO$_4$, filtered and concentrated. The crude product was purified by flash column chromatography (Petroleum Ether:Ethyl Acetate=3:1) to get 4-(benzo[d]thiazol-2-yloxy)-3-methylaniline (0.48 g, 1.88 mmol) (Yield 48.5%) as a brown solid. LC-MS (ESI$^+$): m/z 257.1 (M+H)$^+$.

N-((4-(benzo[d]thiazol-2-yloxy)-3-methylphenyl)carbamoyl)-3-methoxycyclobutane-1-carboxamide (Compound 56). N-((4-(benzo[d]thiazol-2-yloxy)-3-methylphenyl)carbamoyl)-3-methoxycyclobutane-1-carboxamide was prepared using procedure similar to compound 1. Yield 12.8%. NMR and HPLC analysis were performed as described in exemplary methods herein. LC-MS (ESI$^+$): m/z 412.3 (M+H)$^+$. $^1$H NMR (400 MHz, DMSO-d$_6$) δ 10.73-10.56 (m, 2H), 7.82-7.76 (m, 1H), 7.51-7.46 (m, 1H), 7.45-7.39 (m, 1H), 7.28-7.21 (m, 1H), 7.00-6.95 (m, 1H), 3.42-3.37 (m, 0.5H), 3.26-3.18 (m, 3H), 3.16-3.03 (m, 0.5H), 2.48-2.29 (m, 1H), 2.15 (s, 3H), 2.11-2.01 (m, 1H), 1.95-1.82 (m, 2H), 1.75-1.51 (m, 2H), 1.48-1.33 (m, 2H), 1.15-1.00 (m, 1H).

Example 14

In another exemplary method, N-((4-((1,2,4-thiadiazol-5-yl)oxy)-3-methylphenyl)carbamoyl)-3-methoxycyclobutane-1-carboxamide (Compound 57) was synthesized. FIG. 14 illustrates the chemical reaction equation for synthesis of Compound 57.

tert-butyl (4-((1,2,4-thiadiazol-5-yl)oxy)-3-methylphenyl)carbamate. A three-necked bottom flask were charged with NaH (255.0 mg, 6.4 mmol) and DMF (10 mL), a solution of tert-butyl (4-hydroxy-3-methylphenyl)carbamate (1.2 g, 5.4 mmol) in DMF (10 mL) was added dropwise, the reaction mixture was stirred at room temperature for 2 hours under N$_2$, then KI (85.0 mg, 0.54 mmol) and a solution of 5-bromo-1,2,4-thiadiazole (900.0 mg, 5.4 mmol) in DMF (5 mL) was added, the reaction mixture was stirred at room temperature for 16 hours. After completion, the reaction mixture was poured into H$_2$O (60 mL) and extracted with ethyl acetate (40 mL×3), dried over Na$_2$SO$_4$, filtered and concentrated under reduced pressure. The residue was purified via column chromatography (Combiflash) (Ethyl Acetate:Petroleum Ether=1:4) to get the title compound tert-butyl (4-((1,2,4-thiadiazol-5-yl)oxy)-3-methylphenyl)carbamate (1.5 g, 16.28 mmol) (yield 90%) as a white solid.

4-((1,2,4-thiadiazol-5-yl)oxy)-3-methylaniline. A solution of tert-butyl (4-((1,2,4-thiadiazol-5-yl)oxy)-3-methylphenyl)carbamate (800.0 mg, 2.6 mmol) in MeOH (10 mL) was added 1,4-dioxane (4 mL), the reaction mixture was stirred at room temperature for 16 hours under $N_2$. After completion, the reaction mixture was concentrated under reduced pressure to dryness, the residue was used directly for the next step without purification to get the title compound 4-((1,2,4-thiadiazol-5-yl)oxy)-3-methylaniline (510.0 mg, 2.5 mmol) (yield 94%) as a white solid.

N-((4-((1,2,4-thiadiazol-5-yl)oxy)-3-methylphenyl)carbamoyl)-3-methoxycyclobutane-1-carboxamide (Compound 57). A three-necked round bottom flask equipped with magnetic stirrer were charged with 3-methoxycyclobutane-1-carboxamide (175.0 mg, 1.35 mmol) in DCE (10 mL) was added oxalyl chloride (189.0 mg, 1.49 mmol), the reaction mixture was stirred at 85° C. for 3 hours under $N_2$ then cooled to room temperature. A solution of 4-((1,2,4-thiadiazol-5-yl)oxy)-3-methylaniline (140.0 mg, 0.68 mmol) and pyridine (428.0 mg, 5.4 mmol) in THF (5 mL) was added. The reaction mixture was stirred at room temperature for 2 hours. After completion, the mixture was concentrated and the residue was purified by preparative HPLC to afford N-((4-((1,2,4-thiadiazol-5-yl)oxy)-3-methylphenyl)carbamoyl)-3-methoxycyclobutane-1-carboxamide (25.0 mg, 0.07 mmol) (Yield 11%) as a white solid. LC-MS (ESI$^+$): m/z 363.2 (M+H)$^+$. $^1$H NMR (400 MHz, DMSO-d6) δ 10.74 (s, 1H), 10.67 (s, 1H), 8.41 (s, 1H), 7.60 (d, J=2.4 Hz, 1H), 7.56-7.53 (m, 1H), 7.42 (d, J=8.8 Hz, 1H), 3.81-3.78 (m, 1H), 3.14 (s, 3H), 2.84-2.80 (m, 1H), 2.47-2.37 (m, 2H), 2.19 (s, 3H), 2.06-1.99 (m, 2H).

Example 15

In another exemplary method, N-((4-((4,5-dimethylthiazol-2-yl)oxy)-3-methylphenyl)carbamoyl)-3-methoxycyclobutane-1-carboxamide (Compound 59) was synthesized. FIG. 15 illustrates the chemical reaction equation for synthesis of Compound 59.

4-((4,5-dimethylthiazol-2-yl)oxy)-3-methylaniline. A solution of 4-amino-2-methylphenol (481.2 mg, 3.91 mmol), 2-bromo-4,5-dimethylthiazole (500.2 mg, 2.60 mmol), cesium carbonate (1.69 g, 5.21 mmol), in N-methyl pyrrolidone (3.0 mL) was stirred under microwave at 180° C. for 6 hours. After quenching the reaction, the reaction mixture was extracted with ethyl acetate (10.0 mL×3). The organic layer was washed with brine (30.0 mL), dried over $Na_2SO_4$, filtered and concentrated. The crude product was purified by flash column chromatography (PE:EA=1:1) to afford 4-((4,5-dimethylthiazol-2-yl)oxy)-3-methylaniline (450.3 mg, 1.92 mmol) (Yield 73.9%) as a black solid. LC-MS (ESI$^+$): m/z 235.0 (M+H)$^+$.

N-((4-((4,5-dimethylthiazol-2-yl)oxy)-3-methylphenyl)carbamoyl)-3-methoxycyclobutane-1-carboxamide (Compound 59). To a solution of 3-methoxycyclobutane-1-carboxamide (124.2 mg, 0.96 mmol) in 1,2-dichloroethane (5.0 mL) at room temperature was added oxalyl chloride (121.3 mg, 0.96 mmol). The reaction mixture was heated at 80° C. for 3 hours. The mixture was cooled to room temperature, then added dropwise to a solution of 4-((4,5-dimethylthiazol-2-yl)oxy)-3-methylaniline (150.1 mg, 0.64 mmol) and pyridine (253.4 mg, 3.20 mmol) in THF (5.0 mL) and stirred at room temperature for overnight. After quenching the reaction, the reaction mixture was extracted with ethyl acetate (10.0 mL×3). The organic layer was washed with brine (20.0 mL), dried over $Na_2SO_4$, filtered and concentrated. The residue was purified by Prep-HPLC to afford N-((4-((4,5-dimethylthiazol-2-yl)oxy)-3-methylphenyl)carbamoyl)-3-methoxycyclobutane-1-carboxamide 7190: (160.5 mg, 0.41 mmol) (Yield 63.4%) as a white solid. NMR and HPLC analysis were performed as described in exemplary methods herein. LC-MS (ESI$^+$): m/z 390.2 (M+H)$^+$. $^1$H NMR (400 MHz, DMSO-d$_6$) δ 10.70 (s, 1H), 10.57 (s, 1H), 7.50 (s, 1H), 7.49-7.43 (m, 1H), 7.20-7.18 (d, J=8.0 Hz, 1H), 4.00-3.91 (m, 0.2H), 3.82-3.75 (m, 0.8H), 3.21-3.17 (m, 0.2H), 3.14-3.13 (d, J=4.0 Hz, 3H), 2.85-2.77 (m, 0.8H), 2.44-2.38 (m, 2H), 2.19 (s, 3H), 2.16 (s, 3H), 2.13-2.12 (m, 0.5H), 2.10 (s, 3H), 2.07-1.98 (m, 1.6H).

Example 16

In another exemplary method, 3-methoxy-N-((3-methyl-4-((5-methylthiazol-2-yl)oxy)phenyl)carbamoyl)cyclobutane-1-carboxamide (Compound 60) was synthesized. FIG. 16 illustrates the chemical reaction equation for synthesis of Compound 60.

3-methyl-4-((5-methylthiazol-2-yl)oxy)aniline. A solution of 4-amino-2-methylphenol (527.3 mg, 4.28 mmol), 2-bromo-5-methylthiazole (500.1 mg, 2.81 mmol), cesium carbonate (1.83 g, 5.62 mmol) in N-methyl pyrrolidone (13.0 mL) was stirred under microwave at 180° C. for 6 hours. After quenching the reaction, the reaction mixture was extracted with ethyl acetate (40.0 mL×3). The organic layer was washed with brine (50.0 mL), dried over $Na_2SO_4$, filtered and concentrated. The crude product was purified by flash column chromatography (Petroleum Ether:Ethyl Acetate=9:11) to get 3-methyl-4-((5-methylthiazol-2-yl)oxy)aniline (400.2 mg, 1.82 mmol) (Yield 64.6%) as a black solid. LC-MS (ESI$^+$): m/z 221.0 (M+H)$^+$.

3-methoxy-N-((3-methyl-4-((5-methylthiazol-2-yl)oxy)phenyl)carbamoyl)cyclobutane-1-carboxamide (Compound 60). NMR and HPLC analysis were performed as described in exemplary methods herein. LC-MS (ESI$^+$): m/z 376.1 (M+H)$^+$. $^1$H NMR (400 MHz, DMSO-d$_6$) δ 10.71 (s, 1H), 10.58 (s, 1H), 7.50 (m, 1H), 7.47-7.44 (d, J=8.8 Hz, 1H), 7.22-7.20 (d, J=8.4 Hz, 1H), 6.93 (s, 1H), 4.01-3.97 (m, 0.2H), 3.82-3.75 (m, 0.8H), 3.21-3.17 (m, 0.3H), 3.14-3.13 (s, 3H), 2.86-2.77 (m, 0.7H), 2.42-2.40 (m, 2H), 2.29 (s, 3H), 2.16 (s, 3H), 2.03-2.00 (m, 2H).

Example 17

In another exemplary method, 3-methoxy-N-((3-methyl-4-((5-(trifluoromethyl)thiazol-2-yl)oxy)phenyl)carbamoyl)cyclobutane-1-carboxamide (Compound 61) was synthesized. FIG. 17 illustrates the chemical reaction equation for synthesis of Compound 61.

3-methyl-4-((5-(trifluoromethyl)thiazol-2-yl)oxy)aniline. A mixture of 4-amino-2-methylphenol (0.35 g, 2.89 mmol), 2-chloro-5-(trifluoromethyl)thiazole (0.45 g, 2.41 mmol), $Cs_2CO_3$ (1.17 g, 3.61 mmol), in DMA (10 mL) was stirred at 25° C. for overnight. After quenching the reaction, the reaction mixture was extracted with ethyl acetate (30.0 mL×3). The organic layer was washed with brine (50.0 mL), dried over $Na_2SO_4$, filtered and concentrated. The crude product was purified by flash column chromatography (Petroleum Ether:Ethyl Acetate=3:1) to get 3-methyl-4-((5-(trifluoromethyl)thiazol-2-yl)oxy)aniline (0.31 g, 1.13 mmol) (Yield 42.1%) as a brown solid. LC-MS (ESI$^+$): m/z 275.0 (M+H)$^+$.

3-methoxy-N-((3-methyl-4-((5-(trifluoromethyl)thiazol-2-yl)oxy)phenyl)carbamoyl)cyclobutane-1-carboxamide (Compound 61). 3-Methoxy-N-((3-methyl-4-((5-(trifluoromethyl)thiazol-2-yl)oxy)phenyl)carbamoyl)cyclobutane-1-carboxamide was synthesized using procedure for compound 1. Yield 53.9%. NMR and HPLC analysis were performed as described in exemplary methods herein. LC-MS (ESI$^+$): m/z 430.14 (M+H)$^+$. $^1$H NMR (400 MHz, DMSO-d$_6$) δ 10.79-10.61 (m, 2H), 7.99 (s, 1H), 7.61-7.56 (m, 1H), 7.55-7.49 (m, 1H), 7.41-7.34 (m, 1H), 4.03-3.74 (m, 1H), 3.23-3.15 (m, 0.3H), 3.15-3.09 (m, 3H), 2.88-2.74 (m, 1H), 2.47-2.36 (m, 2H), 2.21-2.15 (s, 3H), 2.15-1.96 (m, 2H).

Example 18

In another exemplary method, N-((3-fluoro-4-((5-fluoropyridin-2-yl)oxy)-5-methylphenyl)carbamoyl)-3-methoxycyclobutane-1-carboxamide (Compound 72) was synthesized. FIG. 18 illustrates the chemical reaction equation for synthesis of Compound 72.

2-bromo-6-fluoro-4-nitrophenol. To a solution of 2-fluoro-4-nitrophenol (10.02 g, 64.22 mmol) in acetic acid (50.0 mL) was added bromine (15.03 g, 95.54 mmol) dropwise during a period of 30 minutes at 0° C. The solution was warmed up to room temperature and kept stirring overnight. The reaction was quenched with sodium thiosulfate (100.0 mL), the mixture was filtrated and washed with water three times, the filter cake was concentrated under reduced pressure to afford 2-bromo-6-fluoro-4-nitrophenol (11.52 g, 48.72 mmol) (yield 75.8%) as a yellow solid.

2-(benzyloxy)-1-bromo-3-fluoro-5-nitrobenzene. To a solution of 2-bromo-6-fluoro-4-nitrophenol (8.03 g, 46.82 mmol) in DMF (100.0 mL) was added potassium carbonate (19.44 g, 140.45 mmol) was stirred at room temperature for 0.5 hours. Benzyl bromide (9.61 g, 56.16 mmol) in DMF (30.0 mL) dropwise during a period of 30 minutes at 0° C. The solution was warmed up to room temperature and kept stirring overnight. After quenching with water (200.0 mL), the reaction mixture was extracted with ethyl acetate (100.0 mL×3). The organic layer was washed with brine (150.0 mL), dried over Na$_2$SO$_4$, filtered and concentrated. The crude product was purified by flash column chromatography (PE:EA=6:1) to get 2-(benzyloxy)-1-bromo-3-fluoro-5-nitrobenzene (7.62 g, 23.31 mmol) (yield 49.8%) as a yellow solid.

2-(benzyloxy)-1-fluoro-3-methyl-5-nitrobenzene. To a solution of 2-(benzyloxy)-1-bromo-3-fluoro-5-nitrobenzene (7.42 g, 22.69 mmol) in DME (80.0 mL) was added 2,4,6-trimethyl-1,3,5,2,4,6-trioxatriborinane (8.40 g, 68.07 mmol), K$_3$PO$_4$ (14.41 g, 68.07 mmol) and Pd(dppf)Cl$_2$ (168.3 mg, 0.23 mmol), the reaction mixture was stirred at 100° C. for 20 hours under N$_2$, then petroleum ether was added and the precipitate was filtered. The filtrated was concentrated to dryness and was purified by flash column chromatography (Petroleum Ether:Ethyl Acetate=10:1) to afford 2-(benzyloxy)-1-fluoro-3-methyl-5-nitrobenzene (4.21 g, 16.09 mmol) (yield 70.9%) as a white solid.

2-fluoro-6-methyl-4-nitrophenol. To a solution of 2-(benzyloxy)-1-fluoro-3-methyl-5-nitrobenzene (1.21 g, 4.62 mmol), in DCM (20.0 mL) was added BBr$_3$ (2.23 g, 9.26 mmol) dropwise during a period of 30 minutes at 0° C. The solution was warmed up to room temperature for 2 hours. After quenching the reaction with MeOH (20.0 mL), the reaction mixture was concentrated. The crude product was purified by flash column chromatography (PE:EA=5:1) to get 2-fluoro-6-methyl-4-nitrophenol (760.1 mg, 4.44 mmol) (Yield 96.6%) as a yellow solid.

5-fluoro-2-(2-fluoro-6-methyl-4-nitrophenoxy)pyridine. To a solution of 2-fluoro-6-methyl-4-nitrophenol (300.2 mg, 1.75 mmol), 2,5-difluoropyridine (240.2 mg, 2.15 mmol), p-toluene sulfonic acid (600.4 mg, 2.53 mmol) in DMA (4.0 mL) was stirred at 150° C. microwave for 10 hours. After quenching the reaction, the reaction mixture was extracted with ethyl acetate (10.0 mL×3). The organic layer was washed with brine (20.0 mL), dried over Na$_2$SO$_4$, filtered and concentrated. The crude product was purified by flash column chromatography (PE:EA=7:1) to get 5-fluoro-2-(2-fluoro-6-methyl-4-nitrophenoxy)pyridine (143.3 mg, 0.53 mmol) (Yield 30.7%) as a yellow solid. LC-MS (ESI$^+$): m/z 267.2 (M+H)$^+$.

3-fluoro-4-((5-fluoropyridin-2-yl)oxy)-5-methylaniline. A suspension of 5-fluoro-2-(2-fluoro-6-methyl-4-nitrophenoxy)pyridine (143.3 mg, 0.53 mmol) and 10% palladium-carbon (14.3 mg) in methanol (2.0 mL) was stirred at room temperature under hydrogen atmosphere for 4 h. The insoluble material was filtered off, and the filtrate was concentrated purified by flash column chromatography (DCM:MeOH=20:1) to afford 3-fluoro-4-((5-fluoropyridin-2-yl)oxy)-5-methylaniline (119.3 mg, 0.50 mmol) (Yield 94.3%) as a yellow solid. LC-MS (ESI$^+$): m/z 237.2 (M+H)$^+$.

N-((3-fluoro-4-((5-fluoropyridin-2-yl)oxy)-5-methylphenyl)carbamoyl)-3-methoxycyclobutanecarboxamide (Compound 72). To a solution of 3-methoxycyclobutanecarboxamide (79.1 mg, 0.60 mmol) in 1,2-dichloroethane (4.0 mL) at room temperature was added oxalyl chloride (0.08 mL, 0.60 mmol). The reaction solution was heated at 80° C. for 4 hours. The solution was cooled to room temperature, then was added dropwise to a solution of 3-fluoro-4-((5-fluoropyridin-2-yl)oxy)-5-methylaniline (119.3 mg, 0.50 mmol) and pyridine (0.14 mL, 2.3 mmol) in THF (5.0 mL) and stirred at room temperature for overnight. After quenching the reaction, the reaction mixture was extracted with ethyl acetate (10.0 mL×3). The organic layer was washed with brine (20.0 mL), dried over Na$_2$SO$_4$, filtered and concentrated. The residue was purified by preparative HPLC to afford N-((3-fluoro-4-((5-fluoropyridin-2-yl)oxy)-5-methylphenyl)carbamoyl)-3-methoxycyclobutanecarboxamide (84.2 mg, 0.22 mmol) (Yield 43.0%) as a white solid. NMR and HPLC analysis were performed as described in exemplary methods herein. LC-MS (ESI$^+$): m/z 375 (M+H)$^+$. $^1$H NMR (400 MHz, DMSO-d$_6$) δ 10.74 (s, 1H), 10.64-10.61 (m, 1H), 8.09-8.08 (m, 2H), 7.87-7.82 (m, 1H), 7.52 (d, J=14.4 Hz, 1H), 7.23 (s, 1H), 7.23-7.20 (m, 2H), 4.00-3.97 (m, 0.3H), 3.82-3.75 (m, 0.7H), 3.21-3.15 (m, 0.3H), 3.09 (s, 3H), 2.86-2.77 (m, 0.7H), 2.51-2.50 (m, 2H), 2.16-2.14 (m, 0.4H), 2.10 (s, 3H), 2.05-1.98 (m, 1.6H).

Example 19

In another exemplary method, N-((4-((5-chloropyrimidin-2-yl)oxy)-3-fluoro-5-methylphenyl)carbamoyl)-3-methoxycyclobutane-1-carboxamide (Compound 73) was synthesized. FIG. 19 illustrates the chemical reaction equation for synthesis of Compound 73.

5-chloro-2-(2-fluoro-6-methyl-4-nitrophenoxy)pyrimidine. To a solution of 2-fluoro-6-methyl-4-nitrophenol (320.2 mg, 1.87 mmol), 2,5-difluoropyridine (334.1 mg, 2.24 mmol), p-toluene sulfonic acid (483.3 mg, 2.80 mmol) in DMA (4.0 mL) was stirred at 150° C. microwave for 10 hours. After quenching the reaction with water (20.0 mL), the reaction mixture was extracted with ethyl acetate (10.0 mL×3). The organic layer was washed with brine (20.0 mL), dried over Na$_2$SO$_4$, filtered and concentrated. The crude product was purified by flash column chromatography (PE: EA=6:1) to get 5-chloro-2-(2-fluoro-6-methyl-4-nitrophenoxy) pyrimidine (156.1 mg, 0.55 mmol) (Yield 29.4%) as a yellow solid. LC-MS (ESI+): m/z 284.2 (M+H)+.

4-((5-chloropyrimidin-2-yl)oxy)-3-fluoro-5-methylaniline. A suspension of 5-chloro-2-((2-fluoro-6-methyl-4-nitrophenoxy) pyrimidine (156.1 mg, 0.55 mmol), ammonium chloride (291.2 mg, 5.53 mmol) and iron powder (154.2 mg, 2.75 mmol) in methanol (5.0 mL) was stirred at 80° C. for 4 h. The insoluble material was filtered off, and the filtrate was concentrated then purified by flash column chromatography (Petroleum Ether:Ethyl Acetate=1:2) to afford 4-((5-chloropyrimidin-2-yl)oxy)-3-fluoro-5-methylaniline (110.2 mg, 0.43 mmol) (Yield 78.9%) as a yellow solid. LC-MS (ESI+): m/z 254.1 (M+H)+.

N-((4-((5-chloropyrimidin-2-yl)oxy)-3-fluoro-5-methylphenyl)carbamoyl)-3-methoxycyclobutane carboxamide (Compound 73). N-((4-((5-chloropyrimidin-2-yl)oxy)-3-fluoro-5-methylphenyl)carbamoyl)-3-methoxycyclobutane carboxamide was prepared using procedure similar to compound 72. Yield 16.2%. NMR and HPLC analysis were performed as described in exemplary methods herein. LC-MS (ESI+): m/z 410.1 (M+H)+. $^1$H NMR (400 MHz, DMSO-$d_6$) δ 10.75 (s, 1H), 10.66-10.63 (m, 1H), 8.78 (s, 2H), 7.57-7.54 (m, 1H), 7.24 (s, 1H), 4.00-3.97 (m, 0.3H), 3.82-3.75 (m, 0.7H), 3.21-3.15 (m, 0.3H), 3.15 (s, 3H), 2.85-2.77 (m, 0.7H), 2.45-2.40 (m, 2H), 2.16-2.14 (m, 0.4H), 2.10 (s, 3H), 2.05-1.96 (m, 1.6H).

Example 20

In another exemplary method, N-((3-fluoro-5-methyl-4-(pyrimidin-2-yloxy)phenyl)carbamoyl)-3-methoxycyclobutane-1-carboxamide (Compound 74) was synthesized. FIG. 20 illustrates the chemical reaction equation for synthesis of Compound 74.

2-(2-fluoro-6-methyl-4-nitrophenoxy)pyrimidine. To a solution of 2-fluoro-6-methyl-4-nitrophenol (300.1 mg, 1.75 mmol), 2-chloropyrimidine (241.4 mg, 2.15 mmol), p-toluenesulfonic acid (600.5 mg, 2.53 mmol) in DMA (4.0 mL) was extracted with ethyl acetate (10.0 mL*3). The organic layer was washed with brine (20.0 mL), dried over $Na_2SO_4$, filtered and concentrated. The crude product was purified by flash column chromatography (Petroleum Ether:Ethyl Acetate=6:1) to get 2-(2-fluoro-6-methyl-4-nitrophenoxy) pyrimidine (129.2 mg, 0.52 mmol) (Yield 29.6%) as a yellow solid. LC-MS (ESI+): m/z 250.2 (M+H)+.

3-fluoro-5-methyl-4-(pyrimidin-2-yloxy)aniline. A suspension of 2-(2-fluoro-6-methyl-4-nitrophenoxy)pyrimidine (129.2 mg, 0.52 mmol) and 10% palladium-carbon (12.9 mg) in methanol (2.0 mL) was stirred at room temperature under hydrogen atmosphere for 4 hours. The insoluble material was filtered off, and the filtrate was concentrated purified by flash column chromatography (DCM: MeOH=20:1) to afford 6-(4-fluorophenoxy) pyridin-3-amine (103.2 mg, 0.47 mmol) (Yield 90.4%) as a brown oil. LC-MS (ESI+): m/z 220.3 (M+H)+.

N-((3-fluoro-5-methyl-4-(pyrimidin-2-yloxy)phenyl)carbamoyl)-3-methoxycyclobutane carboxamide (Compound 74). N-((3-fluoro-5-methyl-4-(pyrimidin-2-yloxy)phenyl) carbamoyl)-3-methoxycyclobutanecarboxamide was obtained as a white solid in 15.1% yield. NMR and HPLC analysis were performed as described in exemplary methods herein. LC-MS (ESI+): m/z 375 (M+H)+. $^1$H NMR (400 MHz, DMSO-$d_6$) δ 10.75 (s, 1H), 10.65-10.61 (m, 1H), 8.66 (d, J=4.4 Hz, 2H), 7.56-7.53 (m, 1H), 7.32-7.29 (m, 1H), 7.23 (s, 1H), 4.00-3.97 (m, 0.3H), 3.83-3.75 (m, 0.7H), 3.20-3.17 (m, 0.3H), 3.14-3.10 (s, 3H), 2.84-2.77 (m, 0.7H), 2.47-2.38 (m, 2H), 2.16-2.14 (m, 0.4H), 2.13 (s, 3H), 2.05-1.98 (m, 1.6H).

Example 21

In another exemplary method, N-((4-((5-chloropyridin-2-yl)oxy)-3-fluoro-5-methylphenyl)carbamoyl)-3-methoxycyclobutane-1-carboxamide (Compound 76) was synthesized. FIG. 21 illustrates the chemical reaction equation for synthesis of Compound 76. LC-MS (ESI+): m/z 408.19 (M+H)+. $^1$H NMR (400 MHz, DMSO-$d_6$) δ 10.76 (s, 1H), 10.64-10.61 (m, 1H), 8.15 (s, 1H), 8.07 (d, 1H), 7.52-7.51 (m, 1H), 7.22-7.20 (m, 1H), 4.00-3.97 (m, 0.3H), 3.80-3.79 (m, 0.7H), 3.33-3.18 (m, 0.3H), 3.13 (s, 3H), 2.85-2.75 (m, 0.7H), 2.44-2.42 (m, 2H), 2.30-2.00 (m, 5H).

Example 22

In another exemplary method, N-((3-fluoro-5-methyl-4-(thiazol-2 yloxy)phenyl)carbamoyl)-3-methoxycyclobutanecarboxamide (Compound 77) was synthesized. FIG. 22 illustrates the chemical reaction equation for synthesis of Compound 77.

2-(2-bromo-6-fluoro-4-nitrophenoxy)thiazole. To a solution of 1-bromo-2,3-difluoro-5-nitrobenzene (1.21 g, 4.91 mmol) in DMF (20.0 mL) was added thiazol-2-ol (500.5 mg, 4.91 mmol), potassium iodide (81.3 mg, 0.49 mmol) and cesium carbonate (4.81 g, 14.73 mmol). The mixture was warmed up to 100° C. for 2 h and quenched with water (100 mL). The reaction mixture was extracted with ethyl acetate (100 mL×3). The organic layer was washed with brine (150.0 mL), dried over $Na_2SO_4$, filtered and concentrated. The crude product was purified by flash column chromatography (Petroleum ether:ethyl acetate=8:1) to afford 2-(2-bromo-6-fluoro-4-nitrophenoxy)thiazole (446.2 mg, 1.39 mmol) (yield 26.75%) as a yellow solid. LC-MS (ESI+): m/z 320.1 (M+H)+

2-(2-fluoro-6-methyl-4-nitrophenoxy)thiazole. To a solution of 2-(2-bromo-6-fluoro-4-nitrophenoxy)thiazole (446.2 g, 3.26 mmol) in DME (10.0 mL) was added 2,4,6-trimethyl-1,3,5,2,4,6-trioxatriborinane (523.3 mg, 4.19 mmol), $K_3PO_4$ (884.0 mg, 4.19 mmol) and Pd(dppf)$Cl_2$ (101.6 mg, 1.39 mmol), the reaction mixture was stirred at 100° C. for 20 hours under $N_2$, then petroleum ether was added and the precipitate was filtered. The reaction mixture was extracted with ethyl acetate (100.0 mL×3). The organic layer was washed with brine (150.0 mL), dried over $Na_2SO_4$, filtered and concentrated. The crude product was purified by flash column chromatography (Petroleum ether:ethyl Acetate=9:1) to afford 2-(2-fluoro-6-methyl-4-nitrophenoxy)thiazole (220.3 mg, 0.87 mmol) (Yield 62.31%) as a white solid. LC-MS (ESI+): m/z 255.2 (M+H)+

3-Fluoro-5-methyl-4-(thiazol-2-yloxy)aniline. A suspension of 2-(2-fluoro-6-methyl-4-nitrophenoxy)thiazole (135.3 mg, 0.48 mmol), ammonium chloride (379.3 mg, 4.81 mmol) and iron powder (134.5 mg, 2.38 mmol) in methanol (5.0 mL) was stirred at 80° C. for 4 h. The insoluble material was filtered, the filtrate was concentrated, and then purified by flash column chromatography (PE: EA=1:1) to afford 3-fluoro-5-methyl-4-(thiazol-2-yloxy) aniline (97.6 mg, 0.38 mmol) (yield 80.68%) as a yellow solid. LC-MS (ESI+): m/z 225.2 (M+H)+.

N-((3-fluoro-5-methyl-4-(thiazol-2-yloxy)phenyl)carbamoyl)-3-methoxycyclobutanecarboxamide. To a solution of 3-methoxycyclobutanecarboxamide (89.3 mg, 0.69 mmol) in 1,2-dichloroethane (4.0 mL) at room temperature was added oxalyl chloride (0.08 mL, 0.60 mmol). The reaction mixture was heated at 80° C. for 4 hours. The mixture was cooled to room temperature, then was added dropwise to a solution of 3-fluoro-5-methyl-4-(thiazol-2-yloxy)aniline (97.6 mg, 0.38 mmol) and pyridine (0.14 mL, 3.45 mmol) in THF (5.0 mL). The reaction stirred at room temperature for overnight. After quenching the reaction, the reaction mixture was extracted with ethyl acetate (10.0 mL×3). The organic layer was washed with brine (20.0 mL), dried over $Na_2SO_4$, filtered and concentrated. The residue was purified by HPLC to afford N-((3-fluoro-5-methyl-4-(thiazol-2-yloxy)phenyl)carbamoyl)-3-methoxycyclobutan-ecarboxamide (34.5 mg, 0.09 mmol) (Yield 23.68%) as a white solid. LC-MS (ESI$^+$): m/z 380.2 (M+H)$^+$. $^1$H NMR (400 MHz, DMSO-d$_6$) δ 10.80-10.74 (m, 2H), 7.64-7.60 (m, 1H), 7.31 (s, 1H), 7.11-7.08 (m, 1H), 6.71-6.67 (m, 1H), 4.01-3.97 (m, 0.2H), 3.79-3.77 (m, 0.8H), 3.20-3.19 (m, 0.3H), 3.18 (s, 3H), 2.84-2.82 (m, 0.7H), 2.50-2.49 (m, 2H), 2.40 (s, 3H), 2.39-2.38 (m, 0.5H), 2.12-2.00 (m, 1.5H).

Example 23

Compound 78. In another exemplary method, N-((4-((5-chloropyridin-2-yl)oxy) 3-methylphenyl)carbamoyl)-3-methoxy-1-methylcyclobutane-1-carboxamide Compound 78 was synthesized. FIG. 23 illustrates a chemical reaction equation for synthesis of Compound 78.

Methyl 3-hydroxy-3-methylcyclobutane-1-carboxylate. A solution of methyl 3-oxocyclobutane-1-carboxylate (8.0 g, 62.44 mmol) in THF (100 mL) was dropped $CH_3MgBr$ (24 mL, 75 mmol) into the solution at −78° C. under nitrogen. The reaction mixture was stirred at −78° C. for 16 hours. After quenching the reaction, the reaction mixture was extracted with ethyl acetate (100 mL×3). The organic layer was washed with brine (300 mL), dried over $Na_2SO_4$ to afford methyl 3-hydroxy-3-methylcyclobutane-1-carboxylate (7.1 g, 48.55 mmol) (Yield 79.0%) as a yellow oil. LC-MS (ESI$^+$): m/z 144.1 (M+H)$^+$.

Methyl 3-methoxy-3-methylcyclobutane-1-carboxylate. A solution of methyl 3-hydroxy-3-methylcyclobutane-1-carboxylate (7.1 g, 48.55 mmol) and NaH (2.33 g, 97.11 mmol) in THF (20 mL), the mixture was stirred at 0° C. for 40 mins. Then $CH_3I$ (4.53 mL, 72.88 mmol) was dropped into the solution, then stirred at 0° C. for overnight. After quenching the reaction, the reaction mixture was extracted with ethyl acetate (100 mL×3). The organic layer was washed with brine (300 mL), dried over $Na_2SO_4$ to afford methyl 3-methoxy-3-methylcyclobutane-1-carboxylate (3.9 g, 24.65 mmol) (yield 51.3%) as a yellow oil. LC-MS (ESI$^+$): m/z 158.1 (M+H)$^+$.

3-Methoxy-3-methylcyclobutane-1-carboxylic acid. A solution of methyl 3-methoxy-3-methylcyclobutane-1-carboxylate (3.9 g, 24.65 mmol) and NaOH (3.0 g, 75.85 mmol) in THF (20 mL) were added MeOH/H$_2$O (10 mL, v/v=4:1), the mixture was stirred at 0° C. for 40 mins. Then $CH_3I$ (4.53 mL, 72.88 mmol) was added into the solution, then stirred at room temperature for overnight. After quenching the reaction, the reaction mixture was extracted with ethyl acetate (100 mL×3). The organic layer was washed with brine (300 mL), dried over $Na_2SO_4$ to afford 3-methoxy-3-methylcyclobutane-1-carboxylic acid (2.8 g, 19.44 mmol) (Yield 80.0%) as a yellow oil. LC-MS (ESI$^+$): m/z 144.1 (M+H)$^+$.

3-methoxy-3-methylcyclobutane-1-carboxamide. A solution of 3-methoxy-3-methylcyclobutane-1-carboxylic acid (300.0 mg, 2.08 mmol), pyridine (486.7 mg, 6.24 mmol), di-tert-butyl dicarbonate (680.16 mg, 3.12 mmol) and ammonium bicarbonate (328.6 mg, 4.16 mmol) were added to THF (5 mL). The reaction mixture was stirred at room temperature for 16 hours. The reaction mixture was concentrated and purified by flash column chromatography (DCM: MeOH=15:1) to afford 3-methoxy-3-methylcyclobutane-1-carboxamide (200.0 mg, 0.78 mmol) (yield 55.7%) as a white solid. LC-MS (ESI$^+$): m/z 143.2 (M+H)$^+$.

4-((5-chloropyridin-2-yl)oxy)-3-methylaniline. A solution of 4-amino-2-methylphenol (3.72 g, 30.21 mmol), 2,5-dichloropyridine (4.5 g, 30.21 mmol), potassium carbonate (12.5 g, 90.63 mmol) in DMF (60 mL) was stirred at 100° C. for 16 hours under nitrogen. After quenching the reaction, the reaction mixture was extracted with ethyl acetate (300 mL×3). The organic layer was washed with brine (300 mL), dried over $Na_2SO_4$, filtered and concentrated. The crude product was purified by flash column chromatography (Petroleum ether:ethyl Acetate=2:1) to get 4-((5-chloropyridin-2-yl)oxy)-3-methylaniline (5.0 g, 21.22 mmol) (yield 70.2%) as a brown oily liquid. LC-MS (ESI$^+$): m/z 236.07 (M+H)$^+$.

N-((4-((5-chloropyridin-2-yl)oxy)-3-methylphenyl)carbamoyl)-3-methoxy-1-methylcyclobutane-1-carboxamide. To a solution of 3-methoxy-1-methylcyclobutane-1-carboxamide (200 mg, 1.40 mmol) in 1,2-dichloroethane (4 mL) at room temperature was added oxalyl chloride (264.2 mg, 2.09 mmol). The reaction mixture was heated at 80° C. for 3 hours. The mixture was cooled to room temperature, then was added dropwise to a solution of 4-((5-chloropyridin-2-yl)oxy)-3-methylaniline (200.0 mg, 0.85 mmol) and pyridine (552.9 mg, 6.99 mmol) in THF (4 mL) and stirred at room temperature for overnight. After quenching the reaction, the reaction mixture was extracted with ethyl acetate (100 mL×3). The organic layer was washed with brine (300 mL), dried over $Na_2SO_4$, filtered and concentrated. The residue was purified by HPLC to afford N-((4-((5-chloropyridin-2-yl)oxy)-3-methylphenyl)carbamoyl)-3-methoxy-1-methylcyclobutane-1-carboxamide (141.7 mg, 0.35 mmol) (Yield: 41.4%) as a yellow solid. LC-MS (ESI$^+$): m/z 403.1 (M+H)$^+$. $^1$H NMR (400 MHz, DMSO-d6) δ 10.63 (s, 1H), 10.53 (s, 1H), 8.16 (s, 1H), 7.95-7.92 (m, 1H), 7.45-7.39 (m, 2H), 7.08-7.01 (m, 2H), 3.09-3.08 (m, 3H), 2.94-2.89 (m, 1H), 2.28-2.23 (m, 2H), 2.09-2.05 (m, 2H), 2.02 (s, 3H), 1.28-1.24 (m, 3H).

Example 24

Compound 79. In another exemplary method, N-((4-((5-chloropyridin-2-yl)oxy)-3-methylphenyl)carbamoyl)-3-methoxy-1-methylcyclobutane-1-carboxamide (Compound 79) was synthesized. FIG. 24 illustrates a chemical reaction equation for synthesis of Compound 79.

3-Methoxy-1-methylcyclobutane-1-carboxamide. 3-methoxy-1-methylcyclobutane-1-carboxylic acid (300.0 mg, 2.08 mmol), pyridine (486.7 mg, 6.24 mmol), di-tert-butyl dicarbonate (680.16 g, 3.12 mmol) and ammonium bicarbonate (328.6 g, 4.16 mmol) were added to THF (5 mL). The reaction mixture was stirred at room temperature for 16 hours. The reaction mixture was concentrated and purified by flash column chromatography (DCM: MeOH=15:1) to afford 3-methoxy-1-methylcyclobutane-1-carboxamide (200.0 mg, 1.40 mmol) (Yield 67.3%) as a white solid. LC-MS (ESI$^+$): m/z 143.1 (M+H)$^+$.

4-((5-chloropyridin-2-yl)oxy)-3-methylaniline. A solution of 4-amino-2-methylphenol (3.72 g, 30.21 mmol), 2,5-dichloropyridine (4.5 g, 30.21 mmol), potassium carbonate (12.5 g, 90.63 mmol) in DMF (60 mL) was stirred at 100° C. for 16 h under nitrogen. After quenching the reaction, the reaction mixture was extracted with ethyl acetate (300 mL×3). The organic layer was washed with brine (300 mL), dried over $Na_2SO_4$, filtered and concentrated. The crude product was purified by flash column chromatography (petroleum ether:ethyl acetate=2:1) to get 4-((5-chloropyridin-2-yl)oxy)-3-methylaniline (5.0 g, 21.22 mmol) (yield 70.2%) as a brown oily liquid. LC-MS (ESI$^+$): m/z 236.07 (M+H)$^+$.

N-((4-((5-chloropyridin-2-yl)oxy)-3-methylphenyl)carbamoyl)-3-methoxy-1-methylcyclobutane-1-carboxamide. To a solution of 3-methoxy-1-methylcyclobutane-1-carboxamide (200 mg, 1.40 mmol), in 1,2-dichloroethane (4 mL) at room temperature was added oxalyl chloride (264.2 mg, 2.09 mmol). The reaction mixture was heated at 80° C. for 3 hours. The mixture was cooled to room temperature, then was added dropwise to a solution of 4-((5-chloropyridin-2-yl)oxy)-3-methylaniline (200.0 mg, 0.85 mmol) and pyridine (552.9 mg, 6.99 mmol) in THF (4 mL) and stirred at room temperature for overnight. After quenching the reaction, the reaction mixture was extracted with ethyl acetate (100 mL×3). The organic layer was washed with brine (300 mL), dried over $Na_2SO_4$, filtered and concentrated. The residue was purified by HPLC to afford N-((4-((5-chloropyridin-2-yl)oxy)-3-methylphenyl)carbamoyl)-3-methoxy-1-methylcyclobutane-1-carboxamide (141.7 mg, 0.35 mmol) (yield 41.4%) as a yellow solid. LC-MS (ESI$^+$): m/z 403.1 (M+H)$^+$. $^1$H NMR (400 MHz, DMSO-d$_6$) δ 10.60-10.58 (m, 1.5H), 10.43 (s, 0.3H), 8.15 (d, J=2.4 Hz, 1H), 7.96-7.93 (m, 1H), 7.44-7.40 (m, 2H), 7.08-7.02 (m, 2H), 3.90-3.8 (m, 0.3H), 3.69-3.67 (m, 0.5H), 3.12 (d, J=4.0 Hz, 3H), 3.78-3.73 (m, 1H), 2.23-2.18 (m, 1.6H), 2.05 (s, 3H), 1.83 (s, 0.3H), 1.82-1.78 (m, 1H), 1.45-1.40 (m, 3H).

Example 25

Compound 83 In another exemplary method, 3-methoxy-N-((3-methyl-4-(thiazol-2-yloxy)phenyl)carbamoyl)bicyclo[1.1.1]pentane-1-carboxamide (Compound 83) was synthesized. FIG. 25 illustrates the chemical reaction equation for synthesis of Compound 83.

3-methyl-4-(thiazol-2-yloxy)aniline. A solution of 4-amino-2-methylphenol (751.0 mg, 6.10 mmol), 2-bromothiazole (1.10 g, 6.10 mmol), cesium carbonate (6.00 g, 18.30 mmol), in N-methylpyrrolidone (10 mL) was stirred at 180° C. for 8 hours under microwave. After quenching the reaction, the reaction mixture was extracted with ethyl acetate (50 mL×3). The organic layer was washed with brine (100 mL), dried over $Na_2SO_4$, filtered and concentrated. The crude product was purified by flash column chromatography (petroleum ether:ethyl acetate=2:1) to get 3-methyl-4-(thiazol-2-yloxy)aniline (950.0 mg, 4.61 mmol) (Yield 75.5%) as a brown liquid. LC-MS (ESI$^+$): m/z 207.0 (M+H)$^+$.

3-methoxy-N-((3-methyl-4-(thiazol-2-yloxy)phenyl)carbamoyl)bicyclo[1.1.1]pentane-1-carboxamide. To a solution of 3-methoxybicyclo[1.1.1]pentane-1-carboxamide (55.0 mg, 0.40 mmol) in 1,2-dichloroethane (4 mL) at room temperature was added oxalyl chloride (61.0 mg, 0.48 mmol). The reaction mixture was heated at 80° C. for 3 hours. The mixture was cooled to room temperature, then was added dropwise to a solution of 3-methyl-4-(thiazol-2-yloxy)aniline (74.0 mg, 0.36 mmol) and pyridine (160.0 mg, 2.0 mmol) in THF (3 mL) and stirred at room temperature for overnight. After quenching the reaction, the reaction mixture was extracted with ethyl acetate (50 mL×3). The organic layer was washed with brine (100 mL), dried over $Na_2SO_4$, filtered and concentrated. The residue was purified by HPLC to afford 3-methoxy-N-((3-methyl-4-(thiazol-2-yloxy)phenyl)carbamoyl)bicyclo[1.1.1]pentane-1-carboxamide (10.4 mg, 0.03 mmol) (Yield 8.3%) as a white solid. LC-MS (ESI$^+$): m/z 374.1 (M+H)$^+$. $^1$H NMR (400 MHz, DMSO-d$_6$) δ 10.71 (s, 1H), 10.56 (s, 1H), 7.50 (s, 1H), 7.47-7.45 (m, 1H), 7.26-7.24 (m, 2H), 7.17 (s, 1H), 3.21 (s, 3H), 2.20 (s, 6H), 2.16 (s, 3H).

Example 26

In another exemplary method, N-((4-((5-chloropyridin-2-yl)oxy)-3-methylphenyl)carbamoyl)-3-methoxybicyclo[1.1.1]pentane-1-carboxamide (Compound 84) was synthesized. FIG. 26 illustrates the chemical reaction equation for synthesis of Compound 84.

3-Methoxybicyclo[1.1.1]pentane-1-carboxamide. A solution of 3-methoxybicyclo[1.1.1]pentane-1-carboxylic acid (200.0 mg, 1.41 mmol), pyridine (335.0 mg, 4.23 mmol), di-tert-butyl dicarbonate (463.0 mg, 2.12 mmol) and ammonium bicarbonate (223.0 mg, 2.82 mmol) in THF (5 mL) was stirred at room temperature for 16 hours. The reaction mixture was concentrated and purified by flash column chromatography (DCM:MeOH=10:1) to afford 3-methoxybicyclo[1.1.1]pentane-1-carboxamide (110.0 mg, 0.78 mmol) (Yield 55.7%) as a white solid. LC-MS (ESI$^+$): m/z 142.2 (M+H)$^+$.

4-((5-chloropyridin-2-yl)oxy)-3-methylaniline. A solution of 4-amino-2-methylphenol (3.70 g, 30.21 mmol), 2,5-dichloropyridine (4.50 g, 30.21 mmol) and potassium carbonate (12.50 g, 90.63 mmol) in DMF (60 mL) was stirred at 100° C. for 16 hours under nitrogen. The reaction mixture was extracted with ethyl acetate (100 mL×3). The organic layer was washed with brine (100 mL), dried over $Na_2SO_4$, filtered and concentrated. The crude product was purified by flash column chromatography (petroleum ether:ethyl acetate=2:1) to get 4-((5-chloropyridin-2-yl)oxy)-3-methylaniline (5.00 g, 21.22 mmol) (Yield 70.2%) as a brown liquid. LC-MS (ESI$^+$): m/z 236.1 (M+H)$^+$.

N-((4-((5-chloropyridin-2-yl)oxy)-3-methylphenyl)carbamoyl)-3-methoxybicyclo[1.1.1]pentane-1-carboxamide. To a solution of 3-methoxybicyclo[1.1.1]pentane-1-carboxamide (55.0 mg, 0.40 mmol) in 1,2-dichloroethane (4 mL) at room temperature was added oxalyl chloride (61.0 mg, 0.48 mmol), The reaction mixture was heated at 80° C. for 3 hours. The mixture was cooled to room temperature, added dropwise to a solution of 4-((5-chloropyridin-2-yl)oxy)-3-methylaniline (85.0 mg, 0.36 mmol) and pyridine (160.0 mg, 2.0 mmol) in THF (2 mL) and stirred at room temperature for overnight. After quenching the reaction, the reaction mixture was extracted with ethyl acetate (50 mL×3). The organic layer was washed with brine (100 mL), dried over $Na_2SO_4$, filtered and concentrated. The residue was purified by HPLC to afford N-((4-((5-chloropyridin-2-yl)oxy)-3-methylphenyl)carbamoyl)-3-methoxybicyclo[1.1.1]pentane-1-carboxamide (23.8 mg, 0.06 mmol) (yield: 16.7%) as a white solid. LC-MS (ESI$^+$): m/z 402.2 (M+H)$^+$.

$^1$H NMR (400 MHz, DMSO-d6) δ 10.67 (s, 1H), 10.49 (s, 1H), 8.16 (s, 1H), 7.95-7.93 (m, 1H), 7.43 (s, 1H), 7.40-7.38 (m, 1H), 7.09-7.06 (m, 1H), 7.04-7.03 (m, 1H), 3.21 (s, 3H), 2.20 (s, 6H), 2.05 (s, 3H).

Example 27

In another exemplary method, N-((4-((5-chloropyrimidin-2-yl)oxy)-3-methylphenyl)carbamoyl)-3-methoxybicyclo[1.1.1]pentane-1-carboxamide (Compound 85) was synthesized. FIG. 27 illustrates the chemical reaction equation for synthesis of compound 85.

4-((5-chloropyrimidin-2-yl)oxy)-3-methylaniline. A solution of 4-amino-2-methylphenol (830.0 mg, 6.71 mmol), 2,5-dichloropyrimidine (1.00 g, 6.71 mmol), potassium carbonate (2.80 g, 20.13 mmol) in N,N-dimethylformamide (20 mL) was stirred at 100° C. for 16 hours. The reaction mixture was extracted with ethyl acetate (50 mL×3). After quenching the reaction, the organic layer was washed with brine (100 mL), dried over $Na_2SO_4$, and concentrated. The crude product was purified by flash column chromatography (petroleum ether:methyl t-butyl ether=11:9) to get 4-((5-chloropyrimidin-2-yl)oxy)-3-methylaniline (1.20 g, 5.09 mmol) (yield 75.9%) as a brown solid. LC-MS (ESI$^+$): m/z 236.1 (M+H)$^+$.

N-((4-((5-chloropyrimidin-2-yl)oxy)-3-methylphenyl)carbamoyl)-3-methoxybicyclo[1.1.1]pentane-1-carboxamide. To a solution of 3-methoxybicyclo[1.1.1]pentane-1-carboxamide (100.0 mg, 0.70 mmol) in 1,2-dichloroethane (4 mL) at room temperature was added oxalyl chloride (107.0 mg, 0.84 mmol). The reaction mixture was heated at 80° C. for 3 hours. The mixture was cooled to room temperature, added dropwise to a solution of 4-((5-chloropyrimidin-2-yl)oxy)-3-methylaniline (151.0 mg, 0.64 mmol) and pyridine (233.0 mg, 3.20 mmol) in THF (3 mL) and stirred at room temperature for overnight. After quenching the reaction, the reaction mixture was extracted with ethyl acetate (50 mL×3). The organic layer was washed with brine (100 mL), dried over $Na_2SO_4$, filtered and concentrated. The residue was purified by HPLC to afford N-((4-((5-chloropyrimidin-2-yl)oxy)-3-methylphenyl)carbamoyl)-3-methoxybicyclo[1.1.1]pentane-1-carboxamide (133.0 mg, 0.33 mmol) (yield 51.6%) as a white solid. LC-MS (ESI$^+$): m/z 403.2 (M+H)$^+$. $^1$H NMR (400 MHz, DMSO-d$_6$) δ 10.68 (s, 1H), 10.51 (s, 1H), 8.74 (s, 2H), 7.45-7.44 (m, 1H), 7.41-7.39 (m, 1H), 7.11-7.09 (m, 1H), 3.21 (s, 3H), 2.20 (s, 6H), 2.05 (s, 3H).

Example 28

In another exemplary method, 3-methoxy-N-((3-methyl-4-(pyridin-2-yloxy)phenyl)carbamoyl)bicyclo[1.1.1]pentane-1-carboxamide (Compound 86) was synthesized. FIG. 28 illustrates the chemical reaction equation for synthesis of compound 86.

3-methyl-4-(pyridin-2-yloxy)aniline. A solution of 4-amino-2-methylphenol (1.00 mg, 8.12 mmol), 2-bromopyridine (1.30 g, 8.12 mmol), cesium carbonate (7.94 g, 24.36 mmol) in N,N-dimethylacetamide (20 mL) was stirred at 130° C. for 16 hours. After quenching the reaction, the reaction mixture was extracted with ethyl acetate (100 mL×3). The organic layer was washed with brine (100 mL), dried over $Na_2SO_4$, filtered and concentrated. The crude product was purified by flash column chromatography (petroleum ether:ethyl acetate=1:1) to get 3-methyl-4-(pyridin-2-yloxy)aniline (1.30 g, 6.49 mmol) (Yield 80.0%) as a brown solid. LC-MS (ESI$^+$): m/z 201.2 (M+H)$^+$.

3-Methoxy-N-((3-methyl-4-(pyridin-2-yloxy)phenyl)carbamoyl)bicyclo[1.1.1]pentane-1-carboxamide. To a solution of 3-methoxybicyclo[1.1.1]pentane-1-carboxamide (80.0 mg, 0.57 mmol) in 1,2-dichloroethane (5 mL) at room temperature was added oxalyl chloride (79.0 mg, 0.82 mmol). The reaction mixture was heated at 80° C. for 3 hours. The mixture was cooled to room temperature, added dropwise to a solution of 3-methyl-4-(pyridin-2-yloxy)aniline (104.0 mg, 0.52 mmol) and pyridine (205.0 mg, 2.60 mmol) in THF (4 mL) and stirred at room temperature for overnight. After quenching the reaction, the reaction mixture was extracted with ethyl acetate (50 mL×3). The organic layer was washed with brine (100 mL), dried over $Na_2SO_4$, filtered and concentrated. The residue was purified by HPLC to afford 3-methoxy-N-((3-methyl-4-(pyridin-2-yloxy)phenyl)carbamoyl)bicyclo[1.1.1]pentane-1-carboxamide (60.3 mg, 0.16 mmol) (yield 31.6%) as a white solid. LC-MS (ESI$^+$): m/z 368.3 (M+H)$^+$. $^1$H NMR (400 MHz, DMSO-d$_6$) δ 10.66 (s, 1H), 10.48 (s, 1H), 8.10-8.09 (m, 1H), 7.85-7.81 (m, 1H), 7.42 (s, 1H), 7.39-7.36 (m, 1H), 7.10-7.07 (m, 1H), 7.02-6.98 (m, 2H), 3.21 (s, 3H), 2.20 (s, 6H), 2.05 (s, 3H).

Example 29

In another exemplary method, 3-methoxy-N-((3-methyl-4-(pyrimidin-2-yloxy)phenyl)carbamoyl)bicyclo[1.1.1]pentane-1-carboxamide (Compound 87) was synthesized. FIG. 29 illustrates the chemical reaction equation for synthesis of compound 87.

3-methyl-4-(pyrimidin-2-yloxy)aniline. A solution of 4-amino-2-methylphenol (1.00 g, 8.12 mmol), 2-chloropyrimidine (928.0 mg, 8.12 mmol), cesium carbonate (7.94 g, 24.36 mmol) in acetonitrile (20 mL) was stirred at room temperature for 16 hours. After quenching the reaction, the reaction mixture was extracted with ethyl acetate (100 mL×3). The organic layer was washed with brine (100 mL), dried over $Na_2SO_4$, filtered and concentrated. The crude product was purified by flash column chromatography (petroleum ether:ethyl acetate=3:2) to get 4-((5-fluoropyrimidin-2-yl)oxy)-3-methylaniline (1.2 g, 5.48 mmol) (Yield 67.5%) as a brown solid. LC-MS (ESI$^+$): m/z 202.2 (M+H)$^+$.

3-methoxy-N-((3-methyl-4-(pyrimidin-2-yloxy)phenyl)carbamoyl)bicyclo[1.1.1]pentane-1-carboxamide. To a solution of 3-methoxybicyclo[1.1.1]pentane-1-carboxamide (80.0 mg, 0.57 mmol) in 1,2-dichloroethane (5 mL) at room temperature was added oxalyl chloride (79 mg, 0.82 mmol). The reaction mixture was heated at 80° C. for 3 hours. The mixture was cooled to room temperature, added dropwise to a solution of 3-methyl-4-(pyrimidin-2-yloxy)aniline (105.0 mg, 0.52 mmol) and pyridine (205.0 mg, 2.6 mmol) in THF (4 mL) and stirred at room temperature overnight. After quenching the reaction, the reaction mixture was extracted with ethyl acetate (50 mL×3). The organic layer was washed with brine (100 mL), dried over $Na_2SO_4$, filtered and concentrated. The residue was purified by HPLC to afford 3-methoxy-N-((3-methyl-4-(pyrimidin-2-yloxy)phenyl)carbamoyl)bicyclo[1.1.1]pentane-1-carboxamide (7482) (51.9 mg, 0.14 mmol) (yield 27.1%) as a white solid. LC-MS (ESI$^+$): m/z 369.3 (M+H)$^+$. $^1$H NMR (400 MHz, DMSO-d$_6$) δ 10.50 (s, 1H), 8.63-8.62 (m, 2H), 7.43 (s, 1H), 7.41-7.38 (m, 1H), 7.25 (t, J=4.8, 1H), 7.08-7.06 (m, 1H), 3.20 (s, 3H), 2.20 (s, 6H), 2.04 (s, 3H).

Example 30

In another exemplary method, N-((4-((5-fluoropyrimidin-2-yl)oxy)-3-methylphenyl)carbamoyl)-3-methoxybicyclo[1.1.1]pentane-1-carboxamide (Compound 88) was synthesized. FIG. 30 illustrates the chemical reaction equation for synthesis of compound 88.

4-((5-fluoropyrimidin-2-yl)oxy)-3-methylaniline. A solution of 4-amino-2-methylphenol (1.00 g, 8.12 mmol), 2-chloro-5-fluoropyrimidine (1.08 g, 8.12 mmol), cesium carbonate (7.94 g, 24.36 mmol) in acetonitrile (20 mL) was stirred at 100° C. for 16 hours. After quenching the reaction, the reaction mixture was extracted with ethyl acetate (100 mL×3). The organic layer was washed with brine (100 mL), dried over $Na_2SO_4$, filtered and concentrated. The crude product was purified by flash column chromatography (petroleum ether:methyl t-butyl ether=6:1) to get 4-((5-fluoropyrimidin-2-yl)oxy)-3-methylaniline (1.20 g, 5.48 mmol) (Yield 67.5%) as a brown solid. LC-MS (ESI⁺): m/z 220.1 (M+H)⁺.

N-((4-((5-fluoropyrimidin-2-yl)oxy)-3-methylphenyl)carbamoyl)-3-methoxybicyclo[1.1.1]pentane-1-carboxamide. To a solution of 3-methoxybicyclo[1.1.1]pentane-1-carboxamide (80.0 mg, 0.57 mmol) in 1,2-dichloroethane (5 mL) at room temperature was added oxalyl chloride (79 mg, 0.82 mmol). The reaction mixture was heated at 80° C. for 3 hours. The mixture was cooled to room temperature, added dropwise to a solution of 4-((5-fluoropyrimidin-2-yl)oxy)-3-methylaniline (114.0 mg, 0.52 mmol) and pyridine (205.0 mg, 2.60 mmol) in THF (4 mL) and stirred at room temperature overnight. After quenching the reaction, the reaction mixture was extracted with ethyl acetate (50 mL×3). The organic layer was washed with brine (100 mL), dried over Na₂SO₄, filtered and concentrated. The residue was purified by HPLC to afford N-((4-((5-fluoropyrimidin-2-yl)oxy)-3-methylphenyl)carbamoyl)-3-methoxybicyclo[1.1.1]pentane-1-carboxamide (7469) (27.6 mg, 0.07 mmol) (Yield 13.7%) as a white solid. LC-MS (ESI⁺): m/z 387.2 (M+H)⁺. ¹H NMR (400 MHz, DMSO-d₆) δ 10.67 (s, 1H), 10.50 (s, 1H), 8.71 (s, 2H), 7.44-7.43 (m, 1H), 7.41-7.38 (m, 1H), 7.09-7.07 (m, 1H), 3.21 (s, 3H), 2.20 (s, 6H), 2.05 (s, 3H).

Example 31

In another exemplary method, N-((4-((5-fluoropyridin-2-yl)oxy)-3-methylphenyl)carbamoyl)-3-methoxybicyclo[1.1.1]pentane-1-carboxamide (Compound 89) was synthesized. FIG. 31 illustrates the chemical reaction equation for synthesis of compound 89.

4-((5-fluoropyridin-2-yl)oxy)-3-methylaniline. A solution of 4-amino-2-methylphenol (1.00 g, 8.12 mmol), 2-chloro-5-fluoropyridine (1.07 g, 8.12 mmol), cesium carbonate (7.94 g, 24.36 mmol) in N,N-dimethylformamide (20 mL) was stirred at 100° C. for 16 hours. After quenching the reaction, the reaction mixture was extracted with ethyl acetate (100 mL×3). The organic layer was washed with brine (100 mL), dried over Na₂SO₄, filtered and concentrated. The crude product was purified by flash column chromatography (petroleum ether:methyl t-butyl ether=9:1) to get 4-((5-fluoropyridin-2-yl)oxy)-3-methylaniline (900.0 mg, 5.09 mmol) (Yield 50.7%) as a brown solid. LC-MS (ESI⁺): m/z 219.2 (M+H)⁺.

N-((4-((5-fluoropyridin-2-yl)oxy)-3-methylphenyl)carbamoyl)-3-methoxybicyclo[1.1.1]pentane-1-carboxamide. To a solution of 3-methoxybicyclo[1.1.1]pentane-1-carboxamide (80.0 mg, 0.57 mmol) in 1,2-dichloroethane (5 mL) at room temperature was added oxalyl chloride (79 mg, 0.82 mmol), The reaction mixture was heated at 80° C. for 3 hours. The mixture was cooled to room temperature, added dropwise to a solution of 4-((5-fluoropyridin-2-yl)oxy)-3-methylaniline (114.0 mg, 0.52 mmol) and pyridine (205.0 mg, 2.6 mmol) in THF (4 mL) and stirred at room temperature for overnight. After quenching the reaction, the reaction mixture was extracted with ethyl acetate (50 mL×3). The organic layer was washed with brine (100 mL), dried over Na₂SO₄, filtered and concentrated. The residue was purified by HPLC to afford N-((4-((5-fluoropyridin-2-yl)oxy)-3-methylphenyl)carbamoyl)-3-methoxybicyclo[1.1.1]pentane-1-carboxamide (63.3 mg, 0.16 mmol) (yield 31.6%) as a white solid. LC-MS (ESI⁺): m/z 386.3 (M+H)⁺.

¹H NMR (400 MHz, DMSO-d₆) δ 10.66 (s, 1H), 10.48 (s, 1H), 8.10-8.09 (m, 1H), 7.83-7.78 (m, 1H), 7.42 (s, 1H), 7.39-7.36 (m, 1H), 7.09-7.06 (m, 1H), 7.02-7.00 (m, 1H), 3.20 (s, 3H), 2.20 (s, 6H), 2.06 (s, 3H).

Example 32

In another exemplary method, 3-methoxy-N-((4-methyl-3-(thiazol-2-yloxy)phenyl)carbamoyl)cyclobutane-1-carboxamide (Compound 93) was synthesized. FIG. 32 illustrates the chemical reaction equation for synthesis of compound 93.

4-methyl-3-(thiazol-2-yloxy)aniline. A solution of 5-amino-2-methylphenol (200 mg, 1.63 mmol), 2-bromothiazole (266.6 mg, 1.63 mmol), cesium carbonate (1.60 g, 4.8 mmol) in DMF (5 mL) was stirred at 70° C. for 3 hours. After quenching the reaction, the reaction mixture was extracted with ethyl acetate (100 mL×3). The organic layer was washed with brine (300 mL), dried over Na₂SO₄, filtered and concentrated. The crude product was purified by flash column chromatography (petroleum ether:ethyl acetate=1:1) to get 4-methyl-3-(thiazol-2-yloxy)aniline (256.4 mg, 1.24 mmol) (yield 76.2%) as a yellow solid. LC-MS (ESI⁺): m/z 206.05 (M+H)⁺.

3-methoxy-N-((4-methyl-3-(thiazol-2-yloxy)phenyl)carbamoyl)cyclobutane-1-carboxamide. To a solution of 3-methoxycyclobutane-1-carboxamide (200.0 mg, 1.55 mmol) in 1,2-dichloroethane (4 mL) at room temperature was added oxalyl chloride (261.9 mg, 2.10 mmol). The reaction mixture was heated at 80° C. for 3 hours. The mixture was cooled to room temperature, then was added dropwise to a solution of 4-methyl-3-(thiazol-2-yloxy)aniline (256.4 mg, 1.24 mmol) and pyridine (552.9 mg, 6.99 mmol) in THF (4 mL) and stirred at room temperature for overnight. After quenching the reaction, the reaction mixture was extracted with ethyl acetate (100 mL×3). The organic layer was washed with brine (300 mL), dried over Na₂SO₄, and concentrated. The residue was purified by HPLC to afford 3-methoxy-N-((4-methyl-3-(thiazol-2-yloxy)phenyl)carbamoyl)cyclobutane-1-carboxamide (123.4 mg, 0.34 mmol) (yield: 26.62%) as a yellow solid. LC-MS (ESI⁺): m/z 361.11 (M+H)⁺. ¹H NMR (400 MHz, DMSO-d6) δ 10.67-10.60 (m, 2H), 7.61 (s, 1H), 7.31 (s, 2H), 7.27-7.26 (m, 1H), 7.20-7.19 (m, 1H), 3.99-3.96 (m, 0.3H), 3.78 (s, 0.8H), 3.18 (s, 0.3H), 3.12 (s, 3H), 2.83-2.78 (m, 0.8H), 2.41-2.39 (m, 2H), 2.14 (s, 3H), 2.04-1.97 (m, 2H).

Example 33

In another exemplary method, 3-methoxy-N-((4-methyl-3-(pyridin-2-yloxy)phenyl)carbamoyl)cyclobutane-1-carboxamide (Compound 94) was synthesized. FIG. 33 illustrates the chemical reaction equation for synthesis of compound 94.

4-methyl-3-(pyridin-2-yloxy)aniline. A solution of 5-amino-2-methylphenol (600.0 mg, 4.88 mmol), 2-bromopyridine (771.0 g, 4.88 mmol), cesium carbonate (7.77 g, 14.64 mmol) and CuI (95.2 mg, 0.5 mmol) in N,N-dimethylacetamide (10 mL) was stirred at 80° C. for 16 hours. After quenching the reaction, the reaction mixture was extracted with ethyl acetate (100 mL×3). The organic layer was washed with brine (100 mL), dried over Na₂SO₄, filtered and concentrated. The crude product was purified by flash column chromatography (petroleum ether:ethyl acetate=1:1) to get 4-methyl-3-(pyridin-2-yloxy)aniline (150 g, 0.75 mmol) (Yield 15.4%) as a brown solid. LC-MS (ESI⁺): m/z 201.1 (M+H)⁺.

3-methoxy-N-((4-methyl-3-(pyridin-2-yloxy)phenyl)carbamoyl)cyclobutane-1-carboxamide. To a solution of 3-methoxycyclobutane-1-carboxamide (116.0 mg, 0.90 mmol) in 1,2-dichloroethane (8 mL) at room temperature was added oxalyl chloride (133.0 mg, 1.05 mmol). The reaction mixture was heated at 80° C. for 3 hours. The mixture was cooled to room temperature, added dropwise to a solution of 4-methyl-3-(pyridin-2-yloxy)aniline (150.0 mg, 0.75 mmol) and pyridine (296.0 mg, 3.75 mmol) in THF (8 mL) and stirred at room temperature for overnight. After quenching the reaction, the reaction mixture was extracted with ethyl acetate (50 mL×3). The organic layer was washed with brine (100 mL), dried over $Na_2SO_4$, filtered and concentrated. The residue was purified by HPLC to afford 3-methoxy-N-((4-methyl-3-(pyridin-2-yloxy)phenyl)carbamoyl)cyclobutane-1-carboxamide (60.3 mg, 0.17 mmol) (Yield 22.6%) as a white solid. LC-MS (ESI$^+$): m/z 356.3 (M+H)$^+$. $^1$H NMR (400 MHz, DMSO_d$_6$) δ 10.63 (s, 1H), 10.57-10.54 (m, 1H), 8.12-8.11 (m, 1H) 7.87-7.83 (m, 1H), 7.37 (m, 1H), 7.25-7.19 (m, 2H), 7.12-7.09 (m, 1H), 7.02-7.00 (m, 1H), 3.99-3.95 (m, 0.4H), 3.79-3.75 (m, 0.6H), 3.21-3.16 (m, 0.4H), 3.12 (s, 3H), 2.82-2.78 (m, 0.6H), 2.41-2.38 (m, 2H), 2.14-2.11 (m, 1H), 2.07 (s, 3H), 2.02-1.98 (m, 1H).

Example 34

In another exemplary method, 3-methoxy-N-((4-methyl-3-(pyrimidin-2-yloxy)phenyl)carbamoyl)cyclobutane-1-carboxamide (Compound 95) was synthesized. FIG. 34 illustrates the chemical reaction equation for synthesis of compound 95.

4-methyl-3-(pyrimidin-2-yloxy)aniline. A solution of 5-amino-2-methylphenol (200 mg, 1.63 mmol), 2,5-difluoropyridine (186.9 mg, 1.63 mmol), cesium carbonate (1.60 g, 4.8 mmol) in DMF (5 mL) was stirred at 70° C. for 3 hours. After quenching the reaction, the reaction mixture was extracted with ethyl acetate (100 mL×3). The organic layer was washed with brine (300 mL), dried over $Na_2SO_4$, filtered and concentrated. The crude product was purified by flash column chromatography (petroleum ether:ethyl acetate=1:1) to get 3-((5-fluoropyridin-2-yl)oxy)-4-methylaniline (116.2 mg, 0.53 mmol) (Yield 34.6%) as a yellow solid. LC-MS (ESI$^+$): m z 218.09 (M+H)$^+$.

3-methoxy-N-((4-methyl-3-(pyrimidin-2-yloxy)phenyl)carbamoyl)cyclobutane-1-carboxamide. To a solution of 3-methoxycyclobutane-1-carboxamide (200.0 mg, 1.55 mmol) in 1,2-dichloroethane (4 mL) at room temperature was added oxalyl chloride (261.9 mg, 2.10 mmol). The reaction mixture was heated at 80° C. for 3 hours. The mixture was cooled to room temperature, then was added dropwise to a solution of 3-((5-fluoropyridin-2-yl)oxy)-4-methylaniline (116.2 mg, 0.53 mmol) and pyridine (552.9 mg, 6.99 mmol) in THF (4 mL) and stirred at room temperature for overnight. After quenching the reaction, the reaction mixture was extracted with ethyl acetate (100 mL×3). The organic layer was washed with brine (300 mL), dried over $Na_2SO_4$, filtered and concentrated. The residue was purified by HPLC to afford N-((3-((5-fluoropyridin-2-yl)oxy)-4-methylphenyl)carbamoyl)-3-methoxycyclobutane-1-carboxamide (24.8 mg, 0.07 mmol) (yield 12.59%) as a white solid. LC-MS (ESI$^+$): m/z 373.14 (M+H)$^+$. $^1$H NMR (400 MHz, DMSO-d$_6$) δ 10.63 (s, 1H), 10.56-10.54 (m, 1H), 8.12-8.11 (d, J=3.2 Hz, 1H), 7.84-7.79 (m, 1H), 7.37 (s, 1H), 7.25-7.19 (m, 2H), 7.11-7.08 (m, 1H), 3.98-3.95 (m, 0.2H), 3.79-3.76 (m, 0.8H), 3.19-3.12 (m, 0.3H), 3.11 (s, 3H), 2.81-2.77 (m, 0.8H), 2.42-2.36 (m, 2H), 2.14-2.10 (m, 0.7H), 2.03 (s, 3H), 2.01-1.96 (m, 1.3H).

Example 35

In another exemplary method, 3-methoxy-N-((4-methyl-3-(pyrimidin-2-yloxy)phenyl)carbamoyl)cyclobutane-1-carboxamide (Compound 96) was synthesized. FIG. 35 illustrates the chemical reaction equation for synthesis of compound 96.

4-methyl-3-(pyrimidin-2-yloxy)aniline. A solution of 5-amino-2-methylphenol (200 mg, 1.63 mmol), 2-(methylsulfonyl)pyrimidine (256.9 mg, 1.63 mmol), cesium carbonate (1.60 g, 4.8 mmol) in DMF (5 mL) was stirred at room temperature for 3 hours. After quenching the reaction, the reaction mixture was extracted with ethyl acetate (100 mL×3). The organic layer was washed with brine (300 mL), dried over $Na_2SO_4$, filtered and concentrated. The crude product was purified by flash column chromatography (PE:EA=1:1) to get 4-methyl-3-(pyrimidin-2-yloxy)aniline (300.0 mg, 1.62 mmol) (Yield 91.7%) as a yellow solid. LC-MS (ESI$^+$): m/z 201.09 (M+H)$^+$.

3-methoxy-N-((4-methyl-3-(pyrimidin-2-yloxy)phenyl)carbamoyl)cyclobutane-1-carboxamide. To a solution of 3-methoxycyclobutane-1-carboxamide (200.0 mg, 1.55 mmol) in 1,2-dichloroethane (4 mL) at room temperature was added oxalyl chloride (261.9 mg, 2.10 mmol). The reaction mixture was heated at 80° C. for 3 hours. The mixture was cooled to room temperature, then was added dropwise to a solution of 4-methyl-3-(pyrimidin-2-yloxy)aniline (200.0 mg, 0.99 mmol) and pyridine (552.9 mg, 6.99 mmol) in THF (4 mL) and stirred at room temperature for overnight. After quenching the reaction, the reaction mixture was extracted with ethyl acetate (100 mL×3). The organic layer was washed with brine (300 mL), dried over $Na_2SO_4$, filtered and concentrated. The residue was purified by HPLC to afford 3-methoxy-N-((4-methyl-3-(pyrimidin-2-yloxy)phenyl)carbamoyl)cyclobutane-1-carboxamide (72.9 mg, 0.20 mmol) (Yield 21.0%) as a white solid. LC-MS (ESI$^+$): m/z 356.2 (M+H)$^+$. $^1$H NMR (400 MHz, DMSO-d$_6$) δ 10.65 (s, 1H), 10.58-10.56 (m, 1H), 8.65-8.63 (m, 2H), 7.44 (s, 1H), 7.27-7.25 (m, 3H), 3.99-3.96 (m, 0.2H), 3.79-3.76 (m, 0.8H), 3.37-3.13 (m, 0.2H), 3.12 (s, 3H), 2.82-2.77 (m, 0.8H), 2.42-2.38 (m, 2H), 2.11-2.03 (m, 1.2H), 2.01 (s, 3H), 1.98-1.96 (m, 0.8H).

Example 36

In another exemplary method, N-((4-((5-chloropyrimidin-2-yl)oxy)-3-fluoro-5-methylphenyl)carbamoyl)-3-methoxybicyclo[1.1.1]pentane-1-carboxamide (Compound 90) was synthesized. FIG. 36 illustrates the chemical reaction equation for synthesis of compound 90.

1-bromo-2,3-difluoro-5-nitrobenzene. A solution of 1,2-difluoro-4-nitrobenzene (48.0 g, 301.72 mmol), NBS (53.7 g, 301.72 mmol) in $H_2SO_4$ (200 mL) was stirred at 0° C. for 12 hours. After quenching the reaction, the reaction mixture was extracted with ethyl acetate (500 mL×4). The organic layer was washed with brine (600 mL), dried over $Na_2SO_4$, filtered and concentrated. The crude product was purified by flash column chromatography (petroleum ether:ethyl acetate=30:1) to get 1-bromo-2,3-difluoro-5-nitrobenzene (68.0 g, 285.73 mmol) (Yield 94.7%) as a yellow solid.

2-(benzyloxy)-1-bromo-3-fluoro-5-nitrobenzene. To a solution of 1-bromo-2,3-difluoro-5-nitrobenzene (30.0 g, 126.06 mmol) in DMF (200 mL) at room temperature was added phenyl methanol (13.63 g, 126.06 mmol) and $Cs_2CO_3$ (82.14 g, 252.16 mmol). The reaction mixture was stirred at r.t for 6 hours. After quenching the reaction, the reaction mixture was extracted with ethyl acetate (500 mL×4). The organic layer was washed with brine (600 mL), dried over $Na_2SO_4$, filtered and concentrated. The crude product was purified by flash column chromatography (petroleum ether: ethyl acetate=30:1) to get 2-(benzyloxy)-1-bromo-3-fluoro-5-nitrobenzene (34.3 g, 105.18 mmol) (Yield 83.4%) as a yellow solid.

2-(benzyloxy)-1-fluoro-3-methyl-5-nitrobenzene. To a solution of 2-(benzyloxy)-1-bromo-3-fluoro-5-nitrobenzene (34.3 g, 105.18 mmol) in DMF (200 mL) at room temperature was added 2,4,6-trimethyl-1,3,5,2,4,6-trioxatriborinane (26.41 g, 210.36 mmol) and $K_2PO_4$ (66.98 g, 315.54 mmol) and Pd(dppf)Cl$_2$ (3.84 g, 5.26 mmol) under $N_2$. The reaction mixture was heated at 100° C. for 12 hours. After quenching the reaction, the reaction mixture was extracted with ethyl acetate (500 mL×4). The organic layer was washed with brine (600 mL), dried over $Na_2SO_4$, filtered and concentrated. The crude product was purified by flash column chromatography (petroleum ether:ethyl acetate=19:1) to get 2-(benzyloxy)-1-fluoro-3-methyl-5-nitrobenzene (9.3 g, 35.6 mmol) (Yield 33.8%) as a yellow solid.

2-fluoro-6-methyl-4-nitrophenol. To a solution of 2-(benzyloxy)-1-fluoro-3-methyl-5-nitrobenzene (9.3 g, 35.6 mmol) in DCM (20 mL) at 0° C. was added BBr$_3$ (2 M, 35.6 mL, 71.2 mmol). The reaction mixture was stirred at 0° C. for 8 hours. After quenching the reaction with aq. NaHCO$_3$, the reaction mixture was extracted with ethyl acetate (500 mL×4). The organic layer was washed with brine (600 mL), dried over $Na_2SO_4$, filtered and concentrated. The crude product was purified by flash column chromatography (petroleum ether:ethyl acetate=15:1) to get 2-fluoro-6-methyl-4-nitrophenol (4.3 g, 25.13 mmol) (Yield 71.67%) as a yellow solid.

5-chloro-2-(2-fluoro-6-methyl-4-nitrophenoxy)pyrimidine. To a solution of 2-fluoro-6-methyl-4-nitrophenol (4.0 g, 23.39 mmol), 2,5-dichloropyrimidine (6.96 g, 46.78 mmol) and 4-toluene sulfonic acid (12.06 g, 70.17 mmol) in DMA (10 mL) under microwave (150° C., 12 h). After quenching the reaction, the reaction mixture was extracted with ethyl acetate (100 mL×3). The organic layer was washed with brine (300 mL), dried over $Na_2SO_4$, filtered and concentrated. The crude product was purified by flash column chromatography (petroleum ether:ethyl acetate=15: 1) to get 5-chloro-2-(2-fluoro-6-methyl-4-nitrophenoxy)pyrimidine (1.65 g, 5.83 mmol) (Yield 25.1%) as a yellow solid.

4-((5-chloropyrimidin-2-yl)oxy)-3-fluoro-5-methylaniline. To a solution of 5-chloro-2-(2-fluoro-6-methyl-4-nitrophenoxy)pyrimidine (1.65 mg, 5.83 mmol), Iron powder (1.6 g, 29.15 mmol) and NH$_4$Cl (1.55 g, 29.15 mmol) in EtOH (20 mL) and H$_2$O (10 mL). The reaction mixture was stirred at 80° C. for 3 hours. After quenching the reaction, the reaction mixture was extracted with ethyl acetate (100 mL×3). The organic layer was washed with brine (300 mL), dried over $Na_2SO_4$, filtered and concentrated. The crude product was purified by flash column chromatography (petroleum ether:ethyl acetate=2:1) to get 4-((5-chloropyrimidin-2-yl)oxy)-3-fluoro-5-methylaniline (754.9 mg, 2.98 mmol) (Yield 51.02%) as a yellow solid.

N-((4-((5-chloropyrimidin-2-yl)oxy)-3-fluoro-5-methylphenyl)carbamoyl)-3-methoxybicyclo[1.1.1]pentane-1-carboxamide. To a solution of 3-methoxybicyclo[1.1.1]pentane-1-carboxamide (80.0 mg, 0.57 mmol) in 1,2-dichloroethane (4 mL) at room temperature was added oxalyl chloride (143.64 mg, 1.14 mmol). The reaction mixture was heated at 80° C. for 3 hours. The mixture was cooled to room temperature and added dropwise to a solution of 4-((5-chloropyrimidin-2-yl)oxy)-3-fluoro-5-methylaniline (80 mg, 0.32 mmol) and pyridine (101.3 mg, 1.28 mmol) in THF (4 mL), then stirred at room temperature for overnight. After quenching the reaction, the reaction mixture was extracted with ethyl acetate (100 mL×3). The organic layer was washed with brine (300 mL), dried over $Na_2SO_4$, filtered and concentrated. The residue was purified by HPLC to afford N-((4-((5-chloropyrimidin-2-yl)oxy)-3-fluoro-5-methylphenyl)carbamoyl)-3-methoxybicyclo[1.1.1]pentane-1-carboxamide (36.4 mg, 0.02 mmol) (Yield: 8.6%) as a yellow solid. LC-MS (ESI$^+$): m/z 421.3 (M+H)$^+$. $^1$H NMR (400 MHz, DMSO-d$_6$) δ 10.75 (s, 1H), 10.59 (s, 1H), 8.78 (s, 2H), 7.56-7.55 (m, 1H), 7.22 (s, 1H), 3.21 (s, 3H), 2.21-2.20 (d, J=5.6 Hz, 6H), 2.12 (s, 3H).

Example 37

In another exemplary method, N-((3-fluoro-4-((5-fluoropyridin-2-yl)oxy)-5-methylphenyl)carbamoyl)-3-methoxybicyclo[1.1.1]pentane-1-carboxamide (Compound 91) was synthesized. FIG. 37 illustrates the chemical reaction equation for synthesis of compound 91.

5-fluoro-2-(2-fluoro-6-methyl-4-nitrophenoxy)pyridine. To a solution of 2-fluoro-6-methyl-4-nitrophenol (500 mg, 2.92 mmol), 2,5-difluoropyridine (672.47 mg, 5.84 mmol) and 4-toluene sulfonic acid (1.5 g, 8.76 mmol) in DMA (5 mL) under microwave (150° C., 12 h). After quenching the reaction, the reaction mixture was extracted with ethyl acetate (100 mL×3). The organic layer was washed with brine (300 mL), dried over $Na_2SO_4$, filtered and concentrated. The crude product was purified by flash column chromatography (petroleum ether:ethyl acetate=15:1) to get 5-fluoro-2-(2-fluoro-6-methyl-4-nitrophenoxy)pyridine (323.3 mg, 1.22 mmol) (Yield 41.6%) as a yellow solid.

3-fluoro-4-((5-fluoropyridin-2-yl)oxy)-5-methylaniline. To a solution of 5-fluoro-2-(2-fluoro-6-methyl-4-nitrophenoxy)pyridine (323.3 mg, 1.22 mmol), Iron powder (340.68 mg, 6.1 mmol) and NH$_4$Cl (326.29 mg, 6.1 mmol) in EtOH (4 mL) and H$_2$O (2 mL). The reaction mixture was stirred at 80° C. for 3 hours. After quenching the reaction, the reaction mixture was extracted with ethyl acetate (100 mL×3). The organic layer was washed with brine (300 mL), dried over $Na_2SO_4$, filtered and concentrated. The crude product was purified by flash column chromatography (petroleum ether: ethyl acetate=2:1) to get 3-fluoro-4-((5-fluoropyridin-2-yl)oxy)-5-methylaniline (100 mg, 0.42 mmol) (Yield 34.7%) as a yellow solid. LC-MS (ESI$^+$): m/z 237.1 (M+H)$^+$.

N-((3-fluoro-4-((5-fluoropyridin-2-yl)oxy)-5-methylphenyl)carbamoyl)-3-methoxybicyclo[1.1.1]pentane-1-carboxamide. To a solution of 3-methoxybicyclo[1.1.1]pentane-1-carboxamide (100.0 mg, 0.71 mmol) in 1,2-dichloroethane (4 mL) at room temperature was added oxalyl chloride (105.84 mg, 0.84 mmol). The reaction mixture was heated at 80° C. for 3 hours. The mixture was cooled to room temperature and added dropwise to a solution of 3-fluoro-4-((5-fluoropyridin-2-yl)oxy)-5-methylaniline (100 mg, 0.42 mmol) and pyridine (166.11 mg, 2.1 mmol) in THF (4 mL), then stirred at room temperature for overnight. After quenching the reaction, the reaction mixture was extracted with ethyl acetate (100 mL×3). The organic layer was washed with brine (300 mL), dried over $Na_2SO_4$, filtered and concentrated. The residue was purified by HPLC to afford N-((3-fluoro-4-((5-fluoropyridin-2-yl)oxy)-5-methylphenyl)carbamoyl)-3-methoxybicyclo[1.1.1]pentane-1-carboxamide (6.2 mg, 0.02 mmol) (Yield 2.2%) as a yellow solid. LC-MS (ESI⁺): m/z 404.3 (M+H)⁺. ¹H NMR (400 MHz, DMSO-d₆) δ 10.73 (s, 1H), 10.56 (s, 1H), 8.08-8.07 (d, J=3.2 Hz, 1H), 7.85-7.83 (m, 1H), 7.52-7.48 (m, 1H), 7.23-7.19 (m, 2H), 3.21 (s, 3H), 2.33-2.32 (m, 6H), 2.20-2.07 (m, 3H).

Example 38

In another exemplary method, 3-methoxy-N-((4-methyl-3-(pyrimidin-2-yloxy)phenyl)carbamoyl)bicyclo[1.1.1]pentane-1-carboxamide (Compound 97) was synthesized. FIG. 38 illustrates the chemical reaction equation for synthesis of compound 97.

4-methyl-3-(pyrimidin-2-yloxy)aniline. A solution of 5-amino-2-methylphenol (1.00 g, 8.12 mmol), 2-chloropyrimidine (928.0 mg, 8.12 mmol), cesium carbonate (7.94 g, 24.36 mmol) in acetonitrile (20 mL) was stirred at room temperature for 16 hours. After quenching the reaction, the reaction mixture was extracted with ethyl acetate (100 mL×3). The organic layer was washed with brine (100 mL), dried over Na₂SO₄, filtered and concentrated. The crude product was purified by flash column chromatography (petroleum ether:ethyl acetate=3:2) to get 4-methyl-3-(pyrimidin-2-yloxy)aniline (0.6 g, 2.98 mmol) (Yield 36.8%) as a pale yellow solid. LC-MS (ESI⁺): m/z 202.2 (M+H)⁺.

3-methoxy-N-((4-methyl-3-(pyrimidin-2-yloxy)phenyl) carbamoyl)bicyclo[1.1.1]pentane-1-carboxamide. To a solution of 3-methoxybicyclo[1.1.1]pentane-1-carboxamide (105.0 mg, 0.75 mmol) in 1,2-dichloroethane (5 mL) at room temperature was added oxalyl chloride (141 mg, 1.12 mmol). The reaction mixture was heated at 80° C. for 3 hours. The mixture was cooled to room temperature, added dropwise to a solution of 3-methyl-4-(pyrimidin-2-yloxy)aniline (150.0 mg, 0.75 mmol) and pyridine (296.0 mg, 3.75 mmol) in THF (4 mL) and stirred at room temperature overnight. After quenching the reaction, the reaction mixture was extracted with ethyl acetate (50 mL×3). The organic layer was washed with brine (100 mL), dried over Na₂SO₄, filtered and concentrated. The residue was purified by HPLC to afford 3-methoxy-N-((4-methyl-3-(pyrimidin-2-yloxy)phenyl)carbamoyl)bicyclo[1.1.1]pentane-1-carboxamide (7553) (81.5 mg, 0.22 mmol) (Yield 29.7%) as a white solid. LC-MS (ESI⁺): m/z 369.3 (M+H)⁺. ¹H NMR (400 MHz, DMSO d₆) δ 10.65 (s, 1H), 10.52 (s, 1H), 8.64 (m, 2H), 7.43-7.40 (m, 1H), 7.29-7.22 (m, 3H), 3.20 (s, 3H), 2.18 (s, 6H), 2.00 (s, 3H).

Example 39

In another exemplary method, 3-methoxy-N-((4-methyl-3-(pyridin-2-yloxy)phenyl)carbamoyl)bicyclo[1.1.1]pentane-1-carboxamide (Compound 98) was synthesized. FIG. 39 illustrates the chemical reaction equation for synthesis of compound 98.

4-methyl-3-(pyridin-2-yloxy)aniline. A solution of 5-amino-2-methylphenol (500.0 mg, 4.06 mmol), 2-bromopyridine (638.2 mg, 4.06 mmol), cesium carbonate (2.64 g, 8.13 mmol) in N,N-dimethylacetamide (20 mL) was stirred at 100° C. for 16 hours. After quenching the reaction, the reaction mixture was extracted with ethyl acetate (100 mL×3). The organic layer was washed with brine (100 mL), dried over Na₂SO₄, filtered and concentrated. The crude product was purified by flash column chromatography (petroleum ether:ethyl acetate=1:1) to get 4-methyl-3-(pyridin-2-yloxy)aniline (110.0 mg, 0.55 mmol) (Yield 13.5%) as a brown solid. LC-MS (ESI⁺): m/z 201.2 (M+H)⁺.

3-methoxy-N-((4-methyl-3-(pyridin-2-yloxy)phenyl)carbamoyl)bicyclo[1.1.1]pentane-1-carboxamide. To a solution of 3-methoxybicyclo[1.1.1]pentane-1-carboxamide (78.0 mg, 0.55 mmol) in 1,2-dichloroethane (5 mL) at room temperature was added oxalyl chloride (79.0 mg, 0.83 mmol). The reaction mixture was heated at 80° C. for 3 hours. The mixture was cooled to room temperature, added dropwise to a solution of 4-methyl-3-(pyridin-2-yloxy)aniline (110.0 mg, 0.55 mmol) and pyridine (350.0 mg, 2.75 mmol) in THF (4 mL) and stirred at room temperature overnight. After quenching the reaction, the reaction mixture was extracted with ethyl acetate (50 mL×3). The organic layer was washed with brine (100 mL), dried over Na₂SO₄, filtered and concentrated. The residue was purified by HPLC to afford 3-methoxy-N-((4-methyl-3-(pyridin-2-yloxy)phenyl)carbamoyl)bicyclo[1.1.1]pentane-1-carboxamide (7554) (60.3 mg, 0.16 mmol) (Yield 29.8%) as a white solid. LC-MS (ESI⁺): m/z 368.7 (M+H)⁺. ¹H NMR (400 MHz, DMSO d₆) δ 10.63 (s, 1H), 10.51 (s, 1H), 8.13-8.08 (m, 1H), 7.87-7.81 (m, 1H), 7.37-7.33 (m, 1H), 7.27-7.21 (m, 1H), 7.21-7.16 (m, 1H), 7.15-7.06 (m, 1H), 7.04-6.98 (m, 1H), 3.20 (s, 3H), 2.17 (s, 6H), 2.02 (s, 3H).

Example 40

In another exemplary method, N-((3-fluoro-5-methyl-4-(pyrimidin-2-yloxy)phenyl)carbamoyl)-3-methoxybicyclo[1.1.1]pentane-1-carboxamide (Compound 92) was synthesized. FIG. 40 illustrates the chemical reaction equation for synthesis of compound 92.

2-(benzyloxy)-1-bromo-3-fluoro-5-nitrobenzene. A solution of 1-bromo-2,3-difluoro-5-nitrobenzene (33.0 g, 138.13 mmol) and cesium carbonate (90.4 g, 277.32 mmol) in DMF (200 mL) was added dropwise to a solution of phenyl methanol (15.7 g, 145.59 mmol) at 0° C. The mixture was stirred at room temperature for overnight. After quenching the reaction, the reaction mixture was extracted with ethyl acetate (500 mL×3). The organic layer was washed with brine (500 mL), dried over Na₂SO₄, filtered and concentrated. The crude product was purified by flash column chromatography (petroleum ether:ethyl acetate=10:1) to get 2-(benzyloxy)-1-bromo-3-fluoro-5-nitrobenzene (14.1 g, 43.24 mmol) (Yield 32.6%) as a yellow solid.

2-(benzyloxy)-1-fluoro-3-methyl-5-nitrobenzene. To a solution of 2-(benzyloxy)-1-bromo-3-fluoro-5-nitrobenzene (14.1 g, 43.24 mmol) in DMF (200 mL) was added potassium carbonate (17.9 g, 130.17 mmol) and 2,4,6-trimethyl-1,3,5,2,4,6-trioxatriborinane (10.9 g, 96.78 mmol), Pd(dppf)Cl₂ (3.17 g, 4.34 mmol) at room temperature under N₂. The reaction mixture was heated 100° C. for overnight. The mixture was cooled to room temperature. After diluting the reaction, the reaction mixture was extracted with ethyl acetate (400 mL×3). The organic layer was washed with brine (500 mL), dried over Na₂SO₄, filtered and concentrated. The crude product was purified by flash column chromatography (petroleum ether:ethyl acetate=3:1) to get 2-(benzyloxy)-1-fluoro-3-methyl-5-nitrobenzene (7.0 g, 26.79 mmol) (Yield 62.0%) as a yellow solid.

2-fluoro-6-methyl-4-nitrophenol. To a solution of 2-(benzyloxy)-1-bromo-3-fluoro-5-nitrobenzene (7.0 g, 26.79 mmol) in DCM (100 mL) was added BBr₃ (13.4 g, 53.58 mmol) and stirred at room temperature for overnight. After diluting the reaction, the reaction mixture was extracted with ethyl acetate (400 mL×3). The organic layer was washed with brine (500 mL), dried over Na₂SO₄, filtered and concentrated. The crude product was purified by flash column chromatography (petroleum ether:ethyl acetate=10:1)

to get 2-fluoro-6-methyl-4-nitrophenol (3.0 g, 17.54 mmol) (Yield 32.5%) as a yellow solid.

2-(2-fluoro-6-methyl-4-nitrophenoxy)pyrimidine. To a solution of 2-fluoro-6-methyl-4-nitrophenol (1.0 g, 5.85 mmol) and 2-chloropyrimidine (1.3 g, 11.72 mmol) in DMA (5 mL) was added 4-toluene sulfonic acid (3.3 g, 17.52 mmol) and KI (450.3 mg, 2.92 mmol) at room temperature. The reaction mixture was heated 150° C. for overnight under microwave. The mixture was cooled to room temperature. After diluting the reaction, the reaction mixture was extracted with ethyl acetate (100 mL×3). The organic layer was washed with brine (200 mL), dried over $Na_2SO_4$, filtered and concentrated. The crude product was purified by flash column chromatography (petroleum ether:ethyl acetate=3:1) to get 2-(2-fluoro-6-methyl-4-nitrophenoxy) pyrimidine (90.0 mg, 0.36 mmol) (Yield 6.4%) as a yellow solid.

3-fluoro-5-methyl-4-(pyrimidin-2-yloxy)aniline. To a solution of 2-(2-fluoro-6-methyl-4-nitrophenoxy)pyrimidine (90.0 mg, 0.36 mmol) in $EtOH/H_2O$ (6 mL, v/v=5:1) was added iron powder (201.7 mg, 3.60 mmol) and $NH_4Cl$ (96.3 mg, 1.80 mmol). The mixture was heated to 80° C. for 16 hours. The reaction mixture was cooled to 25° C., filtered and filtrate was concentrated and purified by flash column chromatography (petroleum ether:ethyl acetate=1:2) to give 3-fluoro-5-methyl-4-(pyrimidin-2-yloxy)aniline (50.0 mg, 0.23 mmol) (Yield 63.3%) as a yellow solid. LC-MS ($ESI^+$): m/z 220.1 $(M+H)^+$.

N-((3-fluoro-5-methyl-4-(pyrimidin-2-yloxy)phenyl)carbamoyl)-3-methoxybicyclo[1.1.1]pentane-1-carboxamide. To a solution of 3-methoxybicyclo[1.1.1]pentane-1-carboxamide (39.0 mg, 0.27 mmol) in 1,2-dichloroethane (5 mL) at room temperature was added oxalyl chloride (58.0 mg, 0.46 mmol), then the reaction mixture was heated at 80° C. for 3 hours. The mixture was cooled to room temperature and added dropwise to a solution of 3-fluoro-5-methyl-4-(pyrimidin-2-yloxy)aniline (50.0 mg, 0.23 mmol) and pyridine (91.0 mg, 1.15 mmol) in THF (2 mL) then stirred at room temperature for overnight. After quenching the reaction, the reaction mixture was extracted with ethyl acetate (50 mL×3). The organic layer was washed with brine (100 mL), dried over $Na_2SO_4$, filtered and concentrated. The residue was purified by HPLC to afford N-((3-fluoro-5-methyl-4-(pyrimidin-2-yloxy)phenyl)carbamoyl)-3-methoxybicyclo [1.1.1]pentane-1-carboxamide (11.8 mg, 0.53 mmol) (Yield 58.6%) as a white solid. LC-MS ($ESI^+$): m/z 387.3 $(M+H)^+$. $^1H$ NMR (400 MHz, DMSO-$d_6$) δ 10.75 (s, 1H), 10.58 (s, 1H), 8.67-8.66 (m, 2H), 7.55-7.51 (m, 1H), 7.33-7.30 (m, 1H), 7.22 (s, 1H), 3.22 (s, 3H), 2.20 (s, 6H), 2.12 (s, 3H).

Example 41

In another exemplary method, half maximal effective concentration ($EC_{50}$) was determined for some compounds and their isomers as disclosed herein in a variety of human cancer cell lines. In brief, cells from two prostate cancer cell lines (LNCaP, 22RV1), one glioblastoma cell line (U87), one breast cancer cell line (MCF7), a glioma cell line (LN18), a normal prostate cell line (RWPE1), and a glioblastoma cell line (T98G) were plated in a multi-well plate. After 24 hours, one of the compounds herein was added to the well at increasing concentrations. After 72 hours of treatment, cell viability was assessed using AlamrBlue® (Invitrogen) and fluorescence was read using the CLARIOstar Plus Multilabel Plate Reader (BMG Labtech). Samples were normalized to no treatment controls. EC50 values were determined using GraphPad Prism. The $EC_{50}$ of the compounds tested in each of the cell lines is provided in Tables 5 and 6 where "inactive" means less than 50% inhibition at the highest concentration tested at 50 μM and "NT" means not tested.

TABLE 5

| Compound | $EC_{50}$ (μM) in LNCaP cells | $EC_{50}$ (μM) in 22RV1 cells | $EC_{50}$ (μM) in U87 cells | $EC_{50}$ (μM) in MCF7 cells | $EC_{50}$ (μM) in RWPE1 cells |
| --- | --- | --- | --- | --- | --- |
| 1 | 2.4 | 3.7 | 6.0 | 3.4 | Inactive |
| 1A | 0.55 | 1.5 | 3.2 | NT | Inactive |
| 1B | 13.9 | Inactive | Inactive | NT | Inactive |
| 2 | 19.0 | 41.0 | NT | 20.9 | NT |
| 3 | Inactive | Inactive | NT | NT | NT |
| 4 | Inactive | Inactive | NT | NT | NT |
| 5 | Inactive | Inactive | NT | NT | NT |
| 6A | 6.8 | 3.2 | 18.4 | NT | Inactive |
| 6B | Inactive | Inactive | Inactive | NT | Inactive |
| 7 | 2.8 | 2.9 | 4.4 | 2.4 | Inactive |
| 7A | 0.89 | 2.5 | 2.4 | NT | NT |
| 7B | Inactive | Inactive | Inactive | NT | NT |
| 8 | 27.5 | 26.0 | 36 | 24.3 | Inactive |
| 9 | 11.5 | 5.1 | 4.9 | 8.5 | Inactive |
| 10 | 13 | 12.5 | 33.5 | 12.9 | Inactive |
| 11A | 4.9 | 1.9 | 1.2 | NT | 4.85 |
| 11B | NT | Inactive | Inactive | NT | Inactive |
| 12 | 3.1 | 1.9 | 1.9 | 1.9 | 6.1 |
| 13 | 17.4 | 14.1 |  | 11.3 |  |
| 14A | 1.8 | 1.1 | 1.3 | NT | 1.3 |
| 14B | NT | Inactive | Inactive | NT | Inactive |
| 15A | 1.6 | 4.1 | 5.5 | 11.5 | Inactive |
| 15B | 3.9 | 17.3 | 22 | NT | Inactive |
| 16A | 2.9 | 5.8 | 10 | 12.7 | Inactive |
| 16B | 5.0 | 21.2 | 24 | NT | Inactive |
| 18A | 5.1 | 9.8 | 12.2 | NT | Inactive |
| 18B | 14.4 | 36 | Inactive | NT | Inactive |
| 19A | 0.87 | 0.95 | 2.2 | 2.8 | Inactive |
| 19B | 1.3 | 4.2 | 13.7 | NT | Inactive |
| 20A | 0.87 | 1.5 | 2.6 | 5.8 | Inactive |
| 20B | 5 | 15.3 | 31.2 | NT | Inactive |
| 21 | 19.7 | 24 | 20.8 | NT | 33 |

TABLE 5-continued

| Compound | EC$_{50}$ (μM) in LNCaP cells | EC$_{50}$ (μM) in 22RV1 cells | EC$_{50}$ (μM) in U87 cells | EC$_{50}$ (μM) in MCF7 cells | EC$_{50}$ (μM) in RWPE1 cells |
|---|---|---|---|---|---|
| 22 | Inactive | Inactive | Inactive | NT | Inactive |
| 23 | Inactive | 30.6 | Inactive | NT | Inactive |
| 24 | Inactive | Inactive | Inactive | NT | 31 |
| 27A | 1.3 | 2.8 | 2.1 | NT | NT |
| 27B | 9.8 | 25 | 23.3 | NT | NT |
| 28 | Inactive | Inactive | Inactive | NT | NT |
| 29 | 6.5 | 4.7 | 5.3 | NT | NT |
| 30 | 8.5 | 14.4 | 12.2 | NT | NT |
| 31A | 5 | 3.4 | 2.8 | NT | NT |
| 31B | Inactive | 44 | Inactive | NT | NT |
| 32 | 34 | 35 | Inactive | NT | NT |
| 33 | Inactive | Inactive | Inactive | NT | NT |
| 34A | 1.2 | 5.9 | 5.5 | NT | NT |
| 34B | Inactive | Inactive | Inactive | NT | NT |
| 35 | Inactive | Inactive | 49 | NT | NT |
| 36 | 34 | 34 | 31 | NT | NT |
| 37 | Inactive | Inactive | Inactive | NT | NT |
| 38 | Inactive | Inactive | Inactive | NT | NT |
| 39 | Inactive | Inactive | Inactive | NT | NT |
| 40 | Inactive | Inactive | Inactive | NT | NT |
| 41 | Inactive | 46 | 49 | NT | NT |
| 42 | 19.8 | 37 | 41.5 | NT | NT |
| 43 | 21.8 | 39 | 34 | NT | NT |
| 44 | 6.3 | 17.8 | 22 | 2.5 | NT |
| 45A | 0.90 | 2.8 | 3.7 | | Inactive |
| 45B | 4.0 | 14.2 | 12.2 | NT | Inactive |
| 46 | 2.9 | 8 | Inactive | NT | NT |
| 47 | Inactive | 8.8 | 22.1 | NT | NT |
| 48 | 12.4 | 3.2 | 6.4 | NT | NT |
| 49 | 11.8 | 1.3 | 3.7 | NT | NT |
| 50 | Inactive | Inactive | Inactive | NT | NT |
| 51 | 11.1 | 20 | 29 | NT | NT |
| 52 | 25.3 | 36 | Inactive | NT | NT |
| 53 | Inactive | Inactive | Inactive | NT | NT |
| 54 | Inactive | Inactive | Inactive | NT | NT |
| 55 | Inactive | 30.6 | Inactive | NT | NT |
| 56 | 0.15 | 0.35 | 0.89 | NT | 22.4 |
| 57 | 3.1 | 6.3 | 13.5 | NT | NT |
| 58 | 15.4 | 34 | Inactive | NT | NT |
| 59 | 0.27 | 0.08 | 0.002 | NT | NT |
| 60 | 0.88 | 1.2 | 0.32 | 0.6 | NT |
| 61 | 0.93 | 1.6 | 0.35 | NT | NT |
| 62 | 21 | 1.0 | 5.4 | NT | NT |
| 65 | NT | Inactive | Inactive | NT | NT |
| 66 | Inactive | Inactive | Inactive | NT | NT |
| 68 | Inactive | Inactive | Inactive | NT | NT |
| 69 | Inactive | Inactive | Inactive | NT | NT |
| 70 | Inactive | Inactive | Inactive | NT | Inactive |
| 71 | 10.4 | 12.5 | Inactive | 9.4 | Inactive |
| 72 | NT | 0.91 | 1.1 | NT | NT |
| 73 | NT | 0.068 | 0.12 | NT | NT |
| 74 | NT | 1.65 | 2.5 | NT | NT |
| 75 | NT | NT | Inactive | NT | NT |
| 76 | NT | NT | 0.10 | NT | NT |
| 77 | NT | NT | 22 | NT | NT |
| 78 | NT | NT | 5.9 | NT | NT |
| 79 | NT | NT | Inactive | NT | NT |
| 80 | NT | NT | Inactive | NT | NT |
| 81 | NT | NT | Inactive | NT | NT |
| 82 | NT | NT | Inactive | NT | NT |
| 83 | NT | NT | 0.33 | NT | NT |
| 84 | NT | NT | 0.16 | NT | NI |
| 85 | NT | NT | 0.06 | NT | NT |
| 86 | NT | NT | 0.26 | NT | NT |
| 87 | NT | NT | 1.2 | NT | NT |
| 88 | NT | NT | 1.45 | NT | NT |
| 89 | NT | NT | 0.2 | NT | NT |
| 90 | NT | NT | 0.065 | NT | NT |
| 91 | NT | NT | 0.63 | NT | NT |
| 92 | NT | NT | NT | NT | NT |
| 93 | NT | NT | 0.03 | NT | NT |
| 94 | NT | NT | 0.045 | NT | NT |
| 95 | NT | NT | 0.014 | NT | NT |
| 96 | NT | NT | 0.035 | NT | NT |
| 97 | NT | NT | 0.020 | NT | NT |
| 98 | NT | NT | 0.020 | NT | NT |

TABLE 6

| Compound | EC$_{50}$ (µM) in LN18 cells | EC$_{50}$ (µM) in T98G cells |
|---|---|---|
| 19 | 0.83 | NT |
| 84 | 0.01 | NT |
| 90 | 0.034 | 0.0384 |
| 91 | 0.087 | 0.1674 |
| 97 | 0.011 | 0.026 |
| 98 | 0.07 | 0.0189 |

Example 42

In another exemplary method, central nervous system multiparameter optimization (CNS MPO) score and kinetic solubility of selected compounds was determined. CNS MPO score for compounds and their isomers disclosed herein were calculated using an algorithm that uses a weighted scoring function assessing 6 key physicochemical properties (clogP, clogD, MW, TPSA, HBD, and pKa) for blood-brain-barrier (BBB) penetration). CNS MPO score ranged from 0 and 6.0 with scores≥4.0 used as a cut-off to select compounds that can have a high probability of accumulating in the CNS. Kinetic solubility of a compound is the maximum solubility of the fastest precipitating species of the compound. Kinetic solubility was determined by preparing a concentrated stock solution for compounds and their isomers disclosed herein in an organic solvent (DMSO), after which the solution was mixed with an aqueous PBS buffer and then filtered. Filtrate was tested to quantify the kinetic solubilty using HPLC-MS calibration curve. The CNS MPO Score and kinetic solubility of the compounds tested are provided in Table 7 where "ND" means not determined.

TABLE 7

| Compound | CNS MPO score (Range = 0-6) | Kinetic Solubility (µM) |
|---|---|---|
| 1 | 3.56 | 4.9 |
| 5 | 4.78 | ND |
| 6 | 3.39 | 0.53 |
| 7 | 3.47 | 0.49 |
| 8 | 4.13 | ND |
| 10 | 4.41 | ND |
| 11 | 4.2 | ND |
| 12 | 3.7 | 0.28 |
| 13 | 4.57 | ND |
| 14 | 3.9 | ND |
| 15 | 4.96 | 14.68 |
| 16 | 4.28 | 11.59 |
| 17 | 4.85 | ND |
| 18 | 5.03 | ND |
| 19 | 4.45 | 5.68 |
| 20 | 4.51 | 7.1 |
| 21 | 4.54 | ND |
| 22 | 4.59 | ND |
| 26 | 4.51 | ND |
| 27 | 3.79 | ND |
| 28 | 4.62 | ND |
| 42 | 4.75 | ND |
| 43 | 5.09 | ND |
| 44 | 4.08 | 0.95 |
| 45 | 5.14 | 58.43 |
| 46 | 3.44 | 0.39 |
| 47 | 4.55 | ND |
| 48 | 3.91 | 84.19 |
| 49 | 3.89 | 37.55 |
| 50 | 2.98 | ND |
| 51 | 3.51 | ND |
| 52 | 4 | ND |
| 53 | 3.58 | ND |
| 54 | 3.32 | ND |
| 55 | 5.07 | ND |
| 56 | 3.54 | 1 |
| 57 | 4.87 | 74.95 |
| 58 | 5.09 | ND |
| 85 | 4.42 | 2.21 |
| 87 | 4.96 | 27.5 |
| 88 | 4.76 | 10.9 |
| 90 | 4.22 | 2.17 |
| 93 | 5.14 | 8.9 |
| 94 | 5.13 | 11.8 |
| 95 | 4.96 | 7.2 |
| 96 | 5.03 | 14.8 |
| 97 | 4.96 | 5.80 |
| 85 | 4.42 | 2.21 |
| 87 | 4.96 | 27.5 |

Example 43

In another exemplary method, the effect of the compounds herein on tubulin polymerization was determined. FIG. 41A illustrates effects of compounds 19, 73, 86, 93 and 94 at 5 uM concentration, FIG. 41B illustrates effects of compounds 93, 94, 95 and 96 at 1 uM concentration, or FIG. 41C illustrates effects of compounds 87 and 88 at 5 uM concentration in accordance with certain embodiments of the present disclosure. Colchicine and vincristine are positive controls. The results show that compounds 19, 73, 86, 87, 88, 93, 94, 95 and 96 significantly inhibit tubulin polymerization.

The dose dependent effect of compounds 19 and 73 on tubulin polymerization was also determined. FIG. 42A illustrates effects of compound 19 at 0.3, 1, 3 and 6 uM concentrations, and FIG. 42B illustrates effects of compound 73 at 0.1, 0.3, 1, 3 and 5 uM concentration in accordance with certain embodiments of the present disclosure. Colchicine and nocodazole are positive controls. The results show that compounds 19 and 73 significantly inhibit tubulin polymerization in a dose dependent manner.

These results were further confirmed using the colchicine competitive binding assay (FIG. 43) and the N,N'-ethylene-bis(iodoacetamide) (EBI) competition assay (FIG. 44). Microtubule-targeting agents that bind at the colchicine-site of tubulin are of interest in antitumoral therapy due to their action as anti-mitotics. The results show that compounds 19, 73, and 93 significantly inhibit microtubule assembly (FIG. 43). Nocodazole was used as a positive control. Compounds 19, 73 and 93 were also shown to be inhibitors of EBI binding using the MCF7 cell lines showing binding of compounds in colchicine binding site (FIG. 44). Colchicine (COL) and nocodazole (NOC) are positive controls while vincristine (VINC) is negative control.

Example 44

In another exemplary method, the effect of compounds disclosed herein on cell cycle distribution was determined in a human cancer cell line. In brief, U87 cells were treated with DMSO, Compound 1A (1.2 µM), or Compound 1B (1.2 µM), for 48 hours and examined for cell cycle distribution by flow cytometry after propidium iodide (PI) staining. FIGS. 45A-45C show the fraction of cells in either the G0/G1 phase, the G2/M phase (4n), or the fraction of G2 cells that underwent endoreduplication and became polyploid (the 8n fraction) after treatment with DMSO (FIG. 45A), Compound 1A (FIG. 45B), or Compound 1B (FIG. 45C).

U87 cells were treated with DMSO, Compound 53 (1.2 µM), or Compound 71 (1.2 µM), for 48 hours and examined for cell cycle distribution by flow cytometry after PI staining. FIGS. 46A-46C illustrate the fraction of cells in either the G0/G1 phase, the G2/M phase (4n), or the fraction of G2 cells that underwent endoreduplication and became polyploid (the 8n fraction) after treatment with DMSO (FIG. 46A), Compound 53 (FIG. 46B), or Compound 71 (FIG. 46C).

U87 cells were treated with DMSO, Compound 19A (0.76 µM), or Compound 40 (0.76 µM), for 48 hours and examined for cell cycle distribution by flow cytometry after PI staining. FIGS. 47A-47C illustrate the fraction of cells in either the G0/G1 phase, the G2/M phase (4n), or the fraction of G2 cells that underwent endoreduplication and became polyploid (the 8n fraction) after treatment with DMSO (FIG. 47A), Compound 19A (FIG. 47B), or Compound 40 (FIG. 47C).

U87 cells were treated with DMSO and increasing concentrations of Compound 45A (for 48 hours and examined for cell cycle distribution by flow cytometry after PI staining. FIGS. 48A-48C show the fraction of cells in either the G0/G1 phase, the G2/M phase (4n), or the fraction of G2 cells that underwent endoreduplication and became polyploid (the 8n fraction) after treatment with DMSO (FIG. 48A), 1.0 µM Compound 45A (FIG. 48B), 2.5 µM Compound 45A (FIG. 48C).

Figure 49A:
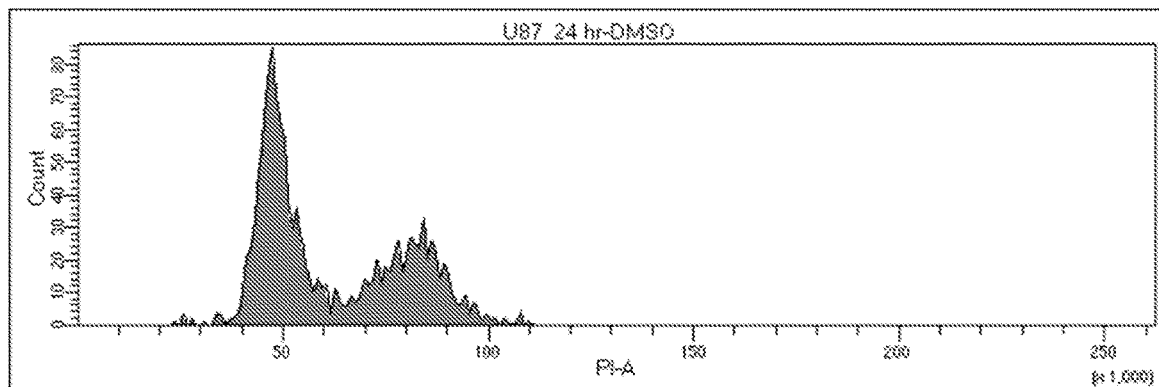
Figure 49B:
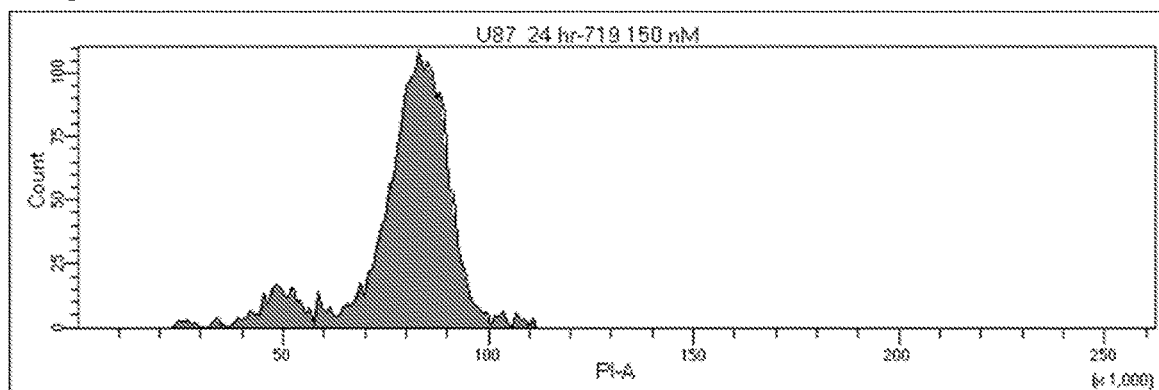
Figure 49C:
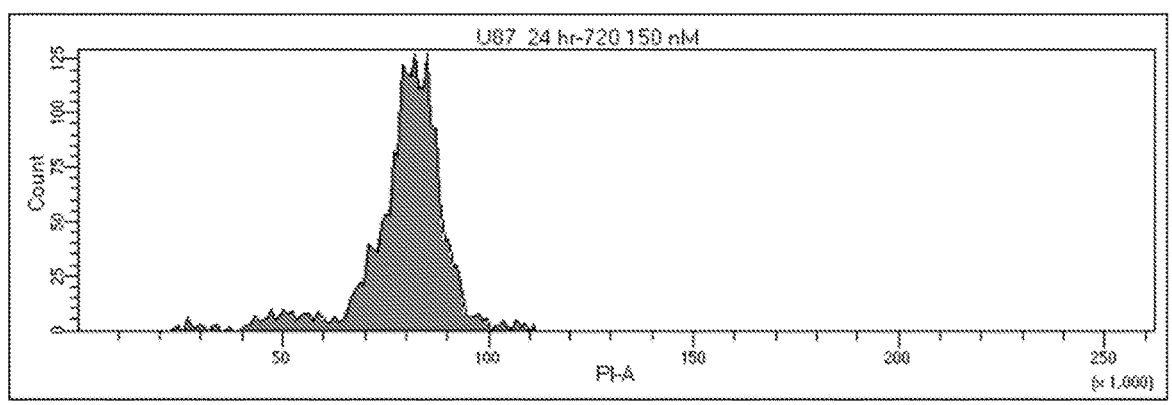
Figure 49D:
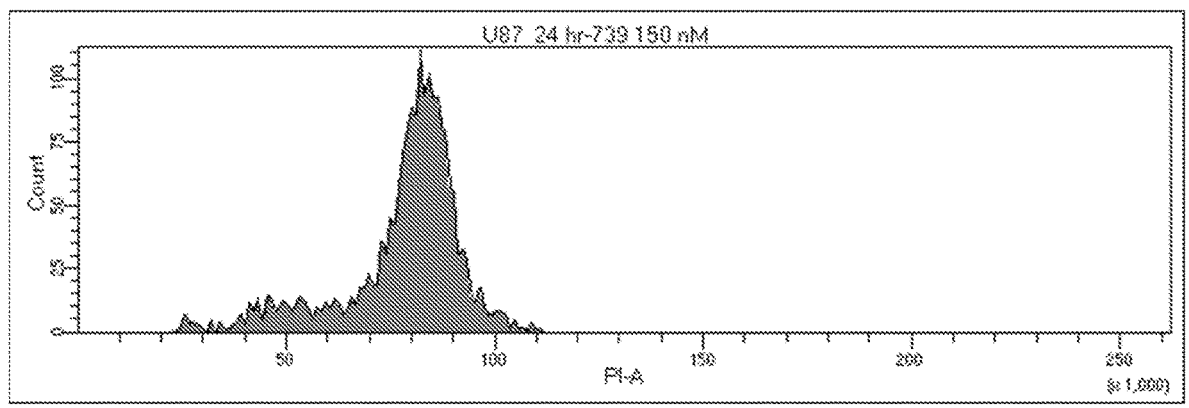
Figure 49E:
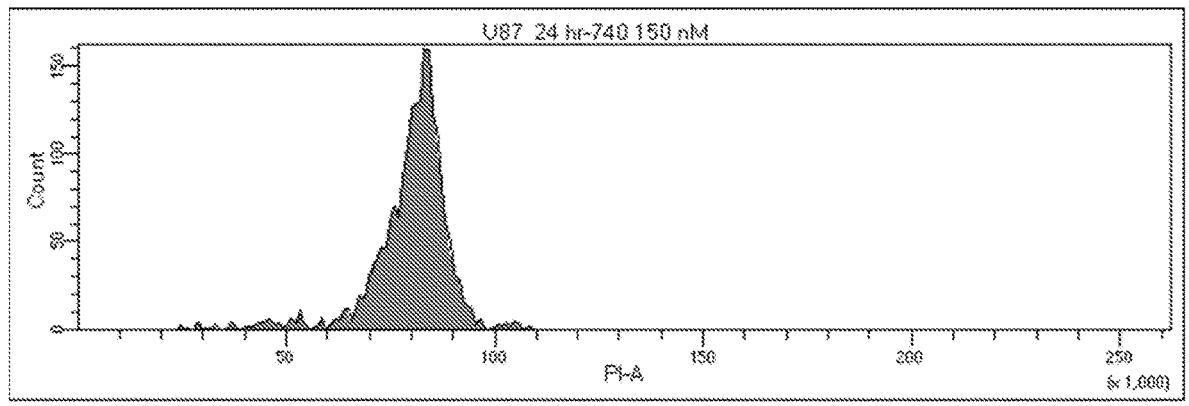
Figure 50A:
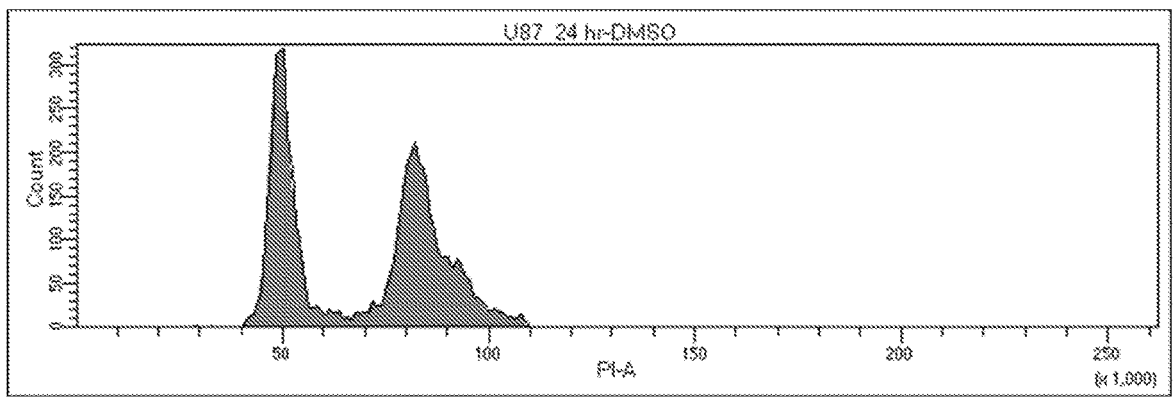
Figure 50B:
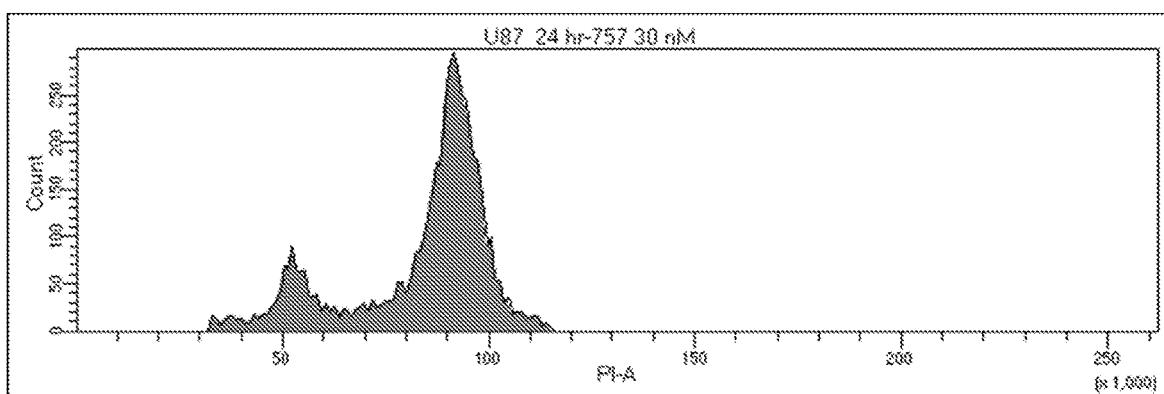
Figure 50C:
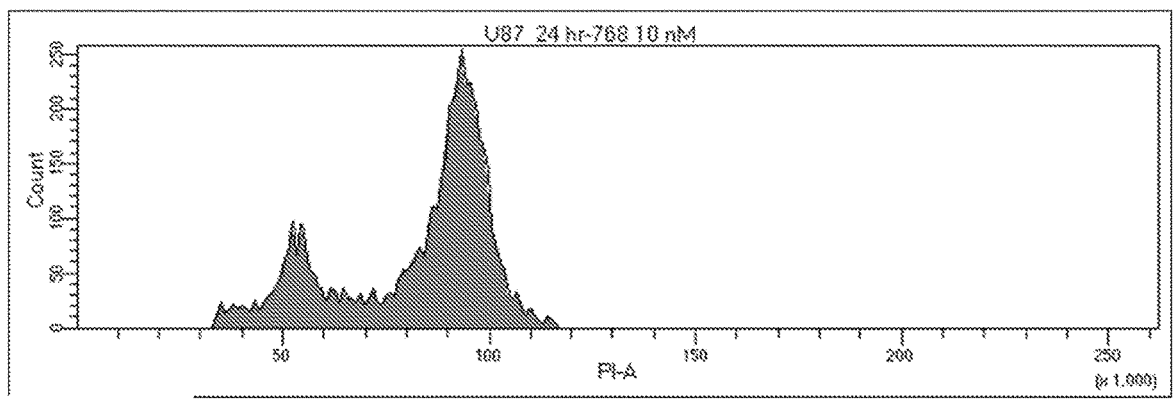
Figure 50D:
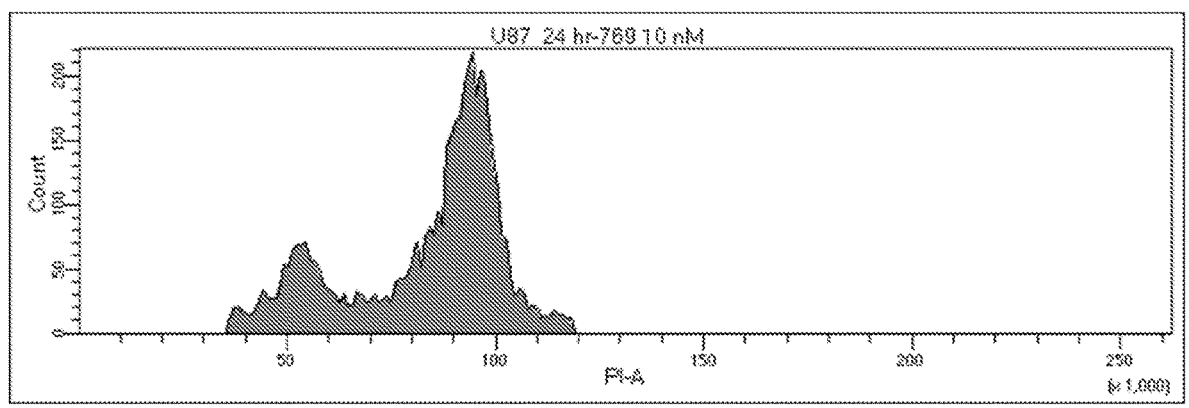

U87 cells were treated with DMSO and increasing concentrations of Compounds 93, 94, 95, or 96 (for 48 hours and examined for cell cycle distribution by flow cytometry after PI staining. FIGS. 49A-49E show the fraction of cells in either the G0/G1 phase, the G2/M phase (4n), or the fraction of G2 cells that underwent endoreduplication and became polyploid (the 8n fraction) after treatment with DMSO (FIG. 49A), 150 nM Compound 93 (FIG. 49B), 150 nM Compound 94 (FIG. 49C), 150 nM Compound 95 (FIG. 49D), and 150 nM Compound 96 (FIG. 49E).

U87 cells were treated with DMSO and increasing concentrations of Compounds 90, 97, or 98 (for 48 hours and examined for cell cycle distribution by flow cytometry after PI staining. FIGS. 50A-50D show the fraction of cells in either the G0/G1 phase, the G2/M phase (4n), or the fraction of G2 cells that underwent endoreduplication and became polyploid (the 8n fraction) after treatment with DMSO (FIG. 50A), 30 nM Compound 90 (FIG. 50B), 30 nM Compound 97 (FIG. 50C), and 10 nM Compound 98 (FIG. 49D) in accordance with certain embodiments of the present disclosure.

Example 45

In another exemplary method, levels of Compound 19A were determined in plasma and brain tissue following administration. For these studies, a CrTac:NCr-Foxn1$^{nu}$ athymic nude mouse strain was used as an acceptable mouse model. For these experiments, CrTac:NCr-Foxn1$^{nu}$ athymic nude mouse received xerographs of tumors implanted into the brain tissues. Compound 19A was then administered to the mice orally as a homogenous suspension in DMSO: (PEG 400: PVP=95:5)=1:4. A single dose of 100 mg/kg of Compound 19A was administered in this manner. Concentrations of the Compound 19A in plasma and brain tissue (after extraction) were measured using HPLC-MS quantitation.

FIG. 51 and Table 8 illustrate increasing concentrations of Compound 19A in both the left, healthy brain tissue and the right experimental brain tissue containing tumor as well as in plasma over time.

TABLE 8

| | Time | | |
|---|---|---|---|
| | 0.5 hours | 1 hour | 6 hours |
| Plasma (ng/mL) | 972.82 | 1342.91 | 1510.62 |
| Brain Tissue Healthy, Left (ng/g) | 766.56 | 1229.59 | 1464.34 |
| Brain Tissue Tumor, right (ng/g) | 828.22 | 1457.45 | 1523.55 |

FIG. 52A illustrates concentrations of Compound 19A in healthy mouse plasma over time and FIG. 52B illustrates concentrations of Compound 19A in healthy mouse plasma and brain at 1, 4 and 8 hrs.

FIG. 53A illustrates concentrations of Compound 98 in healthy mouse plasma over time. FIG. 53B and Table 9 illustrates concentrations of Compound 98 in healthy mouse plasma and brain at 0.5, 1 and 2 hrs.

TABLE 9

| | Time | | |
|---|---|---|---|
| | 0.5 hours | 1 hour | 2 hours |
| Plasma (ng/mL) | 424 | 490 | 399 |
| Healthy Brain (ng/g) | 230 | 234 | 257 |

Example 46 Synergistic Activity of Compounds with Temozolomide

The combination of compound 19 or 59 with Temozolomide resulted in a synergistic decrease in cancer cell viability. Synergy was calculated with the Bliss independence model. Compounds were combined at concentrations of 0 to 1000 uM for Temozolomide and 0.625 to 10 uM for compounds 19 and 59.

TABLE 10

| Bliss Synergy Values of compounds for combination with Temozolomide in LN18 glioblastoma cancer cells | |
|---|---|
| Compound Number | Bliss Synergy value |
| 59 | 20.0 |
| 19 | 29.5 |

Example 47 Synergistic Activity of Compounds with in Combination with a Second Agent The combination of compound 73 or 76 with Rabusertib resulted in a combination of agents leading to a synergistic decrease in cancer cell viability compared to the agents alone or added together. Synergy was calculated with the Bliss independence model. Compounds were combined at concentrations of 0 to 30 uM for Rabusertib and 0.625 to 5 uM for compounds 73 and 76.

TABLE 11

| Bliss Synergy Values of compounds for combination with Synergy with Rabusertib in 22Rv1 prostate cancer cells | |
|---|---|
| Compound Number | Bliss Synergy value |
| 73 | 20.7 |
| 76 | 15.3 |

Example 48 Combination Therapy of Compound 19 with Radiation for Glioblastoma

In this exemplary method, U87 glioblastoma cells treated with 2 Gy (Gray) units of ionizing radiation and 0.04-0.3 uM of compound 19 demonstrate reduced cancer cell viability relative to cells treated with ionizing radiation alone.

The foregoing discussion of the disclosure has been presented for purposes of illustration and description. The foregoing is not intended to limit the disclosure to the form or forms disclosed herein. Although the description of the disclosure has included description of one or more embodiments and certain variations and modifications, other variations and modifications are within the scope of the disclosure, e.g., as can be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

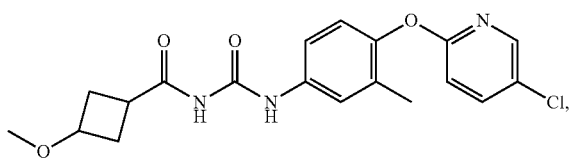

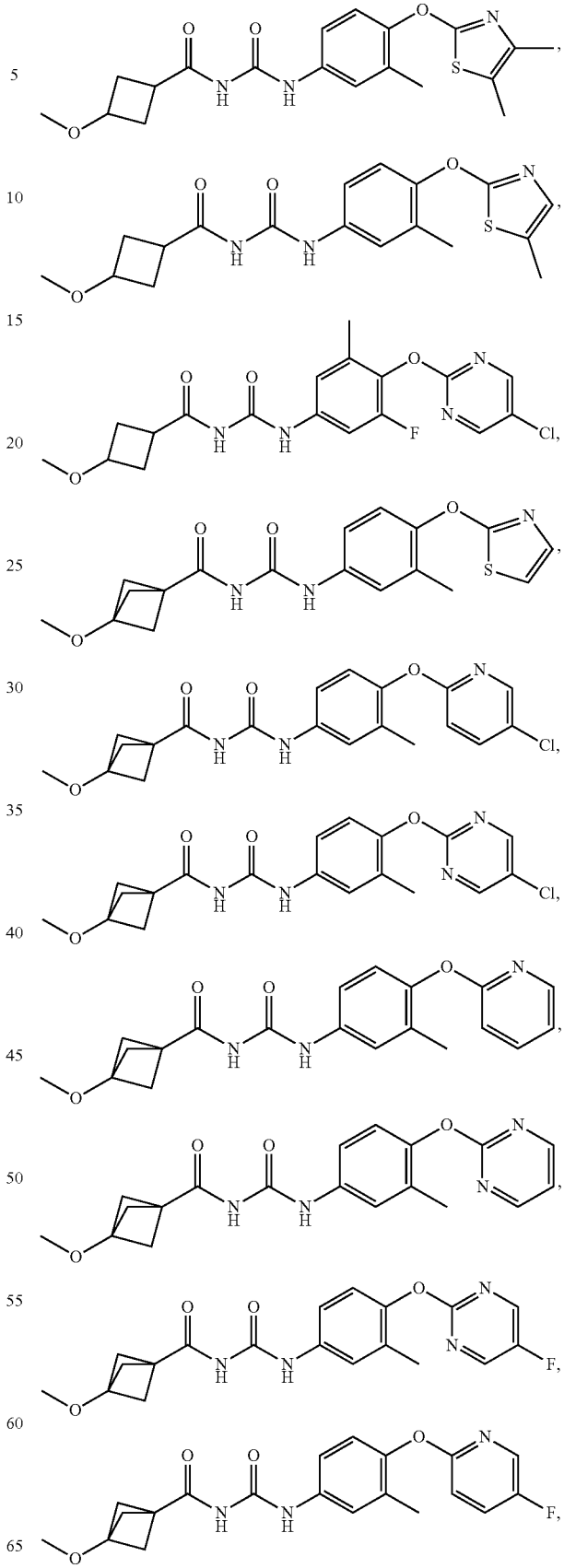

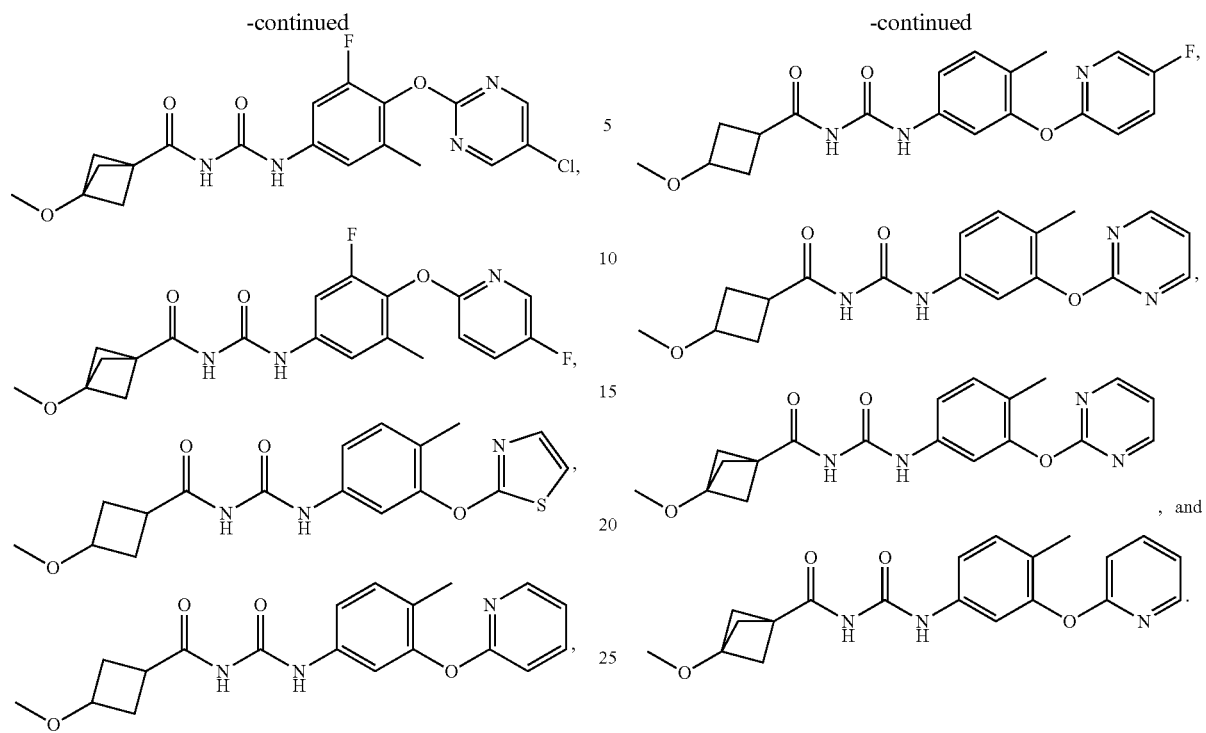

What is claimed is:

1. A compound according to formula (I),

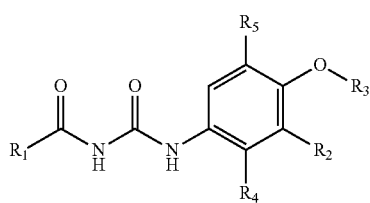

or formula (II),

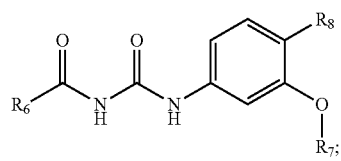

wherein:

$R_1$ and $R_6$ are each independently selected from the group consisting of:

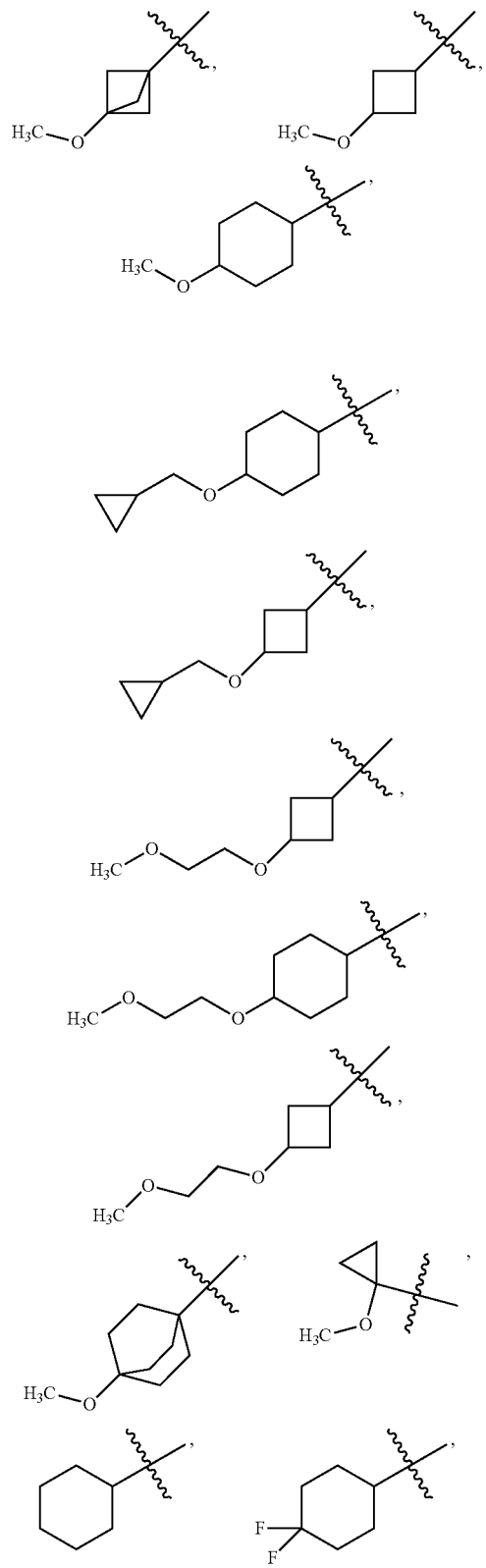

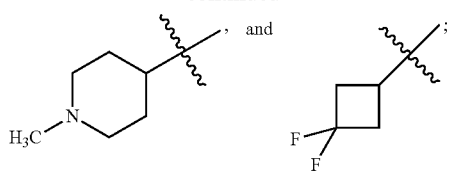

R₂ is selected from the group consisting of CH₃ or F;

wherein R₃ and R₇ are each a 5- or 6-membered heteroaryl unsubstituted or optionally substituted with one or more groups independently selected from the group consisting of alkyl, alkylamino, halogen, alkylhalide, cyano, cycloalkyl, heterocyclic alkyl, aryl, heteroaryl, cycloalkoxyl, heterocyclic alkoxyl, cycloalkylthio, and heterocyclic alkylthio, R₄ and R₅ are each independently selected from the group consisting of H and F; and R₈ is selected from the group consisting of CH₃ and H.

2. The compound according to claim 1, wherein R₃ and R₇ are each independently selected from the group consisting of:

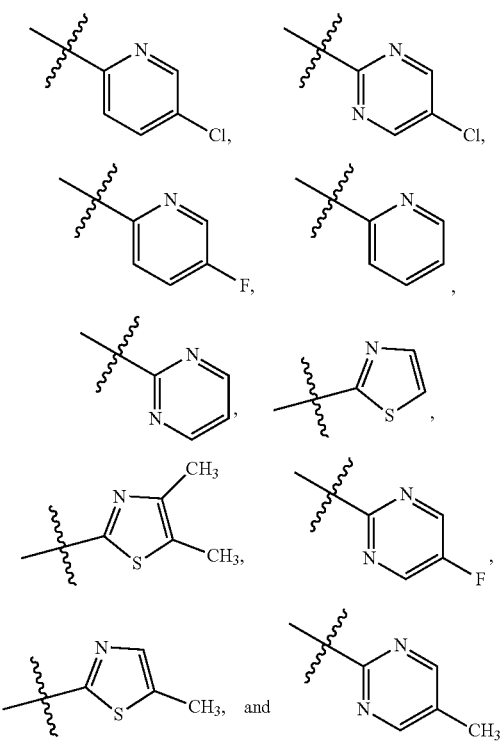

3. A compound selected from the group consisting of: